US012528856B2

(12) United States Patent
Lin et al.

(10) Patent No.: US 12,528,856 B2
(45) **Date of Patent: *Jan. 20, 2026**

(54) CHIMERIC CYTOKINE RECEPTORS COMPRISING TGF β BINDING DOMAINS

(71) Applicant: Allogene Therapeutics, Inc., South San Francisco, CA (US)

(72) Inventors: Regina Junhui Lin, San Mateo, CA (US); Siler Panowski, Berkeley, CA (US); Thomas John Van Blarcom, Oakland, CA (US); Shanshan Lang, San Mateo, CA (US); Barbra Johnson Sasu, San Francisco, CA (US)

(73) Assignee: Allogene Therapeutics, Inc., South San Francisco, CA (US)

( * ) Notice: Subject to any disclaimer, the term of this patent is extended or adjusted under 35 U.S.C. 154(b) by 1124 days.

This patent is subject to a terminal disclaimer.

(21) Appl. No.: 17/005,757

(22) Filed: Aug. 28, 2020

(65) Prior Publication Data

US 2021/0061881 A1 Mar. 4, 2021

Related U.S. Application Data

(60) Provisional application No. 63/053,322, filed on Jul. 17, 2020, provisional application No. 62/894,658, filed on Aug. 30, 2019.

(51) Int. Cl.

| | |
|---|---|
| ***C07K 14/71*** | (2006.01) |
| ***A61K 40/11*** | (2025.01) |
| ***A61K 40/31*** | (2025.01) |
| ***A61K 40/42*** | (2025.01) |
| ***C12N 5/0783*** | (2010.01) |
| ***C12N 15/86*** | (2006.01) |

(52) U.S. Cl.

CPC .............. *C07K 14/71* (2013.01); *A61K 40/11* (2025.01); *A61K 40/31* (2025.01); *A61K 40/4203* (2025.01); *A61K 40/4204* (2025.01); *A61K 40/4214* (2025.01); *C12N 5/0636* (2013.01); *C12N 15/86* (2013.01); *C07K 2319/03* (2013.01); *C07K 2319/70* (2013.01); *C12N 2740/15043* (2013.01)

(58) Field of Classification Search

None

See application file for complete search history.

(56) References Cited

U.S. PATENT DOCUMENTS

| | | | | |
|---|---|---|---|---|
| 6,866,998 | B1 | 3/2005 | Kitamura et al. | |
| 8,389,282 | B2 | 3/2013 | Sadelain et al. | |
| 9,434,935 | B2 | 9/2016 | Spencer et al. | |
| 9,913,882 | B2 | 3/2018 | Slawin et al. | |
| 9,944,690 | B2 | 4/2018 | Spencer et al. | |
| 10,287,354 | B2 | 5/2019 | Brogdon et al. | |
| 10,294,304 | B2 | 5/2019 | Kuo et al. | |
| 10,336,810 | B2 | 7/2019 | Tanaka | |
| 10,548,921 | B2 | 2/2020 | Leen et al. | |
| 2014/0050709 | A1 | 2/2014 | Leen et al. | |
| 2014/0087468 | A1 | 3/2014 | Spencer et al. | |
| 2015/0111294 | A1 | 4/2015 | Spencer et al. | |
| 2016/0175359 | A1 | 6/2016 | Spencer et al. | |
| 2016/0297884 | A1 | 10/2016 | Kuo et al. | |
| 2016/0297885 | A1 | 10/2016 | Kuo et al. | |
| 2018/0037630 | A1 | 2/2018 | Tanaka et al. | |
| 2019/0000881 | A1 | 1/2019 | Sadelain et al. | |
| 2019/0292533 | A1 | 9/2019 | Nager et al. | |
| 2020/0276238 | A1 * | 9/2020 | Lin | A61K 40/11 |
| 2020/0291090 | A1 * | 9/2020 | Lin | A61K 40/4204 |

FOREIGN PATENT DOCUMENTS

| | | | | |
|---|---|---|---|---|
| CA | 2842368 | A1 | 2/2013 | |
| CN | 106399255 | A | 2/2017 | |
| JP | 2016-520302 | A | 7/2016 | |
| JP | 2019-500012 | A | 1/2019 | |
| WO | 1996004389 | A1 | 2/1996 | |
| WO | WO9802558 | A2 | 1/1998 | |
| WO | 1999026978 | A1 | 6/1999 | |
| WO | WO2007075899 | A2 | 7/2007 | |
| WO | WO2011069004 | A1 | 6/2011 | |
| WO | WO2012138858 | A1 | 10/2012 | |
| WO | WO2014151960 | A2 | 9/2014 | |
| WO | WO2016055551 | A1 | 4/2016 | |
| WO | WO-2016061574 | A1 * | 4/2016 | A61K 39/0011 |
| WO | 2016090312 | A1 | 6/2016 | |
| WO | WO2016127257 | A1 | 8/2016 | |
| WO | WO2017029512 | A1 | 2/2017 | |
| WO | 2017068360 | A1 | 4/2017 | |

(Continued)

OTHER PUBLICATIONS

Morris et al. The Molecular Details of Cytokine Signaling via the JAK/STAT Pathway. Protein Science, 2018. 27:1984-2009.*

Bajgain, Pradip , "CAR T Cell Therapy for Breast Cancer: Harnessing the Tumor Milieu to Drive T Cell Activation", Research Article, J Immunother Cancer. May 10, 2018;6(1):34. doi: 10.1186/s40425-018-0347-5.

Behrmann, Iris , et al., "A single STAT recruitment module in a chimeric cytokine receptor complex is sufficient for STAT activation.", J Biol Chem.; 272(8):5269-74., 1997.

Boger, Dale L., et al., "Cytokine receptor dimerization and activation: prospects for small molecule agonists.", Bioorg Med Chem.; 9(3):557-62., 2001.

(Continued)

*Primary Examiner* — Christopher M Babic
*Assistant Examiner* — Kimberly A Aron
(74) *Attorney, Agent, or Firm* — Allogene Therapeutics, Inc.

(57) ABSTRACT

Provided herein are chimeric cytokine receptors bearing a binding domain capable of binding a TGF-β ligand or a TGF-β receptor antibody. When present on chimeric antigen receptor (CAR)-bearing immune cells (CAR-T-cells), such receptors allow for increased CAR-T cell expansion, activity and persistence, constitutively and/or through engagement of a TGF-β ligand or a TGF-β receptor antibody. Also provided are methods of making and using the chimeric cytokine receptors described herein.

40 Claims, 27 Drawing Sheets

Specification includes a Sequence Listing.

(56) References Cited

FOREIGN PATENT DOCUMENTS

| | | | |
|---|---|---|---|
| WO | WO2017103596 | A1 | 6/2017 |
| WO | WO2018038945 | A1 | 3/2018 |
| WO | WO2018094244 | A1 | 5/2018 |
| WO | WO2018104473 | A1 | 6/2018 |
| WO | 2018150187 | A1 | 8/2018 |
| WO | 2018161064 | A1 | 9/2018 |
| WO | 2019055946 | A1 | 3/2019 |
| WO | 2019079520 | A2 | 4/2019 |
| WO | 2019102207 | A1 | 5/2019 |
| WO | WO2019118508 | A1 | 6/2019 |
| WO | 2019169290 | A1 | 9/2019 |
| WO | 2019232425 | A1 | 12/2019 |
| WO | 2019246563 | A1 | 12/2019 |
| WO | 2020044055 | A1 | 3/2020 |
| WO | WO2020180664 | A1 | 9/2020 |
| WO | WO2020180694 | A1 | 9/2020 |
| WO | WO2016168612 | A1 | 10/2020 |

OTHER PUBLICATIONS

Boyerinas, B. , et al., "Abstract 602: A novel TGF-B/IL-12R signal conversion platform that protects Car T cells from TGF-B-mediated immune suppression and concurrently amplifies effector function", Proceedings of the American Association for Cancer Research Annual Meeting 2017; Apr. 1-5, 2017; Washington, DC. Philadelphia (PA): AACR; Cancer Res 2017;77(13 Suppl):Abstract 602, 4 total pages.

Cherkassky, L. , et al., "Human CAR T cells with cell-intrinsic PD-1 checkpoint blockade resist tumor-mediated inhibition", J. Clin. Invest. 126:3130-3144, 2016.

Defour, J P, et al., "Oncogenic activation of MPL/thrombopoietin receptor by 17 mutations at W515: implications for myeloproliferative neoplasms", Leukemia 30, 1214-1216; doi:10.1038/leu.2015.271, 2016.

Defour, J P, et al., "Tryptophan at the transmembrane-cytosolic junction modulates thrombopoietin receptor dimerization and activation", PNAS 110:2540-2545, 2013.

EPO , "International Search Report & Written Opinion", mailed for PCT/US2020/048402 on Nov. 27, 2020; 23 bages.

EPO , "International Search Report & Written Opinion", mailed on May 29, 2020 for PCT Application No. PCT/US2020/020415; 17 pages.

EPO , "International Search Report and Written Opinion", mailed on Jun. 4, 2020 for PCT Application No. PCT/US2020/020340; 15 pages.

EPO , "International Search Report and Written Opinion", mailed on May 31, 2019 for PCT Application No. PCT/US2019/020340; 18 pages.

Friedmann, Michael C., et al., "Different interleukin 2 receptor beta-chain tyrosines couple to at least two signaling pathways and synergistically mediate interleukin 2-induced proliferation", Immunology; Proc. Natl. Acad. Sci. USA, vol. 93, pp. 2077-2082, Mar. 1996.

Hoyos, V. , et al., "Engineering CD19-specific T lymphocytes with interleukin-15 and a suicide gene to enhance their anti-lymphoma/leukemia effects and safety", Leukemia 24:1160-1170, 2010.

Hurton, L. V., et al., "Tethered IL-15 augments antitumor activity and promotes a stem-cell memory subset in tumor-specific T cells", PNAS E7788-E7797, 2016.

Johnson, L.A. , et al., "Rational development and characterization of humanized anti-EGFR variant III chimeric antigen receptor T cells for glioblastoma", Science Translational Medicine, vol. 7, No. 275, Feb. 18, 2015, pp. 1-16, XP055362795, US ISSN: 1946-6234, DOI: 10.1126/scitranslmed.aaa4963.

Kagoya, Yuki , et al., "A Novel Chimeric Antigen Receptor Containing a JAK-STAT Signaling Domain Mediates Superior Antitumor Effects", Nat Med. Feb. 2018; 24(3): 352-359; doi: 10.1038/nm.4478, Feb. 5, 2018.

Kloss, C. , "TGFBeta signaling blockade within PSMA targeted CAR human T cells for the eradication of metastatic prostate cancer", Abstract 638, Molucular Therapy vol. 24, Supplement 1, 2 total pages, 2016.

Leen, Ann M, et al., "Reversal of Tumor Immune Inhibition Using a Chimeric Cytokine Receptor", Molecular Therapy vol. 22 No. 6, 1211-1220 Jun. 2014, Mar. 2014.

Leroy, Emilie , et al., "His 499 Regulates Dimerization and Prevents Oncogenic Activation by Asparagine Mutations of the Human Thrombopoietin Receptor", Journal of Biological Chemistry, vol. 291, No. 6, pp. 2974-2987, XP055696813, US ISSN: 0021-9258, DOI: 10.1074/jbc.M115.696534, 2015.

Liu, X. , et al., "A chimeric switch-receptor targeting PD1 augments the efficacy of second-generation CAR T cells in advanced solid tumors", Cancer Res. 76:1578-1590, 2016.

Lu, Xiaohui , et al., "Dimerization by a Cytokine Receptor Is Necessary for Constitutive Activation of JAK2V617F", J Biol Chem; Feb. 29, 2008;283(9):5258-66. doi: 10.1074/jbc.M707125200; Epub Dec. 23, 2007.

Malek, Thomas R., et al., "Interleukin-2 Receptor Signaling: At the Interface between Tolerance and Immunity", Immunity. Aug. 27, 2010; 33(2): 153-165. doi:10.1016/j.immuni.2010.08.004, 2010.

Matthews, E E, et al., "Thrombopoietin receptor activation: Transmembrane helix dimerization, rotation, and allosteric modulation", FASEB J. 25:2234-2244, 2011.

Maute, Rl, "Engineering high-affinity PD-1 variants for optimized immunotherapy and immuno-PET imaging", PNAS 112:E6506-E6514, 2015.

Murray, P J, "The JAK-STAT signaling pathway: input and output integration.", J Immunol. Mar. 1, 2007;178(5):2623-9., Feb. 2007.

Nakamura, T , et al., "A selective switch-on system for self-renewal of embryonic stem cells using chimeric cytokine receptors.", Biochem Biophys Res Commun. Jul. 9, 1998;248(1):22-7., Jul. 1998.

Saur, Sebastian J., et al., "Ubiquitination and degradation of the thrombopoietin receptor c-Mpl", Blood, Feb. 11, 2010 vol. 115, No. 6, pp. 1254-1263.

Shum, T , et al., "Constitutive signaling from an engineered IL7 receptor promotes durable tumor elimination by tumor-redirected T cells", Cancer Discovery 7:1-10, 2017.

Sukumaran, S. , "Enhancing the potency and specificity of engineered T cells for cancer treatment", Cancer Discovery 8:972-987, 2018.

Tokarew, Nicholas , et al., "Teaching an old dog new tricks: next-generation CAR T cells", British Journal Cancer, Nature Publishing Group; 120, 26-37. https://doi.org/10.1038/s41416-018-0325-1, Nov. 6, 2018.

Varghese, Lelia N., et al., "The Thrombopoietin Receptor: Structural Basis of Traffic and Activation by Ligand, Mutations, Agonists, and Mutated Calreticulin", Frontiers in Endocrinology, Mar. 2017, vol. 8, Article 59; doi: 10.3389/fendo.2017.00059.

Vong, Q, et al., "Inhibiting TGFbeta signaling in CAR T-cells may significantly enhance efficacy of tumor immunotherapy", Blood 130:1791, 5 total pages, 2017.

Wu, C-Y , et al., "Remote control of therapeutic T cells through a small molecule-gated chimeric receptor", Science 350:aab4077, 21 total pages, 2015.

EPO , "International Search Report & Written Opinion", Mailed on Jun. 21, 2021 for International Application No. PCT/US2021/019362.

Morris, Rhiannon , et al., "The molecular details of cytokine signaling via the JAK/STAT pathway", Protein Science 2018 ; vol. 27; pp. 1984-2009;, Dec. 1, 2018.

Babon, Jeffrey J., et al., "The molecular regulation of Janus kinase (JAK) activation", Biochem J. Aug. 15, 2014;462 (1):1-13. doi: 10.1042/BJ20140712.

Clackson, Tim , et al., "Redesigning an FKBP-ligand interface to generate chemical dimerizers with novel specificity", Proc. Natl. Acad. Sci. USA, vol. 95, Sep. 1998, pp. 10437-10442.

Floss, Dorreen , et al., "Naturally occurring and synthetic constitutive-active cytokine receptors in disease and therapy", Cytokine & Growth Factor Reviews; vol. 47, Jun. 2019, pp. 1-20.

Genbank , Accession No. AAB08425; thrombopoietin receptor [*Homo sapiens*]; 2016.

(56) References Cited

OTHER PUBLICATIONS

Genbank , Accession No. MN366105.1Synthetic construct 11D5-3-CD8BBZ gene, complete cds; 2019.
Intellectual Property Office of Singapore, Written Opinion mailed for Singaporean application No. 11202107984R on Jul. 4, 2023.
Itaya, Miki , "Regulation of Dimerization and Activation of the Thrombopoietin Receptor", PHD Thesis, Dec. 1, 2012; Stony Brook University; https://dspace.sunyconnect.suny.edu/bitstream/handle/1951/59699/Itaya_grad.sunysb_0771E_11150.pdf?sequence=1&isAllowed=y.
Miyazaki, H., "The thrombopoietin receptor", Japanese Journal of Thrombosis and Hemostasis, 2015, vol. 26, No. 1, p. 35-41, DOI: 10.2491/jjsth.26.35.
Moraga, I., et al., "Tuning Cytokine Receptor Signaling by Re-orienting Dimer Geometry with Surrogate Ligands", Cell. 2015. vol. 160. No. 6. p. 1196-1208.
Plo, Isabelle, et al., "Genetic Alterations of the Thrombopoietin/MPL/JAK2 Axis Impacting Megakaryopoiesis", Frontiers in Endocrinology; Review; Sep. 12, 2017; doi: 10.3389/fendo.2017.00234.
Saka, K., et al., "Activation of target signal transducers utilizing chimeric receptors with signaling-molecule binding motifs", Biotechnology and Bioengineering, Jan. 7, 2012, vol. 109, No. 6, p. 1528-1537, DOI: 10.1002/bit.24421.
Shaposhnikov, A.V., et al., "Molecular components of JAK/STAT signaling pathway and its connection with transcription machinery", Molecular Biology, 2013, vol. 47, No. 3, p. 388-397. (Russian language article with English language abstract).
Silvennoinen, Olli , et al., "Cytokine receptor signal transduction through Jak tyrosine kinases and Stat transcription factor", APMIS, vol. 105, Issue7-12, Jul. 1997, pp. 497-509.
Wang, X. et al., Structural biology of shared cytokine receptors. Annu Rev Immunol. 2009. vol. 27. p. 29-60.
Wilmes, Stephan , et al., "Mechanism of homodimeric cytokine receptor activation and dysregulation by oncogenic mutations", Science; Feb. 7, 2020;367(6478):643-652. doi: 10.1126/science.aaw3242.
Xie, et al. "Construction of an anti-programmed death-ligand 1 chimeric antigen receptor and determination of its antitumor function with transduced cells", Oncology Letter, 2018, 16:157-166.
Ajina, Adam, et al., "Strategies to Address Chimeric Antigen Receptor Tonic Signaling", Mol Cancer Ther; . Sep. 2018;17(9):1795-1815. doi: 10.1158/1535-7163.MCT-17-1097.
Behncken, Stuart N.., et al. "Growth Hormone (GH)-independent Dimerization of GH Receptor by a Leucine Zipper Results in Constitutive Activation" Journal of Biological Chemistry; vol. 275 Issue 22 pp. 17000-17007 (Jun. 2000) DOI: 10.1074/jbc.275.22.17000.
Ding, Jiamin, et al., "Asn 505 Mutation of the C-MPL Gene, A Cause of Familial Essential Thrombocythemia, Induces the Autonomous Homodimerizaton of the C-Mpl Independent of Ligand Stimulation." Blood; vol. 104, Issue 11, Nov. 16, 2004, p. 738.
Gacerez, Albert T.., et al., "How Chimeric Antigen Receptor Design Affects Adoptive T Cell Therapy" J Cell Physiol; Dec. 2016;231(12):2590-8. doi: 10.1002/jcp.25419. Epub Jun. 2, 2016.
Grotzinger, Joachim, "Molecular mechanisms of cytokine receptor activation" Biochim Biophys Acta; Nov. 11, 2002;1592(3):215-23.
Hu, Yuan, et al., "Chimeric antigen receptor (CAR)-transduced natural killer cells in tumor immunotherapy" Acta Pharmacol Sin; Feb. 2018;39(2):167-176. doi: 10.1038/aps.2017.125. Epub Sep. 7, 2017.
Kim, Jin Hee., et al., "High cleavage efficiency of a 2A peptide derived from porcine teschovirus-1 in human cell lines, zebrafish and mice" PLoS One; 2011;6(4):e18556. doi: 10.1371/journal.pone.0018556. Epub Apr. 29, 2011.
Metcalfe, Riley D.., et al. "Structural Understanding of Interleukin 6 Family Cytokine Signaling and Targeted Therapies: Focus on Interleukin 11" Front. Immunol., Jul. 16, 2020; Sec. Cytokines and Soluble Mediators in Immunity https://doi.org/10.3389/fimmu.2020.01424.
Shao, Huang, Structural requirements for signal transducer and activator of transcription 3 binding to phosphotyrosine ligands containing the YXXQ motif J. Biol Chem; Apr. 30, 2004;279(18):18967-73. doi: 10.1074/jbc.M314037200. Epub Feb. 13, 2004.
Shochat, Chen, et al.,"Gain-of-function mutations in interleukin-7 receptor-α (IL7R) in childhood acute lymphoblastic leukemias" Journal of Experimental Medicine; 2(2011) 208 (5): 901-908; https://doi.org/10.1084/jem.20110580.
Suthaus, Jan, et al., "Forced *Homo*- and Heterodimerization of All gp130-Type Receptor Complexes Leads to Constitutive Ligand-independent Signaling and Cytokine-independent Growth" Molecular Biology of the Cellvol. 21, No. 15; 2797-2807; Aug. 1, 2010; https://doi.org/10.1091/mbc.e10-03-0240.
Xie, Jiasen, et al., "Construction of an anti-programmed death-ligand 1 chimeric antigen receptor and determination of its antitumor function with transduced cells" Oncology Letters; Jul. 2018; vol. 16 Issue 1; DOI: https://doi.org/10.3892/ol.2018.8617.
Zenatti, Priscila P.., et al., "Oncogenic IL7R gain-of-function mutations in childhood T-cell acute lymphoblastic leukemia" Nature Genetics; Sep. 4, 2011;43(10):932-9. doi: 10.1038/ng.924.
Zhang, Cheng, et al., "Engineering CAR-T cells" Biomarker Research vol. 5, Article No. 22 (2017).

* cited by examiner

Underlined: wildtype TpoR TM region
Bold: means insertion

FIG. 9A (4138 - 4302 bp)

| | | |
|---|---|---|
| Template: | SDPTRVETATETAWISLVTALHLVLGLSAVLGLLLLRWQFPAHYRRLRHALWPSL | SEQ ID NO. 235 |
| N-1: | SDPTRVETATET-WISLVTALHLVLGLSAVLGLLLLRWQFPAHYRRLRHALWPSL | SEQ ID NO. 236 |
| N-2: | SDPTRVETATET--ISLVTALHLVLGLSAVLGLLLLRWQFPAHYRRLRHALWPSL | SEQ ID NO. 237 |
| N-2+1: | SDPTRVETATET-**L**ISLVTALHLVLGLSAVLGLLLLRWQFPAHYRRLRHALWPSL | SEQ ID NO. 238 |
| N-3: | SDPTRVETATET---SLVTALHLVLGLSAVLGLLLLRWQFPAHYRRLRHALWPSL | SEQ ID NO. 239 |
| N-4: | SDPTRVETATET----LVTALHLVLGLSAVLGLLLLRWQFPAHYRRLRHALWPSL | SEQ ID NO. 240 |
| N-4+1: | SDPTRVETATET---**I**LVTALHLVLGLSAVLGLLLLRWQFPAHYRRLRHALWPSL | SEQ ID NO. 241 |
| N-5: | SDPTRVETATET-----VTALHLVLGLSAVLGLLLLRWQFPAHYRRLRHALWPSL | SEQ ID NO. 242 |
| N-6: | SDPTRVETATET------TALHLVLGLSAVLGLLLLRWQFPAHYRRLRHALWPSL | SEQ ID NO. 243 |
| N-7: | SDPTRVETATET-------ALHLVLGLSAVLGLLLLRWQFPAHYRRLRHALWPSL | SEQ ID NO. 244 |
| N-8: | SDPTRVETATET--------LHLVLGLSAVLGLLLLRWQFPAHYRRLRHALWPSL | SEQ ID NO. 245 |
| N-9: | SDPTRVETATET---------HLVLGLSAVLGLLLLRWQFPAHYRRLRHALWPSL | SEQ ID NO. 246 |

FIG. 9B (4138 - 4302 bp)

| | | |
|---|---|---|
| Template: | SDPTRVETATETAW--------ISLVTALHLVLGLSAVLGLLLLRWQFPAHYRRLRHALWPSL | SEQ ID NO. 235 |
| N+1: | SDPTRVETATETAW-------**L**ISLVTALHLVLGLSAVLGLLLLRWQFPAHYRRLRHALWPSL | SEQ ID NO. 247 |
| N+2: | SDPTRVETATETAW------**VL**ISLVTALHLVLGLSAVLGLLLLRWQFPAHYRRLRHALWPSL | SEQ ID NO. 248 |
| N+3: | SDPTRVETATETAW-----**LVL**ISLVTALHLVLGLSAVLGLLLLRWQFPAHYRRLRHALWPSL | SEQ ID NO. 249 |
| N+4: | SDPTRVETATETAW----**ILVL**ISLVTALHLVLGLSAVLGLLLLRWQFPAHYRRLRHALWPSL | SEQ ID NO. 250 |
| N+5: | SDPTRVETATETAW---**LILVL**ISLVTALHLVLGLSAVLGLLLLRWQFPAHYRRLRHALWPSL | SEQ ID NO. 251 |
| N+6: | SDPTRVETATETAW--**LLILVL**ISLVTALHLVLGLSAVLGLLLLRWQFPAHYRRLRHALWPSL | SEQ ID NO. 252 |
| N+7: | SDPTRVETATETAW-**VLLILVL**ISLVTALHLVLGLSAVLGLLLLRWQFPAHYRRLRHALWPSL | SEQ ID NO. 253 |
| N+8: | SDPTRVETATETAW**LVLLILVL**ISLVTALHLVLGLSAVLGLLLLRWQFPAHYRRLRHALWPSL | SEQ ID NO. 254 |

FIG. 10A (4114 - 4278 bp)

| | | |
|---|---|---|
| Template: | **SDPTRVETATETAWISLVTALHLVLG**LSAVLGLLLLRWQFPAHYRRLRHALWPSL | SEQ ID NO. 235 |
| N-10: | SDPTRVETATET----------LVLGLSAVLGLLLLRWQFPAHYRRLRHALWPSL | SEQ ID NO. 255 |
| N-11: | SDPTRVETATET-----------VLGLSAVLGLLLLRWQFPAHYRRLRHALWPSL | SEQ ID NO. 256 |
| N-12: | SDPTRVETATET------------LGLSAVLGLLLLRWQFPAHYRRLRHALWPSL | SEQ ID NO. 257 |
| N-13: | SDPTRVETATET-------------GLSAVLGLLLLRWQFPAHYRRLRHALWPSL | SEQ ID NO. 258 |
| N-14: | SDPTRVETATET--------------LSAVLGLLLLRWQFPAHYRRLRHALWPSL | SEQ ID NO. 259 |
| N-9-1: | SDPTRVETATE----------HLVLGLSAVLGLLLLRWQFPAHYRRLRHALWPSL | SEQ ID NO. 260 |
| N-9-2: | SDPTRVETAT-----------HLVLGLSAVLGLLLLRWQFPAHYRRLRHALWPSL | SEQ ID NO. 261 |
| N-9-3: | SDPTRVETA------------HLVLGLSAVLGLLLLRWQFPAHYRRLRHALWPSL | SEQ ID NO. 262 |
| N-9-4: | SDPTRVET-------------HLVLGLSAVLGLLLLRWQFPAHYRRLRHALWPSL | SEQ ID NO. 263 |
| N-9-5: | SDPTRVE--------------HLVLGLSAVLGLLLLRWQFPAHYRRLRHALWPSL | SEQ ID NO. 264 |
| N-9-6: | SDPTRV---------------HLVLGLSAVLGLLLLRWQFPAHYRRLRHALWPSL | SEQ ID NO. 265 |
| N-9-7: | SDPTR----------------HLVLGLSAVLGLLLLRWQFPAHYRRLRHALWPSL | SEQ ID NO. 266 |
| N-9-8: | SDPT-----------------HLVLGLSAVLGLLLLRWQFPAHYRRLRHALWPSL | SEQ ID NO. 267 |
| N-9-9: | SDP------------------HLVLGLSAVLGLLLLRWQFPAHYRRLRHALWPSL | SEQ ID NO. 268 |
| N-9-10: | SD-------------------HLVLGLSAVLGLLLLRWQFPAHYRRLRHALWPSL | SEQ ID NO. 269 |
| N-9-11: | S--------------------HLVLGLSAVLGLLLLRWQFPAHYRRLRHALWPSL | SEQ ID NO. 270 |
| N-9-12: | ---------------------HLVLGLSAVLGLLLLRWQFPAHYRRLRHALWPSL | SEQ ID NO. 271 |

CHIMERIC CYTOKINE RECEPTORS COMPRISING TGF β BINDING DOMAINS

CROSS REFERENCE TO RELATED APPLICATIONS

The present application claims the benefit of priority to U.S. Provisional Application No. 62/894,658, filed on Aug. 30, 2019; and U.S. Provisional Application No. 63/053,322, filed on Jul. 17, 2020, the contents of both of which are hereby incorporated by reference in their entireties.

SEQUENCE LISTING

This application is being filed electronically via EFS-Web and includes an electronically submitted sequence listing in .txt format. The .txt file contains a sequence listing entitled "AT-030_03US_SL.txt" created on Aug. 27, 2020, and having a size of 570,950 bytes. The sequence listing contained in this .txt file is part of the specification and is incorporated herein by reference in its entirety.

BACKGROUND

Adoptive transfer of immune cells (e.g. T-cells) genetically modified to recognize malignancy-associated antigens is showing promise as a new approach to treating cancer. For example, T-cells can be genetically modified to express chimeric antigen receptors (CARs), which are fusion proteins comprised of an antigen recognition moiety and T-cell activation domains.

T-cell proliferation, cytotoxic potency and persistence is driven by signal transduction pathways. Conventional CAR designs provide two signals—CD3zeta activation (Signal 1) and co-stimulation (Signal 2, e.g. via 4-1BB, OX40, and/or CD28 expression). In some contexts, a third signal (Signal 3), cytokine-induced cytokine receptor signaling (e.g. cytokine support for immune potentiation), may be desirable. Approaches to provide Signal 3 have however been met with significant limitations.

One approach to provide cytokine support includes combining CAR-T-cell therapy with systemic infusions of recombinant cytokines/cytokine mimetics, and engineering CAR-T-cells to secrete/express cytokines extracellularly. As cytokines have pleiotropic effects and can also impact the function of other cell types, the systemic administration or production of immune-potentiating cytokines by CAR-T-cells have at least two major drawbacks: (i) these approaches can cause systemic toxicity in humans, and (ii) in the context of allogeneic CAR-T-cell therapy, these approaches may cause bystander host immune-activation that could accelerate the rejection of allogeneic CAR-T-cells, thereby compromising therapeutic efficacy. Another approach to provide cytokine support was based on introducing a constitutively activated dimerized cytokine receptor, an IL-7Ra—this limits the nature (IL-7 signaling only) and magnitude of signaling output. Yet another approach to provide cytokine support involved incorporating Signal 3 directly into the CAR molecule (Nat Med. 2018 March; 24(3):352-359.). A limitation of this approach is that the strength of Signal 3 is dependent on the strength of CAR activation. In the absence of target (and CAR activation), Signal 3 would not be transduced.

Needed are solutions to circumvent these drawbacks by targeting cytokine signals specifically to CAR-T-cells in a context-dependent manner, thus allowing for an improved safety profile and therapeutic efficacy. Provided herein and compositions and methods that address this need.

SUMMARY

Provided herein are chimeric cytokine receptors comprising TGF-β binding domains. Provided herein are inducible TGF-β-driven chimeric cytokine receptors, active when engaged with a ligand of the transforming growth factor beta cytokine family (TGF-β ligands, e.g., TGF-β1, TGF-β2, and TGF-β3) or activation with an anti-TGF-β-receptor antibody. When present on chimeric antigen receptor (CAR)-bearing immune cells, and engaged with TGF-β ligands and/or activation with an anti-TGF-βR antibody, such receptors allow for increased cytokine receptor signaling (Signal 3), leading to increased immune cell activation, proliferation, persistence, and/or potency of the CAR-bearing immune cells. Accordingly, the chimeric cytokine receptors of the disclosure allow for cytokine signals to be transmitted into the immune cell with endogenous TGF-β ligands, whereby blocking their immune-suppressive signals, and converting them into immune-potentiating signals that can work in concert with, or synergize, CAR-driven activity. Moreover, as clinically approved anti-TGF-β receptor antibodies can cluster and activate the chimeric cytokine receptors of the disclosures, patients treated with anti-TGF-β receptor may benefit not only from the blockage of the endogenous TGF-β signaling, but from also the activation of cytokine signaling in cells bearing the chimeric cytokine receptors. Also provided herein are constitutively active TGF-β-driven of TGF-β binding domain-containing chimeric cytokine receptors; such receptors continue to signal in the absence of an inducer, but can be further induced or can exhibit further improved properties or activities, for example, in the presence of a TGF-β ligand or an anti-TGF-βR antibody. In some embodiments, the TGF-βR is TGF-βR2, and the antibody is an anti-TGF-βR2 antibody. As used herein, "TGF-beta" is used interchangeably with "TGF-β."

Accordingly, in one aspect, provided herein is a chimeric cytokine receptor comprising: (a) a binding domain comprising an extracellular portion of a TGF-β receptor, or a TGF-β antigen binding domain; (b) a transmembrane domain; (c) a Janus Kinase (JAK)-binding domain; and (d) a recruiting domain. As used herein, "extracellular portion" refers to any portion of an extracellular domain of a TGF-β receptor.

In a related aspect provided herein is a polynucleotide encoding any one of the chimeric cytokine receptors of the disclosure, and an expression vector comprising such a polynucleotide. In some embodiments, the polynucleotide further encodes for a chimeric antigen receptor (CAR), wherein the CAR binds to a target of interest. The target of interest can be any molecule of interest, including, for example, without limitation any one or more of those presented in Table 8.

In a further aspect, provided herein is an engineered immune cell comprising at least one chimeric cytokine receptor of the disclosure. In another aspect, provided herein is an engineered immune cell comprising at least one chimeric antigen receptor (CAR) and at least one chimeric cytokine receptor of the disclosure. In some embodiments the immune cell is a T-cell. In some embodiments the immune cell is an allogeneic immune cell. In other embodiments, the immune cell is an autologous immune cell. The immune cell may be selected from the group consisting of: T-cell, dendritic cell, killer dendritic cell, mast cell, NK-cell, macrophage, monocyte, B-cell and an immune cell derived from a stem cell. In a related aspect, provided herein is a pharmaceutical composition comprising any of the engineered immune cells of the disclosure, and a kit comprising such a pharmaceutical composition. Also provided herein is a method of making the immune cell.

In another aspect, provided herein is a method of treating a cancer in a subject, comprising administering to the subject a therapeutically effective amount of any of the engineered immune cells described herein.

BRIEF DESCRIPTION OF THE DRAWINGS

FIGS. 9A-9B show the amino acid sequences for the wild type TPOR and the various transmembrane deletion or insertion variants. FIGS. 9A-B disclose SEQ ID NOS 235-246, 235, and 247-254, respectively, in order of appearance.

FIG. 10A shows the amino acid sequences for the wild type TPOR and additional transmembrane variants. FIG. 10A discloses SEQ ID NOS 235 and 255-271, respectively, in order of appearance.

DETAILED DESCRIPTION

Figure 1:
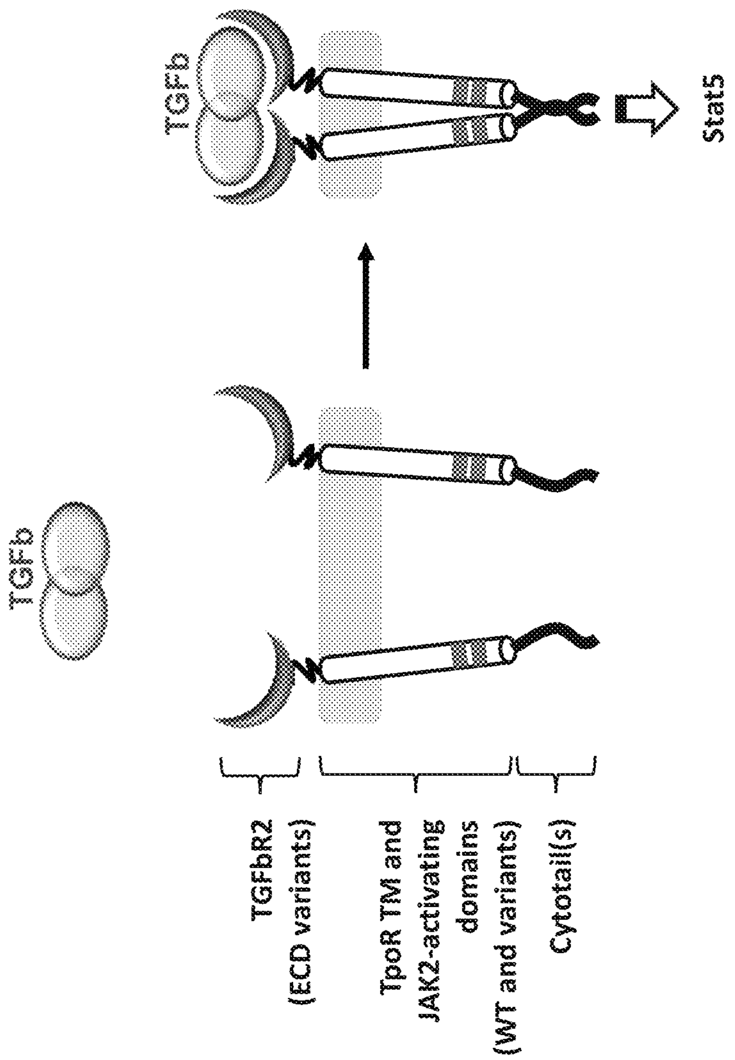
FIG. 1 shows a schematic of the inducible chimeric cytokine receptor of the disclosure.

Provided herein are chimeric cytokine receptors comprising TGF-β binding domains. Provided herein are inducible chimeric cytokine receptors, active when engaged with TGF-β ligands (e.g. TGF-β1, TGF-β2, and/or TGF-β3) or activation with an anti-TGF-β-receptor antibody. Also provided herein are constitutively active chimeric cytokine receptors comprising TGF-β binding domains. Also provided herein are chimeric antigen receptor (CAR)-bearing immune cells (CAR-I-cells, e.g. CAR-T-cells), expressing the chimeric cytokine receptors of the disclosure. In some embodiments, the constitutively active chimeric cytokine receptors exhibit improved properties or activities when engaged with a TGF-β ligand or activation with an anti-TGF-β-receptor antibody, as compared with constitutively active chimeric cytokine receptors without a TGF-β binding domain. Also provided herein are methods of making and using the chimeric cytokine receptors.

I. TGF-β-Bearing Chimeric Cytokine Receptors

The chimeric cytokine receptors of the disclosure activate signaling upon binding of a TGF-β ligand (for example, TGF-β1, TGF-β2, and/or TGF-β3), or an anti-TGF-β-receptor antibody. These receptors activate signaling when monomers of the receptor cluster and/or dimerize. The chimeric cytokine receptors of the disclosure are dual-function chimeric cytokine receptors which can simultaneously neutralize the immune-suppressive effects of a TGF-β ligand, and mimic the transmission of an immune-potentiating cytokine signal.

In some embodiments, a monomer of the chimeric cytokine receptor of the disclosure comprises: (a) a binding domain capable of binding a TGF-β ligand or an anti-TGF-β-receptor antibody; (b) a transmembrane domain; (c) a Janus Kinase (JAK)-binding domain; and; (d) a STAT-recruiting domain (e.g. from the cytoplasmic domain of a receptor; e.g. from a cytokine receptor). Each domain can be linked either directly or via one or more peptide linkers. In some embodiments, a monomer of the chimeric cytokine receptor of the disclosure comprises: (a) a binding domain capable of binding a TGF-β ligand or an anti-TGF-β-receptor antibody; (b) a transmembrane domain; (c) a Janus Kinase (JAK)-binding domain; and; (d) a recruiting domain (e.g. from the cytoplasmic domain of a receptor; e.g. from a cytokine receptor). The recruiting domain can be a STAT-recruiting domain, an AP1—recruiting domain, a Myc/Max recruiting domain; or a NFkB-recruiting domain. In some embodiments, the chimeric cytokine receptors are clustered and activated when they bind to TGF-β ligands, and/or are clustered and activated with an anti-TGF-β-receptor antibody. The chimeric cytokine receptors activate signaling upon for example binding a TGF-β ligand, and/or a TGF-β-receptor antibody. In some embodiments, the TGF-β receptor antibody is, without limitation, PF-03446962 or LY3022859. In some embodiments, the chimeric cytokine receptors are constitutively clustered or dimerized.

As used herein, "TGF-β ligand," refers to TGF-β1, TGF-β2, and TGF-β3, and isoforms and derivatives thereof. It should be understood that "TGF-β ligand" and "TGF-β" are used interchangeably herein.

A. Binding Domains

The chimeric cytokine receptors of the disclosure comprise a binding domain capable of binding a TGF-β ligand or an anti-TGF-β-receptor antibody. As referred to herein, a binding domain is the domain of the chimeric cytokine receptor that extends into the extracellular space. The binding domain binds and sequesters TGF-β away from the endogenous TGF-β receptor, thereby preventing or reducing TGF-β-induced immune-suppression. The binding domains of the disclosure bind with TGF-β ligands and anti-TGF-β-receptor antibodies, leading to binding-induced signal transduction.

In some embodiments, the binding domain comprises an extracellular portion of a TGF-β receptor, for example the extracellular portion of TGFβR1 or TGFβR2.

In some embodiments, the binding domain comprises an extracellular portion of a wild type TGFβ receptor. In some embodiments, the TGF-β receptor comprises one or more mutations that enhance or alter the affinity to the binding to the TGFβ ligands.

In some embodiments, the binding domain comprises the extracellular portion of a wild type TGFβR1 or TGFβR2; in some embodiments, the binding domain comprises the extracellular portion of a wild type TGFβR1 or TGFβR2 and comprises the amino acid sequence of SEQ ID NOS: 2 or 3, respectively.

In some embodiments, the binding domain comprises mutations to the extracellular portion of a wild type TGF-β receptor. In some embodiments, the binding domain comprises mutations to the extracellular portion of a wild type TGF-β receptor, and comprises the amino acid sequences of any one of SEQ ID NO: 4 to SEQ ID NO: 20. In some embodiments, the chimeric cytokine receptor comprises a binding domain that is at least 80%, 85%, 90%, 95%, 98%, or 99%, or 100% identical to any one of the amino acid sequences of SEQ ID NOs: 4-20. In some embodiments, the binding domain does not comprise a signal sequence.

Table 1 shows exemplary binding domain amino acid sequences of the disclosure. It is noted that the expression and extracellular location of the exemplary binding domain sequences, such as TGF-β receptor amino acid sequences, can be achieved with the use of a signal sequence. In an exemplary embodiment, a CD8 signal sequence (CD8SS) MALPVTALLLPLALLLHAARP (SEQ ID NO: 1) is utilized. In some embodiments, the binding domain comprises the extracellular domain of wild type TGFβR2 comprising the amino acid sequence of SEQ ID NO:159. In some embodiments, the signal sequence is the endogenous signal sequence of human TGF-βR2.

TABLE 1

Exemplary Binding Domain Sequences

| Binding Domain | Amino acid sequence | SEQ ID NO: |
|---|---|---|
| TGFβR1 (1-126) | MEAAVAAPRPRLLLLVLAAAAAAAAALLPGAT ALQCFCHLCTKDNFTCVTDGLCFVSVTETTDKVI HNSMCIAEIDLIPRDRPFVCAPSSKTGSVTTTYCC NQDHCNKIELPTTVKSSPGLGPVEL | 2 |
| TGFβR2 (1-166) Underlined TGFβR2 signal sequence | MGRGLLRGLWPLHIVLWTRIASTIPPHVQKSVNN DMIVTDNNGAVKFPQLCKFCDVRFSTCDNQKSC MSNCSITSICEKPQEVCVAVWRKNDENITLETVC HDPKLPYHDFILEDAASPKCIMKEKKKPGETFFM CSCSSDECNDNIIFSEEYNTSNPDLLLVIFQ | 3 |
| TGFβR2ΔN25 | QLCKFCDVRFSTCDNQKSCMSNCSITSICEKPQE VCVAVWRKNDENITLETVCHDPKLPYHDFILED AASPKCIMKEKKKPGETFFMCSCSSDECNDNIIFS EEYNTSNPDLLLVIFQ | 4 |
| TGFβR2ΔN25FSE-N8 | QLCKFCDVRFSTCDNQKSCMSNCSITSICEKPQE VCVAVWRKNDENITLETVCHDPKLPYHDFILED AASPKCIMKEKKKPGETFFMCSCSSDECNDNIIFS ELLLVIFQ | 5 |
| TGFβR2ΔN25FSE-N6 | QLCKFCDVRFSTCDNQKSCMSNCSITSICEKPQE VCVAVWRKNDENITLETVCHDPKLPYHDFILED | 6 |

TABLE 1-continued

Exemplary Binding Domain Sequences

| Binding Domain | Amino acid sequence | SEQ ID NO: |
|---|---|---|
| | AASPKCIMKEKKKPGETFFMCSCSSDECNDNIIFS EPDLLLVIFQ | |
| TGFβR2ΔN25FSE-N5 | QLCKFCDVRFSTCDNQKSCMSNCSITSICEKPQE VCVAVWRKNDENITLETVCHDPKLPYHDFILED AASPKCIMKEKKKPGETFFMCSCSSDECNDNIIFS EEPDLLLVIFQ | 7 |
| TGFβR2ΔN25FSE-N4 | QLCKFCDVRFSTCDNQKSCMSNCSITSICEKPQE VCVAVWRKNDENITLETVCHDPKLPYHDFILED AASPKCIMKEKKKPGETFFMCSCSSDECNDNIIFS EEYPDLLLVIFQ | 8 |
| TGFβR2ΔN25FSE-N3 | QLCKFCDVRFSTCDNQKSCMSNCSITSICEKPQE VCVAVWRKNDENITLETVCHDPKLPYHDFILED AASPKCIMKEKKKPGETFFMCSCSSDECNDNIIFS EEYNPDLLLVIFQ | 9 |
| TGFβR2ΔN25.Glyc33 | QLCKFCD**NRT**STCDNQKSCMSNCSITSICEKPQE VCVAVWRKNDENITLETVCHDPKLPYHDFILED AASPKCIMKEKKKPGETFFMCSCSSDECNDNIIFS EEYNTSNPDLLLVIFQ | 10 |
| TGFβR2ΔN25.Glyc40 | QLCKFCDVRFSTCDNQ**T**SCMSNCSITSICEKPQEV CVAVWRKNDENITLETVCHDPKLPYHDFILEDA ASPKCIMKEKKKPGETFFMCSCSSDECNDNIIFSE EYNTSNPDLLLVIFQ | 11 |
| TGFβR2ΔN25.Glyc56 | QLCKFCDVRFSTCDNQKSCMSNCSITSICE**NPT**EV CVAVWRKNDENITLETVCHDPKLPYHDFILEDA ASPKCIMKEKKKPGETFFMCSCSSDECNDNIIFSE EYNTSNPDLLLVIFQ | 12 |
| TGFβR2ΔN25.Glyc58 | QLCKFCDVRFSTCDNQKSCMSNCSITSICEKP**NET** CVAVWRKNDENITLETVCHDPKLPYHDFILEDA ASPKCIMKEKKKPGETFFMCSCSSDECNDNIIFSE EYNTSNPDLLLVIFQ | 13 |
| TGFβR2ΔN25.V33K | QLCKFCD**K**RFSTCDNQKSCMSNCSITSICEKPQE VCVAVWRKNDENITLETVCHDPKLPYHDFILED AASPKCIMKEKKKPGETFFMCSCSSDECNDNIIFS EEYNTSNPDLLLVIFQ | 14 |
| TGFβR2ΔN25.E70K | QLCKFCDVRFSTCDNQKSCMSNCSITSICEKPQE VCVAVWRKND**K**NITLETVCHDPKLPYHDFILED AASPKCIMKEKKKPGETFFMCSCSSDECNDNIIFS EEYNTSNPDLLLVIFQ | 15 |
| TGFβR2ΔN25.Glyc87 | QLCKFCDVRFSTCDNQKSCMSNCSITSICEKPQE VCVAVWRKNDENITLETVCHDPKLPYH**NFT**LED AASPKCIMKEKKKPGETFFMCSCSSDECNDNIIF | 16 |
| TGFβR2ΔN25.Glyc89 | QLCKFCDVRFSTCDNQKSCMSNCSITSICEKPQE VCVAVWRKNDENITLETVCHDPKLPYHDF**NLT**D AASPKCIMKEKKKPGETFFMCSCSSDECNDNIIF | 17 |
| TGFβR2ΔN25.Glyc102 | QLCKFCDVRFSTCDNQKSCMSNCSITSICEKPQE VCVAVWRKNDENITLETVCHDPKLPYHDFILED AASPKCIMK**NKT**KPGETFFMCSCSSDECNDNIIF | 18 |
| TGFβR2ΔN25.Glyc123 | QLCKFCDVRFSTCDNQKSCMSNCSITSICEKPQE VCVAVWRKNDENITLETVCHDPKLPYHDFILED AASPKCIMKEKKKPGETFFMCSCSSDECNDNI**T**F | 19 |
| TGFβR2ΔN25.I89E | QLCKFCDVRFSTCDNQKSCMSNCSITSICEKPQE VCVAVWRKNDENITLETVCHDPKLPYHDF**E**LED AASPKCIMKEKKKPGETFFMCSCSSDECNDNIIF | 20 |
| TGFβR2 (without the signal sequence) | IPPHVQKSVNNDMIVTDNNGAVKFPQLCKFCDV RFSTCDNQKSCMSNCSITSICEKPQEVCVAVWRK NDENITLETVCHDPKLPYHDFILEDAASPKCIMKE KKKPGETFFMCSCSSDECNDNIIFSEEYNTSNPDL LLVIFQ | 159 |

Figure 2A:
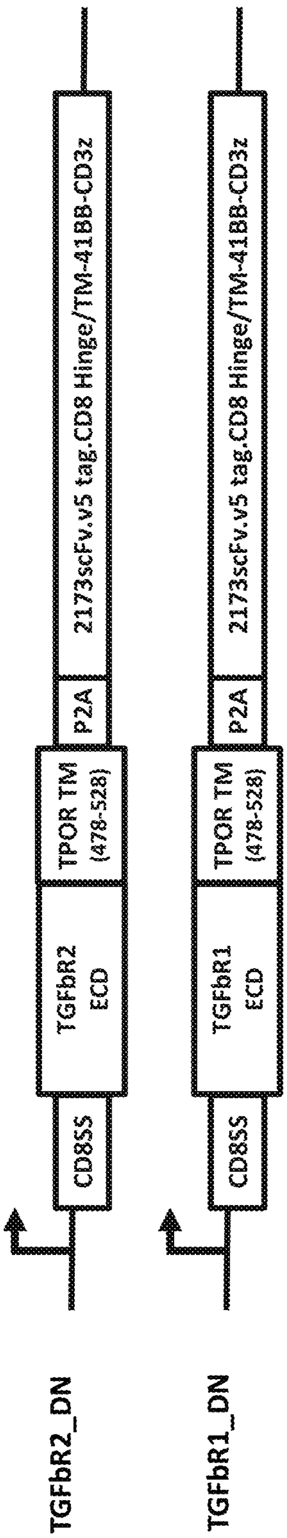
FIG. 2A shows a schematic of the lentiviral vector used to co-express the dominant negative truncations of the TGFβR1 or TGFβR2 cytokine receptor with the $2^{nd}$ generation EGFRvIII CAR.

In some embodiments, the chimeric cytokine receptor is a dominant negative (DN) wherein the binding domain of the TGF-β receptor is expressed, but the chimeric cytokine receptor does not comprise an intracellular signaling domain—the chimeric cytokine receptor can bind TGF-β but does not transmit a positive signal (DN chimeric cytokine receptor). In some embodiments, the TGF-β receptor is TGFβR1 (dominant-negative TGFβR1, or TGFβR1 DN) and comprises the amino acid sequence of SEQ ID NO: 2. In some embodiments, the TGF-β receptor is TGFβR2 (dominant-negative TGFβR2, or TGFβR2 DN) and comprises the amino acid sequence of SEQ ID NO: 3. TGF-β receptor dominant negative sequences may be expressed with the aid of a signal sequence, e.g. a CD8SS signal sequence of SEQ ID NO: 1. Example schematics of a DN chimeric cytokine receptor are shown in FIG. 2A.

In other embodiments, the binding domain comprises a TGF-β antigen binding domain. Such antigen binding domains include, but are not limited to, a single chain variable fragment (scFv) that can bind the TGF-β ligands, and single domain antibodies (nanobodies). These scFvs and single domain antibodies may include commercially available scFvs and single domain antibodies, and those derived from, for example, camelid and shark antibodies.

In other embodiments, the binding domain comprises a TGF-β antigen binding domain, wherein the antigen binding domain comprises a Fab fragment.

B. Transmembrane Domains

The chimeric cytokine receptors of the disclosure comprise transmembrane domains. Such transmembrane domains are coupled to the extracellular binding domain on the N-terminus, and to additional intracellular/cytoplasmic domains on the C-terminus. In some embodiments, the coupling is achieved optionally through a linker.

As used herein, the transmembrane domains are capable of insertion into the membrane of a cell in which it is expressed. In some embodiments, the transmembrane domains of the disclosure span a cellular membrane, and comprise an extracellular portion, and/or an intracellular portion.

In some embodiments, the transmembrane domains of the disclosure are engineered and do not resemble any naturally occurring transmembrane domain, e.g. they are non-naturally occurring.

In other embodiments, the transmembrane domains of the disclosure are derived from naturally occurring receptors.

In some embodiments, the transmembrane and/or JAK domains of the disclosure are derived from, for example, one or more of the following receptors: erythropoietin receptor (EpoR), Interleukin 6 signal transducer (GP130 or IL6ST), prolactin receptor (PrlR), growth hormone receptor (GHR), granulocyte colony-stimulating factor receptor (GCSFR), and thrombopoietin receptor/myeloproliferative leukemia protein receptor (TPOR/MPLR). When derived from naturally occurring receptors, the entire receptor, or the entire transmembrane sequence of the receptor may not be necessary to effectuate constitutive activation and constitutive JAK binding/activation on the intracellular portion. Accordingly fragments of naturally occurring receptors may be utilized. Furthermore, certain mutations may be introduced into the transmembrane domains derived from naturally occurring receptors, to further tune the downstream JAK-dependent signaling. In some embodiments, the chimeric cytokine receptor of the disclosure comprises a portion or a fragment of a naturally occurring receptor, e.g., the transmembrane and/or JAK binding/activation domain of the naturally occurring receptor, optionally comprising one or more mutations therein (e.g., one or more deletions, insertions and/or substitutions).

In some embodiments, the transmembrane and/or JAK domains of the disclosure is derived from the naturally occurring EpoR receptor.

In some embodiments, the transmembrane and/or JAK domains of the disclosure is derived from the naturally occurring GP130 receptor.

In some embodiments, the transmembrane and/or JAK domains of the disclosure is derived from the naturally occurring PrlR receptor.

In some embodiments, the transmembrane and/or JAK domains of the disclosure is derived from the naturally occurring GHR receptor.

In some embodiments, the transmembrane and/or JAK domains of the disclosure is derived from the naturally occurring GCSF receptor.

In some embodiments, the transmembrane and/or JAK domains of the disclosure is derived from the naturally occurring TPOR receptor. When the TPOR transmembrane domain assumes a permissive homodimeric conformation, such as in response to a ligand or forced activation resulting from the introduction of engineered modifications, it is capable of activating downstream cytokine signaling in a JAK2-dependent fashion. The introduction of various modifications to the TPOR transmembrane domain can result in the following: the immune-potentiating cytokine signal may either be (a) quiescent until induced to activate in the presence of extracellular TGF-β, or (b) constitutively active regardless of TGF-β availability.

Table 2 provides exemplary full length sequences of naturally occurring receptors provided in the disclosure, from which the transmembrane and/or JAK domains are derived.

TABLE 2

Exemplary Naturally Occurring Receptors

| Naturally Occurring Receptor Name | SEQ ID NO: |
|---|---|
| >AAI12154.1 Erythropoietin receptor [*Homo sapiens*]<br>MDHLGASLWPQVGSLCLLLAGAAWAPPPNLPDPKFESKAALLAARGPEELLCFTE<br>RLEDLVCFWEEAASAGVGPGNYSFSYQLEDEPWKLCRLHQAPTARGAVRFWCSLP<br>TADTSSFVPLELRVTAASGAPRYHRVIHINEVVLLDAPVGLVARLADESGHVVLR<br>WLPPPETPMTSHIRYEVDVSAGNGAGSVQRVEILEGRTECVLSNLRGRTRYTFAV<br>RARMAEPSFGGFWSAWSEPVSLLTPSDLDPLILTLSLILVVILVLLTVLALLSHR<br>RALKQKIWPGIPSPESEFEGLFTTHKGNFQLWLYQNDGCLWWSPCTPFTEDPPAS<br>LEVLSERCWGTMQAVEPGTDDEGPLLEPVGSEHAQDTYLVLDKWLLPRNPPSEDL<br>PGPGGSVDIVAMDEGSEASSCSSALASKPSPEGASAASFEYTILDPSSQLLRPWT<br>LCPELPPTPPHLKYLYLVVSDSGISTDYSSGDSQGAQGGLSDGPYSNPYENSLIP<br>AAEPLPPSYVACS | 21 |

TABLE 2-continued

Exemplary Naturally Occurring Receptors

| Naturally Occurring Receptor Name | SEQ ID NO: |
|---|---|
| >AAI17403.1 Interleukin 6 signal transducer (GP130, oncostatin M receptor) [*Homo sapiens*]<br>MLTLQTWLVQALFIFLTTESTGELLDPCGYISPESPVVQLHSNFTAVCVLKEKCM<br>DYFHVNANYIVWKTNHFTIPKEQYTIINRTASSVTFTDIASLNIQLTCNILTFGQ<br>LEQNVYGITIISGLPPEKPKNLSCIVNEGKKMRCEWDRGRETHLETNFTLKSEWA<br>THKFADCKAKRDTPTSCTVDYSTVYFVNIEVWVEAENALGKVTSDHINFDPVYKV<br>KPNPPHNLSVINSEELSSILKLTWTNPSIKSVIILKYNIQYRTKDASTWSQIPPE<br>DTASTRSSFTVQDLKPFTEYVFRIRCMKEDGKGYWSDWSEEASGITYEDRPSKAP<br>SFWYKIDPSHTQGYRTVQLVWKTLPPFEANGKILDYEVTLTRWKSHLQNYTVNAT<br>KLTVNLTNDRYVATLTVRNLVGKSDAAVLTIPACDFQATHPVMDLKAFPKDNMLW<br>VEWTTPRESVKKYILEWCVLSDKAPCITDWQQEDGTVHRTYLRGNLAESKCYLIT<br>VTPVYADGPGSPESIKAYLKQAPPSKGPTVRTKKVGKNEAVLEWDQLPVDVQNGF<br>IRNYTIFYRTIIGNETAVNVDSSHTEYTLSSLTSDTLYMVRMAAYTDEGGKDGPE<br>FTFTTPKFAQGEIEAIVVPVCLAFLLTTLLGVLFCFNKRDLIKKHIWPNVPDPSK<br>SHIAQWSPHTPPRHNFNSKDQMYSDGNFTDVSVVEIEANDKKPFPEDLKSLDLFK<br>KEKINTEGHSSGIGGSSCMSSSRPSISSSDENESSQNTSSTVQYSTVVHSGYRHQ<br>VPSVQVFSRSESTQPLLDSEERPEDLQLVDHVDGGDGILPRQQYFKQNCSQHESS<br>PDISHFERSKQVSSVNEEDFVRLKQQISDHISQSCGSGQMKMFQEVSAADAFGPG<br>TEGQVERFETVGMEAATDEGMPKSYLPQTVRQGGYMPQ | 22 |
| >XP_011512371.1 prolactin receptor isoform X2 [*Homo sapiens*]<br>MKENVASATVFTLLLFLNTCLLNGQLPPGKPEIFKCRSPNKETFTCWWRPGTDGG<br>LPTNYSLTYHREGETLMHECPDYITGGPNSCHFGKQYTSMWRTYIMMVNATNQMG<br>SSFSDELYVDVTYIV0PDPPLELAVEVK0PEDRKPYLWIKWSPPTLIDLKTGWFT<br>LLYEIRLKPEKAAEWEIHFAGQQTEFKILSLHPGQKYLVQVRCKPDHGYWSAWSP<br>ATFIQIPSDFTMNDTTVWISVAVLSAVICLIIVWAVALKGYSMVTCIFPPVPGPK<br>IKGFDAHLLEKGKSEELLSALGCQDFPPTSDYEDLLVEYLEVDDSEDQHLMSVHS<br>KEHPSQGMKPTYLDPDTDSGRGSCDSPSLLSEKCEEPQANPSTFYDPEVIEKPEN<br>PETTHTWDPQCISMEGKIPYFHAGGSKCSTWPLPQPSQHNPRSSYHNITDVCELA<br>VGPAGAPATLLNEAGKDALKSSQTIKSREEGKATQQREVESFHSETDQDTPWLLP<br>QEKTPFGSAKPLDYVEIHKVNKDGALSLLPKQRENSGKPKKPGTPENNKEYAKVS<br>GVMDNNILVLVPDPHAKNVACFEESAKEAPPSLEQNQAEKALANFTATSSKCRLQ<br>LGGLDYLDPACFTHSFH | 23 |
| >NP_000154.1 growth hormone receptor isoform 1 precursor [*Homo sapiens*]<br>MDLWQLLLTLALAGSSDAFSGSEATAAILSRAPWSLQSVNPGLKTNSSKEPKFTK<br>CRSPERETFSCHWTDEVHHGTKNLGPIQLFYTRRNTQEWTQEWKECPDYVSAGEN<br>SCYFNSSFTSIWIPYCIKLTSNGGTVDEKCFSVDEIVQPDPPIALNWTLLNVSLT<br>GIHADIQVRWEAPRNADIQKGWMVLEYELQYKEVNETKWKMMDPILTTSVPVYSL<br>KVDKEYEVRVRSKQRNSGNYGEFSEVLYVTLPQMSQFTCEEDFYFPWLLIIIFGI<br>FGLTVMLFVFLFSKQQRIKMLILPPVPVPKIKGIDPDLLKEGKLEEVNTILAIHD<br>SYKPEFHSDDSWVEFIELDIDEPDEKTEESDTDRLLSSDHEKSHSNLGVKDGDSG<br>RTSCCEPDILETDFNANDIHEGTSEVAQPQRLKGEADLLCLDQKNQNNSPYHDAC<br>PATQQPSVIQAEKNKPQPLPTEGAESTHQAAHIQLSNPSSLSNIDFYAQVSDITP<br>AGSVVLSPGQKNKAGMSQCDMHPEMVSLCQENFLMDNAYFCEADAKKCIPVAPHI<br>KVESHIQPSLNQEDIYITTESLTTAAGRPGTGEHVPGSEMPVPDYTSIHIVQSPQ<br>GLILNATALPLPDKEFLSSCGYVSTDQLNKIMP | 24 |
| >XP_016855859.1 granulocyte colony-stimulating factor receptor isoform X1 [*Homo sapiens*]<br>MARLGNCSLTWAALIILLLPGSLEECGHISVSAPIVHLGDPITASCIIKQNCSHL<br>DPEPQILWRLGAELQPGGRQQRLSDGTQESIITLPHLNHTQAFLSCCLNWGNSLQ<br>ILDQVELRAGYPPAIPHNLSCLMNLTTSSLICQWEPGPETHLPTSFTLKSFKSRG<br>NCQTQGDSILDCVPKDGQSHCCIPRKHLLLYQNMGIWVQAENALGTSMSPQLCLD<br>PMDVVKLEPPMLRTMDPSPEAAPPQAGCLQLCWEPWQPGLHINQKCELRHKPQRG<br>EASWALVGPLPLEALQYELCGLLPATAYTLQIRCIRWPLPGHWSDWSPSLELRTT<br>ERAPTVRLDTWVVRQRQLDPRTVQLFWKPVPLEEDSGRIQGYVVSWRPSGQAGAI<br>LPLCNTTELSCTFHLPSEAQEVALVAYNSAGTSRPTPVVFSESRGPALTRLHAMA<br>RDPHSLWVGWEPPNPWPQGYVIEWGLGPPSASNSNKTWRMEQNGRATGFLLKENI<br>RPFQLYEIIVTPLYQDTMGPSQHVYAYSQEMAPSHAPELHLKHIGKTWAQLEWVP<br>EPPELGKSPLTHYTIFWTNAQNQSFSAILNASSRGFVLHGLEPASLYHIHLMAAS<br>QAGATNSTVLTLMTLTPEGSELHIILGLFGLLLLLTCLCGTAWLCCSPNRKNPLW<br>PSVPDPAHSSLGSWVPTIMEELPGPRQGQWLGQTSEMSRALTPHPCVQDAFQLPG<br>LGTPPITKLTVLEEDEKKPVPWESHNSSETCGLPTLVQTYVLQGDPRAVSTQPQS<br>QSGTSDQVLYGQLLGSPTSPGPGHYLRCDSTQPLLAGLTPSPKSYENLWFQASPLGTLVT-<br>PAP<br>SQEDDCVFGPLLNFPLLQGIRVHGMEALGSF | 25 |
| >NP_005364.1 thrombopoietin receptor precursor [Homo sapiens]<br>MPSWALFMVTSCLLLAPQNLAQVSSQDVSLLASDSEPLKCFSRTFEDLTCFWDEEE<br>AAPSGTYQLLYAYPREKPRACPLSSQSMPHFGTRYVCQFPDQEEVRLFFPLHLWVK | 26 |

TABLE 2-continued

| Exemplary Naturally Occurring Receptors | |
|---|---|
| Naturally Occurring Receptor Name | SEQ ID NO: |
| NVFLNQTRTQRVLFVDSVGLPAPPSIIKAMGGSQPGELQISWEEPAPEISDFLRYELR<br>YGPRDPKNSTGPTVIQLIATETCCPALQRPHSASALDQSPCAQPTMPWQDGPKQTSP<br>SREASALTAEGGSCLISGLQPGNSYWLQLRSEPDGISLGGSWGSWSLPVTVDLPGDA<br>VALGLQCFTLDLKNVTCQWQQQDHASSQGFFYHSRARCCPRDRYPIWENCEEEEK<br>TNPGLQTPQFSRCHFKSRNDSIIHILVEVTTAPGTVHSYLGSPFWIHQAVRLPTPNLH<br>WREISSGHLELEWQHPSSWAAQETCYQLRYTGEGHQDWKVLEPPLGARGGTLELR<br>PRSRYRLQLRARLNGPTYQGPWSSWSDPTRVETATETAWISLVTALHLVLGLSAVL<br>GLLLLRWQFPAHYRRLRHALWPSLPDLHRVLGQYLRDTAALSPPKATVSDTCEEVE<br>PSLLEILPKSSERTPLPLCSSQAQMDYRRLQPSCLGTMPLSVCPPMAESGSCCTTHIA<br>NHSYLPLSYWQQP | |

In some embodiments, the transmembrane domain of the disclosure is derived from a truncated, or otherwise modified version of the naturally occurring TPOR/MPLR receptor shown in Table 2.

FIGS. 9A-9B and 10A show the amino acid sequences for the wild type TPOR and the various transmembrane deletion (FIGS. 9A, 10A) or insertion (FIG. 9B) variants.

Table 3 shows exemplary transmembrane amino acid sequences, coupled to intracellular JAK2 binding domain sequences.

In some embodiments, the transmembrane domain of the chimeric cytokine receptor comprises the amino acid sequence of SEQ ID NO: 27. In some embodiments, the transmembrane domain of the chimeric cytokine receptor comprises the amino acid sequence of SEQ ID NO: 28. In some embodiments, the transmembrane domain of the chimeric cytokine receptor comprises the amino acid sequence of SEQ ID NO: 29. In some embodiments, the transmembrane domain of the chimeric cytokine receptor comprises the amino acid sequence of SEQ ID NO: 30. In some embodiments, the transmembrane domain of the chimeric cytokine receptor comprises the amino acid sequence of SEQ ID NO: 31. In some embodiments, the transmembrane domain of the chimeric cytokine receptor comprises the amino acid sequence of SEQ ID NO: 32. In some embodiments, the transmembrane domain of the chimeric cytokine receptor comprises the amino acid sequence of SEQ ID NO: 33. In some embodiments, the transmembrane domain of the chimeric cytokine receptor comprises the amino acid sequence of SEQ ID NO: 34. In some embodiments, the transmembrane domain of the chimeric cytokine receptor comprises the amino acid sequence of SEQ ID NO: 35. In some embodiments, the transmembrane domain of the chimeric cytokine receptor comprises the amino acid sequence of SEQ ID NO: 36. In some embodiments, the transmembrane domain of the chimeric cytokine receptor comprises the amino acid sequence of SEQ ID NO: 37. In some embodiments, the transmembrane domain of the chimeric cytokine receptor comprises the amino acid sequence of SEQ ID NO: 38. In some embodiments, the transmembrane domain of the chimeric cytokine receptor comprises the amino acid sequence of SEQ ID NO: 39. In some embodiments, the transmembrane domain of the chimeric cytokine receptor comprises the amino acid sequence of SEQ ID NO: 40. In some embodiments, the transmembrane domain of the chimeric cytokine receptor comprises the amino acid sequence of SEQ ID NO: 41. In some embodiments, the transmembrane domain of the chimeric cytokine receptor comprises the amino acid sequence of SEQ ID NO: 42. In some embodiments, the transmembrane domain of the chimeric cytokine receptor comprises the amino acid sequence of SEQ ID NO: 43. In some embodiments, the transmembrane domain of the chimeric cytokine receptor comprises the amino acid sequence of SEQ ID NO: 44. In some embodiments, the transmembrane domain of the chimeric cytokine receptor comprises the amino acid sequence of SEQ ID NO: 45. In some embodiments, the transmembrane domain of the chimeric cytokine receptor comprises the amino acid sequence of SEQ ID NO: 46. In some embodiments, the transmembrane domain of the chimeric cytokine receptor comprises the amino acid sequence of SEQ ID NO: 47. In some embodiments, the transmembrane domain of the chimeric cytokine receptor comprises the amino acid sequence of SEQ ID NO: 48. In some embodiments, the transmembrane domain of the chimeric cytokine receptor comprises the amino acid sequence of SEQ ID NO: 49. In some embodiments, the transmembrane domain of the chimeric cytokine receptor comprises the amino acid sequence of SEQ ID NO: 50. In some embodiments, the transmembrane domain of the chimeric cytokine receptor comprises the amino acid sequence of SEQ ID NO: 51. In some embodiments, the transmembrane domain of the chimeric cytokine receptor comprises the amino acid sequence of SEQ ID NO: 52. In some embodiments, the transmembrane domain of the chimeric cytokine receptor comprises the amino acid sequence of SEQ ID NO: 53. In some embodiments, the transmembrane domain of the chimeric cytokine receptor comprises the amino acid sequence of SEQ ID NO: 54. In some embodiments, the transmembrane domain of the chimeric cytokine receptor comprises the amino acid sequence of SEQ ID NO: 55. In some embodiments, the transmembrane domain of the chimeric cytokine receptor comprises the amino acid sequence of SEQ ID NO: 56. In some embodiments, the transmembrane domain of the chimeric cytokine receptor comprises the amino acid sequence of SEQ ID NO: 57. In some embodiments, the transmembrane domain of the chimeric cytokine receptor comprises the amino acid sequence of SEQ ID NO: 58. In some embodiments, the transmembrane domain of the chimeric cytokine receptor comprises the amino acid sequence of SEQ ID NO: 59. In some embodiments, the transmembrane domain of the chimeric cytokine receptor comprises the amino acid sequence of SEQ ID NO: 60. In some embodiments, the transmembrane domain of the chimeric cytokine receptor comprises the amino acid sequence of SEQ ID NO: 61. In some embodiments, the transmembrane domain of the chimeric cytokine receptor comprises the amino acid sequence of SEQ ID NO: 62. In some embodiments, the transmembrane domain of the chimeric cytokine receptor comprises the amino acid sequence of SEQ ID NO: 63. In some embodiments, the transmembrane domain of the chimeric cytokine receptor comprises the amino acid sequence of SEQ ID NO: 64. In some embodiments, the transmembrane domain of the chimeric cytokine receptor comprises the amino acid sequence of SEQ ID NO: 65. In some embodiments, the transmembrane domain of the chimeric cytokine receptor comprises the amino acid sequence of SEQ ID NO: 66. In some embodiments, the transmembrane domain of the chimeric cytokine receptor comprises the amino acid sequence of SEQ ID NO: 67. In some embodiments, the transmembrane domain of the chimeric cytokine receptor comprises the amino acid sequence of SEQ ID NO: 68. In some embodiments, the transmembrane domain of the chimeric cytokine receptor comprises the amino acid sequence of SEQ ID NO: 69. In some embodiments, the transmembrane domain of the chimeric cytokine receptor comprises the amino acid sequence of SEQ ID NO: 70. In some embodiments, the transmembrane domain of the chimeric cytokine receptor comprises the amino acid sequence of SEQ ID NO: 71. In some embodiments, the transmembrane domain of the chimeric cytokine receptor comprises the amino acid sequence of SEQ ID NO: 72. In some embodiments, the transmembrane domain of the chimeric cytokine receptor comprises the amino acid sequence of SEQ ID NO: 73. In some embodiments, the transmembrane domain of the chimeric cytokine receptor comprises the amino acid sequence of SEQ ID NO: 74. In some embodiments, the transmembrane domain of the chimeric cytokine receptor comprises the amino acid sequence of SEQ ID NO: 75. In some embodiments, the transmembrane domain of the chimeric cytokine receptor comprises the amino acid sequence of SEQ ID NO: 76. In some embodiments, the transmembrane domain of the chimeric cytokine receptor comprises the amino acid sequence of SEQ ID NO: 77. In some embodiments, the transmembrane domain of the chimeric cytokine receptor comprises the amino acid sequence of SEQ ID NO: 78. In some embodiments, the transmembrane domain of the chimeric cytokine receptor comprises the amino acid sequence of SEQ ID NO: 79. In some embodiments, the transmembrane domain of the chimeric cytokine receptor comprises the amino acid sequence of SEQ ID NO: 160. In some embodiments, the transmembrane domain of the chimeric cytokine receptor comprises the amino acid sequence of SEQ ID NO: 217. In some embodiments, the transmembrane domain of the chimeric cytokine receptor comprises the amino acid sequence of SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, SEQ ID NO: 230, SEQ ID NO: 231, SEQ ID NO: 232, SEQ ID NO: 233, or SEQ ID NO: 234. In some embodiments, the transmembrane domain of the chimeric cytokine receptor comprises an amino acid sequence that is at least 80%, 85%, 90%, 95%, 98%, or 99%, or 100% identical to the amino acid sequence of any one of SEQ ID NOs: 27-79, 160, and 217-234.

In some embodiments, the chimeric cytokine receptor (CCR) comprises the binding domain comprising the amino acid sequence of SEQ ID NO: 3, 4 or 159, and the transmembrane and JAK2 binding domain comprising the amino acid sequence of SEQ ID NO: 64, 69, or 70. In some embodiments, the CCR is inducible. In some embodiments, the CCR comprises the binding domain comprising the amino acid sequence of SEQ ID NO: 3, 4 or 159, and the transmembrane and JAK2 binding domain comprising the amino acid sequence of SEQ ID NO: 38, 39, 40 or 53. In some embodiments, the CCR comprises the binding domain comprising the amino acid sequence of SEQ ID NO: 3, 4 or 159, and the transmembrane and JAK2 binding domain comprising the amino acid sequence of SEQ ID NO: 59, 60, 160, or 217. In some embodiments, the CCR is constitutively active. In some embodiments, the constitutively active CCR of the disclosure dimerizes without a TGF-β ligand.

TABLE 3

Exemplary Transmembrane + JAK2 Binding Domain Sequences

| Transmembrane and JAK2 binding domain | Amino acid sequence | SEQ ID NO: |
|---|---|---|
| GCSFR(614-710) | LTLMTLTPEGSELHIILGLFGLLLLLTCLCGTAWLCCSPNRKNPLWP SVPDPAHSSLGSWVPTIMEEDAFQLPGLGTPPITKLTVLEEDEKKP VPWE | 27 |
| GP130(609-700) | TTPKFAQGEIEAIVVPVCLAFLLTTLLGVLFCFNKRDLIKKHIWPNV PDPSKSHIAQWSPHTPPRHNFNSKDQMYSDGNFTDVSWEIEAN D | 28 |
| TPOR/MPLR(478-582) | SDPTRVETATETAWISLVTALHLVLGLSAVLGLLLLRWQFPAHYRR LRHALWPSLPDLHRVLGQYLRDTAALSPPKATVSDTCEEVEPSLLEI LPKSSERTPLPL | 29 |
| TPOR/MPLR(N - 1) | SDPTRVETATETWISLVTALHLVLGLSAVLGLLLLRWQFPAHYRRL RHALWPSLPDLHRVLGQYLRDTAALSPPKATVSDTCEEVEPSLLEIL PKSSERTPLPL | 30 |
| TPOR/MPLR(N - 2) | SDPTRVETATETISLVTALHLVLGLSAVLGLLLLRWQFPAHYRRLRH ALWPSLPDLHRVLGQYLRDTAALSPPKATVSDTCEEVEPSLLEILPK SSERTPLPL | 31 |
| TPOR/MPLR(N - 2 + 1) | SDPTRVETATETLISLVTALHLVLGLSAVLGLLLLRWQFPAHYRRLR HALWPSLPDLHRVLGQYLRDTAALSPPKATVSDTCEEVEPSLLEILP KSSERTPLPL | 32 |
| TPOR/MPLR(N - 3) | SDPTRVETATETSLVTALHLVLGLSAVLGLLLLRWQFPAHYRRLRH ALWPSLPDLHRVLGQYLRDTAALSPPKATVSDTCEEVEPSLLEILPK SSERTPLPL | 33 |

TABLE 3-continued

| Exemplary Transmembrane + JAK2 Binding Domain Sequences | | |
|---|---|---|
| Transmembrane and JAK2 binding domain | Amino acid sequence | SEQ ID NO: |
| TPOR/MPLR(N - 4) | SDPTRVETATETLVTALHLVLGLSAVLGLLLLRWQFPAHYRRLRHALWPSLPDLHRVLGQYLRDTAALSPPKATVSDTCEEVEPSLLEILPKSSERTPLPL | 34 |
| TPOR/MPLR(N - 4 + 1) | SDPTRVETATETILVTALHLVLGLSAVLGLLLLRWQFPAHYRRLRHALWPSLPDLHRVLGQYLRDTAALSPPKATVSDTCEEVEPSLLEILPKSSERTPLPL | 35 |
| TPOR/MPLR(N - 5) | SDPTRVETATETVTALHLVLGLSAVLGLLLLRWQFPAHYRRLRHALWPSLPDLHRVLGQYLRDTAALSPPKATVSDTCEEVEPSLLEILPKSSERTPLPL | 36 |
| TPOR/MPLR(N - 6) | SDPTRVETATETTALHLVLGLSAVLGLLLLRWQFPAHYRRLRHALWPSLPDLHRVLGQYLRDTAALSPPKATVSDTCEEVEPSLLEILPKSSERTPLPL | 37 |
| TPOR/MPLR(N - 7) | SDPTRVETATETALHLVLGLSAVLGLLLLRWQFPAHYRRLRHALWPSLPDLHRVLGQYLRDTAALSPPKATVSDTCEEVEPSLLEILPKSSERTPLPL | 38 |
| TPOR/MPLR(N - 8) | SDPTRVETATETLHLVLGLSAVLGLLLLRWQFPAHYRRLRHALWPSLPDLHRVLGQYLRDTAALSPPKATVSDTCEEVEPSLLEILPKSSERTPLPL | 39 |
| TPOR/MPLR(N - 9) | SDPTRVETATETHLVLGLSAVLGLLLLRWQFPAHYRRLRHALWPSLPDLHRVLGQYLRDTAALSPPKATVSDTCEEVEPSLLEILPKSSERTPLPL | 40 |
| TPOR/MPLR(N - 10) | SDPTRVETATETLVLGLSAVLGLLLLRWQFPAHYRRLRHALWPSLPDLHRVLGQYLRDTAALSPPKATVSDTCEEVEPSLLEILPKSSERTPLPL | 41 |
| TPOR/MPLR(N - 11) | SDPTRVETATETVLGLSAVLGLLLLRWQFPAHYRRLRHALWPSLPDLHRVLGQYLRDTAALSPPKATVSDTCEEVEPSLLEILPKSSERTPLPL | 42 |
| TPOR/MPLR(N - 12) | SDPTRVETATETLGLSAVLGLLLLRWQFPAHYRRLRHALWPSLPDLHRVLGQYLRDTAALSPPKATVSDTCEEVEPSLLEILPKSSERTPLPL | 43 |
| TPOR/MPLR(N - 13) | SDPTRVETATETGLSAVLGLLLLRWQFPAHYRRLRHALWPSLPDLHRVLGQYLRDTAALSPPKATVSDTCEEVEPSLLEILPKSSERTPLPL | 44 |
| TPOR/MPLR(N - 14) | SDPTRVETATETLSAVLGLLLLRWQFPAHYRRLRHALWPSLPDLHRVLGQYLRDTAALSPPKATVSDTCEEVEPSLLEILPKSSERTPLPL | 45 |
| TPOR/MPLR(N - 15) | SDPTRVETATETSAVLGLLLLRWQFPAHYRRLRHALWPSLPDLHRVLGQYLRDTAALSPPKATVSDTCEEVEPSLLEILPKSSERTPLPL | 46 |
| TPOR/MPLR(N - 16) | SDPTRVETATETAVLGLLLLRWQFPAHYRRLRHALWPSLPDLHRVLGQYLRDTAALSPPKATVSDTCEEVEPSLLEILPKSSERTPLPL | 47 |
| TPOR/MPLR(N - 17) | SDPTRVETATETVLGLLLLRWQFPAHYRRLRHALWPSLPDLHRVLGQYLRDTAALSPPKATVSDTCEEVEPSLLEILPKSSERTPLPL | 48 |
| TPOR/MPLR(N - 18) | SDPTRVETATETLGLLLLRWQFPAHYRRLRHALWPSLPDLHRVLGQYLRDTAALSPPKATVSDTCEEVEPSLLEILPKSSERTPLPL | 49 |
| TPOR/MPLR(N + 1) | SDPTRVETATETAWLISLVTALHLVLGLSAVLGLLLLRWQFPAHYRRLRHALWPSLPDLHRVLGQYLRDTAALSPPKATVSDTCEEVEPSLLEILPKSSERTPLPL | 50 |
| TPOR/MPLR(N + 2) | SDPTRVETATETAWVLISLVTALHLVLGLSAVLGLLLLRWQFPAHYRRLRHALWPSLPDLHRVLGQYLRDTAALSPPKATVSDTCEEVEPSLLEILPKSSERTPLPL | 51 |
| TPOR/MPLR(N + 3) | SDPTRVETATETAWLVLISLVTALHLVLGLSAVLGLLLLRWQFPAHYRRLRHALWPSLPDLHRVLGQYLRDTAALSPPKATVSDTCEEVEPSLLEILPKSSERTPLPL | 52 |
| TPOR/MPLR(N + 4) | SDPTRVETATETAWILVLISLVTALHLVLGLSAVLGLLLLRWQFPAHYRRLRHALWPSLPDLHRVLGQYLRDTAALSPPKATVSDTCEEVEPSLLEILPKSSERTPLPL | 53 |

TABLE 3-continued

Exemplary Transmembrane + JAK2 Binding Domain Sequences

| Transmembrane and JAK2 binding domain | Amino acid sequence | SEQ ID NO: |
|---|---|---|
| TPOR/MPLR(N + 5) | SDPTRVETATETAWLILVLISLVTALHLVLGLSAVLGLLLLRWQFPAHYRRLRHALWPSLPDLHRVLGQYLRDTAALSPPKATVSDTCEEVEPSLLEILPKSSERTPLPL | 54 |
| TPOR/MPLR(N + 6) | SDPTRVETATETAWLLILVLISLVTALHLVLGLSAVLGLLLLRWQFPAHYRRLRHALWPSLPDLHRVLGQYLRDTAALSPPKATVSDTCEEVEPSLLEILPKSSERTPLPL | 55 |
| TPOR/MPLR(N + 7) | SDPTRVETATETAWVLLILVLISLVTALHLVLGLSAVLGLLLLRWQFPAHYRRLRHALWPSLPDLHRVLGQYLRDTAALSPPKATVSDTCEEVEPSLLEILPKSSERTPLPL | 56 |
| TPOR/MPLR(N + 8) | SDPTRVETATETAWLVLLILVLISLVTALHLVLGLSAVLGLLLLRWQFPAHYRRLRHALWPSLPDLHRVLGQYLRDTAALSPPKATVSDTCEEVEPSLLEILPKSSERTPLPL | 57 |
| TPOR/MPLR(478-582; W515K) | SDPTRVETATETAWISLVTALHLVLGLSAVLGLLLLRKQFPAHYRRLRHALWPSLPDLHRVLGQYLRDTAALSPPKATVSDTCEEVEPSLLEILPKSSERTPLPL | 58 |
| TPOR/MPLR(478-582; H499L, S505N, W515K) | SDPTRVETATETAWISLVTALLLVLGLNAVLGLLLLRKQFPAHYRRLRHALWPSLPDLHRVLGQYLRDTAALSPPKATVSDTCEEVEPSLLEILPKSSERTPLPL | 59 |
| TPOR/MPLR(478-582;S505N,W515K) | SDPTRVETATETAWISLVTALHLVLGLNAVLGLLLLRKQFPAHYRRLRHALWPSLPDLHRVLGQYLRDTAALSPPKATVSDTCEEVEPSLLEILPKSSERTPLPL | 60 |
| TPOR/MPLR(N - 9 - 1) | SDPTRVETATEHLVLGLSAVLGLLLLRWQFPAHYRRLRHALWPSLPDLHRVLGQYLRDTAALSPPKATVSDTCEEVEPSLLEILPKSSERTPLPL | 61 |
| TPOR/MPLR(N - 9 - 2) | SDPTRVETATHLVLGLSAVLGLLLLRWQFPAHYRRLRHALWPSLPDLHRVLGQYLRDTAALSPPKATVSDTCEEVEPSLLEILPKSSERTPLPL | 62 |
| TPOR/MPLR(N - 9 - 3) | SDPTRVETAHLVLGLSAVLGLLLLRWQFPAHYRRLRHALWPSLPDLHRVLGQYLRDTAALSPPKATVSDTCEEVEPSLLEILPKSSERTPLPL | 63 |
| TPOR/MPLR(N - 9 - 4) | SDPTRVETHLVLGLSAVLGLLLLRWQFPAHYRRLRHALWPSLPDLHRVLGQYLRDTAALSPPKATVSDTCEEVEPSLLEILPKSSERTPLPL | 64 |
| TPOR/MPLR(N - 9 - 5) | SDPTRVEHLVLGLSAVLGLLLLRWQFPAHYRRLRHALWPSLPDLHRVLGQYLRDTAALSPPKATVSDTCEEVEPSLLEILPKSSERTPLPL | 65 |
| TPOR/MPLR(N - 9 - G) | SDPTRVHLVLGLSAVLGLLLLRWQFPAHYRRLRHALWPSLPDLHRVLGQYLRDTAALSPPKATVSDTCEEVEPSLLEILPKSSERTPLPL | 66 |
| TPOR/MPLR(N - 9 - 7) | SDPTRHLVLGLSAVLGLLLLRWQFPAHYRRLRHALWPSLPDLHRVLGQYLRDTAALSPPKATVSDTCEEVEPSLLEILPKSSERTPLPL | 67 |
| TPOR/MPLR(N - 9 - 8) | SDPTHLVLGLSAVLGLLLLRWQFPAHYRRLRHALWPSLPDLHRVLGQYLRDTAALSPPKATVSDTCEEVEPSLLEILPKSSERTPLPL | 68 |
| TPOR/MPLR(N - 9 - 9) | SDPHLVLGLSAVLGLLLLRWQFPAHYRRLRHALWPSLPDLHRVLGQYLRDTAALSPPKATVSDTCEEVEPSLLEILPKSSERTPLPL | 69 |
| TPOR/MPLR(N - 9 - 10) | SDHLVLGLSAVLGLLLLRWQFPAHYRRLRHALWPSLPDLHRVLGQYLRDTAALSPPKATVSDTCEEVEPSLLEILPKSSERTPLPL | 70 |
| TPOR/MPLR(N - 9 - 11) | SHLVLGLSAVLGLLLLRWQFPAHYRRLRHALWPSLPDLHRVLGQYLRDTAALSPPKATVSDTCEEVEPSLLEILPKSSERTPLPL | 71 |
| TPOR/MPLR(N - 9 - 12) | HLVLGLSAVLGLLLLRWQFPAHYRRLRHALWPSLPDLHRVLGQYLRDTAALSPPKATVSDTCEEVEPSLLEILPKSSERTPLPL | 72 |
| TPOR/MPLR(N - C3) | SDPTRVETATETAWISLVHLVLGLSAVLGLLLLRWQFPAHYRRLRHALWPSLPDLHRVLGQYLRDTAALSPPKATVSDTCEEVEPSLLEILPKSSERTPLPL | 73 |
| TPOR/MPLR(N - C5) | SDPTRVETATETAWISHLVLGLSAVLGLLLLRWQFPAHYRRLRHALWPSLPDLHRVLGQYLRDTAALSPPKATVSDTCEEVEPSLLEILPKSSERTPLPL | 74 |

TABLE 3-continued

| Exemplary Transmembrane + JAK2 Binding Domain Sequences | | |
|---|---|---|
| Transmembrane and JAK2 binding domain | Amino acid sequence | SEQ ID NO: |
| TPOR/MPLR(N − C5P) | SDPTRVETATETAWISPHLVLGLSAVLGLLLLRWQFPAHYRRLRHALWPSLPDLHRVLGQYLRDTAALSPPKATVSDTCEEVEPSLLEILPKSSERTPLPL | 75 |
| TPOR/MPLR(N − C5PP) | SDPTRVETATETAWISPPHLVLGLSAVLGLLLLRWQFPAHYRRLRHALWPSLPDLHRVLGQYLRDTAALSPPKATVSDTCEEVEPSLLEILPKSSERTPLPL | 76 |
| TPOR/MPLR(N − C6) | SDPTRVETATETAWIHLVLGLSAVLGLLLLRWQFPAHYRRLRHALWPSLPDLHRVLGQYLRDTAALSPPKATVSDTCEEVEPSLLEILPKSSERTPLPL | 77 |
| TPOR/MPLR(N − C6P) | SDPTRVETATETAWIPHLVLGLSAVLGLLLLRWQFPAHYRRLRHALWPSLPDLHRVLGQYLRDTAALSPPKATVSDTCEEVEPSLLEILPKSSERTPLPL | 78 |
| TPOR/MPLR(N − C6PP) | SDPTRVETATETAWIPPHLVLGLSAVLGLLLLRWQFPAHYRRLRHALWPSLPDLHRVLGQYLRDTAALSPPKATVSDTCEEVEPSLLEILPKSSERTPLPL | 79 |
| TPOR/MPLR(478-582; H499L, S505N, W515K, K553R, K573R) | SDPTRVETATETAWISLVTALLLVLGLNAVLGLLLLRKQFPAHYRRLRHALWPSLPDLHRVLGQYLRDTAALSPPRATVSDTCEEVEPSLLEILPRSSERTPLPL | 217 |
| TPOR/MPLR(478-582) S505N.W515K. K553R.K573R | SDPTRVETATETAWISLVTALHLVLGLNAVLGLLLLRKQFPAHYRRLRHALWPSLPDLHRVLGQYLRDTAALSPPRATVSDTCEEVEPSLLEILPRSSERTPLPL | 160 |
| TPOR/MPLR(478-582) K553R.K573R | SDPTRVETATETAWISLVTALHLVLGLSAVLGLLLLRWQFPAHYRRLRHALWPSLPDLHRVLGQYLRDTAALSPPRATVSDTCEEVEPSLLEILPRSSERTPLPL | 218 |
| TPOR/MPLR(N − 7) S505N.W515K | SDPTRVETATETALHLVLGLNAVLGLLLLRKQFPAHYRRLRHALWPSLPDLHRVLGQYLRDTAALSPPKATVSDTCEEVEPSLLEILPKSSERTPLPL | 219 |
| TPOR/MPLR(N − 7) S505N.W515K. K553R, K573R | SDPTRVETATETALHLVLGLNAVLGLLLLRKQFPAHYRRLRHALWPSLPDLHRVLGQYLRDTAALSPPRATVSDTCEEVEPSLLEILPRSSERTPLPL | 220 |
| TPOR/MPLR(N − 8) S505N.W515K | SDPTRVETATETLHLVLGLNAVLGLLLLRKQFPAHYRRLRHALWPSLPDLHRVLGQYLRDTAALSPPKATVSDTCEEVEPSLLEILPKSSERTPLPL | 221 |
| TPOR/MPLR(N − 8) S505N.W515K. K553R, K573R | SDPTRVETATETLHLVLGLNAVLGLLLLRKQFPAHYRRLRHALWPSLPDLHRVLGQYLRDTAALSPPRATVSDTCEEVEPSLLEILPRSSERTPLPL | 222 |
| TPOR/MPLR(N − 9) S505N.W515K | SDPTRVETATETHLVLGLNAVLGLLLLRKQFPAHYRRLRHALWPSLPDLHRVLGQYLRDTAALSPPKATVSDTCEEVEPSLLEILPKSSERTPLPL | 223 |
| TPOR/MPLR(N − 9) S505N.W515K. K553R,BK573R | SDPTRVETATETHLVLGLNAVLGLLLLRKQFPAHYRRLRHALWPSLPDLHRVLGQYLRDTAALSPPRATVSDTCEEVEPSLLEILPRSSERTPLPL | 224 |
| TPOR/MPLR(N + 4) S505N.W515K | SDPTRVETATETAWILVLISLVTALHLVLGLNAVLGLLLLRKQFPAHYRRLRHALWPSLPDLHRVLGQYLRDTAALSPPKATVSDTCEEVEPSLLEILPKSSERTPLPL | 225 |
| TPOR/MPLR(N + 4) S505N.W515K. K553R, K573R | SDPTRVETATETAWILVLISLVTALHLVLGLNAVLGLLLLRKQFPAHYRRLRHALWPSLPDLHRVLGQYLRDTAALSPPRATVSDTCEEVEPSLLEILPRSSERTPLPL | 226 |
| TPOR/M PLR(N − 9 − 1) S505N.W515K | SDPTRVETATEHLVLGLNAVLGLLLLRKQFPAHYRRLRHALWPSLPDLHRVLGQYLRDTAALSPPKATVSDTCEEVEPSLLEILPKSSERTPLPL | 227 |
| TPOR/MPLR(N − 9 − 1) S505N.W515K. K553R, K573R | SDPTRVETATEHLVLGLNAVLGLLLLRKQFPAHYRRLRHALWPSLPDLHRVLGQYLRDTAALSPPRATVSDTCEEVEPSLLEILPRSSERTPLPL | 228 |
| TPOR/M PLR(N − 9 − 4) S505N.W515K | SDPTRVETHLVLGLNAVLGLLLLRKQFPAHYRRLRHALWPSLPDLHRVLGQYLRDTAALSPPKATVSDTCEEVEPSLLEILPKSSERTPLPL | 229 |

TABLE 3-continued

Exemplary Transmembrane + JAK2 Binding Domain Sequences

| Transmembrane and JAK2 binding domain | Amino acid sequence | SEQ ID NO: |
|---|---|---|
| TPOR/MPLR(N - 9 - 4) S505N.W515K. K553R, K573R | SDPTRVETHLVLGL**N**AVLGLLLLR**K**QFPAHYRRLRHALWPSLPDLH RVLGQYLRDTAALSPP**R**ATVSDTCEEVEPSLLEILP**R**SSERTPLPL | 230 |
| TPOR/M PLR(N - 9 - 9) S505N.W515K | SDPHLVLGL**N**AVLGLLLLR**K**QFPAHYRRLRHALWPSLPDLHRVLG QYLRDTAALSPPKATVSDTCEEVEPSLLEILPKSSERTPLPL | 231 |
| TPOR/MPLR(N - 9 - 9) S505N.W515K. K553R, K573R | SDPHLVLGL**N**AVLGLLLLR**K**QFPAHYRRLRHALWPSLPDLHRVLG QYLRDTAALSPP**R**ATVSDTCEEVEPSLLEILP**R**SSERTPLPL | 232 |
| TPOR/MPLR(N - 9 - 10) S505N.W515K | SDHLVLGL**N**AVLGLLLLR**K**QFPAHYRRLRHALWPSLPDLHRVLGQ YLRDTAALSPPKATVSDTCEEVEPSLLEILPKSSERTPLPL | 233 |
| TPOR/MPLR(N - 9 - 10) S505N.W515K. K553R, K573R | SDHLVLGL**N**AVLGLLLLR**K**QFPAHYRRLRHALWPSLPDLHRVLGQ YLRDTAALSPP**R**ATVSDTCEEVEPSLLEILP**R**SSERTPLPL | 234 |

C. Janus Kinase (JAK)-Binding Domains

The chimeric cytokine receptors of the disclosure comprise intracellular JAK-binding domains. The JAK-binding domain is coupled to the C-terminus of the transmembrane domain, either directly, or via a linker. The JAK-binding domain is coupled to the transmembrane domain on the intracellular side of the chimeric cytokine receptor.

In some embodiments, the JAK-binding domain is a JAK-1-binding domain, a JAK-2 binding domain, a JAK-3 binding domain, or a TYK2 binding domain.

In some embodiments, the JAK-binding domains of the chimeric cytokine receptors of the disclosure are naturally occurring, and derived from a naturally occurring receptor.

In some embodiments, the JAK-binding domains of the chimeric cytokine receptors of the disclosure are synthetic.

In some embodiments, the chimeric cytokine receptor comprises a transmembrane and JAK2 binding domain that is at least 80%, 85%, 90%, 95%, 98% or 99%, or 100% identical to any one of the amino acid sequences of SEQ ID NOs: 27-79, 160 and 217-234.

Table 3 provides exemplary amino acid sequences for the transmembrane and JAK2 binding domains of the disclosure. In some embodiments, the transmembrane and JAK2 binding domain comprises one or more mutations, e.g., one or more deletions, insertions and/or substitutions of the wild type sequences. In some embodiments, the transmembrane and JAK2 binding domain comprises one or more substitutions at amino acid positions H499, S505 and W515 of the wild type TPOR/MPLR sequence. See Table 3. In some embodiments, the transmembrane and JAK2 binding domain comprises one or more substitutions at the amino acid positions K533 and K573 of the wild type TPOR/MPLR sequence. In some embodiments, the transmembrane and JAK2 binding domain, e.g., as shown in Table 3, may be combined with a TGFβR2 ectodomain as disclosed herein, e.g., in Table 1, or a PD-1 ectodomain (such as a high affinity PD-1 ectodomain, as indicated in SEQ ID NO: 274 or 275 in Table 6) and a recruiting domain to form a chimeric cytokine receptor. In some embodiments, the transmembrane and JAK2 binding domain may be combined with a recruiting domain to form a chimeric cytokine receptor without an ectodomain, see e.g., SEQ ID NOs: 272 or 273. See also U.S. Ser. No. 16/804,917, filed on Feb. 28, 2020, and U.S. Ser. No. 16/804,545, filed on Feb. 28, 2020, both of which are incorporated herein by reference in their entireties.

D. Recruiting Domains

The chimeric cytokine receptors of the disclosure comprise cytoplasmic domains comprising recruiting domains (which may also be referred to as "signaling domains"). The recruiting domain can be a STAT-recruiting domain, an AP1—recruiting domain, a Myc/Max recruiting domain; or an NFkB-recruiting domain. In some embodiments, the recruiting domain is a Signal Transducer and Activator of Transcription (STAT)—recruiting (Stat-activating) domains from receptor tails (cytotails) or from cytokine receptor tails. These intracellular recruiting domains of the chimeric cytokine receptors of the disclosure allow for the propagation of Signal 3 in an immune cell comprising a CAR and a chimeric cytokine receptor (e.g. a CAR-T-cell with a chimeric cytokine receptor of the disclosure). Cytokine signaling propagated through the Stat-recruiting domain allows for the cytokine-based immune potentiation of the cell. In some embodiments, the immune-potentiation is homeostatic, e.g. signaling gives rise to increase in immune cells bearing the CAR. In some embodiments, the immune-potentiation is inflammatory, e.g. signaling gives rise to increase in the potency of the immune cells bearing the CAR. In some embodiments, the immune-potentiation prevents exhaustion, e.g. signaling maintains the long-term functionality of immune cells bearing the CAR.

In some embodiments, the recruiting domains of the disclosure are synthetic, and do not resemble any naturally occurring receptor fragment.

In some embodiments, the Stat-recruiting domains of the disclosure are synthetic, and do not resemble any naturally occurring receptor fragment.

In other embodiments, the Stat-recruiting domains of the disclosure are derived from cytoplasmic tails of naturally occurring receptors, e.g. derived from naturally occurring cytokine receptors. In some embodiments, the chimeric cytokine receptor comprises a portion or a fragment of a naturally occurring receptor, e.g., the intracellular Stat-recruiting domain of the naturally occurring receptor, optionally with one or more mutations therein (e.g., one or more deletions, insertions and/or substitutions). These cytoplasmic tails of naturally occurring receptors may be the regions downstream of the JAK-activating domains of the transmembrane domain of the receptor. The Stat-recruiting domains of the chimeric cytokine receptors comprise at least one STAT-recruiting domain from at least one receptor. In some embodiments, the Stat-recruiting domain comprises at least one STAT1-recruiting domain. In some embodiments, the Stat-recruiting domain comprises at least one STAT2-recruiting domain. In some embodiments, the Stat-recruiting domain comprises at least one STAT3-recruiting domain. In some embodiments, the Stat-recruiting domain comprises at least one STAT4-recruiting domain. In some embodiments, the Stat-recruiting domain comprises at least one STAT5-recruiting domain. In some embodiments, the STAT-recruiting domain comprises at least one STAT6-recruiting domain. In some embodiments, the Stat-recruiting domain comprises at least one STAT7-recruiting domain.

In some embodiments, the naturally occurring receptor from which the STAT-recruiting domain is derived, is a not a cytokine receptor.

In some embodiments, the naturally occurring receptor from which the Stat-recruiting domain is derived, is a cytokine receptor. Exemplary cytokine receptors through which T-cell-immune potentiating cytokines signal include, but are not limited to IL-2 receptor, IL-7 receptor, IL-15 receptor, IL12 receptor, and IL-21 receptor. In some embodiments, the cytokine receptor from which the STAT-recruiting domain is derived contains phosphorylatable tyrosine residues downstream of the cognate JAK-binding motifs, and one or more signaling domains of interest may be fused downstream of the transmembrane domain to generate single or multiple signaling outputs. In alternative embodiments, the receptor from which the Stat-recruiting domain is derived, is not a cytokine receptor. By choosing the Stat-recruiting domain of the chimeric cytokine receptor, the receptor can be redirected to signaling of choice. In some embodiments, the chimeric cytokine receptor comprises two or more Stat-recruiting domains from more than one receptor. In some embodiments, the two or more Stat-recruiting domains are linked with or without a peptide linker.

Table 4 provides exemplary receptors from which Stat-recruiting domains (signaling domains) of the chimeric cytokine receptors of the disclosure are derived. Table 5a provides exemplary amino acid sequences of recruiting domains of the disclosure.

In some embodiments, the chimeric cytokine receptor of the disclosure comprises the amino acid sequence of the STAT-recruiting domain of SEQ ID NO: 80. In some embodiments, the chimeric cytokine receptor of the disclosure comprises the amino acid sequence of the STAT-recruiting domain of SEQ ID NO: 81. In some embodiments, the chimeric cytokine receptor of the disclosure comprises the amino acid sequence of the STAT-recruiting domain of SEQ ID NO: 82. In some embodiments, the chimeric cytokine receptor of the disclosure comprises the amino acid sequence of the STAT-recruiting domain of SEQ ID NO: 83. In some embodiments, the chimeric cytokine receptor of the disclosure comprises the amino acid sequence of the STAT-recruiting domain of SEQ ID NO: 84. In some embodiments, the chimeric cytokine receptor of the disclosure comprises the amino acid sequence of the STAT-recruiting domain of SEQ ID NO: 85. In some embodiments, the chimeric cytokine receptor of the disclosure comprises the amino acid sequence of the STAT-recruiting domain of SEQ ID NO: 86. In some embodiments, the chimeric cytokine receptor of the disclosure comprises the amino acid sequence of the STAT-recruiting domain of SEQ ID NO: 87. In some embodiments, the chimeric cytokine receptor of the disclosure comprises the amino acid sequence of the STAT-recruiting domain of SEQ ID NO: 88. In some embodiments, the chimeric cytokine receptor of the disclosure comprises the amino acid sequence of the STAT-recruiting domain of SEQ ID NO: 89. In some embodiments, the chimeric cytokine receptor of the disclosure comprises the amino acid sequence of the STAT-recruiting domain of SEQ ID NO: 90. In some embodiments, the chimeric cytokine receptor of the disclosure comprises the amino acid sequence of the STAT-recruiting domain of SEQ ID NO: 91. In some embodiments, the chimeric cytokine receptor of the disclosure comprises the amino acid sequence of the STAT-recruiting domain of SEQ ID NO: 92. In some embodiments, the chimeric cytokine receptor of the disclosure comprises the amino acid sequence of the STAT-recruiting domain of SEQ ID NO: 93. In some embodiments, the chimeric cytokine receptor of the disclosure comprises the amino acid sequence of the STAT-recruiting domain of SEQ ID NO: 94. In some embodiments, the chimeric cytokine receptor of the disclosure comprises the amino acid sequence of the STAT-recruiting domain of SEQ ID NO: 95. In some embodiments, the chimeric cytokine receptor of the disclosure comprises the amino acid sequence of the STAT-recruiting domain of SEQ ID NO: 96. In some embodiments, the chimeric cytokine receptor of the disclosure comprises the amino acid sequence of the STAT-recruiting domain of SEQ ID NO: 97. In some embodiments, the chimeric cytokine receptor of the disclosure comprises the amino acid sequence of the STAT-recruiting domain of SEQ ID NO: 98. In some embodiments, the chimeric cytokine receptor of the disclosure comprises the amino acid sequence of the STAT-recruiting domain of SEQ ID NO: 99. In some embodiments, the chimeric cytokine receptor of the disclosure comprises the amino acid sequence of the STAT-recruiting domain of SEQ ID NO: 100. In some embodiments, the chimeric cytokine receptor of the disclosure comprises the amino acid sequence of the STAT-recruiting domain of SEQ ID NO: 101. In some embodiments, the chimeric cytokine receptor of the disclosure comprises the amino acid sequence of the STAT-recruiting domain of SEQ ID NO: 102. In some embodiments, the chimeric cytokine receptor of the disclosure comprises the amino acid sequence of the STAT-recruiting domain of SEQ ID NO: 103. In some embodiments, the chimeric cytokine receptor of the disclosure comprises the amino acid sequence of the STAT-recruiting domain of SEQ ID NO: 104. In some embodiments, the chimeric cytokine receptor of the disclosure comprises the amino acid sequence of the STAT-recruiting domain of SEQ ID NO: 105. In some embodiments, the chimeric cytokine receptor of the disclosure comprises the amino acid sequence of the STAT-recruiting domain of SEQ ID NO: 106. In some embodiments, the chimeric cytokine receptor of the disclosure comprises the amino acid sequence of the STAT-recruiting domain of SEQ ID NO: 107. In some embodiments, the chimeric cytokine receptor of the disclosure comprises the amino acid sequence of the STAT-recruiting domain of SEQ ID NO: 108. In some embodiments, the chimeric cytokine receptor of the disclosure comprises the amino acid sequence of the STAT-recruiting domain of SEQ ID NO: 109. In some embodiments, the chimeric cytokine receptor of the disclosure comprises the amino acid sequence of the STAT-recruiting domain of SEQ ID NO: 110. In some embodiments, the chimeric cytokine receptor of the disclosure comprises the amino acid sequence of the STAT-recruiting domain of SEQ ID NO: 111. In some embodiments, the chimeric cytokine receptor of the disclosure comprises the amino acid sequence of the STAT-recruiting domain of SEQ ID NO: 112. In some embodiments, the chimeric cytokine receptor of the disclosure comprises the amino acid sequence of the STAT-recruiting domain of SEQ ID NO: 113. In some embodiments, the chimeric cytokine receptor of the disclosure comprises the amino acid sequence of the STAT-recruiting domain of SEQ ID NO: 114. In some embodiments, the chimeric cytokine receptor of the disclosure comprises the amino acid sequence of the STAT-recruiting domain of SEQ ID NO: 115. In some embodiments, the chimeric cytokine receptor of the disclosure comprises the amino acid sequence of the STAT-recruiting domain of SEQ ID NO: 116. In some embodiments, the chimeric cytokine receptor of the disclosure comprises the amino acid sequence of the STAT-recruiting domain of SEQ ID NO: 117. In some embodiments, the chimeric cytokine receptor of the disclosure comprises the amino acid sequence of the STAT-recruiting domain of SEQ ID NO: 118. In some embodiments, the chimeric cytokine receptor of the disclosure comprises the amino acid sequence of the STAT-recruiting domain of SEQ ID NO: 119. In some embodiments, the chimeric cytokine receptor of the disclosure comprises the amino acid sequence of the STAT-recruiting domain of SEQ ID NO: 120. In some embodiments, the chimeric cytokine receptor of the disclosure comprises the amino acid sequence of the STAT-recruiting domain of SEQ ID NO: 121. In some embodiments, the chimeric cytokine receptor of the disclosure comprises the amino acid sequence of the STAT-recruiting domain of SEQ ID NO: 122. In some embodiments, the chimeric cytokine receptor of the disclosure comprises the amino acid sequence of the STAT-recruiting domain of SEQ ID NO: 161. In some embodiments, the chimeric cytokine receptor comprises a recruiting domain that comprises an amino acid sequence that is at least 80%, 85%, 90%, 95%, 98%, or 99%, or 100% identical to any one of the amino acid sequences of SEQ ID NOs: 80-122 and SEQ ID NO: 161.

TABLE 4

| Recruiting domain sources<br>Source for recruiting domains |
|---|
| BLNK |
| IL2RG |
| EGFR |
| EpoR |
| GHR |
| IFNAR1 |
| IFNAR2 |
| IFNAR1/2 |
| IFNLR1 |
| IL10R1 |
| IL12Rb1 |
| IL12Rb2 |
| IL21R |
| IL2Rb |
| IL2small |
| IL7R |
| IL7Ra |
| IL9R |
| IL15R |
| IL21R |

TABLE 5a

Recruiting Domain Sequences (Cytotail Sequences)

| Recruiting domain | Amino acid sequence | SEQ ID NO: |
|---|---|---|
| IL7R(316-459) | ARDEVEGFLQDTFPQQLEESEKQRLGGDVQSPNCPSEDVVITPES FGRDSSLTCLAGNVSACDAPILSSSRSLDCRESGKNGPHVYQDLLL SLGTTNSTLPPPFSLQSGILTLNPVAQGQPILTSLGSNQEEAYVTM SSFYQNQ | 80 |
| IL2Rb(333-551) | VTQLLLQQDKVPEPASLSSNHSLTSCFTNQGYFFFHLPDALEIEAC QVYFTYDPYSEEDPDEGVAGAPTGSSPQPLQPLSGEDDAYCTFPS RDDLLLFSPSLLGGPSPPSTAPGGSGAGEERMPPSLQERVPRDW DPQPLGPPTPGVPDLVDFQPPPELVLREAGEEVPDAGPREGVSFP WSRPPGQGEFRALNARLPLNTDAYLSLQELQGQDPTHLV | 81 |
| IFNAR1(508-557) | ISTIATVEETNQTDEDHKKYSSQTSQDSGNYSNEDESESKTSEELQ QDFV | 82 |
| IFNAR2(310-515) | KKKVWDYNYDDESDSDTEAAPRTSGGGYTMHGLTVRPLGQASA TSTESQLIDPESEEEPDLPEVDVELPTMPKDSPQQLELLSGPCERRK SPLQDPFPEEDYSSTEGSGGRITFNVDLNSVFLRVLDDEDSDDLEA PLMLSSHLEEMVDPEDPDNVQSNHLLASGEGTQPTFPSPSSEGL WSEDAPSDQSDTSESDVDLGDGYIMR | 83 |
| IFNAR1/2(IFNAR1 residues 508-557-IFNAR2 residues 310-515) | ISTIATVEETNQTDEDHKKYSSQTSQDSGNYSNEDESESKTSEELQ QDFVKKKVWDYNYDDESDSDTEAAPRTSGGGYTMHGLTVRPLG QASATSTESQLIDPESEEEPDLPEVDVELPTMPKDSPQQLELLSGP CERRKSPLQDPFPEEDYSSTEGSGGRITFNVDLNSVFLRVLDDEDS DDLEAPLMLSSHLEEMVDPEDPDNVQSNHLLASGEGTQPTFPSP SSEGLWSEDAPSDQSDTSESDVDLGDGYIMR | 84 |
| IFNLR1(300-520) | RGVRPTPRVRAPATQQTRWKKDLAEDEEEEDEEDTEDGVSFQPY IEPPSFLGQEHQAPGHSEAGGVDSGRPRAPLVPSEGSSAWDSSD RSWASTVDSSWDRAGSSGYLAEKGPGQGPGGDGHQESLPPPEF SKDSGFLEELPEDNLSSWATWGTLPPEPNLVPGGPPVSLQTLTFC WESSPEEEEEARESEIEDSDAGSWGAESTQRTEDRGRTLGHYMA R | 85 |

TABLE 5a-continued

| Recruiting Domain Sequences (Cytotail Sequences) | | |
|---|---|---|
| Recruiting domain | Amino acid sequence | SEQ ID NO: |
| Common Gamma Chain (335-369) | IPPKGGALGEGPGASPCNQHSPYWAPPCYTLKPET | 86 |
| IL9R(356-521) | TALLTCGPARPWKSVALEEEQEGPGTRLPGNLSSEDVLPAGCTEW RVQTLAYLPQEDWAPTSLTRPAPPDSEGSRSSSSSSSSNNNNYCA LGCYGGWHLSALPGNTQSSGPIPALACGLSCDHQGLETQQGVA WVLAGHCQRPGLHEDLQGMLLPSVLSKARSWTF | 87 |
| IL21R(322-538) | PRSPAKRLQLTELQEPAELVESDGVPKPSFWPTAQNSGGSAYSEE RDRPYGLVSIDTVTVLDAEGPCTWPCSCEDDGYPALDLDAGLEPS PGLEDPLLDAGTTVLSCGCVSAGSPGLGGPLGSLLDRLKPPLADGE DWAGGLPWGGRSPGGVSESEAGSPLAGLDMDTFDSGFVGSDCS SPVECDFTSPGDEGPPRSYLRQWVVIPPPLSSPGPQAS | 88 |
| GHR(353-638) | PDEKTEESDTDRLLSSDHEKSHSNLGVKDGDSGRTSCCEPDILETD FNANDIHEGTSEVAQPQRLKGEADLLCLDQKNQNNSPYHDACPA TQQPSVIQAEKNKPQPLPTEGAESTHQAAHIQLSNPSSLSNIDFYA QVSDITPAGSVVLSPGQKNKAGMSQCDMHPEMVSLCQENFLM DNAYFCEADAKKCIPVAPHIKVESHIQPSLNQEDIYITTESLTTAAG RPGTGEHVPGSEMPVPDYTSIHIVQSPQGLILNATALPLPDKEFLS SCGYVSTDQLNKIMP | 89 |
| EpoR(339-508) | WGTMQAVEPGTDDEGPLLEPVGSEHAQDTYLVLDKWLLPRNPP SEDLPGPGGSVDIVAMDEGSEASSCSSALASKPSPEGASAASFEYT ILDPSSQLLRPWTLCPELPPTPPHLKYLYLVVSDSGISTDYSSGDSQ GAQGGLSDGPYSNPYENSLIPAAEPLPPSYVACS | 90 |
| murine IL2Rb(337-539) | AVQLLLLQKDSAPLPSPSGHSQASCFTNQGYFFFHLPNALEIESCQ VYFTYDPCVEEEVEEDGSRLPEGSPHPPLLPLAGEQDDYCAFPPRD DLLLFSPSLSTPNTAYGGSRAPEERSPLSLHEGLPSLASRDLMGLQR PLERMPEGDGEGLSANSSGEQASVPEGNLHGQDQDRGQGPILTL NTDAYLSLQELQAQDSVHLI | 91 |
| murine IL7Ra(316-459) | ARDEVESFLPNDLPAQPEELETQGHRAAVHSANRSPETSVSPPET VRRESPLRCLARNLSTCNAPPLLSSRSPDYRDGDRNRPPVYQDLLP NSGNTNVPVPVPQPLPFQSGILIPVSQRQPISTSSVLNQEEAYVTM SSFYQNK | 92 |
| EGFR(955-1186) | VIQGDERMHLPSPTDSNFYRALMDEEDMDDVVDADEYLIPQQG FFSSPSTSRTPLLSSLSATSNNSTVACIDRNGLQSCPIKEDSFLQRYS SDPTGALTEDSIDDTFLPVPEYINQSVPKRPAGSVQNPVYHNQPL NPAPSRDPHYQDPHSTAVGNPEYLNTVQPTCVNSTFDSPAHWA QKGSHQISLDNPDYQQDFFPKEAKPNGIFKGSTAENAEYLRVAPQ SSEFIGA | 93 |
| EGFR(955-1186; Y974F, d1045-1057) | VIQGDERMHLPSPTDSNFFRALMDEEDMDDVVDADEYLIPQQG FFSSPSTSRTPLLSSLSATSNNSTVACIDRNGLQSCPIKEDSFLQRID DTFLPVPEYINQSVPKRPAGSVQNPVYHNQPLNPAPSRDPHYQD PHSTAVGNPEYLNTVQPTCVNSTFDSPAHWAQKGSHQISLDNPD YQQDFFPKEAKPNGIFKGSTAENAEYLRVAPQSSEFIGA | 94 |
| EGFR(955-1009; Y974F) | VIQGDERMHLPSPTDSNFFRALMDEEDMDDVVDADEYLIPQQG FFSSPSTSRTP | 95 |
| EGFR(1019-1085) | NNSTVACIDRNGLQSCPIKEDSFLQRIDDTFLPVPEYINQSVPKRPA GSVQNPV | 96 |
| EGFR(1037-1103; Y1068/1101F, d1045-1057) | KEDSFLQRIDDTFLPVPEFINQSVPKRPAGSVQNPVYHNQPLNPA PSRDPHFQD | 97 |
| EGFR(1066-1118; Y1068/1086F) | VPEFINQSVPKRPAGSVQNPVFHNQPLNPAPSRDPHYQDPHSTA VGNPEYLNTV | 98 |
| EGFR(1122-1165) | PEYLNTVQPTCVNSTFDSPAHWAQKGSHQISLDNPDYQQDFFPK EAKPNGIFKG | 99 |
| EGFR(1133-1186; Y1148F) | WAQKGSHQISLDNPDFQQDFFPKEAKPNGIFKGSTAENAEYLRV APQSSEFIGA | 100 |
| IL12Rb2(775-825) | SDPKPENPACPWTVLPAGDLPTHDGYLPSNIDDLPSHEAPLADSL EELEPQ | 101 |

TABLE 5a-continued

Recruiting Domain Sequences (Cytotail Sequences)

| Recruiting domain | Amino acid sequence | SEQ ID NO: |
|---|---|---|
| IL7R(376-416) | ACDAPILSSSRSLDCRESGKNGPHVYQDLLLSLGTTNSTLP | 102 |
| IL7R(424-459) | GILTLNPVAQGQPILTSLGSNQEEAYVTMSSFYQNQ | 103 |
| IL7R(376-416, 424-459) | ACDAPILSSSRSLDCRESGKNGPHVYQDLLLSLGTTNSTLPQGQPIL TSLGSNQEEAYVTMSSFYQNQ | 104 |
| IL7R(424-459; Y456F) | GILTLNPVAQGQPILTSLGSNQEEAYVTMSSFFQNQ | 105 |
| IL7R(376-416, 424-459, Y456F) | ACDAPILSSSRSLDCRESGKNGPHVYQDLLLSLGTTNSTLPQGQPIL TSLGSNQEEAYVTMSSFFQNQ | 106 |
| IL2Rbsmall(393-433) | DEGVAGAPTGSSPQPLQPLSGEDDAYCTFPSRDDLLLFSPS | 107 |
| IL2Rbsmall(518-551) | GQGEFRALNARLPLNTDAYLSLQELQGQDPTHLV | 108 |
| IL2Rbsmall(339-379, 393-433) | QQDKVPEPASLSSNHSLTSCFTNQGYFFFHLPDALEIEACQDEGV AGAPTGSSPQPLQPLSGEDDAYCTFPSRDDLLLFSPS | 109 |
| IL2Rbsmall(339-379, 518-551) | QQDKVPEPASLSSNHSLTSCFTNQGYFFFHLPDALEIEACQ GQGEFRALNARLPLNTDAYLSLQELQGQDPTHLV | 110 |
| IL2Rbsmall(393-433, 518-551) | DEGVAGAPTGSSPQPLQPLSGEDDAYCTFPSRDDLLLFSPSGQGE FRALNARLPLNTDAYLSLQELQGQDPTHLV | 111 |
| IL2Rbsmall(339-379, 393-433, 518-551) | QQDKVPEPASLSSNHSLTSCFTNQGYFFFHLPDALEIEACQDEGV AGAPTGSSPQPLQPLSGEDDAYCTFPSRDDLLLFSPSGQGEFRAL NARLPLNTDAYLSLQELQGQDPTHLV | 112 |
| IFNAR2small(310-352) | KKKVWDYNYDDESDSDTEAAPRTSGGGYTMHGLTVRPLGQASA | 113 |
| IFNAR2small(486-515) | EGLWSEDAPSDQSDTSESDVDLGDGYIMR | 114 |
| IFNAR2small(310-352, 486-515) | KKKVWDYNYDDESDSDTEAAPRTSGGGYTMHGLTVRPLGQASA EGLWSEDAPSDQSDTSESDVDLGDGYIMR | 115 |
| BLNK(53-208) | ASESPADEEEQWSDDFDSDYENPDEHSDSEMYVMPAEENADDS YEPPPVEQETRPVHPALPFARGEYIDNRSSQRHSPPFSKTLPSKPS WPSEKARLTSTLPALTALQKPQVPPKPKGLLEDEADYVVPVEDND ENYIHPTESSSPPPEKAPMVNR | 116 |
| BLNK(53-208; Y72F) | ASESPADEEEQWSDDFDSDFENPDEHSDSEMYVMPAEENADDS YEPPPVEQETRPVHPALPFARGEYIDNRSSQRHSPPFSKTLPSKPS WPSEKARLTSTLPALTALQKPQVPPKPKGLLEDEADYVVPVEDND ENYIHPTESSSPPPEKAPMVNR | 117 |
| BLNK(53-208; Y72F, Y96F) | ASESPADEEEQWSDDFDSDFENPDEHSDSEMYVMPAEENADDS FEPPPVEQETRPVHPALPFARGEYIDNRSSQRHSPPFSKTLPSKPS WPSEKARLTSTLPALTALQKPQVPPKPKGLLEDEADYVVPVEDND ENYIHPTESSSPPPEKAPMVNR | 118 |
| EpoR(339-508) | WGTMQAVEPGTDDEGPLLEPVGSEHAQDTYLVLDKWLLPRNPP SEDLPGPGGSVDIVAMDEGSEASSCSSALASKPSPEGASAASFEYT ILDPSSQLLRPWTLCPELPPTPPHLKYLYLVVSDSGISTDYSSGDSQ GAQGGLSDGPYSNPYENSLIPAAEPLPPSYVACS | 119 |
| IL12Rb2(714-862) | VTPVFRHPPCSNWPQREKGIQGHQASEKDMMHSASSPPPPRAL QAESRQLVDLYKVLESRGSDPKPENPACPWTVLPAGDLPTHDGYL PSNIDDLPSHEAPLADSLEELEPQHISLSVFPSSSLHPLTFSCGDKLT LDQLKMRCDSLML | 120 |
| IL12Rb1(622-662) | WDKGERTEPLEKTELPEGAPELALDTELSLEDGDRCKAKM | 121 |
| IL10R1(304-578) | VSPELKNLDLHGSTDSGFGSTKPSLQTEEPQFLLPDPHPQADRTLG NREPPVLGDSCSSGSSNSTDSGICLQEPSLSPSTGPTWEQQVGSN SRGQDDSGIDLVQNSEGRAGDTQGGSALGHHSPPEPEVPGEEDP AAVAFQGYLRQTRCAEEKATKTGCLEEESPLTDGLGPKFGRCLVD EAGLHPPALAKGYLKQDPLEMTLASSGAPTGQWNQPTEEWSLLA LSSCSDLGISDWSFAHDLAPLGCVAAPGGLLGSFNSDLVTLPLISSL QSSE | 122 |
| IL7Ra(316-459).IL12Rb2(775-825) | ARDEVEGFLQDTFPQQLEESEKQRLGGDVQSPNCPSEDVVITPES FGRDSSLTCLAGNVSACDAPILSSSRSLDCRESGKNGPHVYQDLLL SLGTTNSTLPPPFSLQSGILTLNPVAQGQPILTSLGSNQEEAYVTM | 161 |

TABLE 5a-continued

| Recruiting Domain Sequences (Cytotail Sequences) | | |
|---|---|---|
| Recruiting domain | Amino acid sequence | SEQ ID NO: |
| | SSFYQNQSRSDPKPENPACPWTVLPAGDLPTHDGYLPSNIDDLPS HEAPLADSLEELEPQ | |

*SR indicates an exemplary peptide linker

In some embodiments, the Stat-recruiting domain of a chimeric cytokine receptor of the disclosure comprises a STAT-recruiting domain from one receptor.

In order to generate multiple outputs, one or more STAT-recruiting domains may be joined in tandem to mimic signaling from one or more cytokines.

In some embodiments, the STAT-recruiting domain comprises portions of more than one receptor, e.g. comprising more than one STAT-recruiting domain. In such embodiments, a tandem cytokine signaling domain is provided, allowing for enhanced signaling. Accordingly, in some embodiments, the STAT-recruiting domain of a monomer of the chimeric cytokine receptor of the disclosure comprises the STAT-recruiting domains from more than one receptor, e.g. comprises the STAT-recruiting domains from two, three, four, five, or even six receptors. For example, in some embodiments, STAT-recruiting domains can be linked in tandem to stimulate multiple pathways (e.g., the IL7R(316-459)-IL12Rb2(775-825) fragment fusion for pro-persistence STAT5 and pro-inflammatory STAT4; IL7R(316-459)-IL2Rbsmall(393-433,518-551) for pro-persistence; IL7R (316-459)-EGFR(1122-1165) for pro-persistence and anti-exhaustion; IL2Rbsmall(393-433,518-551)-EGFR(1122-1165) for pro-persistence and anti-exhaustion).

When generating multiple outputs, the proximity of individual STAT-recruiting domains to the cell membrane can influence the strength of their respective signaling outputs. Table 5b shows examples of chimeric cytokine receptors with the dual outputs, where each output can be placed either proximal or distal to the cell membrane.

TABLE 5b

| Examples of chimeric cytokine receptors with dual outputs | | |
|---|---|---|
| Dual output STAT-recruiting domain | Membrane proximal | Membrane distal |
| IL2Rbsmall(393-433, 518-551)/IL21R(322-538) | IL2Rbsmall(393-433, 518-551) | IL21R(322-538) |
| IL21R(322-538)/IL2Rbsmall(393-433, 518-551) | IL21R(322-538) | IL2Rbsmall(393-433, 518-551) |
| IL2Rbsmall(339-379, 393-433, 518-551)/IL21R(322-538) | IL2Rbsmall(339-379, 393-433, 518-551) | IL21R(322-538) |
| IL21R(322-538)/IL2Rbsmall(339-379, 393-433, 518-551) | IL21R(322-538) | IL2Rbsmall(339-379, 393-433, 518-551) |
| IL7R (316-459)/IL21R(322-538) | IL7R (316-459) | IL21R(322-538) |
| IL7R (316-459)/IL12Rb2(775-825) | IL7R (316-459) | IL12Rb2(775-825) |
| IL21R(322-538)/IL7R (316-459) | IL21R(322-538) | IL7R (316-459) |

Without being bound to theory or mechanism, in some embodiments, a JAK-protein (JAK1, JAK2, JAK3, or TYK2) is bound to a chimeric cytokine receptor of the disclosure (comprising a binding domain, a transmembrane domain, a JAK-binding domain, and a recruiting domain). In some embodiments, in the presence of (e.g. binding to) a TGF-β ligand or an anti-TGF-β-receptor antibody, the chimeric cytokine receptor clusters and allows for the two bound JAK-proteins to become activated, which in turn phosphorylate tyrosine residues on the recruiting domain of the chimeric receptor. The phosphorylated recruiting domains are then capable of binding the recruited proteins (e.g. a phosphorylated STAT-recruiting domain binds a STAT-protein), which in turn effectuate transcription events in the nucleus.

E. Exemplary TGF-β-Driven Chimeric Cytokine Receptors

Context-dependent chimeric cytokine receptors of the disclosure may be expressed with a signal sequence, e.g. a CD8SS of SEQ ID NO: 1. Table 6 shows exemplary context-dependent cytokine receptor sequences of the disclosure. The receptors may be expressed with a signal sequence, e.g. a CD8SS of SEQ ID NO: 1.

In some embodiments, the chimeric cytokine receptor of the disclosure comprises a TGF-β binding domain comprising an amino acid sequence of any one of SEQ ID NOs: 3-20, and 159, a transmembrane and JAK2 binding domain comprising an amino acid sequence of any one of SEQ ID NOs: 27-79, 160 and 217-234, and a recruiting domain comprising an amino acid sequences of any one of SEQ ID NOs: 80-122 and 161. In some embodiments, the chimeric cytokine receptor does not comprise a signal sequence.

In some embodiments, the chimeric cytokine receptor of the disclosure comprises a TGF-β binding domain comprising the amino acid sequence selected from the group consisting of SEQ ID NOs: 3, 4, and 159, a TPOR/MPLR transmembrane and JAK2 binding domain comprising the amino acid sequence selected from the group consisting of SEQ ID NOs: 38, 39, 40, 53, 59, 60, 61, 64, 69, 70, 160 and 217-234, and a recruiting domain comprising the amino acid sequence selected from the group consisting of SEQ ID NOs: 80, 99, 111, 112, and 161. Optionally, the chimeric cytokine receptor comprises a signal sequence that comprises for example the amino acid sequence of SEQ ID NO:1.

In some embodiments, the chimeric cytokine receptor comprises a binding domain comprising the amino acid sequence of SEQ ID NO: 3, 4 or 159, a transmembrane and JAK2 binding domain comprising the amino acid sequence of SEQ ID NO: 64, 69, or 70, and a recruiting domain comprising the amino acid sequence of SEQ ID NO: 80, 99, 111, 112, or 161. In some embodiments, the chimeric cytokine receptor is inducible. In some embodiments, the chimeric cytokine receptor comprises a binding domain comprising the amino acid sequence of SEQ ID NO: 3, 4 or 159, a transmembrane and JAK2 binding domain comprising the amino acid sequence of SEQ ID NO: 38, 39, 40 or 53, and a recruiting domain comprising the amino acid sequence of SEQ ID NO: 80, 99, 111, 112, or 161. In some embodiments, the chimeric cytokine receptor comprises a binding domain comprising the amino acid sequence of SEQ ID NO: 3, 4 or 159, a transmembrane and JAK2 binding domain comprising the amino acid sequence of SEQ ID NO:

59, 60, 160, or 217, and a recruiting domain comprising the amino acid sequence of SEQ ID NO: 80, 99, 111, 112, or 161. In some embodiments, the chimeric cytokine receptor is constitutively active. In some embodiments, the constitutively active chimeric cytokine receptor of the disclosure dimerizes without binding to a TGFβ ligand or an anti-TGFβR antibody. In some embodiments, the chimeric cytokine receptor of the disclosure inhibits TGFβR-mediated signaling and/or activates STAT-mediated signaling, either constitutively or induced by TGF-β, or an anti-TGFβR antibody. In some embodiments, the chimeric cytokine receptor is constitutively active and/or exhibits further enhanced activities or properties in the presence of a TGF-βR ligand, e.g., TGF-β, or an anti-TGF-βR antibody. In some embodiments, the TGF-βR is TGF-βR2, and the antibody is an anti-TGF-βR2 antibody.

In some embodiments, the chimeric cytokine receptor does not comprise a signal sequence. In some embodiments, the chimeric cytokine receptor comprises the TGFβR2 endogenous signal sequence or a signal sequence that comprise, e.g., the amino acid sequence of SEQ ID NO:1.

In some embodiments, the chimeric cytokine receptor of the disclosure comprises the amino acid sequence of SEQ ID NO: 123. In some embodiments, the chimeric cytokine receptor of the disclosure comprises the amino acid sequence of SEQ ID NO: 124. In some embodiments, the chimeric cytokine receptor of the disclosure comprises the amino acid sequence of SEQ ID NO: 125. In some embodiments, the chimeric cytokine receptor of the disclosure comprises the amino acid sequence of SEQ ID NO: 126. In some embodiments, the chimeric cytokine receptor of the disclosure comprises the amino acid sequence of SEQ ID NO: 127. In some embodiments, the chimeric cytokine receptor of the disclosure comprises the amino acid sequence of SEQ ID NO: 128. In some embodiments, the chimeric cytokine receptor of the disclosure comprises the amino acid sequence of SEQ ID NO: 129. In some embodiments, the chimeric cytokine receptor of the disclosure comprises the amino acid sequence of SEQ ID NO: 130. In some embodiments, the chimeric cytokine receptor of the disclosure comprises the amino acid sequence of SEQ ID NO: 131. In some embodiments, the chimeric cytokine receptor of the disclosure comprises the amino acid sequence of SEQ ID NO: 132. In some embodiments, the chimeric cytokine receptor of the disclosure comprises the amino acid sequence of SEQ ID NO: 133. In some embodiments, the chimeric cytokine receptor of the disclosure comprises the amino acid sequence of SEQ ID NO: 134. In some embodiments, the chimeric cytokine receptor of the disclosure comprises the amino acid sequence of SEQ ID NO: 135. In some embodiments, the chimeric cytokine receptor of the disclosure comprises the amino acid sequence of SEQ ID NO: 136. In some embodiments, the chimeric cytokine receptor of the disclosure comprises the amino acid sequence of SEQ ID NO: 137. In some embodiments, the chimeric cytokine receptor of the disclosure comprises the amino acid sequence of SEQ ID NO: 138. In some embodiments, the chimeric cytokine receptor of the disclosure comprises the amino acid sequence of SEQ ID NO: 139. In some embodiments, the chimeric cytokine receptor of the disclosure comprises the amino acid sequence of SEQ ID NO: 140. In some embodiments, the chimeric cytokine receptor of the disclosure comprises the amino acid sequence of SEQ ID NO: 141. In some embodiments, the chimeric cytokine receptor of the disclosure comprises the amino acid sequence of SEQ ID NO: 142. In some embodiments, the chimeric cytokine receptor of the disclosure comprises the amino acid sequence of SEQ ID NO: 143. In some embodiments, the chimeric cytokine receptor of the disclosure comprises the amino acid sequence of SEQ ID NO: 144. In some embodiments, the chimeric cytokine receptor of the disclosure comprises the amino acid sequence of SEQ ID NO: 145. In some embodiments, the chimeric cytokine receptor of the disclosure comprises the amino acid sequence of SEQ ID NO: 146. In some embodiments, the chimeric cytokine receptor of the disclosure comprises the amino acid sequence of SEQ ID NO: 147. In some embodiments, the chimeric cytokine receptor of the disclosure comprises the amino acid sequence of SEQ ID NO: 148. In some embodiments, the chimeric cytokine receptor of the disclosure comprises the amino acid sequence of SEQ ID NO: 149. In some embodiments, the chimeric cytokine receptor of the disclosure comprises the amino acid sequence of SEQ ID NO: 150. In some embodiments, the chimeric cytokine receptor of the disclosure comprises the amino acid sequence of SEQ ID NO: 151. In some embodiments, the chimeric cytokine receptor of the disclosure comprises the amino acid sequence of SEQ ID NO: 162. In some embodiments, the chimeric cytokine receptor of the disclosure comprises the amino acid sequence of SEQ ID NO: 163. In some embodiments, the chimeric cytokine receptor of the disclosure comprises the amino acid sequence of SEQ ID NO: 164. In some embodiments, the chimeric cytokine receptor of the disclosure comprises the amino acid sequence of SEQ ID NO:165. In some embodiments, the chimeric cytokine receptor of the disclosure comprises the amino acid sequence of SEQ ID NO:166. In some embodiments, the chimeric cytokine receptor of the disclosure comprises the amino acid sequence of SEQ ID NO:167. In some embodiments, the chimeric cytokine receptor of the disclosure comprises the amino acid sequence of SEQ ID NO:168. In some embodiments, the chimeric cytokine receptor of the disclosure comprises the amino acid sequence of SEQ ID NO:169. In some embodiments, the chimeric cytokine receptor of the disclosure comprises the amino acid sequence of SEQ ID NO:170. In some embodiments, the chimeric cytokine receptor of the disclosure comprises the amino acid sequence of SEQ ID NO:171. In some embodiments, the chimeric cytokine receptor of the disclosure comprises the amino acid sequence of SEQ ID NO:172. In some embodiments, the chimeric cytokine receptor of the disclosure comprises the amino acid sequence of SEQ ID NO:173. In some embodiments, the chimeric cytokine receptor of the disclosure comprises the amino acid sequence of SEQ ID NO:174. In some embodiments, the chimeric cytokine receptor of the disclosure comprises the amino acid sequence of SEQ ID NO:175. In some embodiments, the chimeric cytokine receptor of the disclosure comprises the amino acid sequence of SEQ ID NO:176. In some embodiments, the chimeric cytokine receptor of the disclosure comprises the amino acid sequence of SEQ ID NO:177. In some embodiments, the chimeric cytokine receptor of the disclosure comprises the amino acid sequence of SEQ ID NO:178. In some embodiments, the chimeric cytokine receptor of the disclosure comprises the amino acid sequence of SEQ ID NO:179. In some embodiments, the chimeric cytokine receptor of the disclosure comprises the amino acid sequence of SEQ ID NO:180. In some embodiments, the chimeric cytokine receptor of the disclosure comprises the amino acid sequence of SEQ ID NO:181. In some embodiments, the chimeric cytokine receptor of the disclosure comprises the amino acid sequence of SEQ ID NO:182. In some embodiments, the chimeric cytokine receptor of the disclosure comprises the amino acid sequence of SEQ ID NO:183. In some embodiments, the chimeric cytokine receptor of the disclosure comprises the amino acid sequence of SEQ ID NO:184. In some embodiments, the chimeric cytokine receptor of the disclosure comprises the amino acid sequence of SEQ ID NO:185. In some embodiments, the chimeric cytokine receptor of the disclosure comprises the amino acid sequence of SEQ ID NO:186. In some embodiments, the chimeric cytokine receptor of the disclosure comprises the amino acid sequence of SEQ ID NO:187. In some embodiments, the chimeric cytokine receptor of the disclosure comprises the amino acid sequence of SEQ ID NO:188. In some embodiments, the chimeric cytokine receptor of the disclosure comprises the amino acid sequence of SEQ ID NO:189. In some embodiments, the chimeric cytokine receptor of the disclosure comprises the amino acid sequence of SEQ ID NO:190. In some embodiments, the chimeric cytokine receptor of the disclosure comprises the amino acid sequence of SEQ ID NO:191. In some embodiments, the chimeric cytokine receptor of the disclosure comprises the amino acid sequence of SEQ ID NO:192. In some embodiments, the chimeric cytokine receptor of the disclosure comprises the amino acid sequence of SEQ ID NO:193. In some embodiments, the chimeric cytokine receptor of the disclosure comprises the amino acid sequence of SEQ ID NO:194. In some embodiments, the chimeric cytokine receptor of the disclosure comprises the amino acid sequence of SEQ ID NO:195. In some embodiments, the chimeric cytokine receptor of the disclosure comprises the amino acid sequence of SEQ ID NO:196. In some embodiments, the chimeric cytokine receptor of the disclosure comprises the amino acid sequence of SEQ ID NO:197. In some embodiments, the chimeric cytokine receptor of the disclosure comprises the amino acid sequence of SEQ ID NO:198. In some embodiments, the chimeric cytokine receptor of the disclosure comprises the amino acid sequence of SEQ ID NO:199. In some embodiments, the chimeric cytokine receptor of the disclosure comprises the amino acid sequence of SEQ ID NO:200. In some embodiments, the chimeric cytokine receptor of the disclosure comprises the amino acid sequence of SEQ ID NO:201. In some embodiments, the chimeric cytokine receptor of the disclosure comprises the amino acid sequence of SEQ ID NO:202. In some embodiments, the chimeric cytokine receptor of the disclosure comprises the amino acid sequence of SEQ ID NO:203. In some embodiments, the chimeric cytokine receptor of the disclosure comprises the amino acid sequence of SEQ ID NO:204. In some embodiments, the chimeric cytokine receptor of the disclosure comprises the amino acid sequence of SEQ ID NO:205. In some embodiments, the chimeric cytokine receptor of the disclosure comprises the amino acid sequence of SEQ ID NO:206. In some embodiments, the chimeric cytokine receptor of the disclosure comprises the amino acid sequence of SEQ ID NO:207. In some embodiments, the chimeric cytokine receptor of the disclosure comprises the amino acid sequence of SEQ ID NO:208. In some embodiments, the chimeric cytokine receptor of the disclosure comprises the amino acid sequence of SEQ ID NO:209. In some embodiments, the chimeric cytokine receptor of the disclosure comprises the amino acid sequence of SEQ ID NO:210. In some embodiments, the chimeric cytokine receptor of the disclosure comprises the amino acid sequence of SEQ ID NO:211. In some embodiments, the chimeric cytokine receptor of the disclosure comprises the amino acid sequence of SEQ ID NO:212. In some embodiments, the chimeric cytokine receptor of the disclosure comprises the amino acid sequence of SEQ ID NO:213. In some embodiments, the chimeric cytokine receptor of the disclosure comprises the amino acid sequence of SEQ ID NO:214. In some embodiments, the chimeric cytokine receptor of the disclosure comprises the amino acid sequence of SEQ ID NO:215. In some embodiments, the chimeric cytokine receptor of the disclosure comprises the amino acid sequence of SEQ ID NO:216.

In some embodiments, the chimeric cytokine receptor (CCR) comprises a binding domain comprising the amino acid sequence of SEQ ID NO: 159, a transmembrane and JAK2 binding domain comprising the amino acid sequence of SEQ ID NO: 40, and a recruiting domain comprising the amino acid sequence of SEQ ID NO: 80, 99, 111, 112, or 161. In some embodiments, the CCR comprises a binding domain comprising the amino acid sequence of SEQ ID NO: 159, a transmembrane and JAK2 binding domain comprising the amino acid sequence of SEQ ID NO: 53, and a recruiting domain comprising the amino acid sequence of SEQ ID NO: 80, 99, 111, 112, or 161. In some embodiments, the CCR comprises a binding domain comprising the amino acid sequence of SEQ ID NO: 4, a transmembrane and JAK2 binding domain comprising the amino acid sequence of SEQ ID NO: 38, and a recruiting domain comprising the amino acid sequence of SEQ ID NO: 80, 99, 111, 112, or 161. In some embodiments, the CCR comprises a binding domain comprising the amino acid sequence of SEQ ID NO: 4, a transmembrane and JAK2 binding domain comprising the amino acid sequence of SEQ ID NO: 39, and a recruiting domain comprising the amino acid sequence of SEQ ID NO: 80, 99, 111, 112, or 161. In some embodiments, the CCR comprises a binding domain comprising the amino acid sequence of SEQ ID NO: 4, a transmembrane and JAK2 binding domain comprising the amino acid sequence of SEQ ID NO: 40, and a recruiting domain comprising the amino acid sequence of SEQ ID NO: 80, 99, 111, 112, or 161. In some embodiments, the CCR comprises a binding domain comprising the amino acid sequence of SEQ ID NO: 4, a transmembrane and JAK2 binding domain comprising the amino acid sequence of SEQ ID NO: 53, and a recruiting domain comprising the amino acid sequence of SEQ ID NO: 80, 99, 111, 112, or 161. In some embodiments, the CCR comprises a binding domain comprising the amino acid sequence of SEQ ID NO: 159, a transmembrane and JAK2 binding domain comprising the amino acid sequence of SEQ ID NO: 70, and a recruiting domain comprising the amino acid sequence of SEQ ID NO: 80, 99, 111, 112, or 161. In some embodiments, the CCR comprises a binding domain comprising the amino acid sequence of SEQ ID NO: 159, a transmembrane and JAK2 binding domain comprising the amino acid sequence of SEQ ID NO: 69, and a recruiting domain comprising the amino acid sequence of SEQ ID NO: 80, 99, 111, 112, or 161. In some embodiments, the CCR comprises a binding domain comprising the amino acid sequence of SEQ ID NO: 4, a transmembrane and JAK2 binding domain comprising the amino acid sequence of SEQ ID NO: 64, and a recruiting domain comprising the amino acid sequence of SEQ ID NO: 80, 99, 111, 112, or 161. In some embodiments, the CCR comprises a binding domain comprising the amino acid sequence of SEQ ID NO: 4, a transmembrane and JAK2 binding domain comprising the amino acid sequence of SEQ ID NO: 69, and a recruiting domain comprising the amino acid sequence of SEQ ID NO: 80, 99, 111, 112, or 161. In some embodiments, the CCR comprises a binding domain comprising the amino acid sequence of SEQ ID NO: 4, a transmembrane and JAK2 binding domain comprising the amino acid sequence of SEQ ID NO: 70, and a recruiting domain comprising the amino acid sequence of SEQ ID NO: 80, 99, 111, 112, or 161. In some embodiments, the CCR comprises a binding domain comprising the amino acid sequence of SEQ ID NO: 159, a transmembrane and JAK2 binding domain comprising the amino acid sequence of SEQ ID NO: 160 or 219, and a recruiting domain comprising the amino acid sequence of SEQ ID NO: 80, 99, 111, 112, or 161. In some embodiments, the CCR comprises a binding domain comprising the amino acid sequence of SEQ ID NO: 159, a transmembrane and JAK2 binding domain comprising the amino acid sequence of SEQ ID NO: 223, 224, and a recruiting domain comprising the amino acid sequence of SEQ ID NO: 80, 99, 111, 112, or 161. In some embodiments, the CCR comprises a binding domain comprising the amino acid sequence of SEQ ID NO: 159, a transmembrane and JAK2 binding domain comprising the amino acid sequence of SEQ ID NO: 225 or 226, and a recruiting domain comprising the amino acid sequence of SEQ ID NO: 80, 99, 111, 112, or 161. In some embodiments, the CCR comprises a binding domain comprising the amino acid sequence of SEQ ID NO: 4, a transmembrane and JAK2 binding domain comprising the amino acid sequence of SEQ ID NO: 60 or 160, and a recruiting domain comprising the amino acid sequence of SEQ ID NO: 80, 99, 111, 112, or 161. In some embodiments, the CCR comprises a binding domain comprising the amino acid sequence of SEQ ID NO: 4, a transmembrane and JAK2 binding domain comprising the amino acid sequence of SEQ ID NO: 223, 224, and a recruiting domain comprising the amino acid sequence of SEQ ID NO: 80, 99, 111, 112, or 161. In some embodiments, the CCR comprises a binding domain comprising the amino acid sequence of SEQ ID NO: 4, a transmembrane and JAK2 binding domain comprising the amino acid sequence of SEQ ID NO: 225 or 226, and a recruiting domain comprising the amino acid sequence of SEQ ID NO: 80, 99, 111, 112, or 161

In some embodiments, the chimeric cytokine receptor of the disclosure comprises the amino acid sequence of SEQ ID NO:272, SEQ ID NO:273, SEQ ID NO:274, or SEQ ID NO:275. In some embodiments, the chimeric cytokine receptor comprises an amino acid sequence that is at least 80%, 85%, 90%, 95%, 98%, or 99%, or 100% identical to any one of the amino acid sequences of SEQ ID NOs: 123-216 and SEQ ID NOs: 272-275.

TABLE 6

Exemplary chimeric cytokine receptor sequences (assembled inducible or constitutively active TGF-β receptor chimeric cytokine receptors):

| Receptor | Amino acid sequence | SEQ ID NO: |
|---|---|---|
| CD8SS-TGFbR2(1-166).TPOR/MPLR(478-582).IL7Ra(316-459).IL12Rb2(775-825) Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETAWISLVTALHLVLGLSAVLGLLLLRWQFPA<br>HYRRLRHALWPSLPDLHRVLGQYLRDTAALSPPKATVSDTCEEVE<br>PSLLEILPKSSERTPLPLARDEVEGFLQDTFPQQLEESEKQRLGGDV<br>QSPNCPSEDVVITPESFGRDSSLTCLAGNVSACDAPILSSSRSLDCR<br>ESGKNGPHVYQDLLLSLGTTNSTLPPPFSLQSGILTLNPVAQGQPIL<br>TSLGSNQEEAYVTMSSFYQNQSDPKPENPACPWTVLPAGDLPTH<br>DGYLPSNIDDLPSHEAPLADSLEELEPQ | 123 |
| CD8SS-TGFbR2(1-166).TPOR/MPLR(478-582; N - 1).IL7Ra(316-459).IL12Rb2(775-825) Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETWISLVTALHLVLGLSAVLGLLLLRWQFPAH<br>YRRLRHALWPSLPDLHRVLGQYLRDTAALSPPKATVSDTCEEVEPS<br>LLEILPKSSERTPLPLARDEVEGFLQDTFPQQLEESEKQRLGGDVQS<br>PNCPSEDVVITPESFGRDSSLTCLAGNVSACDAPILSSSRSLDCRES<br>GKNGPHVYQDLLLSLGTTNSTLPPPFSLQSGILTLNPVAQGQPILTS<br>LGSNQEEAYVTMSSFYQNQSDPKPENPACPWTVLPAGDLPTHD<br>GYLPSNIDDLPSHEAPLADSLEELEPQ | 124 |
| CD8SS-TGFbR2(1-166).TPOR/MPLR(478-582; N - 2).IL7Ra(316-459).IL12Rb2(775-825) Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETISLVTALHLVLGLSAVLGLLLLRWQFPAHYR<br>RLRHALWPSLPDLHRVLGQYLRDTAALSPPKATVSDTCEEVEPSLL<br>EILPKSSERTPLPLARDEVEGFLQDTFPQQLEESEKQRLGGDVQSP<br>NCPSEDVVITPESFGRDSSLTCLAGNVSACDAPILSSSRSLDCRESG<br>KNGPHVYQDLLLSLGTTNSTLPPPFSLQSGILTLNPVAQGQPILTSL<br>GSNQEEAYVTMSSFYQNQSDPKPENPACPWTVLPAGDLPTHDG<br>YLPSNIDDLPSHEAPLADSLEELEPQ | 125 |
| CD8SS-TGFbR2(1-166).TPOR/MPLR(478-582; N - 2 + 1).IL7Ra(316-459).IL12Rb2(775-825) Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETLISLVTALHLVLGLSAVLGLLLLRWQFPAHY<br>RRLRHALWPSLPDLHRVLGQYLRDTAALSPPKATVSDTCEEVEPSL<br>LEILPKSSERTPLPLARDEVEGFLQDTFPQQLEESEKQRLGGDVQS<br>PNCPSEDVVITPESFGRDSSLTCLAGNVSACDAPILSSSRSLDCRES<br>GKNGPHVYQDLLLSLGTTNSTLPPPFSLQSGILTLNPVAQGQPILTS | 126 |

TABLE 6-continued

Exemplary chimeric cytokine receptor sequences (assembled inducible or constitutively active TGF-β receptor chimeric cytokine receptors):

| Receptor | Amino acid sequence | SEQ ID NO: |
|---|---|---|
| | LGSNQEEAYVTMSSFYQNQSDPKPENPACPWTVLPAGDLPTHD<br>GYLPSNIDDLPSHEAPLADSLEELEPQ | |
| CD8SS-TGFbR2(1-166).TPOR/MPLR(478-582; N - 3).IL7Ra(316-459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETSLVTALHLVLGLSAVLGLLLLRWQFPAHYRR<br>LRHALWPSLPDLHRVLGQYLRDTAALSPPKATVSDTCEEVEPSLLEI<br>LPKSSERTPLPLARDEVEGFLQDTFPQQLEESEKQRLGGDVQSPN<br>CPSEDVVITPESFGRDSSLTCLAGNVSACDAPILSSSRSLDCRESGK<br>NGPHVYQDLLLSLGTTNSTLPPPFSLQSGILTLNPVAQGQPILTSLG<br>SNQEEAYVTMSSFYQNQSDPKPENPACPWTVLPAGDLPTHDGY<br>LPSNIDDLPSHEAPLADSLEELEPQ | 127 |
| CD8SS-TGFbR2(1-166).TPOR/MPLR(478-582; N - 4).IL7Ra(316-459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETLVTALHLVLGLSAVLGLLLLRWQFPAHYRRL<br>RHALWPSLPDLHRVLGQYLRDTAALSPPKATVSDTCEEVEPSLLEIL<br>PKSSERTPLPLARDEVEGFLQDTFPQQLEESEKQRLGGDVQSPNC<br>PSEDVVITPESFGRDSSLTCLAGNVSACDAPILSSSRSLDCRESGKN<br>GPHVYQDLLLSLGTTNSTLPPPFSLQSGILTLNPVAQGQPILTSLGS<br>NQEEAYVTMSSFYQNQSDPKPENPACPWTVLPAGDLPTHDGYL<br>PSNIDDLPSHEAPLADSLEELEPQ | 128 |
| CD8SS-TGFbR2(1-166).TPOR/MPLR(478-582; N - 4 + 1).IL7Ra(316-459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETILVTALHLVLGLSAVLGLLLLRWQFPAHYRR<br>LRHALWPSLPDLHRVLGQYLRDTAALSPPKATVSDTCEEVEPSLLEI<br>LPKSSERTPLPLARDEVEGFLQDTFPQQLEESEKQRLGGDVQSPN<br>CPSEDVVITPESFGRDSSLTCLAGNVSACDAPILSSSRSLDCRESGK<br>NGPHVYQDLLLSLGTTNSTLPPPFSLQSGILTLNPVAQGQPILTSLG<br>SNQEEAYVTMSSFYQNQSDPKPENPACPWTVLPAGDLPTHDGY<br>LPSNIDDLPSHEAPLADSLEELEPQ | 129 |
| CD8SS-TGFbR2(1-166).TPOR/MPLR(478-582; N - 5).IL7Ra(316-459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETVTALHLVLGLSAVLGLLLLRWQFPAHYRRL<br>RHALWPSLPDLHRVLGQYLRDTAALSPPKATVSDTCEEVEPSLLEIL<br>PKSSERTPLPLARDEVEGFLQDTFPQQLEESEKQRLGGDVQSPNC<br>PSEDVVITPESFGRDSSLTCLAGNVSACDAPILSSSRSLDCRESGKN<br>GPHVYQDLLLSLGTTNSTLPPPFSLQSGILTLNPVAQGQPILTSLGS<br>NQEEAYVTMSSFYQNQSDPKPENPACPWTVLPAGDLPTHDGYL<br>PSNIDDLPSHEAPLADSLEELEPQ | 130 |
| CD8SS-TGFbR2(1-166).TPOR/MPLR(478-582; N - 6).IL7Ra(316-459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETTALHLVLGLSAVLGLLLLRWQFPAHYRRLR<br>HALWPSLPDLHRVLGQYLRDTAALSPPKATVSDTCEEVEPSLLEILP<br>KSSERTPLPLARDEVEGFLQDTFPQQLEESEKQRLGGDVQSPNCP<br>SEDVVITPESFGRDSSLTCLAGNVSACDAPILSSSRSLDCRESGKNG<br>PHVYQDLLLSLGTTNSTLPPPFSLQSGILTLNPVAQGQPILTSLGSN<br>QEEAYVTMSSFYQNQSDPKPENPACPWTVLPAGDLPTHDGYLPS<br>NIDDLPSHEAPLADSLEELEPQ | 131 |
| CD8SS-TGFbR2(1-166).TPOR/MPLR(478-582; N - 7).IL7Ra(316-459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETALHLVLGLSAVLGLLLLRWQFPAHYRRLRH<br>ALWPSLPDLHRVLGQYLRDTAALSPPKATVSDTCEEVEPSLLEILPK<br>SSERTPLPLARDEVEGFLQDTFPQQLEESEKQRLGGDVQSPNCPS<br>EDVVITPESFGRDSSLTCLAGNVSACDAPILSSSRSLDCRESGKNGP<br>HVYQDLLLSLGTTNSTLPPPFSLQSGILTLNPVAQGQPILTSLGSNQ<br>EEAYVTMSSFYQNQSDPKPENPACPWTVLPAGDLPTHDGYLPSN<br>IDDLPSHEAPLADSLEELEPQ | 132 |

TABLE 6-continued

Exemplary chimeric cytokine receptor sequences (assembled inducible or constitutively active TGF-β receptor chimeric cytokine receptors):

| Receptor | Amino acid sequence | SEQ ID NO: |
|---|---|---|
| CD8SS-TGFbR2(1-166).TPOR/MPLR(478-582; N - 8).IL7Ra(316-459).IL12Rb2(775-825) Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETLHLVLGLSAVLGLLLLRWQFPAHYRRLRHA<br>LWPSLPDLHRVLGQYLRDTAALSPPKATVSDTCEEVEPSLLEILPKS<br>SERTPLPLARDEVEGFLQDTFPQQLEESEKQRLGGDVQSPNCPSE<br>DVVITPESFGRDSSLTCLAGNVSACDAPILSSSRSLDCRESGKNGPH<br>VYQDLLLSLGTTNSTLPPPFSLQSGILTLNPVAQGQPILTSLGSNQE<br>EAYVTMSSFYQNQSDPKPENPACPWTVLPAGDLPTHDGYLPSNI<br>DDLPSHEAPLADSLEELEPQ | 133 |
| CD8SS-TGFbR2(1-166).TPOR/MPLR(478-582; N - 9).IL7Ra(316-459).IL12Rb2(775-825) Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETHLVLGLSAVLGLLLLRWQFPAHYRRLRHAL<br>WPSLPDLHRVLGQYLRDTAALSPPKATVSDTCEEVEPSLLEILPKSS<br>ERTPLPLARDEVEGFLQDTFPQQLEESEKQRLGGDVQSPNCPSED<br>VVITPESFGRDSSLTCLAGNVSACDAPILSSSRSLDCRESGKNGPHV<br>YQDLLLSLGTTNSTLPPPFSLQSGILTLNPVAQGQPILTSLGSNQEE<br>AYVTMSSFYQNQSDPKPENPACPWTVLPAGDLPTHDGYLPSNID<br>DLPSHEAPLADSLEELEPQ | 134 |
| CD8SS-TGFbR2(1-166).TPOR/MPLR(478-582; N - 10).IL7Ra(316-459).IL12Rb2(775-825) Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETLVLGLSAVLGLLLLRWQFPAHYRRLRHALW<br>PSLPDLHRVLGQYLRDTAALSPPKATVSDTCEEVEPSLLEILPKSSER<br>TPLPLARDEVEGFLQDTFPQQLEESEKQRLGGDVQSPNCPSEDVV<br>ITPESFGRDSSLTCLAGNVSACDAPILSSSRSLDCRESGKNGPHVYQ<br>DLLLSLGTTNSTLPPPFSLQSGILTLNPVAQGQPILTSLGSNQEEAY<br>VTMSSFYQNQSDPKPENPACPWTVLPAGDLPTHDGYLPSNIDDL<br>PSHEAPLADSLEELEPQ | 135 |
| CD8SS-TGFbR2(1-166).TPOR/MPLR(478-582; N - 11).IL7Ra(316-459).IL12Rb2(775-825) Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETVLGLSAVLGLLLLRWQFPAHYRRLRHALW<br>PSLPDLHRVLGQYLRDTAALSPPKATVSDTCEEVEPSLLEILPKSSER<br>TPLPLARDEVEGFLQDTFPQQLEESEKQRLGGDVQSPNCPSEDVV<br>ITPESFGRDSSLTCLAGNVSACDAPILSSSRSLDCRESGKNGPHVYQ<br>DLLLSLGTTNSTLPPPFSLQSGILTLNPVAQGQPILTSLGSNQEEAY<br>VTMSSFYQNQSDPKPENPACPWTVLPAGDLPTHDGYLPSNIDDL<br>PSHEAPLADSLEELEPQ | 136 |
| CD8SS-TGFbR2(1-166).TPOR/MPLR(478-582; N - 12).IL7Ra(316-459).IL12Rb2(775-825) Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETLGLSAVLGLLLLRWQFPAHYRRLRHALWPS<br>LPDLHRVLGQYLRDTAALSPPKATVSDTCEEVEPSLLEILPKSSERTP<br>LPLARDEVEGFLQDTFPQQLEESEKQRLGGDVQSPNCPSEDVVIT<br>PESFGRDSSLTCLAGNVSACDAPILSSSRSLDCRESGKNGPHVYQD<br>LLLSLGTTNSTLPPPFSLQSGILTLNPVAQGQPILTSLGSNQEEAYVT<br>MSSFYQNQSDPKPENPACPWTVLPAGDLPTHDGYLPSNIDDLPS<br>HEAPLADSLEELEPQ | 137 |
| CD8SS-TGFbR2(1-166).TPOR/MPLR(478-582; N - 13).IL7Ra(316-459).IL12Rb2(775-825) Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETGLSAVLGLLLLRWQFPAHYRRLRHALWPSL<br>PDLHRVLGQYLRDTAALSPPKATVSDTCEEVEPSLLEILPKSSERTPL<br>PLARDEVEGFLQDTFPQQLEESEKQRLGGDVQSPNCPSEDVVITP<br>ESFGRDSSLTCLAGNVSACDAPILSSSRSLDCRESGKNGPHVYQDL<br>LLSLGTTNSTLPPPFSLQSGILTLNPVAQGQPILTSLGSNQEEAYVT<br>MSSFYQNQSDPKPENPACPWTVLPAGDLPTHDGYLPSNIDDLPS<br>HEAPLADSLEELEPQ | 138 |

TABLE 6-continued

Exemplary chimeric cytokine receptor sequences (assembled inducible or constitutively active TGF-β receptor chimeric cytokine receptors):

| Receptor | Amino acid sequence | SEQ ID NO: |
|---|---|---|
| CD8SS-TGFbR2(1-166).TPOR/MPLR(478-582; N - 14).IL7Ra(316-459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETLSAVLGLLLLRWQFPAHYRRLRHALWPSLP<br>DLHRVLGQYLRDTAALSPPKATVSDTCEEVEPSLLEILPKSSERTPLP<br>LARDEVEGFLQDTFPQQLEESEKQRLGGDVQSPNCPSEDVVITPE<br>SFGRDSSLTCLAGNVSACDAPILSSSRSLDCRESGKNGPHVYQDLL<br>LSLGTTNSTLPPPFSLQSGILTLNPVAQGQPILTSLGSNQEEAYVTM<br>SSFYQNQSDPKPENPACPWTVLPAGDLPTHDGYLPSNIDDLPSHE<br>APLADSLEELEPQ | 139 |
| CD8SS-TGFbR2(1-166).TPOR/MPLR(478-582; N - 15).IL7Ra(316-459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETSAVLGLLLLRWQFPAHYRRLRHALWPSLPD<br>LHRVLGQYLRDTAALSPPKATVSDTCEEVEPSLLEILPKSSERTPLPL<br>ARDEVEGFLQDTFPQQLEESEKQRLGGDVQSPNCPSEDVVITPES<br>FGRDSSLTCLAGNVSACDAPILSSSRSLDCRESGKNGPHVYQDLLL<br>SLGTTNSTLPPPFSLQSGILTLNPVAQGQPILTSLGSNQEEAYVTM<br>SSFYQNQSDPKPENPACPWTVLPAGDLPTHDGYLPSNIDDLPSHE<br>APLADSLEELEPQ | 140 |
| CD8SS-TGFbR2(1-166).TPOR/MPLR(478-582; N - 16).IL7Ra(316-459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETAVLGLLLLRWQFPAHYRRLRHALWPSLPDL<br>HRVLGQYLRDTAALSPPKATVSDTCEEVEPSLLEILPKSSERTPLPLA<br>RDEVEGFLQDTFPQQLEESEKQRLGGDVQSPNCPSEDVVITPESF<br>GRDSSLTCLAGNVSACDAPILSSSRSLDCRESGKNGPHVYQDLLLS<br>LGTTNSTLPPPFSLQSGILTLNPVAQGQPILTSLGSNQEEAYVTMS<br>SFYQNQSDPKPENPACPWTVLPAGDLPTHDGYLPSNIDDLPSHE<br>APLADSLEELEPQ | 141 |
| CD8SS-TGFbR2(1-166).TPOR/MPLR(478-582; N - 17).IL7Ra(316-459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETVLGLLLLRWQFPAHYRRLRHALWPSLPDLH<br>RVLGQYLRDTAALSPPKATVSDTCEEVEPSLLEILPKSSERTPLPLAR<br>DEVEGFLQDTFPQQLEESEKQRLGGDVQSPNCPSEDVVITPESFG<br>RDSSLTCLAGNVSACDAPILSSSRSLDCRESGKNGPHVYQDLLLSL<br>GTTNSTLPPPFSLQSGILTLNPVAQGQPILTSLGSNQEEAYVTMSS<br>FYQNQSDPKPENPACPWTVLPAGDLPTHDGYLPSNIDDLPSHEA<br>PLADSLEELEPQ | 142 |
| CD8SS-TGFbR2(1-166).TPOR/MPLR(478-582; N - 18).IL7Ra(316-459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETLGLLLLRWQFPAHYRRLRHALWPSLPDLHR<br>VLGQYLRDTAALSPPKATVSDTCEEVEPSLLEILPKSSERTPLPLARD<br>EVEGFLQDTFPQQLEESEKQRLGGDVQSPNCPSEDVVITPESFGR<br>DSSLTCLAGNVSACDAPILSSSRSLDCRESGKNGPHVYQDLLLSLGT<br>TNSTLPPPFSLQSGILTLNPVAQGQPILTSLGSNQEEAYVTMSSFY<br>QNQSDPKPENPACPWTVLPAGDLPTHDGYLPSNIDDLPSHEAPL<br>ADSLEELEPQ | 143 |
| CD8SS-TGFbR2(1-166).TPOR/MPLR(478-582; N + 1).IL7Ra(316-459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETAWLISLVTALHLVLGLSAVLGLLLLRWQFPA<br>HYRRLRHALWPSLPDLHRVLGQYLRDTAALSPPKATVSDTCEEVE<br>PSLLEILPKSSERTPLPLARDEVEGFLQDTFPQQLEESEKQRLGGDV<br>QSPNCPSEDVVITPESFGRDSSLTCLAGNVSACDAPILSSSRSLDCR<br>ESGKNGPHVYQDLLLSLGTTNSTLPPPFSLQSGILTLNPVAQGQPIL<br>TSLGSNQEEAYVTMSSFYQNQSDPKPENPACPWTVLPAGDLPTH<br>DGYLPSNIDDLPSHEAPLADSLEELEPQ | 144 |

TABLE 6-continued

Exemplary chimeric cytokine receptor sequences (assembled inducible or constitutively active TGF-β receptor chimeric cytokine receptors):

| Receptor | Amino acid sequence | SEQ ID NO: |
|---|---|---|
| CD8SS-TGFbR2(1-166).TPOR/MPLR(478-582; N + 2).IL7Ra(316-459).IL12Rb2(775-825) Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETAWVLISLVTALHLVLGLSAVLGLLLLRWQFP<br>AHYRRLRHALWPSLPDLHRVLGQYLRDTAALSPPKATVSDTCEEV<br>EPSLLEILPKSSERTPLPLARDEVEGFLQDTFPQQLEESEKQRLGGD<br>VQSPNCPSEDVVITPESFGRDSSLTCLAGNVSACDAPILSSSRSLDC<br>RESGKNGPHVYQDLLLSLGTTNSTLPPPFSLQSGILTLNPVAQGQP<br>ILTSLGSNQEEAYVTMSSFYQNQSDPKPENPACPWTVLPAGDLPT<br>HDGYLPSNIDDLPSHEAPLADSLEELEPQ | 145 |
| CD8SS-TGFbR2(1-166).TPOR/MPLR(478-582; N + 3).IL7Ra(316-459).IL12Rb2(775-825) Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETAWLVLISLVTALHLVLGLSAVLGLLLLRWQF<br>PAHYRRLRHALWPSLPDLHRVLGQYLRDTAALSPPKATVSDTCEE<br>VEPSLLEILPKSSERTPLPLARDEVEGFLQDTFPQQLEESEKQRLGG<br>DVQSPNCPSEDVVITPESFGRDSSLTCLAGNVSACDAPILSSSRSLD<br>CRESGKNGPHVYQDLLLSLGTTNSTLPPPFSLQSGILTLNPVAQGQ<br>PILTSLGSNQEEAYVTMSSFYQNQSDPKPENPACPWTVLPAGDLP<br>THDGYLPSNIDDLPSHEAPLADSLEELEPQ | 146 |
| CD8SS-TGFbR2(1-166).TPOR/MPLR(478-582; N + 4).IL7Ra(316-459).IL12Rb2(775-825) Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETAWILVLISLVTALHLVLGLSAVLGLLLLRWQ<br>FPAHYRRLRHALWPSLPDLHRVLGQYLRDTAALSPPKATVSDTCE<br>EVEPSLLEILPKSSERTPLPLARDEVEGFLQDTFPQQLEESEKQRLG<br>GDVQSPNCPSEDVVITPESFGRDSSLTCLAGNVSACDAPILSSSRSL<br>DCRESGKNGPHVYQDLLLSLGTTNSTLPPPFSLQSGILTLNPVAQG<br>QPILTSLGSNQEEAYVTMSSFYQNQSDPKPENPACPWTVLPAGD<br>LPTHDGYLPSNIDDLPSHEAPLADSLEELEPQ | 147 |
| CD8SS-TGFbR2(1-166).TPOR/MPLR(478-582; N + 5).IL7Ra(316-459).IL12Rb2(775-825) Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETAWLILVLISLVTALHLVLGLSAVLGLLLLRW<br>QFPAHYRRLRHALWPSLPDLHRVLGQYLRDTAALSPPKATVSDTC<br>EEVEPSLLEILPKSSERTPLPLARDEVEGFLQDTFPQQLEESEKQRLG<br>GDVQSPNCPSEDVVITPESFGRDSSLTCLAGNVSACDAPILSSSRSL<br>DCRESGKNGPHVYQDLLLSLGTTNSTLPPPFSLQSGILTLNPVAQG<br>QPILTSLGSNQEEAYVTMSSFYQNQSDPKPENPACPWTVLPAGD<br>LPTHDGYLPSNIDDLPSHEAPLADSLEELEPQ | 148 |
| CD8SS-TGFbR2(1-166).TPOR/MPLR(478-582; N + 6).IL7Ra(316-459).IL12Rb2(775-825) Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETAWLLILVLISLVTALHLVLGLSAVLGLLLLRW<br>QFPAHYRRLRHALWPSLPDLHRVLGQYLRDTAALSPPKATVSDTC<br>EEVEPSLLEILPKSSERTPLPLARDEVEGFLQDTFPQQLEESEKQRLG<br>GDVQSPNCPSEDVVITPESFGRDSSLTCLAGNVSACDAPILSSSRSL<br>DCRESGKNGPHVYQDLLLSLGTTNSTLPPPFSLQSGILTLNPVAQG<br>QPILTSLGSNQEEAYVTMSSFYQNQSDPKPENPACPWTVLPAGD<br>LPTHDGYLPSNIDDLPSHEAPLADSLEELEPQ | 149 |
| CD8SS-TGFbR2(1-166).TPOR/MPLR(478-582; N + 7).IL7Ra(316-459).IL12Rb2(775-825) Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETAWVLLILVLISLVTALHLVLGLSAVLGLLLLR<br>WQFPAHYRRLRHALWPSLPDLHRVLGQYLRDTAALSPPKATVSD<br>TCEEVEPSLLEILPKSSERTPLPLARDEVEGFLQDTFPQQLEESEKQR<br>LGGDVQSPNCPSEDVVITPESFGRDSSLTCLAGNVSACDAPILSSS<br>RSLDCRESGKNGPHVYQDLLLSLGTTNSTLPPPFSLQSGILTLNPVA<br>QGQPILTSLGSNQEEAYVTMSSFYQNQSDPKPENPACPWTVLPA<br>GDLPTHDGYLPSNIDDLPSHEAPLADSLEELEPQ | 150 |

TABLE 6-continued

Exemplary chimeric cytokine receptor sequences (assembled inducible or constitutively active TGF-β receptor chimeric cytokine receptors):

| Receptor | Amino acid sequence | SEQ ID NO: |
|---|---|---|
| CD8SS-TGFbR2(1-166).TPOR/MPLR(478-582; N + 8).IL7Ra(316-459).IL12Rb2(775-825) Underlined indicates CD8SS | MALPVTALLLPLALLLHAARPMGRGLLRGLWPLHIVLWTRIASTIPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPDLLLVIFQSDPTRVETATETAWLVLLILVLISLVTALHLVLGLSAVLGLLLLRWQFPAHYRRLRHALWPSLPDLHRVLGQYLRDTAALSPPKATVSDTCEEVEPSLLEILPKSSERTPLPLARDEVEGFLQDTFPQQLEESEKQRLGGDVQSPNCPSEDVVITPESFGRDSSLTCLAGNVSACDAPILSSSRSLDCRESGKNGPHVYQDLLLSLGTTNSTLPPPFSLQSGILTLNPVAQGQPILTSLGSNQEEAYVTMSSFYQNQSDPKPENPACPWTVLPAGDLPTHDGYLPSNIDDLPSHEAPLADSLEELEPQ | 151 |
| CD8SS-TGFbR2(1-166).TPOR/MPLR(478-582).IL7Ra(316-459).IL12Rb2(775-825) Underlined indicates CD8SS | MALPVTALLLPLALLLHAARPMGRGLLRGLWPLHIVLWTRIASTIPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPDLLLVIFQSDPTRVETATETAWISLVTALHLVLGLSAVLGLLLLLRWQFPAHYRRLRHALWPSLPDLHRVLGQYLRDTAALSPPKATVSDTCEEVEPSLLEILPKSSERTPLPLLEARDEVEGFLQDTFPQQLEESEKQRLGGDVQSPNCPSEDVVITPESFGRDSSLTCLAGNVSACDAPILSSSRSLDCRESGKNGPHVYQDLLLSLGTTNSTLPPPFSLQSGILTLNPVAQGQPILTSLGSNQEEAYVTMSSFYQNQSRSDPKPENPACPWTVLPAGDLPTHDGYLPSNIDDLPSHEAPLADSLEELEPQ | 162 |
| CD8SS-TGFbR2(1-166).TPOR/MPLR(478-582) S505N.W515K.IL7Ra(316-459).IL12Rb2(775-825) Underlined indicates CD8SS | MALPVTALLLPLALLLHAARPMGRGLLRGLWPLHIVLWTRIASTIPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPDLLLVIFQSDPTRVETATETAWISLVTALHLVLGLNAVLGLLLLLRKQFPAHYRRLRHALWPSLPDLHRVLGQYLRDTAALSPPKATVSDTCEEVEPSLLEILPKSSERTPLPL*LE*ARDEVEGFLQDTFPQQLEESEKQRLGGDVQSPNCPSEDVVITPESFGRDSSLTCLAGNVSACDAPILSSSRSLDCRESGKNGPHVYQDLLLSLGTTNSTLPPPFSLQSGILTLNPVAQGQPILTSLGSNQEEAYVTMSSFYQNQ*SR*SDPKPENPACPWTVLPAGDLPTHDGYLPSNIDDLPSHEAPLADSLEELEPQ | 163 |
| CD8SS-TGFbR2(1-166).TPOR/MPLR(478-582) S505N.W515K.IL2Rbsmall (393-433, 518-551) Underlined indicates CD8SS | MALPVTALLLPLALLLHAARPMGRGLLRGLWPLHIVLWTRIASTIPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPDLLLVIFQSDPTRVETATETAWISLVTALHLVLGLNAVLGLLLLLRKQFPAHYRRLRHALWPSLPDLHRVLGQYLRDTAALSPPKATVSDTCEEVEPSLLEILPKSSERTPLPLLEDEGVAGAPTGSSPQPLQPLSGEDDAYCTFPSRDDLLLFSPSGQGEFRALNARLPLNTDAYLSLQELQGQDPTHLV | 164 |
| CD8SS-TGFbR2(1-166).TPOR/MPLR(478-582) S505N.W515K. K553R.K573R.IL7Ra(316-459).IL12Rb2(775-825) Underlined indicates CD8SS | MALPVTALLLPLALLLHAARPMGRGLLRGLWPLHIVLWTRIASTIPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPDLLLVIFQSDPTRVETATETAWISLVTALHLVLGLNAVLGLLLLLRKQFPAHYRRLRHALWPSLPDLHRVLGQYLRDTAALSPPRATVSDTCEEVEPSLLEILPRSSERTPLPL*LE*ARDEVEGFLQDTFPQQLEESEKQRLGGDVQSPNCPSEDVVITPESFGRDSSLTCLAGNVSACDAPILSSSRSLDCRESGKNGPHVYQDLLLSLGTTNSTLPPPFSLQSGILTLNPVAQGQPILTSLGSNQEEAYVTMSSFYQNQ*SR*SDPKPENPACPWTVLPAGDLPTHDGYLPSNIDDLPSHEAPLADSLEELEPQ | 165 |
| CD8SS-TGFbR2(1-166).TPOR/MPLR(478-582) S505N.W515K. K553R.K573R. IL2Rbsmall(393-433, 518-551) Underlined indicates CD8SS | MALPVTALLLPLALLLHAARPMGRGLLRGLWPLHIVLWTRIASTIPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPDLLLVIFQSDPTRVETATETAWISLVTALHLVLGLNAVLGLLLLLRKQFPAHYRRLRHALWPSLPDLHRVLGQYLRDTAALSPPRATVSDTCEEVEPSLLEILPRSSERTPLPL*LE*DEGVAGAPTGSSPQPLQPLSGEDDAYCTFPSRDDLLLFSPSGQGEFRALNARLPLNTDAYLSLQELQGQDPTHLV | 166 |
| TGFbR2(1-166).TPOR/MPLR(478-582) S505N.W515K.IL2Rbsmall (393-433, 518-551) | MGRGLLRGLWPLHIVLWTRIASTIPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPDLLLVIFQSDPTRVETATETAWISLVTALHLVLGLNAVLGLLLLLRKQFPAHYRRLRHALWPSLPDLHRVLGQYLRDTAALSPPKATVSDTCEEVEPSLLEILPKSSERTPLPL*LE*DEGV | 167 |

TABLE 6-continued

Exemplary chimeric cytokine receptor sequences (assembled inducible or constitutively active TGF-β receptor chimeric cytokine receptors):

| Receptor | Amino acid sequence | SEQ ID NO: |
|---|---|---|
| | AGAPTGSSPQPLQPLSGEDDAYCTFPSRDDLLLFSPSGQGEFRAL<br>NARLPLNTDAYLSLQELQGQDPTHLV | |
| TGFbR2(1-166).TPOR/MPLR(478-582)<br>S505N.W515K.<br>K553R.K573R.<br>IL2Rbsmall(393-433,<br>518-551) | MGRGLLRGLWPLHIVLWTRIASTIPPHVQKSVNNDMIVTDNNGA<br>VKFPQLCKFCDVRFSTCDNQKSCMSNCSITSICEKPQEVCVAVWR<br>KNDENITLETVCHDPKLPYHDFILEDAASPKCIMKEKKKPGETFFM<br>CSCSSDECNDNIIFSEEYNTSNPDLLLVIFQSDPTRVETATETAWISL<br>VTALHLVLGLNAVLGLLLLRKQFPAHYRRLRHALWPSLPDLHRVLG<br>QYLRDTAALSPPRATVSDTCEEVEPSLLEILPRSSERTPLPLLEDEGV<br>AGAPTGSSPQPLQPLSGEDDAYCTFPSRDDLLLFSPSGQGEFRAL<br>NARLPLNTDAYLSLQELQGQDPTHLV | 168 |
| CD8SS-TGFbR2(1-166).TPOR/MPLR(478-582)<br>S505N.W515K.IL7Ra(316-459)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETAWISLVTALHLVLGLNAVLGLLLLRKQFPAH<br>YRRLRHALWPSLPDLHRVLGQYLRDTAALSPPKATVSDTCEEVEPS<br>LLEILPKSSERTPLPLLEARDEVEGFLQDTFPQQLEESEKQRLGGDV<br>QSPNCPSEDVVITPESFGRDSSLTCLAGNVSACDAPILSSSRSLDCR<br>ESGKNGPHVYQDLLLSLGTTNSTLPPPFSLQSGILTLNPVAQGQPIL<br>TSLGSNQEEAYVTMSSFYQNQ | 169 |
| CD8SS-TGFbR2(1-166).TPOR/MPLR(478-582)<br>S505N.W515K.K553R.K573R.<br>IL7Ra(316-459)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETAWISLVTALHLVLGLNAVLGLLLLRKQFPAH<br>YRRLRHALWPSLPDLHRVLGQYLRDTAALSPPRATVSDTCEEVEPS<br>LLEILPRSSERTPLPLLEARDEVEGFLQDTFPQQLEESEKQRLGGDV<br>QSPNCPSEDVVITPESFGRDSSLTCLAGNVSACDAPILSSSRSLDCR<br>ESGKNGPHVYQDLLLSLGTTNSTLPPPFSLQSGILTLNPVAQGQPIL<br>TSLGSNQEEAYVTMSSFYQNQ | 170 |
| CD8SS-TGFbR2(1-166).TPOR/MPLR(478-582)<br>S505N.W515K.<br>IL2Rbsmall(339-379,<br>393-433, 518-551)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETAWISLVTALLLVLGLNAVLGLLLLRKQFPAH<br>YRRLRHALWPSLPDLHRVLGQYLRDTAALSPPKATVSDTCEEVEPS<br>LLEILPKSSERTPLPLLEQQDKVPEPASLSSNHSLTSCFTNQGYFFFH<br>LPDALEIEACQDEGVAGAPTGSSPQPLQPLSGEDDAYCTFPSRDD<br>LLLFSPSGQGEFRALNARLPLNTDAYLSLQELQGQDPTHLV | 171 |
| CD8SS-TGFbR2(1-166).TPOR/MPLR(478-582; N - 1).IL7Ra(316-459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETWISLVTALHLVLGLSAVLGLLLLRWQFPAH<br>YRRLRHALWPSLPDLHRVLGQYLRDTAALSPPKATVSDTCEEVEPS<br>LLEILPKSSERTPLPLLEARDEVEGFLQDTFPQQLEESEKQRLGGDV<br>QSPNCPSEDVVITPESFGRDSSLTCLAGNVSACDAPILSSSRSLDCR<br>ESGKNGPHVYQDLLLSLGTTNSTLPPPFSLQSGILTLNPVAQGQPIL<br>TSLGSNQEEAYVTMSSFYQNQSRSDPKPENPACPWTVLPAGDLP<br>THDGYLPSNIDDLPSHEAPLADSLEELEPQ | 172 |
| CD8SS-TGFbR2(1-166).TPOR/MPLR(478-582; N - 2).IL7Ra(316-459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETISLVTALHLVLGLSAVLGLLLLRWQFPAHYR<br>RLRHALWPSLPDLHRVLGQYLRDTAALSPPKATVSDTCEEVEPSLL<br>EILPKSSERTPLPLLEARDEVEGFLQDTFPQQLEESEKQRLGGDVQ<br>SPNCPSEDVVITPESFGRDSSLTCLAGNVSACDAPILSSSRSLDCRE<br>SGKNGPHVYQDLLLSLGTTNSTLPPPFSLQSGILTLNPVAQGQPILT<br>SLGSNQEEAYVTMSSFYQNQSRSDPKPENPACPWTVLPAGDLPT<br>HDGYLPSNIDDLPSHEAPLADSLEELEPQ | 173 |
| CD8SS-TGFbR2(1-166).TPOR/MPLR(478-582; N - 2 + 1).IL7Ra(316-459).IL12Rb2(775-825) | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETLISLVTALHLVLGLSAVLGLLLLRWQFPAHY<br>RRLRHALWPSLPDLHRVLGQYLRDTAALSPPKATVSDTCEEVEPSL | 174 |

TABLE 6-continued

Exemplary chimeric cytokine receptor sequences (assembled inducible or constitutively active TGF-β receptor chimeric cytokine receptors):

| Receptor | Amino acid sequence | SEQ ID NO: |
|---|---|---|
| | LEILPKSSERTPLPLLEARDEVEGFLQDTFPQQLEESEKQRLGGDVQ<br>SPNCPSEDVVITPESFGRDSSLTCLAGNVSACDAPILSSSRSLDCRE<br>SGKNGPHVYQDLLLSLGTTNSTLPPPFSLQSGILTLNPVAQGQPILT<br>SLGSNQEEAYVTMSSFYQNQSRSDPKPENPACPWTVLPAGDLPT<br>HDGYLPSNIDDLPSHEAPLADSLEELEPQ | |
| CD8SS-TGFbR2(1-<br>166).TPOR/MPLR(478-<br>582; N - 3).IL7Ra(316-<br>459).IL12Rb2(775-825) | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETSLVTALHLVLGLSAVLGLLLLRWQFPAHYRR<br>LRHALWPSLPDLHRVLGQYLRDTAALSPPKATVSDTCEEVEPSLLEI<br>LPKSSERTPLPLLEARDEVEGFLQDTFPQQLEESEKQRLGGDVQSP<br>NCPSEDVVITPESFGRDSSLTCLAGNVSACDAPILSSSRSLDCRESG<br>KNGPHVYQDLLLSLGTTNSTLPPPFSLQSGILTLNPVAQGQPILTSL<br>GSNQEEAYVTMSSFYQNQSRSDPKPENPACPWTVLPAGDLPTH<br>DGYLPSNIDDLPSHEAPLADSLEELEPQ | 175 |
| CD8SS-TGFbR2(1-<br>166).TPOR/MPLR(478-<br>582; N - 4).IL7Ra(316-<br>459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETLVTALHLVLGLSAVLGLLLLRWQFPAHYRRL<br>RHALWPSLPDLHRVLGQYLRDTAALSPPKATVSDTCEEVEPSLLEIL<br>PKSSERTPLPLLEARDEVEGFLQDTFPQQLEESEKQRLGGDVQSP<br>NCPSEDVVITPESFGRDSSLTCLAGNVSACDAPILSSSRSLDCRESG<br>KNGPHVYQDLLLSLGTTNSTLPPPFSLQSGILTLNPVAQGQPILTSL<br>GSNQEEAYVTMSSFYQNQSRSDPKPENPACPWTVLPAGDLPTH<br>DGYLPSNIDDLPSHEAPLADSLEELEPQ | 176 |
| CD8SS-TGFbR2(1-<br>166).TPOR/MPLR(478-<br>582; N - 4 + 1).IL7Ra(316-<br>459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETILVTALHLVLGLSAVLGLLLLRWQFPAHYRR<br>LRHALWPSLPDLHRVLGQYLRDTAALSPPKATVSDTCEEVEPSLLEI<br>LPKSSERTPLPLLEARDEVEGFLQDTFPQQLEESEKQRLGGDVQSP<br>NCPSEDVVITPESFGRDSSLTCLAGNVSACDAPILSSSRSLDCRESG<br>KNGPHVYQDLLLSLGTTNSTLPPPFSLQSGILTLNPVAQGQPILTSL<br>GSNQEEAYVTMSSFYQNQSRSDPKPENPACPWTVLPAGDLPTH<br>DGYLPSNIDDLPSHEAPLADSLEELEPQ | 177 |
| CD8SS-TGFbR2(1-<br>166).TPOR/MPLR(478-<br>582; N - 5).IL7Ra(316-<br>459).IL12Rb2(775-825) | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETVTALHLVLGLSAVLGLLLLRWQFPAHYRRL<br>RHALWPSLPDLHRVLGQYLRDTAALSPPKATVSDTCEEVEPSLLEIL<br>PKSSERTPLPLLEARDEVEGFLQDTFPQQLEESEKQRLGGDVQSP<br>NCPSEDVVITPESFGRDSSLTCLAGNVSACDAPILSSSRSLDCRESG<br>KNGPHVYQDLLLSLGTTNSTLPPPFSLQSGILTLNPVAQGQPILTSL<br>GSNQEEAYVTMSSFYQNQSRSDPKPENPACPWTVLPAGDLPTH<br>DGYLPSNIDDLPSHEAPLADSLEELEPQ | 178 |
| CD8SS-TGFbR2(1-<br>166).TPOR/MPLR(478-<br>582; N - 6).IL7Ra(316-<br>459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETTALHLVLGLSAVLGLLLLRWQFPAHYRRLR<br>HALWPSLPDLHRVLGQYLRDTAALSPPKATVSDTCEEVEPSLLEILP<br>KSSERTPLPLLEARDEVEGFLQDTFPQQLEESEKQRLGGDVQSPN<br>CPSEDVVITPESFGRDSSLTCLAGNVSACDAPILSSSRSLDCRESGK<br>NGPHVYQDLLLSLGTTNSTLPPPFSLQSGILTLNPVAQGQPILTSLG<br>SNQEEAYVTMSSFYQNQSRSDPKPENPACPWTVLPAGDLPTHD<br>GYLPSNIDDLPSHEAPLADSLEELEPQ | 179 |
| CD8SS-TGFbR2(1-<br>166).TPOR/MPLR(478-<br>582; N - 7).IL7Ra(316-<br>459).IL12Rb2(775-825) | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETALHLVLGLSAVLGLLLLRWQFPAHYRRLRH<br>ALWPSLPDLHRVLGQYLRDTAALSPPKATVSDTCEEVEPSLLEILPK<br>SSERTPLPLLEARDEVEGFLQDTFPQQLEESEKQRLGGDVQSPNC<br>PSEDVVITPESFGRDSSLTCLAGNVSACDAPILSSSRSLDCRESGKN | 180 |

TABLE 6-continued

Exemplary chimeric cytokine receptor sequences (assembled inducible or constitutively active TGF-β receptor chimeric cytokine receptors):

| Receptor | Amino acid sequence | SEQ ID NO: |
|---|---|---|
| | GPHVYQDLLLSLGTTNSTLPPPFSLQSGILTLNPVAQGQPILTSLGS NQEEAYVTMSSFYQNQSRSDPKPENPACPWTVLPAGDLPTHDG YLPSNIDDLPSHEAPLADSLEELEPQ | |
| CD8SS-TGFbR2(1-166).TPOR/MPLR(478-582; N - 8).IL7Ra(316-459).IL12Rb2(775-825) Underlined indicates CD8SS | MALPVTALLLPLALLLHAARPMGRGLLRGLWPLHIVLWTRIASTIP PHVQKSVNNDMIVTDNNGAVKFPQLCKFCDVRFSTCDNQKSCM SNCSITSICEKPQEVCVAVWRKNDENITLETVCHDPKLPYHDFILED AASPKCIMKEKKKPGETFFMCSCSSDECNDNIIFSEEYNTSNPDLLL VIFQSDPTRVETATETLHLVLGLSAVLGLLLLRWQFPAHYRRLRHA LWPSLPDLHRVLGQYLRDTAALSPPKATVSDTCEEVEPSLLEILPKS SERTPLPLLEARDEVEGFLQDTFPQQLEESEKQRLGGDVQSPNCP SEDVVITPESFGRDSSLTCLAGNVSACDAPILSSSRSLDCRESGKNG PHVYQDLLLSLGTTNSTLPPPFSLQSGILTLNPVAQGQPILTSLGSN QEEAYVTMSSFYQNQSRSDPKPENPACPWTVLPAGDLPTHDGYL PSNIDDLPSHEAPLADSLEELEPQ | 181 |
| CD8SS-TGFbR2(1-166).TPOR/MPLR(478-582; N - 9).IL7Ra(316-459).IL12Rb2(775-825) Underlined indicates CD8SS | MALPVTALLLPLALLLHAARPMGRGLLRGLWPLHIVLWTRIASTIP PHVQKSVNNDMIVTDNNGAVKFPQLCKFCDVRFSTCDNQKSCM SNCSITSICEKPQEVCVAVWRKNDENITLETVCHDPKLPYHDFILED AASPKCIMKEKKKPGETFFMCSCSSDECNDNIIFSEEYNTSNPDLLL VIFQSDPTRVETATETHLVLGLSAVLGLLLLRWQFPAHYRRLRHAL WPSLPDLHRVLGQYLRDTAALSPPKATVSDTCEEVEPSLLEILPKSS ERTPLPLLEARDEVEGFLQDTFPQQLEESEKQRLGGDVQSPNCPS EDVVITPESFGRDSSLTCLAGNVSACDAPILSSSRSLDCRESGKNGP HVYQDLLLSLGTTNSTLPPPFSLQSGILTLNPVAQGQPILTSLGSNQ EEAYVTMSSFYQNQSRSDPKPENPACPWTVLPAGDLPTHDGYLP SNIDDLPSHEAPLADSLEELEPQ | 182 |
| CD8SS-TGFbR2(1-166).TPOR/MPLR(478-582; N - 10).IL7Ra(316-459).IL12Rb2(775-825) Underlined indicates CD8SS | MALPVTALLLPLALLLHAARPMGRGLLRGLWPLHIVLWTRIASTIP PHVQKSVNNDMIVTDNNGAVKFPQLCKFCDVRFSTCDNQKSCM SNCSITSICEKPQEVCVAVWRKNDENITLETVCHDPKLPYHDFILED AASPKCIMKEKKKPGETFFMCSCSSDECNDNIIFSEEYNTSNPDLLL VIFQSDPTRVETATETLVLGLSAVLGLLLLRWQFPAHYRRLRHALW PSLPDLHRVLGQYLRDTAALSPPKATVSDTCEEVEPSLLEILPKSSER TPLPLLEARDEVEGFLQDTFPQQLEESEKQRLGGDVQSPNCPSED VVITPESFGRDSSLTCLAGNVSACDAPILSSSRSLDCRESGKNGPHV YQDLLLSLGTTNSTLPPPFSLQSGILTLNPVAQGQPILTSLGSNQEE AYVTMSSFYQNQSRSDPKPENPACPWTVLPAGDLPTHDGYLPSN IDDLPSHEAPLADSLEELEPQ | 183 |
| CD8SS-TGFbR2(1-166).TPOR/MPLR(478-582; N - 11).IL7Ra(316-459).IL12Rb2(775-825) Underlined indicates CD8SS | MALPVTALLLPLALLLHAARPMGRGLLRGLWPLHIVLWTRIASTIP PHVQKSVNNDMIVTDNNGAVKFPQLCKFCDVRFSTCDNQKSCM SNCSITSICEKPQEVCVAVWRKNDENITLETVCHDPKLPYHDFILED AASPKCIMKEKKKPGETFFMCSCSSDECNDNIIFSEEYNTSNPDLLL VIFQSDPTRVETATETVLGLSAVLGLLLLRWQFPAHYRRLRHALW PSLPDLHRVLGQYLRDTAALSPPKATVSDTCEEVEPSLLEILPKSSER TPLPLLEARDEVEGFLQDTFPQQLEESEKQRLGGDVQSPNCPSED VVITPESFGRDSSLTCLAGNVSACDAPILSSSRSLDCRESGKNGPHV YQDLLLSLGTTNSTLPPPFSLQSGILTLNPVAQGQPILTSLGSNQEE AYVTMSSFYQNQSRSDPKPENPACPWTVLPAGDLPTHDGYLPSN IDDLPSHEAPLADSLEELEPQ | 184 |
| CD8SS-TGFbR2(1-166).TPOR/MPLR(478-582; N - 12).IL7Ra(316-459).IL12Rb2(775-825) Underlined indicates CD8SS | MALPVTALLLPLALLLHAARPMGRGLLRGLWPLHIVLWTRIASTIP PHVQKSVNNDMIVTDNNGAVKFPQLCKFCDVRFSTCDNQKSCM SNCSITSICEKPQEVCVAVWRKNDENITLETVCHDPKLPYHDFILED AASPKCIMKEKKKPGETFFMCSCSSDECNDNIIFSEEYNTSNPDLLL VIFQSDPTRVETATETLGLSAVLGLLLLRWQFPAHYRRLRHALWPS LPDLHRVLGQYLRDTAALSPPKATVSDTCEEVEPSLLEILPKSSERTP LPLLEARDEVEGFLQDTFPQQLEESEKQRLGGDVQSPNCPSEDVV ITPESFGRDSSLTCLAGNVSACDAPILSSSRSLDCRESGKNGPHVYQ DLLLSLGTTNSTLPPPFSLQSGILTLNPVAQGQPILTSLGSNQEEAY VTMSSFYQNQSRSDPKPENPACPWTVLPAGDLPTHDGYLPSNID DLPSHEAPLADSLEELEPQ | 185 |
| CD8SS-TGFbR2(1-166).TPOR/MPLR(478-582; N - 13).IL7Ra(316-459).IL12Rb2(775-825) Underlined indicates CD8SS | MALPVTALLLPLALLLHAARPMGRGLLRGLWPLHIVLWTRIASTIP PHVQKSVNNDMIVTDNNGAVKFPQLCKFCDVRFSTCDNQKSCM SNCSITSICEKPQEVCVAVWRKNDENITLETVCHDPKLPYHDFILED AASPKCIMKEKKKPGETFFMCSCSSDECNDNIIFSEEYNTSNPDLLL VIFQSDPTRVETATETGLSAVLGLLLLRWQFPAHYRRLRHALWPSL PDLHRVLGQYLRDTAALSPPKATVSDTCEEVEPSLLEILPKSSERTPL PLLEARDEVEGFLQDTFPQQLEESEKQRLGGDVQSPNCPSEDVVI TPESFGRDSSLTCLAGNVSACDAPILSSSRSLDCRESGKNGPHVYQ DLLLSLGTTNSTLPPPFSLQSGILTLNPVAQGQPILTSLGSNQEEAY | 186 |

TABLE 6-continued

Exemplary chimeric cytokine receptor sequences (assembled inducible or constitutively active TGF-β receptor chimeric cytokine receptors):

| Receptor | Amino acid sequence | SEQ ID NO: |
|---|---|---|
| | VTMSSFYQNQSRSDPKPENPACPWTVLPAGDLPTHDGYLPSNID<br>DLPSHEAPLADSLEELEPQ | |
| CD8SS-TGFbR2(1-<br>166).TPOR/MPLR(478-<br>582; N - 14).IL7Ra(316-<br>459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETLSAVLGLLLLRWQFPAHYRRLRHALWPSLP<br>DLHRVLGQYLRDTAALSPPKATVSDTCEEVEPSLLEILPKSSERTPLP<br>LLEARDEVEGFLQDTFPQQLEESEKQRLGGDVQSPNCPSEDVVIT<br>PESFGRDSSLTCLAGNVSACDAPILSSSRSLDCRESGKNGPHVYQD<br>LLLSLGTTNSTLPPPFSLQSGILTLNPVAQGQPILTSLGSNQEEAYVT<br>MSSFYQNQSRSDPKPENPACPWTVLPAGDLPTHDGYLPSNIDDL<br>PSHEAPLADSLEELEPQ | 187 |
| CD8SS-TGFbR2(1-<br>166).TPOR/MPLR(478-<br>582; N - 15).IL7Ra(316-<br>459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETSAVLGLLLLRWQFPAHYRRLRHALWPSLPD<br>LHRVLGQYLRDTAALSPPKATVSDTCEEVEPSLLEILPKSSERTPLPL<br>LEARDEVEGFLQDTFPQQLEESEKQRLGGDVQSPNCPSEDVVITP<br>ESFGRDSSLTCLAGNVSACDAPILSSSRSLDCRESGKNGPHVYQDL<br>LLSLGTTNSTLPPPFSLQSGILTLNPVAQGQPILTSLGSNQEEAYVT<br>MSSFYQNQSRSDPKPENPACPWTVLPAGDLPTHDGYLPSNIDDL<br>PSHEAPLADSLEELEPQ | 188 |
| CD8SS-TGFbR2(1-<br>166).TPOR/MPLR(478-<br>582; N - 16).IL7Ra(316-<br>459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETAVLGLLLLRWQFPAHYRRLRHALWPSLPDL<br>HRVLGQYLRDTAALSPPKATVSDTCEEVEPSLLEILPKSSERTPLPLL<br>EARDEVEGFLQDTFPQQLEESEKQRLGGDVQSPNCPSEDVVITPE<br>SFGRDSSLTCLAGNVSACDAPILSSSRSLDCRESGKNGPHVYQDLL<br>LSLGTTNSTLPPPFSLQSGILTLNPVAQGQPILTSLGSNQEEAYVTM<br>SSFYQNQSRSDPKPENPACPWTVLPAGDLPTHDGYLPSNIDDLPS<br>HEAPLADSLEELEPQ | 189 |
| CD8SS-TGFbR2(1-<br>166).TPOR/MPLR(478-<br>582; N - 17).IL7Ra(316-<br>459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETVLGLLLLRWQFPAHYRRLRHALWPSLPDLH<br>RVLGQYLRDTAALSPPKATVSDTCEEVEPSLLEILPKSSERTPLPLLE<br>ARDEVEGFLQDTFPQQLEESEKQRLGGDVQSPNCPSEDVVITPES<br>FGRDSSLTCLAGNVSACDAPILSSSRSLDCRESGKNGPHVYQDLLL<br>SLGTTNSTLPPPFSLQSGILTLNPVAQGQPILTSLGSNQEEAYVTM<br>SSFYQNQSRSDPKPENPACPWTVLPAGDLPTHDGYLPSNIDDLPS<br>HEAPLADSLEELEPQ | 190 |
| CD8SS-TGFbR2(1-<br>166).TPOR/MPLR(478-<br>582; N - 18).IL7Ra(316-<br>459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETLGLLLLRWQFPAHYRRLRHALWPSLPDLHR<br>VLGQYLRDTAALSPPKATVSDTCEEVEPSLLEILPKSSERTPLPLLEA<br>RDEVEGFLQDTFPQQLEESEKQRLGGDVQSPNCPSEDVVITPESF<br>GRDSSLTCLAGNVSACDAPILSSSRSLDCRESGKNGPHVYQDLLLS<br>LGTTNSTLPPPFSLQSGILTLNPVAQGQPILTSLGSNQEEAYVTMS<br>SFYQNQSRSDPKPENPACPWTVLPAGDLPTHDGYLPSNIDDLPSH<br>EAPLADSLEELEPQ | 191 |
| CD8SS-TGFbR2(1-<br>166).TPOR/MPLR(478-<br>582; N + 1).IL7Ra(316-<br>459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETAWLISLVTALHLVLGLSAVLGLLLLRWQFPA<br>HYRRLRHALWPSLPDLHRVLGQYLRDTAALSPPKATVSDTCEEVE<br>PSLLEILPKSSERTPLPLLEARDEVEGFLQDTFPQQLEESEKQRLGG<br>DVQSPNCPSEDVVITPESFGRDSSLTCLAGNVSACDAPILSSSRSLD<br>CRESGKNGPHVYQDLLLSLGTTNSTLPPPFSLQSGILTLNPVAQGQ<br>PILTSLGSNQEEAYVTMSSFYQNQSRSDPKPENPACPWTVLPAGD<br>LPTHDGYLPSNIDDLPSHEAPLADSLEELEPQ | 192 |

TABLE 6-continued

Exemplary chimeric cytokine receptor sequences (assembled inducible or constitutively active TGF-β receptor chimeric cytokine receptors):

| Receptor | Amino acid sequence | SEQ ID NO: |
|---|---|---|
| CD8SS-TGFbR2(1-166).TPOR/MPLR(478-582; N + 2).IL7Ra(316-459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETAWVLISLVTALHLVLGLSAVLGLLLLLRWQFP<br>AHYRRLRHALWPSLPDLHRVLGQYLRDTAALSPPKATVSDTCEEV<br>EPSLLEILPKSSERTPLPLLEARDEVEGFLQDTFPQQLEESEKQRLGG<br>DVQSPNCPSEDVVITPESFGRDSSLTCLAGNVSACDAPILSSSRSLD<br>CRESGKNGPHVYQDLLLSLGTTNSTLPPPFSLQSGILTLNPVAQGQ<br>PILTSLGSNQEEAYVTMSSFYQNQSRSDPKPENPACPWTVLPAGD<br>LPTHDGYLPSNIDDLPSHEAPLADSLEELEPQ | 193 |
| CD8SS-TGFbR2(1-166).TPOR/MPLR(478-582; N + 3).IL7Ra(316-459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETAWLVLISLVTALHLVLGLSAVLGLLLLRWQF<br>PAHYRRLRHALWPSLPDLHRVLGQYLRDTAALSPPKATVSDTCEE<br>VEPSLLEILPKSSERTPLPLLEARDEVEGFLQDTFPQQLEESEKQRLG<br>GDVQSPNCPSEDVVITPESFGRDSSLTCLAGNVSACDAPILSSSRSL<br>DCRESGKNGPHVYQDLLLSLGTTNSTLPPPFSLQSGILTLNPVAQG<br>QPILTSLGSNQEEAYVTMSSFYQNQSRSDPKPENPACPWTVLPA<br>GDLPTHDGYLPSNIDDLPSHEAPLADSLEELEPQ | 194 |
| CD8SS-TGFbR2(1-166).TPOR/MPLR(478-582; N + 4).IL7Ra(316-459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETAWILVLISLVTALHLVLGLSAVLGLLLLRWQ<br>FPAHYRRLRHALWPSLPDLHRVLGQYLRDTAALSPPKATVSDTCE<br>EVEPSLLEILPKSSERTPLPLLEARDEVEGFLQDTFPQQLEESEKQRL<br>GGDVQSPNCPSEDVVITPESFGRDSSLTCLAGNVSACDAPILSSSR<br>SLDCRESGKNGPHVYQDLLLSLGTTNSTLPPPFSLQSGILTLNPVA<br>QGQPILTSLGSNQEEAYVTMSSFYQNQSRSDPKPENPACPWTVL<br>PAGDLPTHDGYLPSNIDDLPSHEAPLADSLEELEPQ | 195 |
| CD8SS-TGFbR2(1-166).TPOR/MPLR(478-582; N + 5).IL7Ra(316-459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETAWLILVLISLVTALHLVLGLSAVLGLLLLRW<br>QFPAHYRRLRHALWPSLPDLHRVLGQYLRDTAALSPPKATVSDTC<br>EEVEPSLLEILPKSSERTPLPLLEARDEVEGFLQDTFPQQLEESEKQR<br>LGGDVQSPNCPSEDVVITPESFGRDSSLTCLAGNVSACDAPILSSS<br>RSLDCRESGKNGPHVYQDLLLSLGTTNSTLPPPFSLQSGILTLNPVA<br>QGQPILTSLGSNQEEAYVTMSSFYQNQSRSDPKPENPACPWTVL<br>PAGDLPTHDGYLPSNIDDLPSHEAPLADSLEELEPQ | 196 |
| CD8SS-TGFbR2(1-166).TPOR/MPLR(478-582; N + 6).IL7Ra(316-459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETAWLLILVLISLVTALHLVLGLSAVLGLLLLRW<br>QFPAHYRRLRHALWPSLPDLHRVLGQYLRDTAALSPPKAWSDTC<br>EEVEPSLLEILPKSSERTPLPLLEARDEVEGFLQDTFPQQLEESEKQR<br>LGGDVQSPNCPSEDVVITPESFGRDSSLTCLAGNVSACDAPILSSS<br>RSLDCRESGKNGPHVYQDLLLSLGTTNSTLPPPFSLQSGILTLNPVA<br>QGQPILTSLGSNQEEAYVTMSSFYQNQSRSDPKPENPACPWTVL<br>PAGDLPTHDGYLPSNIDDLPSHEAPLADSLEELEPQ | 197 |
| CD8SS-TGFbR2(1-166).TPOR/MPLR(478-582; N + 7).IL7Ra(316-459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETAWVLLILVLISLVTALHLVLGLSAVLGLLLLR<br>WQFPAHYRRLRHALWPSLPDLHRVLGQYLRDTAALSPPKATVSD<br>TCEEVEPSLLEILPKSSERTPLPLLEARDEVEGFLQDTFPQQLEESEK<br>QRLGGDVQSPNCPSEDVVITPESFGRDSSLTCLAGNVSACDAPILS<br>SSRSLDCRESGKNGPHVYQDLLLSLGTTNSTLPPPFSLQSGILTLNP<br>VAQGQPILTSLGSNQEEAYVTMSSFYQNQSRSDPKPENPACPWT<br>VLPAGDLPTHDGYLPSNIDDLPSHEAPLADSLEELEPQ | 198 |

TABLE 6-continued

Exemplary chimeric cytokine receptor sequences (assembled inducible or constitutively active TGF-β receptor chimeric cytokine receptors):

| Receptor | Amino acid sequence | SEQ ID NO: |
|---|---|---|
| CD8SS-TGFbR2(1-166).TPOR/MPLR(478-582; N + 8).IL7Ra(316-459).IL12Rb2(775-825) Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATETAWLVLLILVLISLVTALHLVLGLSAVLGLLLLR<br>WQFPAHYRRLRHALWPSLPDLHRVLGQYLRDTAALSPPKATVSD<br>TCEEVEPSLLEILPKSSERTPLPLLEARDEVEGFLQDTFPQQLEESEK<br>QRLGGDVQSPNCPSEDVVITPESFGRDSSLTCLAGNVSACDAPILS<br>SSRSLDCRESGKNGPHVYQDLLLSLGTTNSTLPPPFSLQSGILTLNP<br>VAQGQPILTSLGSNQEEAYVTMSSFYQNQSRSDPKPENPACPWT<br>VLPAGDLPTHDGYLPSNIDDLPSHEAPLADSLEELEPQ | 199 |
| CD8SS-TGFbR2(1-166).TPOR/MPLR(478-582; N - 9 - 1).IL7Ra(316-459).IL12Rb2(775-825) Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATEHLVLGLSAVLGLLLLRWQFPAHYRRLRHAL<br>WPSLPDLHRVLGQYLRDTAALSPPKATVSDTCEEVEPSLLEILPKSS<br>ERTPLPLLEARDEVEGFLQDTFPQQLEESEKQRLGGDVQSPNCPS<br>EDVVITPESFGRDSSLTCLAGNVSACDAPILSSSRSLDCRESGKNGP<br>HVYQDLLLSLGTTNSTLPPPFSLQSGILTLNPVAQGQPILTSLGSNQ<br>EEAYVTMSSFYQNQSRSDPKPENPACPWTVLPAGDLPTHDGYLP<br>SNIDDLPSHEAPLADSLEELEPQ | 200 |
| CD8SS-TGFbR2(1-166).TPOR/MPLR(478-582; N - 9 - 2).IL7Ra(316-459).IL12Rb2(775-825) Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETATHLVLGLSAVLGLLLLRWQFPAHYRRLRHALW<br>PSLPDLHRVLGQYLRDTAALSPPKATVSDTCEEVEPSLLEILPKSSER<br>TPLPLLEARDEVEGFLQDTFPQQLEESEKQRLGGDVQSPNCPSED<br>VVITPESFGRDSSLTCLAGNVSACDAPILSSSRSLDCRESGKNGPHV<br>YQDLLLSLGTTNSTLPPPFSLQSGILTLNPVAQGQPILTSLGSNQEE<br>AYVTMSSFYQNQSRSDPKPENPACPWTVLPAGDLPTHDGYLPSN<br>IDDLPSHEAPLADSLEELEPQ | 201 |
| CD8SS-TGFbR2(1-166).TPOR/MPLR(478-582; N - 9 - 3).IL7Ra(316-459).IL12Rb2(775-825) Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETAHLVLGLSAVLGLLLLRWQFPAHYRRLRHALWP<br>SLPDLHRVLGQYLRDTAALSPPKATVSDTCEEVEPSLLEILPKSSERT<br>PLPLLEARDEVEGFLQDTFPQQLEESEKQRLGGDVQSPNCPSEDV<br>VITPESFGRDSSLTCLAGNVSACDAPILSSSRSLDCRESGKNGPHVY<br>QDLLLSLGTTNSTLPPPFSLQSGILTLNPVAQGQPILTSLGSNQEEA<br>YVTMSSFYQNQSRSDPKPENPACPWTVLPAGDLPTHDGYLPSNI<br>DDLPSHEAPLADSLEELEPQ | 202 |
| CD8SS-TGFbR2(1-166).TPOR/MPLR(478-582; N - 9 - 4).IL7Ra(316-459).IL12Rb2(775-825) Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVETHLVLGLSAVLGLLLLRWQFPAHYRRLRHALWPSL<br>PDLHRVLGQYLRDTAALSPPKATVSDTCEEVEPSLLEILPKSSERTPL<br>PLLEARDEVEGFLQDTFPQQLEESEKQRLGGDVQSPNCPSEDVVI<br>TPESFGRDSSLTCLAGNVSACDAPILSSSRSLDCRESGKNGPHVYQ<br>DLLLSLGTTNSTLPPPFSLQSGILTLNPVAQGQPILTSLGSNQEEAY<br>VTMSSFYQNQSRSDPKPENPACPWTVLPAGDLPTHDGYLPSNID<br>DLPSHEAPLADSLEELEPQ | 203 |
| CD8SS-TGFbR2(1-166).TPOR/MPLR(478-582; N - 9 - 5).IL7Ra(316-459).IL12Rb2(775-825) Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQSDPTRVEHLVLGLSAVLGLLLLRWQFPAHYRRLRHALWPSLP<br>DLHRVLGQYLRDTAALSPPKATVSDTCEEVEPSLLEILPKSSERTPLP<br>LLEARDEVEGFLQDTFPQQLEESEKQRLGGDVQSPNCPSEDVVIT<br>PESFGRDSSLTCLAGNVSACDAPILSSSRSLDCRESGKNGPHVYQD<br>LLLSLGTTNSTLPPPFSLQSGILTLNPVAQGQPILTSLGSNQEEAYVT<br>MSSFYQNQSRSDPKPENPACPWTVLPAGDLPTHDGYLPSNIDDL<br>PSHEAPLADSLEELEPQ | 204 |

TABLE 6-continued

Exemplary chimeric cytokine receptor sequences (assembled inducible or constitutively active TGF-β receptor chimeric cytokine receptors):

| Receptor | Amino acid sequence | SEQ ID NO: |
|---|---|---|
| CD8SS-TGFbR2(1-166).TPOR/MPLR(478-582; N - 9 - 6).IL7Ra(316-459).IL12Rb2(775-825) Underlined indicates CD8SS | MALPVTALLLPLALLLHAARPMGRGLLRGLWPLHIVLWTRIASTIPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPDLLLVIFQSDPTRVHLVLGLSAVLGLLLLRWQFPAHYRRLRHALWPSLPDLHRVLGQYLRDTAALSPPKATVSDTCEEVEPSLLEILPKSSERTPLPLLEARDEVEGFLQDTFPQQLEESEKQRLGGDVQSPNCPSEDVVITPESFGRDSSLTCLAGNVSACDAPILSSSRSLDCRESGKNGPHVYQDLLLSLGTTNSTLPPPFSLQSGILTLNPVAQGQPILTSLGSNQEEAYVTMSSFYQNQSRSDPKPENPACPWTVLPAGDLPTHDGYLPSNIDDLPSHEAPLADSLEELEPQ | 205 |
| CD8SS-TGFbR2(1-166).TPOR/MPLR(478-582; N - 9 - 7).IL7Ra(316-459).IL12Rb2(775-825) Underlined indicates CD8SS | MALPVTALLLPLALLLHAARPMGRGLLRGLWPLHIVLWTRIASTIPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPDLLLVIFQSDPTRHLVLGLSAVLGLLLLRWQFPAHYRRLRHALWPSLPDLHRVLGQYLRDTAALSPPKATVSDTCEEVEPSLLEILPKSSERTPLPLLEARDEVEGFLQDTFPQQLEESEKQRLGGDVQSPNCPSEDVVITPESFGRDSSLTCLAGNVSACDAPILSSSRSLDCRESGKNGPHVYQDLLLSLGTTNSTLPPPFSLQSGILTLNPVAQGQPILTSLGSNQEEAYVTMSSFYQNQSRSDPKPENPACPWTVLPAGDLPTHDGYLPSNIDDLPSHEAPLADSLEELEPQ | 206 |
| CD8SS-TGFbR2(1-166).TPOR/MPLR(478-582; N - 9 - 8).IL7Ra(316-459).IL12Rb2(775-825) Underlined indicates CD8SS | MALPVTALLLPLALLLHAARPMGRGLLRGLWPLHIVLWTRIASTIPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPDLLLVIFQSDPTHLVLGLSAVLGLLLLRWQFPAHYRRLRHALWPSLPDLHRVLGQYLRDTAALSPPKATVSDTCEEVEPSLLEILPKSSERTPLPLLEARDEVEGFLQDTFPQQLEESEKQRLGGDVQSPNCPSEDVVITPESFGRDSSLTCLAGNVSACDAPILSSSRSLDCRESGKNGPHVYQDLLLSLGTTNSTLPPPFSLQSGILTLNPVAQGQPILTSLGSNQEEAYVTMSSFYQNQSRSDPKPENPACPWTVLPAGDLPTHDGYLPSNIDDLPSHEAPLADSLEELEPQ | 207 |
| CD8SS-TGFbR2(1-166).TPOR/MPLR(478-582; N - 9 - 9).IL7Ra(316-459).IL12Rb2(775-825) Underlined indicates CD8SS | MALPVTALLLPLALLLHAARPMGRGLLRGLWPLHIVLWTRIASTIPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPDLLLVIFQSDPHLVLGLSAVLGLLLLRWQFPAHYRRLRHALWPSLPDLHRVLGQYLRDTAALSPPKATVSDTCEEVEPSLLEILPKSSERTPLPLLEARDEVEGFLQDTFPQQLEESEKQRLGGDVQSPNCPSEDVVITPESFGRDSSLTCLAGNVSACDAPILSSSRSLDCRESGKNGPHVYQDLLLSLGTTNSTLPPPFSLQSGILTLNPVAQGQPILTSLGSNQEEAYVTMSSFYQNQSRSDPKPENPACPWTVLPAGDLPTHDGYLPSNIDDLPSHEAPLADSLEELEPQ | 208 |
| CD8SS-TGFbR2(1-166).TPOR/MPLR(478-582; N - 9 - 10).IL7Ra(316-459).IL12Rb2(775-825) Underlined indicates CD8SS | MALPVTALLLPLALLLHAARPMGRGLLRGLWPLHIVLWTRIASTIPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPDLLLVIFQSDHLVLGLSAVLGLLLLRWQFPAHYRRLRHALWPSLPDLHRVLGQYLRDTAALSPPKATVSDTCEEVEPSLLEILPKSSERTPLPLLEARDEVEGFLQDTFPQQLEESEKQRLGGDVQSPNCPSEDVVITPESFGRDSSLTCLAGNVSACDAPILSSSRSLDCRESGKNGPHVYQDLLLSLGTTNSTLPPPFSLQSGILTLNPVAQGQPILTSLGSNQEEAYVTMSSFYQNQSRSDPKPENPACPWTVLPAGDLPTHDGYLPSNIDDLPSHEAPLADSLEELEPQ | 209 |
| CD8SS-TGFbR2(1-166).TPOR/MPLR(478-582; N - 9 - 11).IL7Ra(316-459).IL12Rb2(775-825) Underlined indicates CD8SS | MALPVTALLLPLALLLHAARPMGRGLLRGLWPLHIVLWTRIASTIPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPDLLLVIFQSHLVLGLSAVLGLLLLRWQFPAHYRRLRHALWPSLPDLHRVLGQYLRDTAALSPPKATVSDTCEEVEPSLLEILPKSSERTPLPLLEARDEVEGFLQDTFPQQLEESEKQRLGGDVQSPNCPSEDVVITPESFGRDSSLTCLAGNVSACDAPILSSSRSLDCRESGKNGPHVYQDLLLSLGTTNSTLPPPFSLQSGILTLNPVAQGQPILTSLGSNQEEAYVTMSSFYQNQSRSDPKPENPACPWTVLPAGDLPTHDGYLPSNIDDLPSHEAPLADSLEELEPQ | 210 |

TABLE 6-continued

Exemplary chimeric cytokine receptor sequences (assembled inducible or constitutively active TGF-β receptor chimeric cytokine receptors):

| Receptor | Amino acid sequence | SEQ ID NO: |
|---|---|---|
| CD8SS-TGFbR2(1-<br>166).TPOR/MPLR(478-<br>582; N - 9 - 12).IL7Ra(316-<br>459).IL12Rb2(775-825)<br>Underlined indicates CD8SS | MALPVTALLLPLALLLHAARPMGRGLLRGLWPLHIVLWTRIASTIP<br>PHVQKSVNNDMIVTDNNGAVKFPQLCKFCDVRFSTCDNQKSCM<br>SNCSITSICEKPQEVCVAVWRKNDENITLETVCHDPKLPYHDFILED<br>AASPKCIMKEKKKPGETFFMCSCSSDECNDNIIFSEEYNTSNPDLLL<br>VIFQHLVLGLSAVLGLLLLRWQFPAHYRRLRHALWPSLPDLHRVL<br>GQYLRDTAALSPPKATVSDTCEEVEPSLLEILPKSSERTPLPLLEARD<br>EVEGFLQDTFPQQLEESEKQRLGGDVQSPNCPSEDVVITPESFGR<br>DSSLTCLAGNVSACDAPILSSSRSLDCRESGKNGPHVYQDLLLSLGT<br>TNSTLPPPFSLQSGILTLNPVAQGQPILTSLGSNQEEAYVTMSSFY<br>QNQSRSDPKPENPACPWTVLPAGDLPTHDGYLPSNIDDLPSHEA<br>PLADSLEELEPQ | 211 |
| CD8SS-<br>TGFbR2AN25.TPOR/MPLR<br>(478-582; N - 9).IL7Ra(316-<br>459).IL12Rb2(775-825)<br>Underlined indicates CD8SS | MALPVTALLLPLALLLHAARPQLCKFCDVRFSTCDNQKSCMSNCSI<br>TSICEKPQEVCVAVWRKNDENITLETVCHDPKLPYHDFILEDAASP<br>KCIMKEKKKPGETFFMCSCSSDECNDNIIFSEEYNTSNPDLLLVIFQ<br>SDPTRVETATETHLVLGLSAVLGLLLLRWQFPAHYRRLRHALWPSL<br>PDLHRVLGQYLRDTAALSPPKATVSDTCEEVEPSLLEILPKSSERTPL<br>PLLEARDEVEGFLQDTFPQQLEESEKQRLGGDVQSPNCPSEDVVI<br>TPESFGRDSSLTCLAGNVSACDAPILSSSRSLDCRESGKNGPHVYQ<br>DLLLSLGTTNSTLPPPFSLQSGILTLNPVAQGQPILTSLGSNQEEAY<br>VTMSSFYQNQSRSDPKPENPACPWTVLPAGDLPTHDGYLPSNID<br>DLPSHEAPLADSLEELEPQ | 212 |
| CD8SS-<br>TGFbR2 ▲ N25.TPOR/MPLR<br>(478-582; N + 4).IL7Ra(316-<br>459).IL12Rb2(775-825)<br>Underlined indicates CD8SS | MALPVTALLLPLALLLHAARPQLCKFCDVRFSTCDNQKSCMSNCSI<br>TSICEKPQEVCVAVWRKNDENITLETVCHDPKLPYHDFILEDAASP<br>KCIMKEKKKPGETFFMCSCSSDECNDNIIFSEEYNTSNPDLLLVIFQ<br>SDPTRVETATETAWILVLISLVTALHLVLGLSAVLGLLLLRWQFPAH<br>YRRLRHALWPSLPDLHRVLGQYLRDTAALSPPKATVSDTCEEVEPS<br>LLEILPKSSERTPLPLLEARDEVEGFLQDTFPQQLEESEKQRLGGDV<br>QSPNCPSEDVVITPESFGRDSSLTCLAGNVSACDAPILSSSRSLDCR<br>ESGKNGPHVYQDLLLSLGTTNSTLPPPFSLQSGILTLNPVAQGQPIL<br>TSLGSNQEEAYVTMSSFYQNQSRSDPKPENPACPWTVLPAGDLP<br>THDGYLPSNIDDLPSHEAPLADSLEELEPQ | 213 |
| CD8SS-<br>TGFbR2 ▲ N25.TPOR/MPLR<br>(478-582; N - 9 - 4).IL7Ra<br>(316-459).IL12Rb2(775-825)<br>Underlined indicates CD8SS | MALPVTALLLPLALLLHAARPQLCKFCDVRFSTCDNQKSCMSNCSI<br>TSICEKPQEVCVAVWRKNDENITLETVCHDPKLPYHDFILEDAASP<br>KCIMKEKKKPGETFFMCSCSSDECNDNIIFSEEYNTSNPDLLLVIFQ<br>SDPTRVETHLVLGLSAVLGLLLLRWQFPAHYRRLRHALWPSLPDL<br>HRVLGQYLRDTAALSPPKATVSDTCEEVEPSLLEILPKSSERTPLPLL<br>EARDEVEGFLQDTFPQQLEESEKQRLGGDVQSPNCPSEDVVITPE<br>SFGRDSSLTCLAGNVSACDAPILSSSRSLDCRESGKNGPHVYQDLL<br>LSLGTTNSTLPPPFSLQSGILTLNPVAQGQPILTSLGSNQEEAYVTM<br>SSFYQNQSRSDPKPENPACPWTVLPAGDLPTHDGYLPSNIDDLPS<br>HEAPLADSLEELEPQ | 214 |
| CD8SS-<br>TGFbR2 ▲ N25.TPOR/MPLR<br>(478-582; N - 9 - 9).IL7Ra<br>(316-459).IL12Rb2(775-825)<br>Underlined indicates CD8SS | MALPVTALLLPLALLLHAARPQLCKFCDVRFSTCDNQKSCMSNCSI<br>TSICEKPQEVCVAVWRKNDENITLETVCHDPKLPYHDFILEDAASP<br>KCIMKEKKKPGETFFMCSCSSDECNDNIIFSEEYNTSNPDLLLVIFQ<br>SDPHLVLGLSAVLGLLLLRWQFPAHYRRLRHALWPSLPDLHRVLG<br>QYLRDTAALSPPKATVSDTCEEVEPSLLEILPKSSERTPLPLLEARDE<br>VEGFLQDTFPQQLEESEKQRLGGDVQSPNCPSEDVVITPESFGRD<br>SSLTCLAGNVSACDAPILSSSRSLDCRESGKNGPHVYQDLLLSLGTT<br>NSTLPPPFSLQSGILTLNPVAQGQPILTSLGSNQEEAYVTMSSFYQ<br>NQSRSDPKPENPACPWTVLPAGDLPTHDGYLPSNIDDLPSHEAPL<br>ADSLEELEPQ | 215 |
| CD8SS-<br>TGFbR2 ▲ N25.TPOR/MPLR<br>(478-582; N - 9 - 10).IL7Ra<br>(316-459).IL12Rb2(775-825)<br>Underlined indicates CD8SS | MALPVTALLLPLALLLHAARPQLCKFCDVRFSTCDNQKSCMSNCSI<br>TSICEKPQEVCVAVWRKNDENITLETVCHDPKLPYHDFILEDAASP<br>KCIMKEKKKPGETFFMCSCSSDECNDNIIFSEEYNTSNPDLLLVIFQ<br>SDHLVLGLSAVLGLLLLRWQFPAHYRRLRHALWPSLPDLHRVLGQ<br>YLRDTAALSPPKATVSDTCEEVEPSLLEILPKSSERTPLPLLEARDEV<br>EGFLQDTFPQQLEESEKQRLGGDVQSPNCPSEDVVITPESFGRDS<br>SLTCLAGNVSACDAPILSSSRSLDCRESGKNGPHVYQDLLLSLGTT<br>NSTLPPPFSLQSGILTLNPVAQGQPILTSLGSNQEEAYVTMSSFYQ<br>NQSRSDPKPENPACPWTVLPAGDLPTHDGYLPSNIDDLPSHEAPL<br>ADSLEELEPQ | 216 |
| CD8SS-TPOR/MPLR(478-<br>582; H499L, S505N, W515K,<br>K553R, K573R).IL2Rb(339-<br>379, 393-433, 518-551)<br>Underlined indicates CD8SS | MALPVTALLLPLALLLHAARPSDPTRVETATETAWISLVTALLLVLG<br>LNAVLGLLLLRKQFPAHYRRLRHALWPSLPDLHRVLGQYLRDTAA<br>LSPPRATVSDTCEEVEPSLLEILPRSSERTPLPLLEQQDKVPEPASLS<br>SNHSLTSCFTNQGYFFFHLPDALEIEACQDEGVAGAPTGSSPQPL<br>QPLSGEDDAYCTFPSRDDLLLFSPSGQGEFRALNARLPLNTDAYLS<br>LQELQGQDPTHLV | 272 |

TABLE 6-continued

Exemplary chimeric cytokine receptor sequences (assembled inducible or constitutively active TGF-β receptor chimeric cytokine receptors):

| Receptor | Amino acid sequence | SEQ ID NO: |
|---|---|---|
| CD8SS-TPOR/MPLR(478-582; S505N, W515K, K553R, K573R).IL2Rb(393-433, 518-551) Underlined indicates CD8SS | MALPVTALLLPLALLLHAARPSDPTRVETATETAWISLVTALHLVLGLNAVLGLLLLRKQFPAHYRRLRHALWPSLPDLHRVLGQYLRDTAALSPPRATVSDTCEEVEPSLLEILPRSSERTPLPLLEDEGVAGAPTGSSPQPLQPLSGEDDAYCTFPSRDDLLLFSPSGQGEFRALNARLPLNTDAYLSLQELQGQDPTHLV | 273 |
| CD8SS-HAPD1.TPOR/MPLR(478-582; H499L, S505N, W515K, K553R, K573R).IL2Rb(339-379, 393-433, 518-551) Underlined indicates CD8SS Italicized marks high-affinity PD-1 ectodomain | MALPVTALLLPLALLLHAARP*PGWFLDSPDRPWNPPTFSPALLVVTEGDNATFTCSFSNTSESFHVIWHRESPSGQTDTLAAFPEDRSQPGQDCRFRVTQLPNGRDFHMSVVRARRNDSGTYVCGVISLAPKIQIKESLRAELRVTERRAEVPTAHPSPSPRPAGQFQTLV*SDPTRVETATETAWISLVTALLLVLGLNAVLGLLLLRKQFPAHYRRLRHALWPSLPDLHRVLGQYLRDTAALSPPRATVSDTCEEVEPSLLEILPRSSERTPLPLLEQQDKVPEPASLSSNHSLTSCFTNQGYFFFHLPDALEIEACQDEGVAGAPTGSSPQPLQPLSGEDDAYCTFPSRDDLLLFSPSGQGEFRALNARLPLNTDAYLSLQELQGQDPTHLV | 274 |
| CD8SS-HAPD1.TPOR/MPLR(478-582; S505N, W515K, K553R, K573R).IL2Rb(393-433, 518-551) Underlined indicates CD8SSItalicized marks high-affinity PD-1 ectodomain | MALPVTALLLPLALLLHAARP*PGWFLDSPDRPWNPPTFSPALLVVTEGDNATFTCSFSNTSESFHVIWHRESPSGQTDTLAAFPEDRSQPGQDCRFRVTQLPNGRDFHMSVVRARRNDSGTYVCGVISLAPKIQIKESLRAELRVTERRAEVPTAHPSPSPRPAGQFQTLVS*DPTRVETATETAWISLVTALHLVLGLNAVLGLLLLRKQFPAHYRRLRHALWPSLPDLHRVLGQYLRDTAALSPPRATVSDTCEEVEPSLLEILPRSSERTPLPLLEDEGVAGAPTGSSPQPLQPLSGEDDAYCTFPSRDDLLLFSPSGQGEFRALNARLPLNTDAYLSLQELQGQDPTHLV | 275 |

*The underlined LE and SR indicate exemplary peptide linkers.

F. Expression of Chimeric Cytokine Receptors

Provided herein are polynucleotides encoding any one of the chimeric cytokine receptors provided herein. Likewise, provided herein are expression vectors comprising such polynucleotides. In some embodiments, the vector is a viral vector. In some embodiments, the vector is not a viral vector.

In some embodiments, the vector comprises a polynucleotide encoding a chimeric cytokine receptor, and a polynucleotide expressing a chimeric antigen receptor (CAR).

In some embodiments, expression of the chimeric cytokine receptor and the CAR are expressed as a single polypeptide chain, separated by a linker. FIGS. 2A, 3, 4A, 5A, 6A, 8A, and 11A show schematics of a vector that can be used to co-express the chimeric cytokine receptor and CAR of the disclosure. One or more STAT-recruiting domains may be joined in tandem to mimic signaling from one or more cytokines.

II. CAR-Bearing Immune Cells

Provided herein are engineered immune cells comprising a polynucleotide encoding a chimeric antigen receptor and a chimeric cytokine receptor of the disclosure; and provided herein are engineered immune cells expressing a chimeric antigen receptor (CAR-I cell) and a chimeric cytokine receptor of the disclosure. Examples of immune cells include T-cells, e.g., alpha/beta T-cells and gamma/delta T-cells, B cells, natural killer (NK) cells, natural killer T (NKT) cells, invariant NKT cells, mast cells, myeloid-derived phagocytes, dendritic cells, killer dendritic cells, macrophages, and monocytes. Immune cells also refer to cells derived from, for example without limitation, a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells.

Accordingly in some embodiments, provided herein are CAR-T cells comprising a chimeric cytokine receptor of the disclosure.

In some embodiments, a CAR can comprise an extracellular ligand-binding domain (e.g., a single chain variable fragment (scFv)), a transmembrane domain, and an intracellular signaling domain. In some embodiments, the extracellular ligand-binding domain, transmembrane domain, and intracellular signaling domain are in one polypeptide, i.e., in a single chain. Multichain CARs and polypeptides are also provided herein. In some embodiments, the multichain CARs comprise: a first polypeptide comprising a transmembrane domain and at least one extracellular ligand-binding domain, and a second polypeptide comprising a transmembrane domain and at least one intracellular signaling domain, wherein the polypeptides assemble together to form a multichain CAR.

The extracellular ligand-binding domain of a CAR specifically binds to a target of interest. The target of interest can be any molecule of interest, including, for example, without limitation any one or more of those presented in Table 8.

TABLE 8

| List of targets of interest |
|---|
| BCMA |
| EGFRvIII |
| Flt-3 |
| WT-1 |
| CD20 |
| CD23 |
| CD30 |
| CD38 |
| CD70 |
| CD33 |
| CD133 |
| MHC- WT1 |
| TSPAN10 |
| MHC-PRAME |
| Liv1 |
| ADAM10 |

TABLE 8-continued

| List of targets of interest |
|---|
| CHRNA2 |
| LeY |
| NKG2D |
| CS1 |
| CD44v6 |
| ROR1 |
| CD19 |
| Claudin-18.2 (Claudin-18A2 or Claudin18 isoform 2) |
| DLL3 (Delta-like protein 3, *Drosophila* Delta homolog 3, Delta3) |
| Muc17 (Mucin17, Muc3, Muc3) |
| FAP alpha (Fibroblast Activation Protein alpha) |
| Ly6G6D (Lymphocyte antigen 6 complex locus protein G6d |
| c6orf23 |
| G6D |
| MEGT1 |
| NG25) |
| RNF43 (E3 ubiquitin-protein ligase RNF43, RING finger protein 43) |
| ErbB2 (HER2/neu) |
| carcinoembryonic antigen (CEA) |
| epithelial cell adhesion molecule (EpCAM) |
| epidermal growth factor receptor (EGFR) |
| CD40 |
| disialoganglioside GD2 |
| GD3 |
| C-type lectin-like molecule-1 (CLL-1) |
| ductal-epithelial mucine |
| gp36 |
| TAG-72 |
| glycosphingolipids |
| glioma-associated antigen |
| β-human chorionic gonadotropin |
| alphafetoprotein (AFP) |
| lectin-reactive AFP |
| thyroglobulin |
| RAGE-1 |
| MN-CA IX |
| human telomerase reverse transcriptase |
| RU1 |
| RU2 (AS) |
| intestinal carboxyl esterase |
| mut hsp70-2 |
| M-CSF |
| prostase |
| prostase specific antigen (PSA) |
| PAP |
| NY-ESO-1 |
| LAGA-la |
| p53 |
| prostein |
| PSMA |
| survivin and telomerase |
| prostate-carcinoma tumor antigen-1 (PCTA-1) |
| MAGE |
| ELF2M |
| neutrophil elastase |
| ephrin B2 |
| CD22 |
| insulin growth factor (IGFl)-l |
| IGF-II |
| IGFI receptor |
| mesothelin |
| a major histocompatibility complex (MHC) molecule presenting a tumor-specific peptide epitope |
| 5T4 |
| O 1 |
| Nkp30 |
| tumor stromal antigens |
| the extra domain A (EDA) and extra domain B (EDB) of fibronectin and the AI domain of tenascin-C (TnC AI) and fibroblast associated protein (fap) |
| LRP6 |
| melamona-associated Chondroitin Sulfate Proteoglycan (MCSP) |
| MARTI |
| MUC1 |
| LMP2 |
| Idiotype |
| NY-ESO-1 |
| Ras mutant |
| gp100 |
| proteinase 3 |
| bcr-abl |
| tyrosinase |
| hTERT |
| EphA2 |
| ML-TAP |
| ERG |
| NA17 |
| PAX3 |
| ALK |
| Androgen receptor |
| a lineage-specific or tissue specific antigen such as CD3 |
| CD4 |
| CD8 |
| CD24 |
| CD25 |
| CD34 |
| CD79 |
| CD116 |
| CD117 |
| CD135 |
| CD123 |
| CD138 |
| CTLA-4 |
| B7-1 (CD80) |
| B7-2 (CD86) |
| endoglin |
| a major histocompatibility complex (MHC) molecule |
| MUC16 |
| PSCA |
| Trop2 |
| CD171 (L1CAM) |
| CA9 |
| STEAP1 |
| VEGFR2 |

In some embodiments, the extracellular ligand-binding domain of a CAR comprises an scFv comprising the light chain variable (VL) region and the heavy chain variable (VH) region of a target antigen specific monoclonal antibody joined by a flexible linker. Single chain variable region fragments are made by linking light and/or heavy chain variable regions by using a short linking peptide (Bird et al., Science 242:423-426, 1988) (e.g. glycine-serine containing linkers). In general, linkers can be short, flexible polypeptides and are generally comprised of about 20 or fewer amino acid residues. Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

The intracellular signaling domain of a CAR according to the invention is responsible for intracellular signaling following the binding of extracellular ligand-binding domain to the target resulting in the activation of the immune cell and immune response (Signals 1 and/or 2). The intracellular signaling domain has the ability to activate at least one of the normal effector functions of the immune cell in which the CAR is expressed. For example, the effector function of a T cell can be a cytolytic activity or helper activity including the secretion of cytokines.

In some embodiments, an intracellular signaling domain for use in a CAR can be the cytoplasmic sequences of, for example without limitation, the T cell receptor and co-receptors that act in concert to initiate signal transduction following antigen receptor engagement, as well as any derivative or variant of these sequences and any synthetic sequence that has the same functional capability. Intracellular signaling domains comprise two distinct classes of cytoplasmic signaling sequences: those that initiate antigen-dependent primary activation, and those that act in an antigen-independent manner to provide a secondary or co-stimulatory signal. Primary cytoplasmic signaling sequences can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non-limiting examples those derived from TCRξ, FcRγ, FcRβ, FcRε, CD3γ, CD3δ, CD3ε, CD5, CD22, CD79a, CD79b and CD66d. In some embodiments, the intracellular signaling domain of the CAR can comprise the CD3ξ signaling domain. In some embodiments the intracellular signaling domain of the CAR of the invention comprises a domain of a co-stimulatory molecule.

In some embodiments, the intracellular signaling domain of a CAR of the invention comprises a part of co-stimulatory molecule selected from the group consisting of fragment of 41BB (GenBank: AAA53133.) and CD28 (NP_006130.1).

CARs are expressed on the surface membrane of the cell. Thus, the CAR comprises a transmembrane domain. Suitable transmembrane domains for a CAR disclosed herein have the ability to (a) be expressed at the surface of a cell, preferably an immune cell such as, for example without limitation, lymphocyte cells or Natural killer (NK) cells, and (b) interact with the ligand-binding domain and intracellular signaling domain for directing cellular response of immune cell against a predefined target cell. The transmembrane domain can be derived either from a natural or from a synthetic source. The transmembrane domain can be derived from any membrane-bound or transmembrane protein. As non-limiting examples, the transmembrane polypeptide can be a subunit of the T cell receptor such as α, β, γ or δ, polypeptide constituting CD3 complex, IL-2 receptor p55 (a chain), p75 (β chain) or γ chain, subunit chain of Fc receptors, in particular Fcγ receptor III or CD proteins. Alternatively, the transmembrane domain can be synthetic and can comprise predominantly hydrophobic residues such as leucine and valine. In some embodiments said transmembrane domain is derived from the human CD8a chain (e.g., NP_001139345.1). The transmembrane domain can further comprise a stalk domain between the extracellular ligand-binding domain and said transmembrane domain. A stalk domain may comprise up to 300 amino acids, preferably 10 to 100 amino acids and most preferably 25 to 50 amino acids. Stalk region may be derived from all or part of naturally occurring molecules, such as from all or part of the extracellular region of CD8, CD4, or CD28, or from all or part of an antibody constant region. Alternatively the stalk domain may be a synthetic sequence that corresponds to a naturally occurring stalk sequence, or may be an entirely synthetic stalk sequence. In some embodiments said stalk domain is a part of human CD8a chain (e.g., NP_001139345.1). In another particular embodiment, said transmembrane and hinge domains comprise a part of human CD8a chain. In some embodiments, CARs disclosed herein can comprise an extracellular ligand-binding domain that specifically binds BCMA, CD8a human hinge and transmembrane domains, the CD3(signaling domain, and 4-1BB signaling domain.

In some embodiments, a CAR can be introduced into an immune cell as a transgene via a plasmid vector. In some embodiments, the plasmid vector can also contain, for example, a selection marker which provides for identification and/or selection of cells which received the vector.

Table 7 provides exemplary sequences of CAR components that can be used in the CARs disclosed herein.

TABLE 7

Exemplary Sequences

| Domain | Amino acid sequence | SEQ ID NO: |
|---|---|---|
| V5 epitope tag | KPIPNPLLGLDST | 152 |
| 2173 scFv | EIQLVQSGAEVKKPGESLRISCKGSGFNIEDYYIR WVRQMPGKGLEWMGRIDPENDETKYGPIFQGH VTISADTSINTVYLQWSSLKASDTAMYYCAFRG GVYWGQGTTVTVSSGGGGSGGGGSGGGGSGGG GSDVVMTQSPDSLAVSLGERATINCKSSQSLLDS DGKTYLNWLQQKPGQPPKRLISLVSKLDSGVPD RFSGSGSGTDFTLTISSLQAEDVAVYYCWQGTHF PGTFGGGTKVEIK | 153 |
| CD8 hinge and transmembrane | TTTPAPRPPTPAPTIASQPLSLRPEACRPAAGGAV HTRGLDFACDIYIWAPLAGTCGVLLLSLVITLYC | 154 |
| 4-1BB intracellular signaling | KRGRKKLLYIFKQPFMRPVQTTQEEDGCSCRFPE EEEGGCEL | 155 |
| CD3z intracellular signaling | RVKFSRSADAPAYQQGQNQLYNELNLGRREEYD VLDKRRGRDPEMGGKPRRKNPQEGLYNELQKD KMAEAYSEIGMKGERRRGKGHDGLYQGLSTAT KDTYDALHMQALPPR | 156 |
| BFP (blue fluorescent protein) | MSELIKENMHMKLYMEGTVDNHHFKCTSEGEG KPYEGTQTMRIKVVEGGPLPFAFDILATSFLYGS KTFINHTQGIPDFFKQSFPEGFTWERVTTYEDGG | 157 |

TABLE 7-continued

Exemplary Sequences

| Domain | Amino acid sequence | SEQ ID NO: |
|---|---|---|
| | VLTATQDTSLQDGCLIYNVKIRGVNFTSNGPVM QKKTLGWEAFTETLYPADGGLEGRNDMALKLV GGSHLIANIKTTYRSKKPAKNLKMPGVYYVDYR LERIKEANNETYVEQHEVAVARYCDLPSKLGHK LN | |
| P2A | GSGATNFSLLKQAGDVEENPGP | 158 |

In some embodiments, the CAR-immune cell (e.g., CAR-T cell) of the disclosure comprises a polynucleotide encoding a suicide polypeptide, such as for example RQR8. See, e.g., WO2013153391A, which is hereby incorporated by reference in its entirety. In some embodiments, a suicide polypeptide is expressed on the surface of the cell. In some embodiments, a suicide polypeptide is included in the CAR construct. In some embodiments, a suicide polypeptide is not part of the CAR construct.

In some embodiments, the extracellular domain of any one of CARs disclosed herein may comprise one or more epitopes specific for (specifically recognized by) a monoclonal antibody. These epitopes are also referred to herein as mAb-specific epitopes. Exemplary mAb-specific epitopes are disclosed in International Patent Publication No. WO 2016/120216, which is incorporated herein in its entirety. In these embodiments, the extracellular domains of the CARs comprise antigen binding domains that specifically bind to a target of interest and one or more epitopes that bind to one or more monoclonal antibodies (mAbs). CARs comprising the mAb-specific epitopes can be single-chain or multi-chain.

The inclusion of epitopes specific for monoclonal antibodies in the extracellular domain of the CARs described herein allows sorting and depletion of engineered immune cells expressing the CARs. In some embodiments, allowing for depletion provides a safety switch in case of deleterious effects, e.g., upon administration to a subject.

Methods of preparing immune cells for use in immunotherapy are also provided herein. In some embodiments, the methods comprise introducing a chimeric cytokine receptor and a CAR into immune cells, and expanding the cells. In some embodiments, the invention relates to a method of engineering an immune cell comprising: providing a cell and expressing a chimeric cytokine receptor, and expressing at the surface of the cell at least one CAR. In some embodiments, the method comprises: transfecting the cell with at least one polynucleotide encoding a chimeric cytokine receptor, and at least one polynucleotide encoding a CAR, and expressing the polynucleotides in the cell. In some embodiments, the method comprises: transfecting the cell with at least one polynucleotide encoding a chimeric cytokine receptor, at least one polynucleotide encoding a CAR, and expressing the polynucleotides in the cell. In some embodiments, the chimeric cytokine receptor and the CAR reside on one polynucleotide.

In some embodiments, the one or more polynucleotides encoding the chimeric cytokine receptor and CAR are present in one or more expression vectors for stable expression in the cells. In some embodiments, the polynucleotides are present in viral vectors for stable expression in the cells. In some embodiments, the one or more polynucleotides are inserted into the cellular genome by random integration, and in other embodiments, inserted into specific locations of the cellular genome by site-specific integration. In some embodiments, the viral vectors may be for example, lentiviral vectors or adenoviral vectors. In some embodiments, the one or more polynucleotides are present in non-viral vectors.

In some embodiments, polynucleotides encoding polypeptides according to the present disclosure can be mRNA which is introduced directly into the cells, for example by electroporation. In some embodiments, CytoPulse electroporation technology, such as PulseAgile, can be used to transiently permeabilize living cells for delivery of material into the cells (e.g. U.S. Pat. No. 6,078,490; PCT/US2011/000827; and PCT/US2004/005237). Parameters can be modified in order to determine conditions for high transfection efficiency with minimal mortality.

Also provided herein are methods of transfecting an immune cell, e.g a T-cell. In some embodiments, the method comprises: contacting a T-cell with RNA and applying to the T-cell an agile pulse sequence. In some embodiments, a method of transfecting an immune cell (e.g. T-cell) comprising contacting the immune cell with RNA and applying to the cell an agile pulse sequence.

In some embodiments, the method can further comprise a step of genetically modifying a cell by inactivating at least one gene expressing, for example without limitation, a component of the TCR, a target for an immunosuppressive agent, an HLA gene, and/or an immune checkpoint protein such as, for example, PDCD1 or CTLA-4. By inactivating a gene it is intended that the gene of interest is not expressed in a functional protein form. In some embodiments, the gene to be inactivated is selected from the group consisting of, for example without limitation, TCRα, TCRβ, CD52, GR, deoxycytidine kinase (DCK), TGF-B, and CTLA-4. In some embodiments the method comprises inactivating one or more genes by introducing into the cells a rare-cutting endonuclease able to selectively inactivate a gene by selective DNA cleavage. In some embodiments the rare-cutting endonuclease can be, for example, a transcription activator-like effector nuclease (TALE-nuclease) or CRISPR-based endonuclease (e.g Cas-9 or Cas12a).

In another aspect, a step of genetically modifying cells can comprise: modifying immune cells (e.g. T-cells) by inactivating at least one gene expressing a target for an immunosuppressive agent, and; expanding the cells, optionally in presence of the immunosuppressive agent.

In some embodiments, the engineered immune cells (e.g. T-cells) provided herein exhibit improved cytotoxicity, increased expansion, and/or increased levels of memory phenotype markers upon contact with a TGF-β ligand or anti-TGF-β-receptor antibody that binds to the binding domain of the chimeric cytokine receptor relative to engineered immune cells that do not express the chimeric cytokine receptor.

In some embodiments, the engineered immune cells (e.g. T-cells) provided herein exhibit (i) increased in vivo persistence, (ii) increased STAT activation, (iii) increased cytotoxicity, (iv) increased levels of memory phenotype markers, (v) increased expansion (proliferation), or combinations of these functional features, upon contact with a TGF-β ligand or anti-TGF-β-receptor antibody that binds to the binding domain of the chimeric cytokine receptor relative to engineered immune cells that do not express the chimeric cytokine receptor. In some embodiments, the improvement in the one or more functional features described herein is dose-dependent, i.e., the functional activity of the immune cell comprising the chimeric cytokine receptors increases upon contact with increasing doses of the PD-L1/PD-L2/TGF-B or an antibody to the respective receptor. In some embodiments, STATs activated by the engineered immune cell comprising one or more chimeric cytokine receptors disclosed are STAT1, STAT2, STAT3, STAT4, STAT5, STAT6, or combinations thereof. In one embodiment, memory phenotype markers that are increased or maintained by the immune cell comprising the chimeric cytokine receptor of the disclosure include stem cell memory (Tscm) markers and central memory (Tcm) markers.

In some embodiments, the improvement in one or more functional features exhibited by an engineered immune cell comprising a chimeric cytokine receptor provided herein is at least about 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 25 fold, 30 fold, 40 fold, 50 fold, 60 fold, 70 fold, 80 fold, 90 fold, 100 fold, 125 fold, 150 fold, 200 fold, 250 fold, 300 fold, 350 fold, 400 fold, 450 fold, or even about 10-500 fold, including values and ranges therebetween, compared to an immune cell that does not express the chimeric cytokine receptor.

In some embodiments, the improvement in one or more functional features exhibited by an engineered immune cell comprising a chimeric cytokine receptor provided herein is at least about 10%, 20%, 25%, 30%, 35%, 40%, 45%, 50%, 55%, 60%, 70%, 75%, 80%, 90%, 100%, 125%, 150%, 200%, 250%, 300%, 350%, 400%, or even about 80%-500%, including values and ranges therebetween, compared to an engineered immune cell that does not express the chimeric cytokine receptor.

III. Therapeutic Methods

Provided herein are pharmaceutical compositions comprising cells bearing the chimeric cytokine receptors and CARs of the disclosure.

Engineered chimeric cytokine receptor-bearing and CAR-bearing immune cells (e.g. T-cells) obtained by the methods described above, or cell lines derived from such engineered immune cells, can be used as a medicament. In some embodiments, such a medicament can be used for treating a disorder such as for example a viral disease, a bacterial disease, a cancer, an inflammatory disease, an immune disease, or an aging—associated disease. In some embodiments, the cancer is a solid cancer. In some embodiments the cancer is a liquid cancer. The cancer can be selected from the group consisting of gastric cancer, sarcoma, lymphoma, leukemia, head and neck cancer, thymic cancer, epithelial cancer, salivary cancer, liver cancer, stomach cancer, thyroid cancer, lung cancer, small cell lung cancer, ovarian cancer, breast cancer, prostate cancer, esophageal cancer, pancreatic cancer, glioma, glioblastoma, leukemia, multiple myeloma, renal cell carcinoma, bladder cancer, cervical cancer, choriocarcinoma, colon cancer, oral cancer, skin cancer, and melanoma. In some embodiments, the subject is a previously treated adult subject with locally advanced or metastatic melanoma, squamous cell head and neck cancer (SCHNC), ovarian carcinoma, sarcoma, or relapsed or refractory classic Hodgkin's Lymphoma (cHL).

In some embodiments, engineered immune cells, or cell line derived from the engineered immune cells, can be used in the manufacture of a medicament for treatment of a disorder in a subject in need thereof. In some embodiments, the disorder can be, for example, a cancer, an autoimmune disorder, or an infection.

Also provided herein are methods for treating subjects in need of such treatment.

As used herein, the term "subject" refers to any vertebrate including, without limitation, humans and other primates (e.g., chimpanzees, cynomologous monkeys, and other apes and monkey species), farm animals (e.g., cattle, sheep, pigs, goats and horses), domestic mammals (e.g., dogs and cats), laboratory animals (e.g., rabbits, rodents such as mice, rats, and guinea pigs), and birds (e.g., domestic, wild and game birds such as chickens, turkeys and other gallinaceous birds, ducks, geese, and the like). In some embodiments, the subject is a mammal. In exemplary embodiments, the subject is a human.

In some embodiments the method comprises providing immune cells of the disclosure, bearing the chimeric cytokine receptors and CARs described herein to a subject in need thereof.

In some embodiments, chimeric cytokine receptor and CAR-bearing T-cells of the invention can undergo robust in vivo T-cell expansion and can persist for an extended amount of time.

Methods of treatment of the invention can be ameliorating, curative or prophylactic. The method of the invention may be either part of an autologous immunotherapy or part of an allogenic immunotherapy treatment.

In another aspect, the invention provides a method of inhibiting tumor growth or progression in a subject who has a tumor, comprising administering to the subject an effective amount of chimeric cytokine receptor-expressing and CAR-expressing immune cells as described herein. In another aspect, the invention provides a method of inhibiting or preventing metastasis of cancer cells in a subject, comprising administering to the subject in need thereof an effective amount of engineered immune cells as described herein. In another aspect, the invention provides a method of inducing tumor regression in a subject who has a tumor, comprising administering to the subject an effective amount of engineered immune cells as described herein. In some embodiments, the subject is further administered with an anti-TGF-βR antibody, in particular, an anti-TGF-βR2 antibody.

In some embodiments, the engineered T-cells herein can be administered parenterally in a subject. In some embodiments, the engineered T-cells disclosed herein can be administered intravenously in a subject.

Also provided is the use of any of the engineered T-cells provided herein in the manufacture of a medicament for the treatment of cancer or for inhibiting tumor growth or progression in a subject in need thereof.

In some embodiments, treatment can be administrated into subjects undergoing an immunosuppressive treatment. Indeed, the invention preferably relies on cells or population of cells, which have been made resistant to at least one immunosuppressive agent due to the inactivation of a gene encoding a receptor for such immunosuppressive agent. In this aspect, the immunosuppressive treatment should help the selection and expansion of the T-cells according to the invention within the subject. The administration of the cells or population of cells according to the invention may be carried out in any convenient manner, including by aerosol inhalation, injection, ingestion, transfusion, implantation or transplantation. The compositions described herein may be administered to a subject subcutaneously, intradermally, intratumorally, intranodally, intramedullary, intramuscularly, by intravenous or intralymphatic injection, or intraperitoneally. Cells bearing the chimeric cytokine receptors and/or CARs of the disclosure or the pharmaceutical compositions thereof may be administered via one or more of the following routes of administration: intravenous, intraocular, intravitreal, intramuscular, subcutaneous, topical, oral, transdermal, intraperitoneal, intraorbital, by implantation, by inhalation, intrathecal, intraventricular, via the ear, or intranasal.

In some embodiments the administration of the cells or population of cells (bearing the chimeric cytokine receptors and CARs of the disclosure) can comprise administration of, for example, about $10^4$ to about $10^9$ cells per kg body weight including all integer values of cell numbers within those ranges. In some embodiments the administration of the cells or population of cells can comprise administration of about $10^4$ to $10^5$ cells per kg body weight, $10^5$ to $10^6$ cells per kg body weight, $10^6$ to $10^7$ cells per kg body weight, $10^7$ to $10^8$ cells per kg body weight, or $10^8$ to $10^9$ cells per kg body weight. The cells or population of cells can be administrated in one or more doses. In some embodiments, said effective amount of cells can be administrated as a single dose. In some embodiments, said effective amount of cells can be administrated as more than one dose over a period time. Timing of administration is within the judgment of managing physician and depends on the clinical condition of the subject. The cells or population of cells may be obtained from any source, such as a blood bank or a donor. While individual needs vary, determination of optimal ranges of effective amounts of a given cell type for a particular disease or condition is within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired. In some embodiments, an effective amount of cells or composition comprising those cells are administrated parenterally. In some embodiments, administration can be an intravenous administration. In some embodiments, administration can be directly done by injection within a tumor.

The methods can further comprise administering one or more agents to a subject prior to administering the engineered immune cells bearing a CAR and a chimeric cytokine receptor provided herein. In certain embodiments, the agent is a lymphodepleting (preconditioning) regimen. For example, methods of lymphodepleting a subject in need of such therapy comprise administering to the subject specified beneficial doses of cyclophosphamide (between 200 mg/m$^2$/day and 2000 mg/m$^2$/day, about 100 mg/m$^2$/day and about 2000 mg/m$^2$/day; e.g., about 100 mg/m$^2$/day, about 200 mg/m$^2$/day, about 300 mg/m$^2$/day, about 400 mg/m$^2$/day, about 500 mg/m$^2$/day, about 600 mg/m$^2$/day, about 700 mg/m$^2$/day, about 800 mg/m$^2$/day, about 900 mg/m$^2$/day, about 1000 mg/m$^2$/day, about 1500 mg/m$^2$/day or about 2000 mg/m$^2$/day) and specified doses of fludarabine (between 20 mg/m$^2$/day and 900 mg/m$^2$/day, between about 10 mg/m$^2$/day and about 900 mg/m$^2$/day; e.g., about 10 mg/m$^2$/day, about 20 mg/m$^2$/day, about 30 mg/m$^2$/day, about 40 mg/m$^2$/day, about 40 mg/m$^2$/day, about 50 mg/m$^2$/day, about 60 mg/m$^2$/day, about 70 mg/m$^2$/day, about 80 mg/m$^2$/day, about 90 mg/m$^2$/day, about 100 mg/m$^2$/day, about 500 mg/m$^2$/day or about 900 mg/m$^2$/day). An exemplary dosing regimen involves treating a subject comprising administering daily to the patient about 300 mg/m$^2$/day of cyclophosphamide in combination or before or after administering about 30 mg/m$^2$/day of fludarabine for three days prior to administration of a therapeutically effective amount of engineered immune cells to the patient.

In some embodiments, notably in the case when the engineered cells provided herein have been gene edited to eliminate or minimize surface expression of CD52, lymphodepletion further comprises administration of an anti-CD52 antibody, such as alemtuzumab. In some embodiments, the CD52 antibody is administered at a dose of about 1-20 mg/day IV, e.g., about 13 mg/day IV for 1, 2, 3 or more days. The antibody can be administered in combination with, before, or after administration of other elements of a lymphodepletion regime (e.g., cyclophosphamide and/or fludarabine).

In certain embodiments, compositions comprising CAR-expressing immune effector cells disclosed herein may be administered in conjunction with any number of chemotherapeutic agents.

IV. Kits and Articles of Manufacture

The present disclosure provides kits comprising any one or more of the chimeric cytokine receptors and chimeric cytokine receptor-bearing cells described herein, and pharmaceutical compositions thereof. The present disclosure also provides articles of manufacture comprising any one or more of the chimeric cytokine receptors and chimeric cytokine receptors-bearing CAR-I-cells described herein, pharmaceutical compositions thereof, and kits described herein.

The following examples are included for illustrative purposes and are not intended to limit the scope of the disclosure.

All patent and non-patent documents referenced throughout this disclosure are incorporated by reference herein in their entirety for all purposes.

EXAMPLES

Example 1: Construction and Testing of Chimeric Cytokine Receptor-CAR Constructs Having a TGFβR1 or TGFβR2 Dominant Negative Truncation FIG. 1 shows a schematic of the inducible chimeric cytokine receptor of the disclosure. To couple simultaneous TGF-β engagement with cytokine signaling, a chimeric cytokine receptor was constructed, composed of the following modules: (i) a binding domain comprising an extracellular portion of a TGF-β receptor, or a TGF-β antigen binding domain; (ii) a transmembrane domain with an intracellular portion having a JAK2-activating domain and (iii) STAT-recruiting domains comprising STAT-recruiting (STAT-activating) domains from cytokine receptor tails (cytotails). As shown as an example in FIG. 1, the binding domain comprises the extracellular domain of TGFβR2.

A HEK293T cell reporter assay was used to test the inducibility and magnitude of cytokine signaling using chimeric cytokine receptors for either neutralizing the TGF-β signaling or activating the STAT response, which can be used as a surrogate measurement for the cytokine ICD activation and cytokine signaling. Briefly, 20,000 HEK293T-cells were plated into each well of a poly-L-lysine-coated 96-well flat-bottom plate and cultured overnight at 37° C. with 5% $CO_2$. A chimeric cytokine receptor-CAR construct (2.5 ng), a TGF-β or STAT-response element that drives Firefly Luciferase (100 ng; Promega), and Renilla Luciferase control reporter vector (1 ng; Promega) were mixed to a final volume of 5 μl in Opti-MEM (Gibco) ("DNA mix").

Cells were transfected with a BFP-EGFRvIII CAR construct where a BFP gene is in place of the chimeric cytokine receptor as a negative control. A dominant negative truncation of TGFβR2 ("TGFβR2 DN") and a dominant negative truncation of TGFβ1 ("TGFβR1 DN") were also constructed as additional controls to examine dominant negative effects in the absence of an intracellular cytokine signal. After incubating the DNA mixes with premixed 0.3 μl Lipofectamine 2000 (Invitrogen) and 5 μl Opti-MEM at room temperature for 20 minutes, the mixture having a total volume of 10 μl was added to each well containing HEK293T cells. One day after transfection, a commercially available TGF-β1 ligand (BioLegend, hereinafter in Examples 1-4 referred to as "TGF-β") was added to the culture for stimulation, to various final concentrations. After 20-24 hours of stimulation, TGF-β or STAT5 reporter activity was evaluated using the Dual-Glo Luciferase Assay System (Promega). Fold induction of TGF-β or STAT5 reporter activity was normalized to that of HEK293T cells that were transfected with only a reporter vector, and left untreated.

FIG. 2A shows a schematic of the lentiviral vector used to co-express the dominant negative truncations of the TGFβR1 or TGFβR2 chimeric cytokine receptor with the 2"a generation EGFRvIII CAR.

Figure 2B:
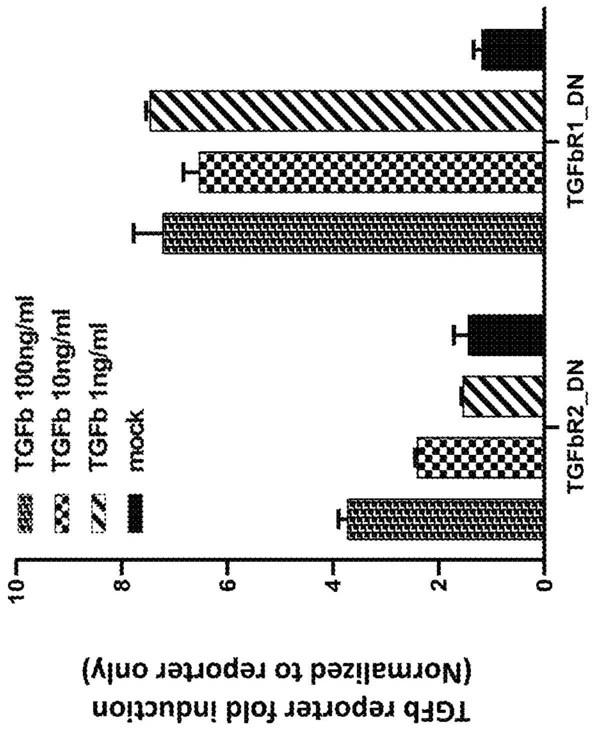
FIG. 2B shows the inhibition of the TGF-β signaling by expression of either the TGFβR1 DN or TGFβR2 DN.

FIG. 2B shows the inhibition of the TGF-β signaling by expression of either the TGFβR1 DN or TGFβR2 DN (shown by FIG. 2A, and comprising the amino acid sequences of SEQ ID NOs 2 and 3, respectively). The data shown indicates that the TGFβR2 DN chimeric cytokine receptor inhibits TGF-β signaling induced by the TGF-β ligand (up to 100 ng/ml), with higher efficacy than the TGFβR1 DN. This is likely due to the higher affinity of TGFβR2 binding to the TGF-β ligand in comparison to the binding affinity of TGFβR1 binding to the TGF-β ligand (described in Groppe et al., 2008, Mol. Cell, 29(2):157-68). Consequentially, the designs of the following examples focus on the chimeric cytokine receptors having the binding domain of TGFβR2.

Example 2: Designs and Testing of Inducible Chimeric Cytokine Receptors Using TGFβR2

A chimeric cytokine receptor was constructed, as briefly described when referring to FIG. 1, having a binding domain derived from TGFβR2 ("TGFβR2 chimeric cytokine receptor"). To investigate the utility of the TGFβR2 chimeric cytokine receptor in the context of CAR-T cells, variants of TGFβR2 extracellular domains (ECD) and variants of TPOR transmembrane (TM) domains were constructed. Fusions of each TGFβR2 ECD variant, each TPOR TM domain variant, and the intracellular domains (ICD) of desired cytokine receptors were cloned into a lentiviral vector encoding a $2^{nd}$ generation EGFRvIII-specific CAR (2173scFv; described in *Sci Transl Med.* 2015 Feb. 18; 7(275): 275ra22), and the activity of these receptor variants was tested. To permit stoichiometric co-expression of the chimeric cytokine receptor and the CAR, both genes were linked via a P2A peptide ("chimeric cytokine receptor-CAR construct"). To facilitate the detection of transduced cells, a v5 epitope tag (SEQ ID NO: 152) was inserted between the scFv and CD8 hinge domain.

Figure 3:
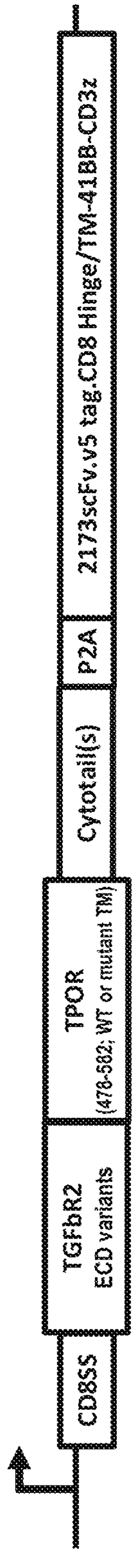
FIG. 3 shows a general schematic of the lentiviral vector used to co-express the TGFβR2 cytokine receptor with the $2^{nd}$ generation EGFRvIII CAR.

FIG. 3 shows a general schematic of the lentiviral vector used to co-express the TGFβR2 chimeric cytokine receptor with the $2^{nd}$ generation EGFRvIII CAR. One or more cytotails or recruiting domains may be joined in tandem to mimic signaling from one or more cytokines.

Figure 4A:
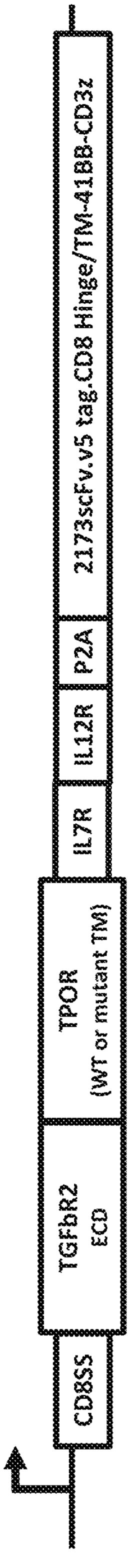
FIG. 4A shows a schematic of the prototypic lentiviral vector used, bearing the IL7R(316-459) and the IL12Rb2 (775-825) recruiting domains to mimic IL7 and IL12 signaling in CAR-T-cells.
Figure 4B:
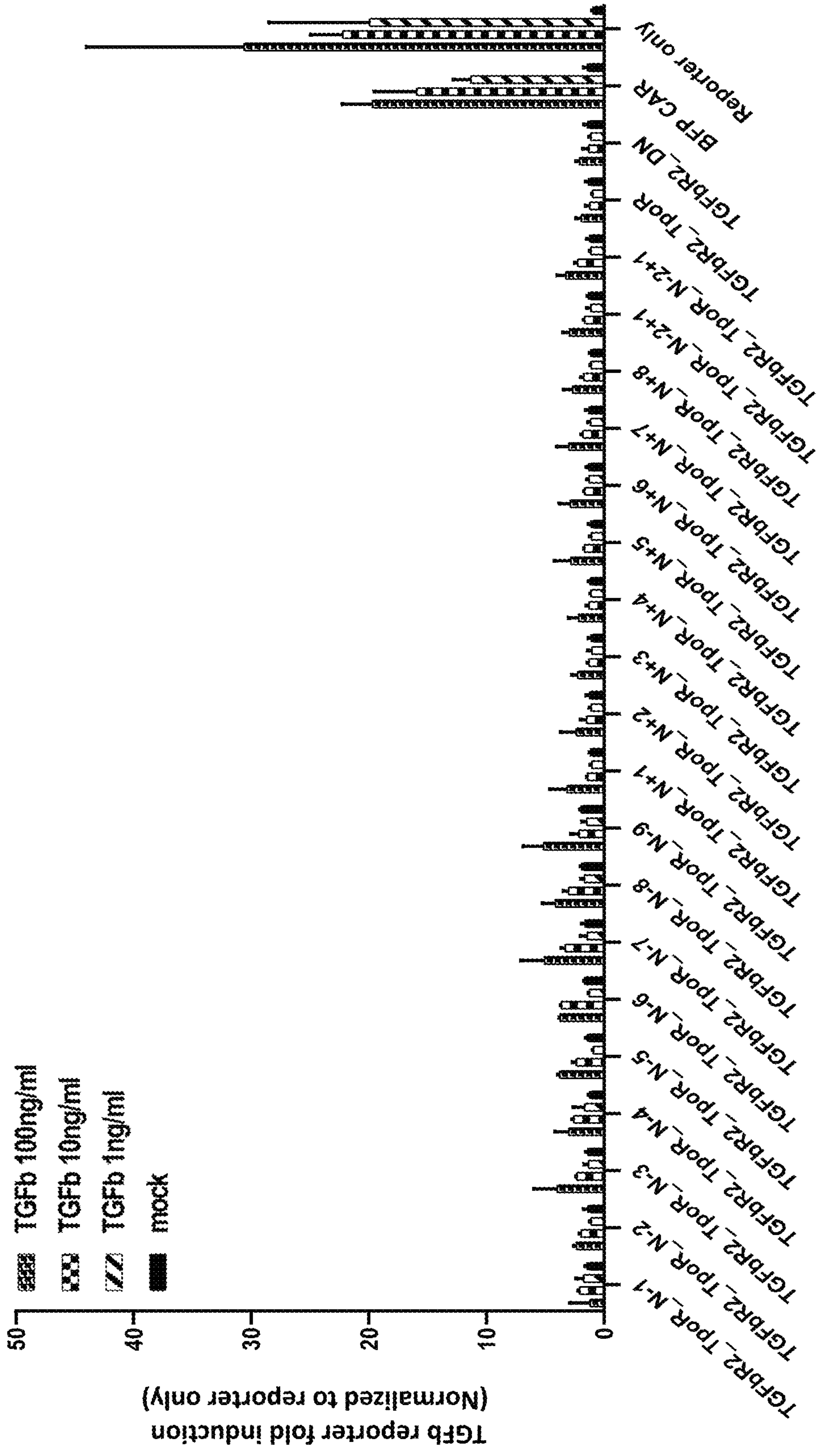
FIG. 4B shows TGF-β signaling activity determined by a luciferase reporter assay.
Figure 4C:
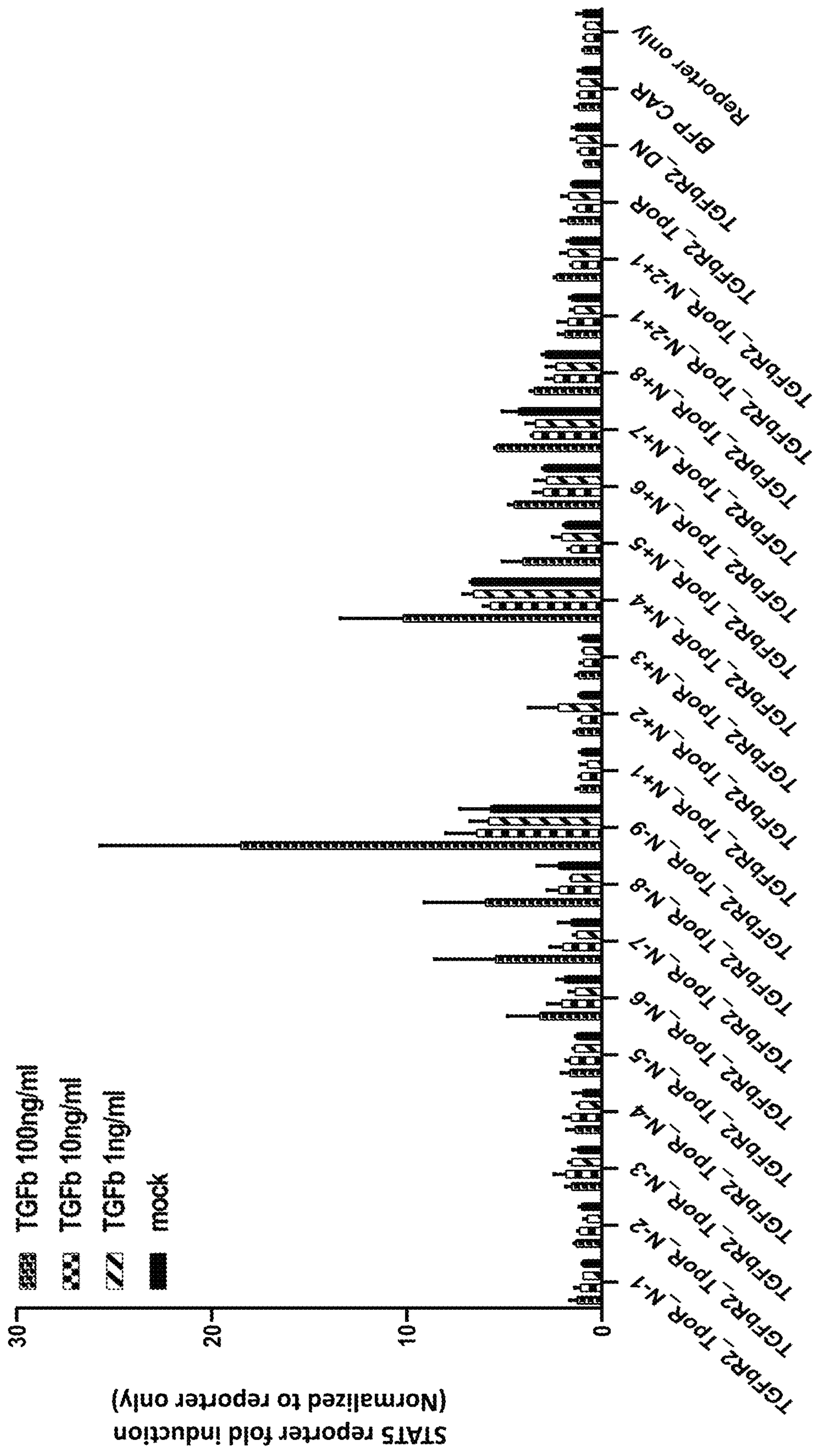
FIG. 4C shows the activation of the chimeric cytokine receptors of FIG. 4A in the presence of TGF-β.

FIGS. 4A-4C show the inhibition of TGF-β signaling by the overexpression of chimeric cytokine receptors constructed using TGFβR2. The lentiviral vectors used were constructed similarly as described in Example 1. FIG. 4A shows a schematic of the prototypic lentiviral vector used, bearing the IL7R(316-459) and the IL12Rb2(775-825) cytotail or recruiting domains to mimic IL7 and IL12 signaling in CAR-T-cells. A variety of truncations in the transmembrane domain of the TpoR cassette were designed (as shown in Table 3). The capacity of these truncations to regulate cytokine signaling was determined. FIG. 4B shows TGF-β signaling activity determined by a luciferase reporter assay. All the tested chimeric cytokine receptors constructed using TGFβR2 were shown to be able to inhibit TGF-β signaling as they compete for binding via the extracellular domain of TGFβR2 in these engineered chimeric receptors. FIG. 4C shows the activation of the chimeric cytokine receptors of FIG. 4A in the presence of TGF-β. The activation of the chimeric cytokine receptor is measured by STAT reporter activity. Several variants were identified to have the ability to induce cytokine signaling by a TGF-β ligand. The amino acid sequences of the transmembrane domains listed in the X-axes of FIGS. 4B-4C are SEQ ID NO: 29 to SEQ ID NO: 40 and SEQ ID NO: 50 to SEQ ID NO: 57, presented in Table 3.

Figure 5A:
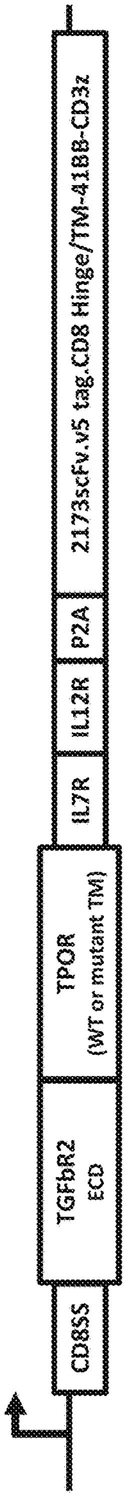
FIG. 5A shows a schematic of the prototypic lentiviral vector used, having truncations in the binding domain.
Figure 5B:
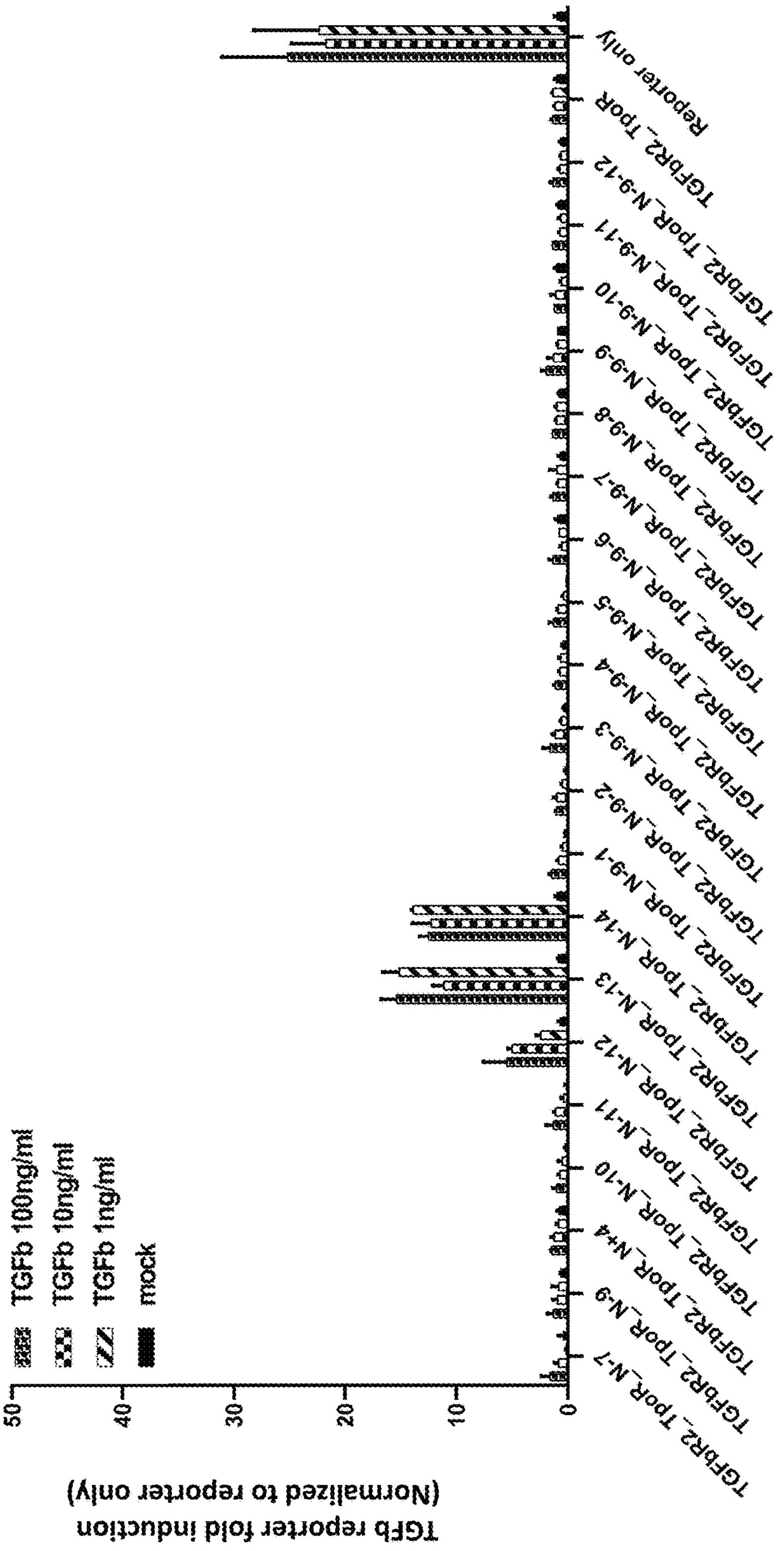
FIG. 5B shows TGF-β signaling activity determined by a luciferase reporter assay.
Figure 5C:
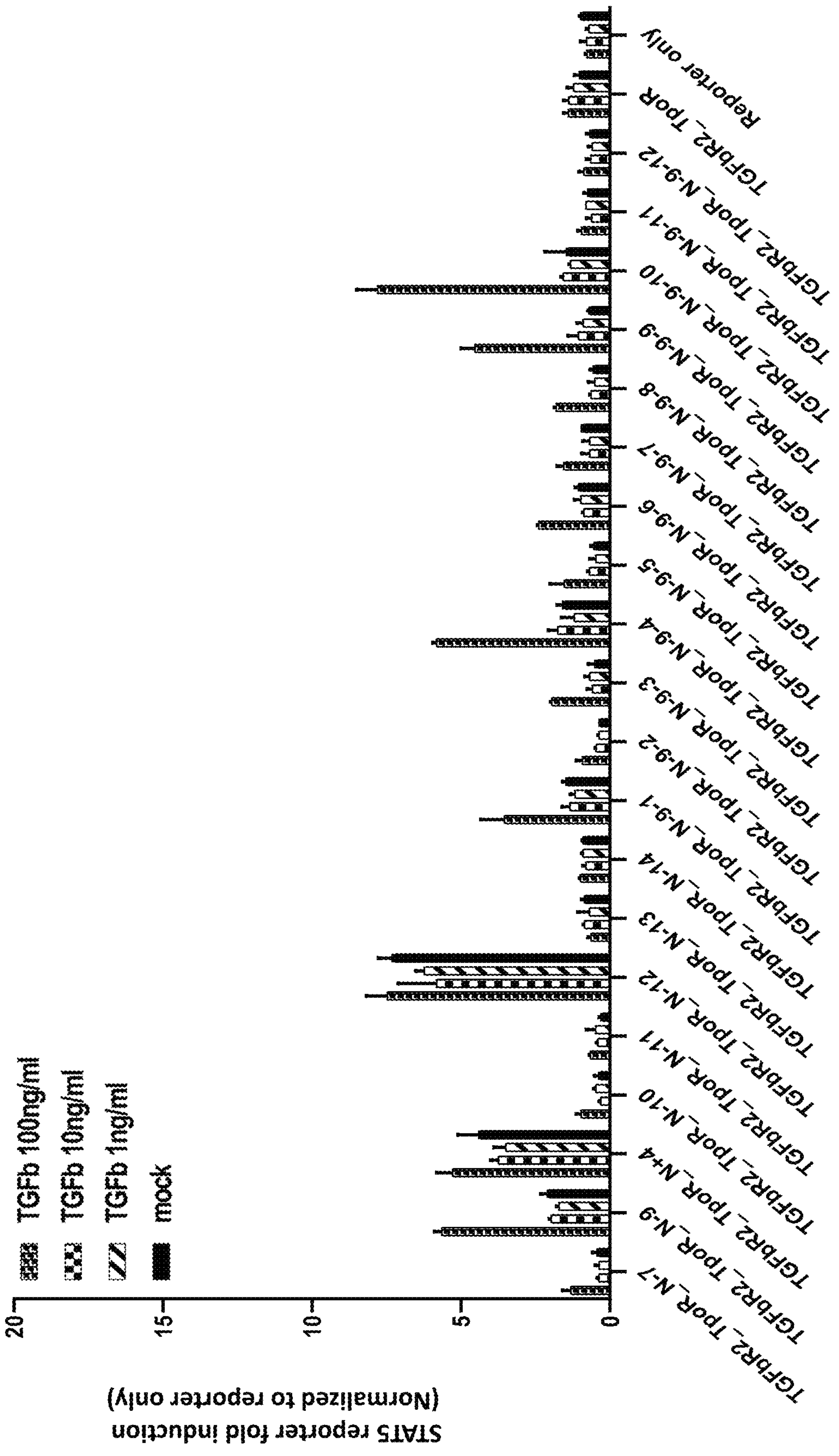
FIG. 5C shows the activation of the chimeric cytokine receptors of FIG. 5A in the presence of TGF-β.

FIGS. 5A-5C show the inhibition of TGF-β signaling by the overexpression of additional chimeric cytokine receptors constructed using TGFβR2. The lentiviral vectors used were constructed similarly as described when referring to FIGS. 4A-4C, and Example 1. FIG. 5A shows a schematic of the prototypic lentiviral vector used, having truncations in the binding domain.

Again, additional truncations (N-10, N-11, N-12, etc.) in the TM domain of TpoR cassette were designed (as shown in Table 3), and their capacity to regulate cytokine signaling was determined. FIG. 5B shows TGF-β signaling activity determined by a luciferase reporter assay. Most of the chimeric cytokine receptors tested were shown to be able to inhibit TGF-β signaling (other than the N-12, N-13, N-14 TM truncations, which show less extent of inhibition). FIG. 5C shows the activation of the chimeric cytokine receptors of FIG. 5A in the presence of TGF-β. The activation of the chimeric cytokine receptors is measured by the STAT reporter activity. Several variants were identified to have the ability to induce cytokine signaling by a TGF-β ligand. The amino acid sequences of the transmembrane domains listed in the X-axes of FIGS. 5B-5C are SEQ ID NOs: 29, 38, 53, SEQ ID NO: 40 to SEQ ID NO: 44, and SEQ ID NO: 61 to SEQ ID NO: 72, presented in Table 3.

Example 3: Modifications of the Chimeric Cytokine Receptor Binding Domain and Testing of the Constructed Chimeric Cytokine Receptors In the absence of TGFβR2, TGFβR1 interacts with the TGF-β ligand with very low affinity. Once the ECD of TGFβR2 binds to the TGF-β ligand, the binary complex has an extended interface to efficiently recruit TGFβR1 to form the ternary complex. The engineered TGFβR2 chimeric cytokine receptor can also engage endogenous TGFβR1, which may sterically intervene the intended signaling though the cytokine receptor ICDs. To abrogate interaction between the TGFβR2 chimeric cytokine receptors and TGFβR1, several variants for the TGFβR1 cassette were designed, and modifications that can enhance cytokine signaling while inhibiting the TGF-β signaling were identified.

Figure 6A:
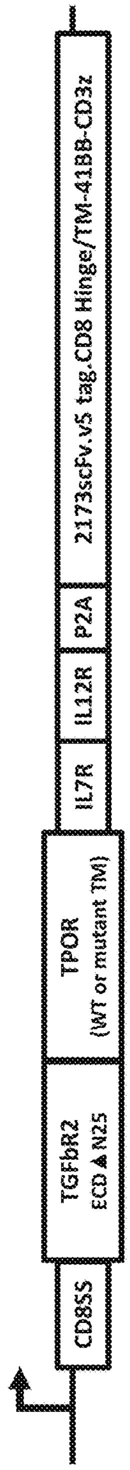
FIG. 6A shows a schematic of the modification introduced into the TGFβR2 cassette.
Figure 6B:
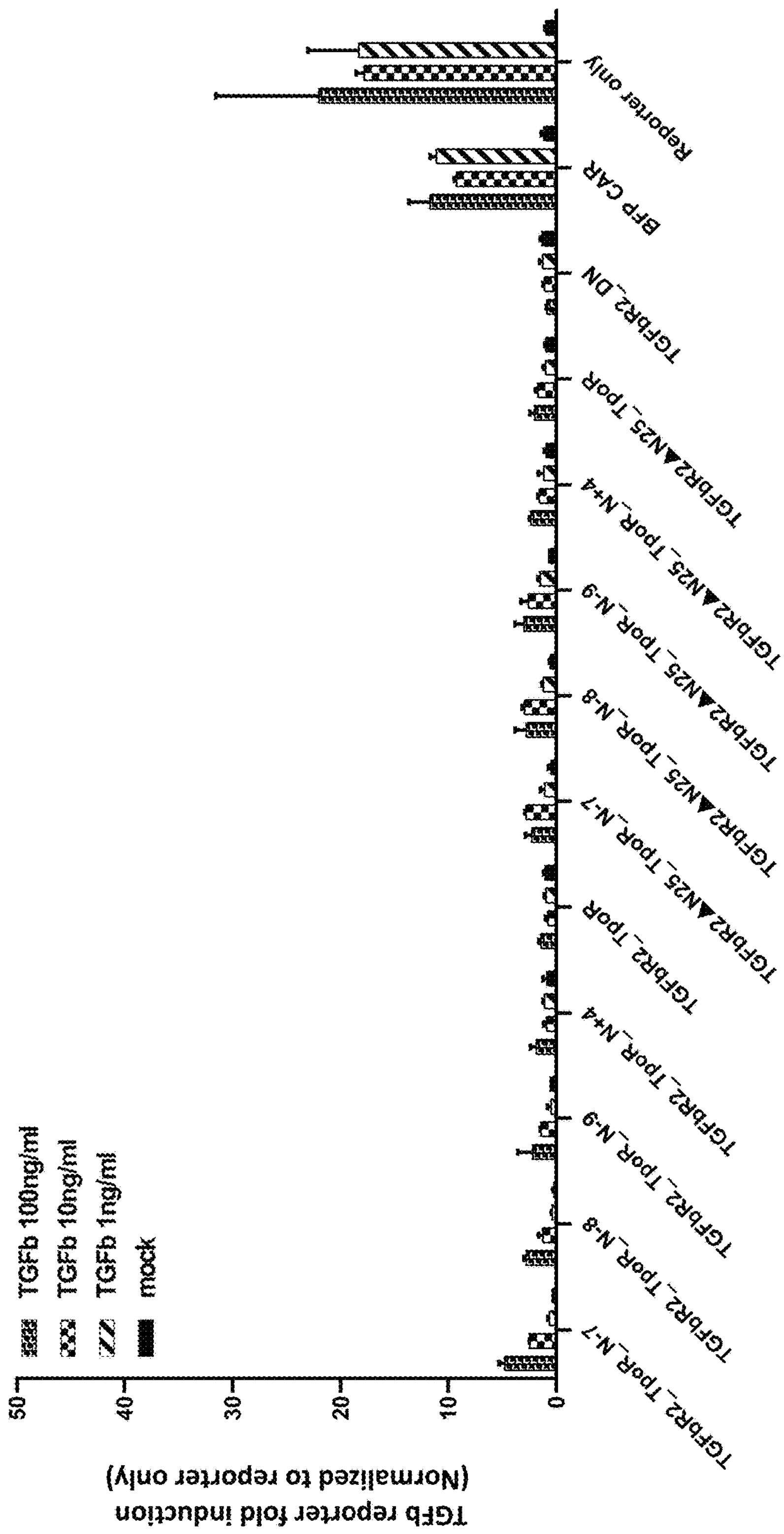
FIG. 6B shows that the TGFβR2ΔN25 chimeric cytokine receptors still retained the ability to inhibit TGF-β signaling.
Figure 6C:
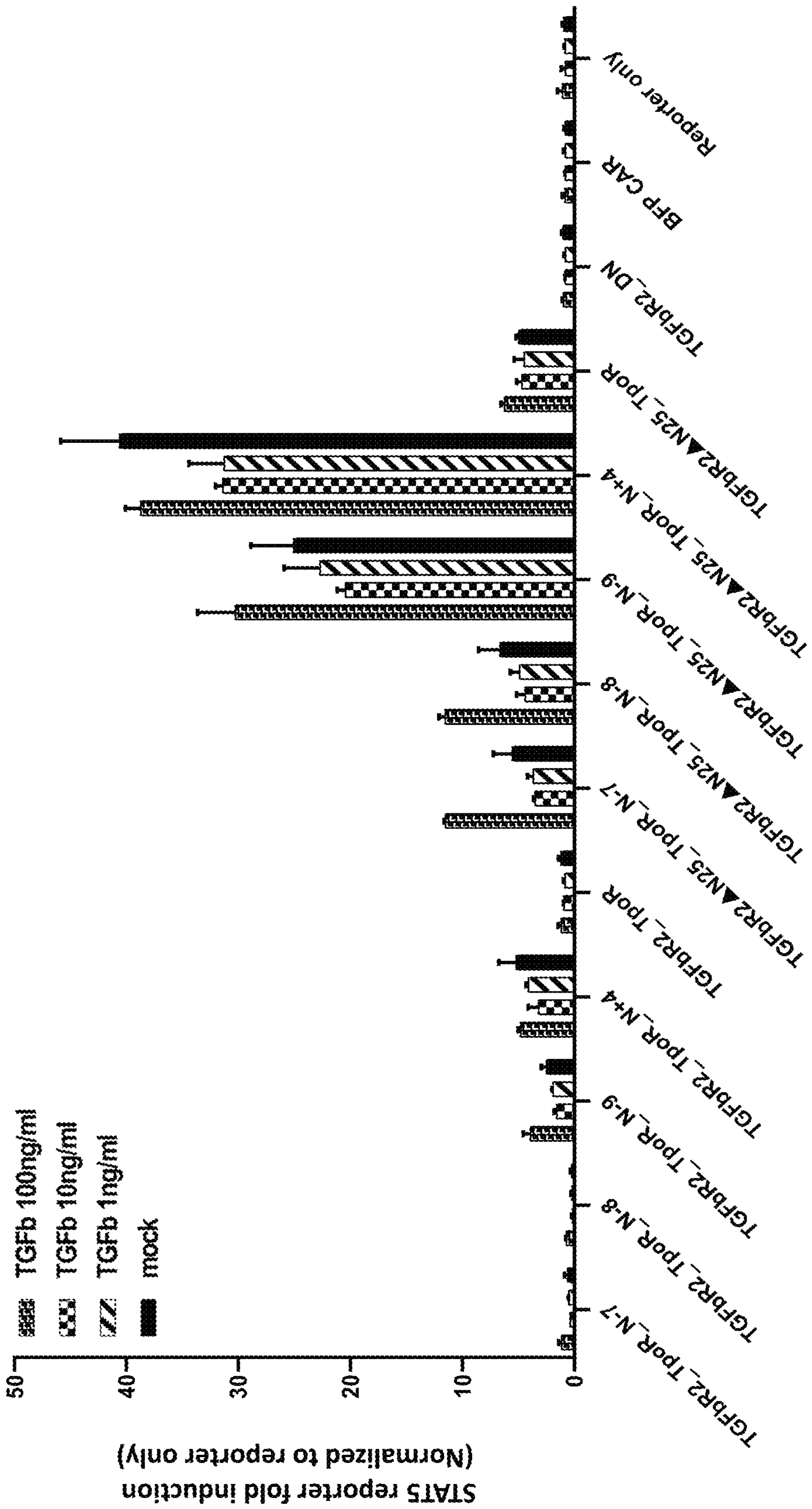
FIG. 6C shows the activation of the chimeric cytokine receptors of FIG. 6A, evaluated by the STAT reporter activity.

FIGS. 6A-6C show the inhibition of TGF-β signaling by the expression of chimeric cytokine receptors constructed with TGFβR2 having modifications. FIG. 6A shows a schematic of the modification introduced into the TGFβR2 cassette. The lentiviral vectors used were constructed similarly as described in Example 1. To abolish the engagement of TGFβR1, a truncation (ΔN25) was introduced into the TGFβR2 binding domain based on the previous constructs described when referring to FIGS. 6A-6C ("TGFβR2ΔN25"), and the inhibition of TGF-β signaling was tested by a TGF-β reporter assay. FIG. 6B shows that the TGFβR2N25 chimeric cytokine receptors still retained the ability to inhibit TGF-β signaling. FIG. 6C shows the activation of the chimeric cytokine receptors of FIG. 6A, evaluated by the STAT reporter activity. The amino acid sequences of the transmembrane domains listed in the X-axes of FIGS. 6B-6C are SEQ ID NOs: 29, 38, 39, 40, and 53, with a binding domain sequence of SEQ ID NO: 4 or SEQ ID NO: 3, presented in Tables 1 and 3.

It was determined that the truncation in the TGFβR2 binding domain enhances the cytokine signaling by 5-10 fold, even in the absence of a TGF-β ligand. Interestingly, the ΔN25 truncation was able to enhance the signaling synergistically with the TpoR TM truncations (e.g. N-7, N-8, N-9 and N+4). This combinatorial use of the TGFβR2 binding domain and TpoR TM truncation mutants represents a novel approach for simultaneously inhibiting immunosuppressive TGF-β signaling while transmitting immune-potentiating cytokine signaling.

Figure 7:
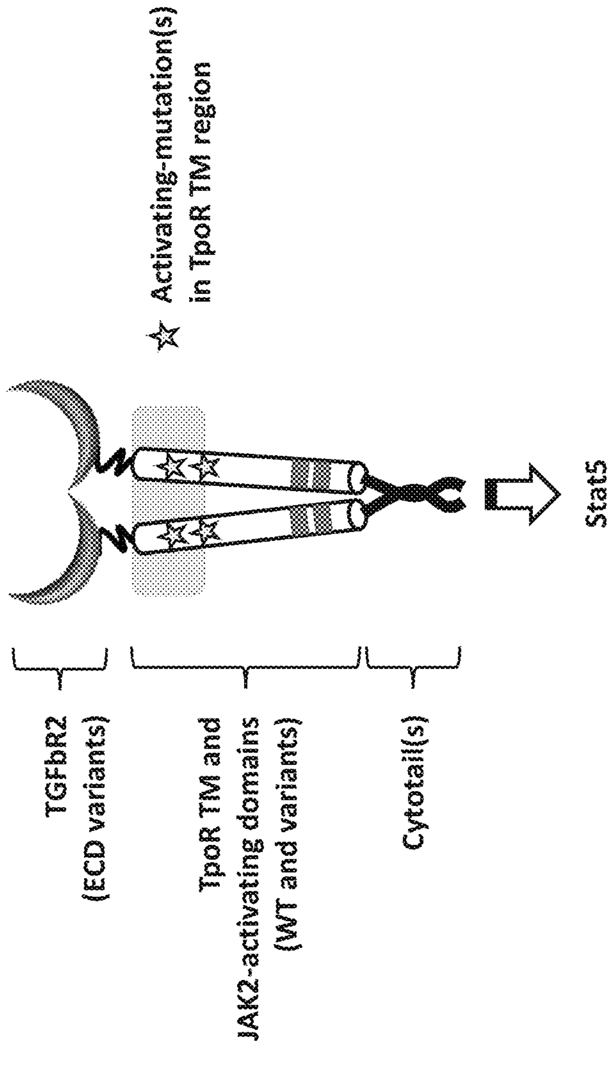
FIG. 7 shows a schematic of the constitutively active chimeric cytokine receptor.

Example 4: Design and Testing of the Constitutively Active Chimeric Cytokine Receptor FIG. 7 shows a schematic of the constitutively active chimeric cytokine receptor. To enable constitutively active signaling of the cytokine intracellular domains, double mutations that inherently dimerize the TPOR transmembrane domain and activate the JAK-STAT pathway were introduced in the TPOR transmembrane domain. As shown as an exemplary construct in FIG. 7, the binding domain comprises the extracellular portion of TGFβR2; exemplary transmembrane domains may comprise the SEQ ID NOs 29, 40, 53 or 60.

Figure 8A:
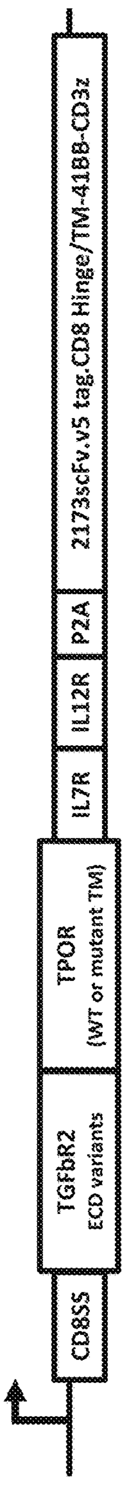
FIG. 8A shows a schematic of the modification introduced into the TGFβR2 cassette.
Figure 8B:
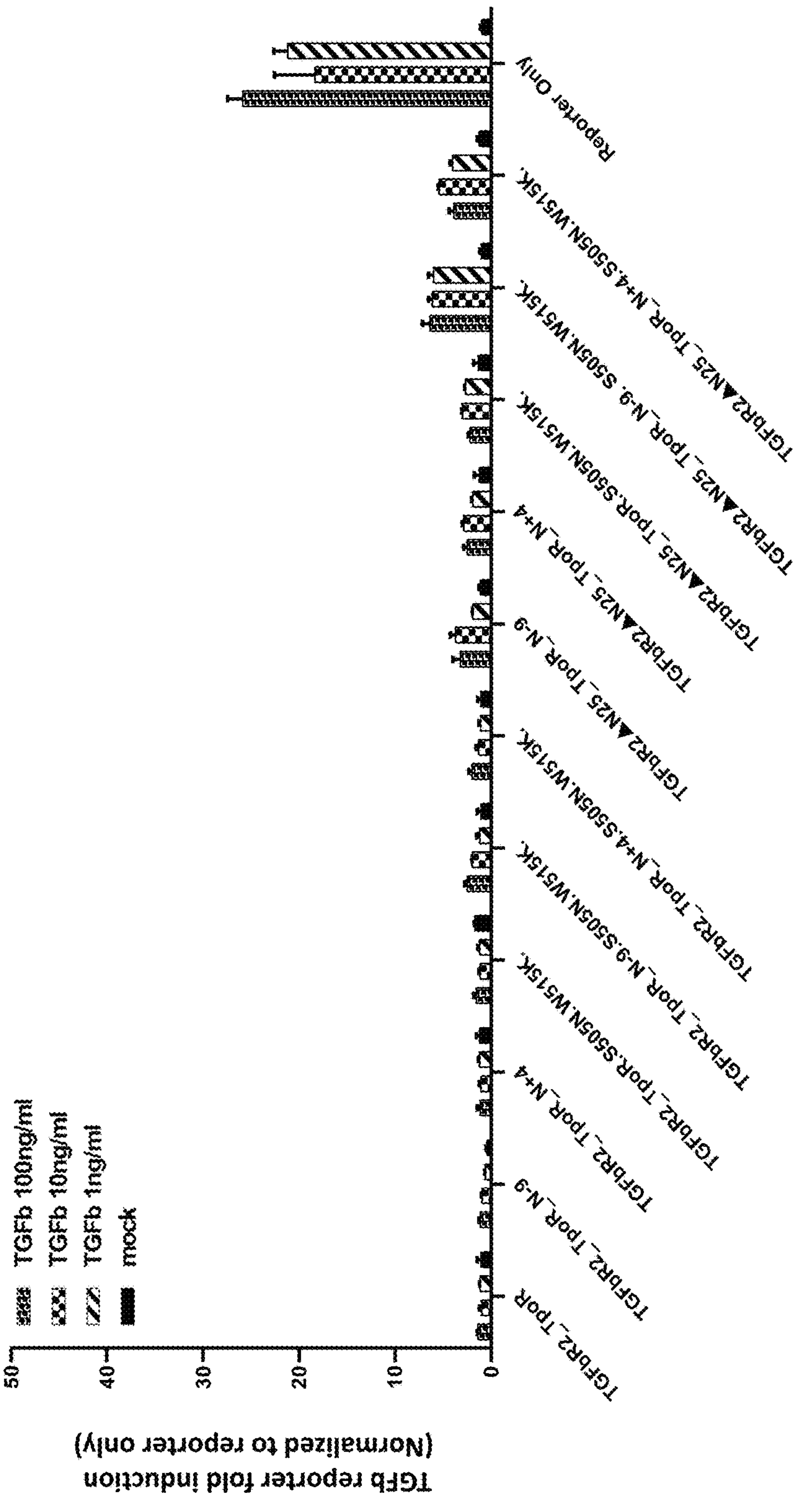
FIG. 8B shows the inhibition of TGF-β signaling by the expression of the chimeric cytokine receptors of FIG. 8A.
Figure 8C:
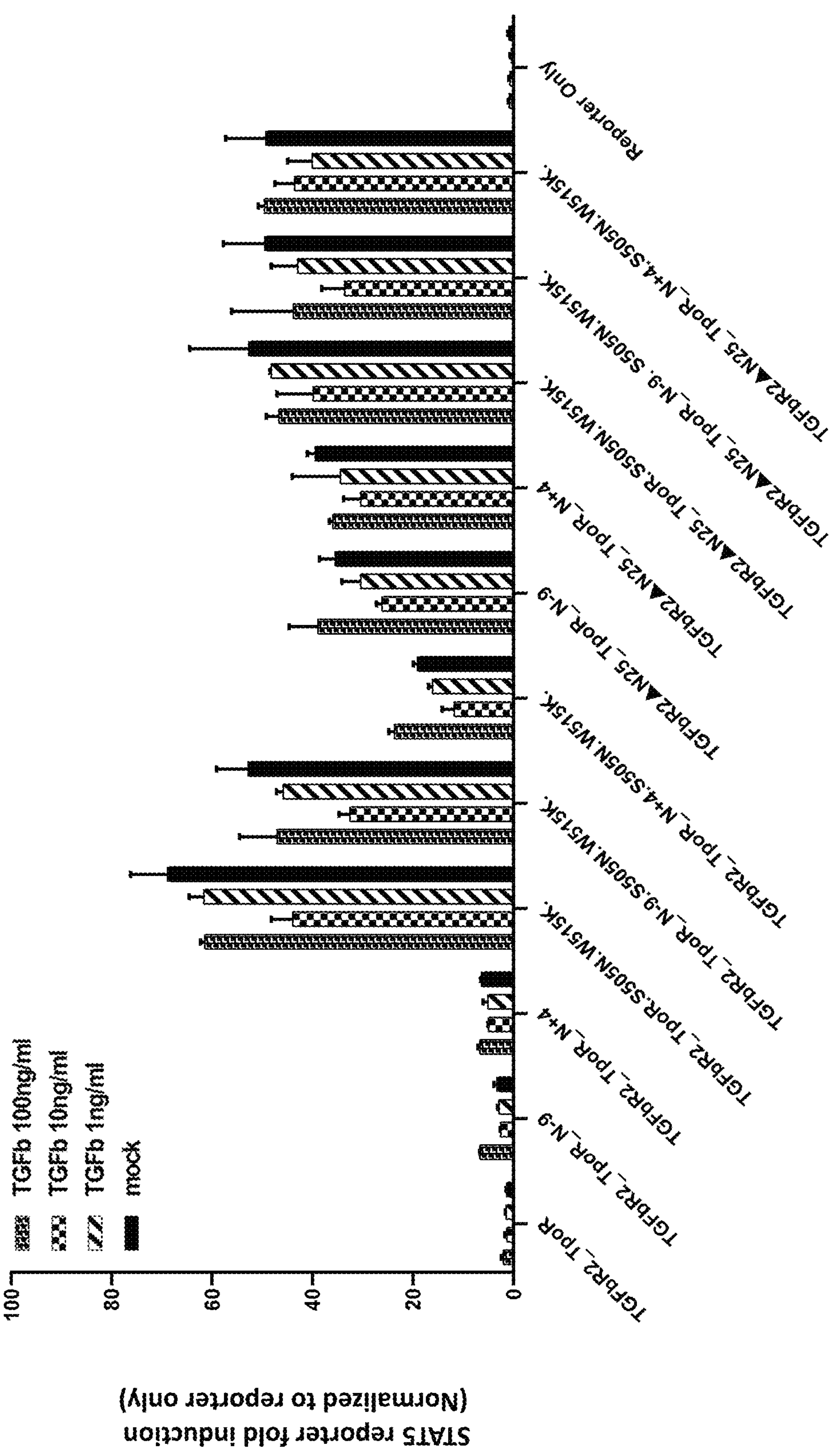
FIG. 8C shows the activation of cytokine signaling via the chimeric cytokine receptors of FIG. 8A, measured by the STAT5 reporter activity.

FIGS. 8A-8C show the design and tested function of the constitutively active chimeric cytokine receptors. The lentiviral vectors used were constructed similarly as described in Example 1. A double mutant (S505N, W515K) was introduced into the TPOR cassette to enforce the dimerization and activation of the receptors, in combination with variants that had shown the most promising functionality (e.g. TGFβR2ΔN25, N-9 and N+4 truncations in the TPOR cassette). FIG. 8A shows a schematic of the modification introduced into the TGFβR2 cassette. FIG. 8B shows the inhibition of TGF-β signaling by the expression of the chimeric cytokine receptors of FIG. 8A. FIG. 8C shows the activation of cytokine signaling via the chimeric cytokine receptors of FIG. 8A, measured by the STAT5 reporter activity in 293 cells. Compared to the parental designs (TGFβR2_TpoR, TGFβR2_TpoR_N-9, and TGFβR2_TpoR_N+4), receptors with the S505N and W515K mutations display substantial cytokine signaling (e.g. TGFβR2_TpoR.S505.W515K, TGFβR2_TpoR_N-9.S505N.W515K). The sequences of the transmembrane domains listed in the X-axes of FIGS. 8B-8C comprise SEQ ID NOs: 40, 53, 59, and 60 with a binding domain sequence of SEQ ID NO: 4 or SEQ ID NO: 3, presented in Tables 1 and 3.

Example 5 Testing of Additional Chimeric Cytokine Receptors

Figure 10B:
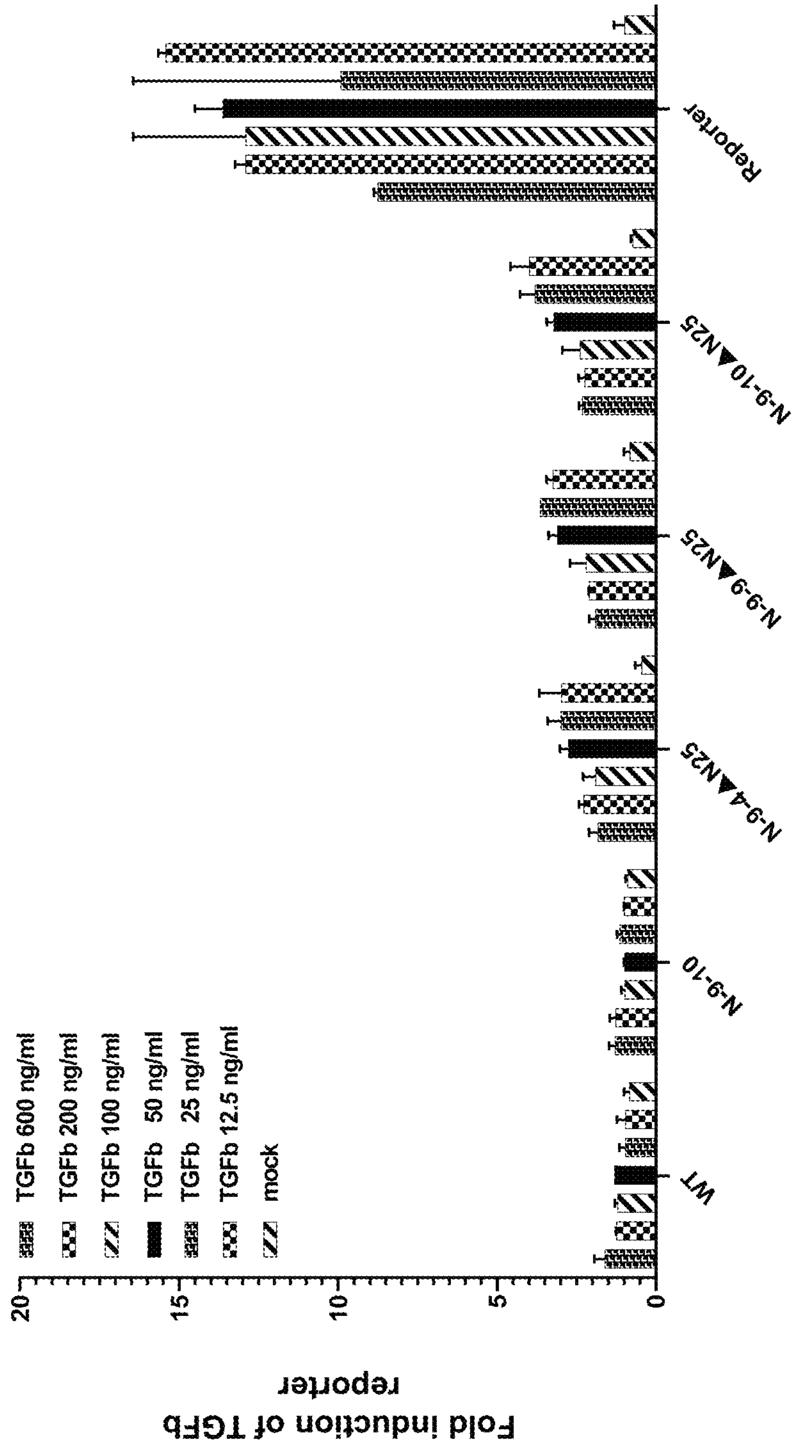
FIG. 10B shows the inhibition of endogenous TGF-β signaling as determined by luciferase assay by the overexpression of TGF-β-driven chimeric cytokine receptors shown in FIG. 10A, in the presence of different concentrations of TGF-β.
Figure 10C:
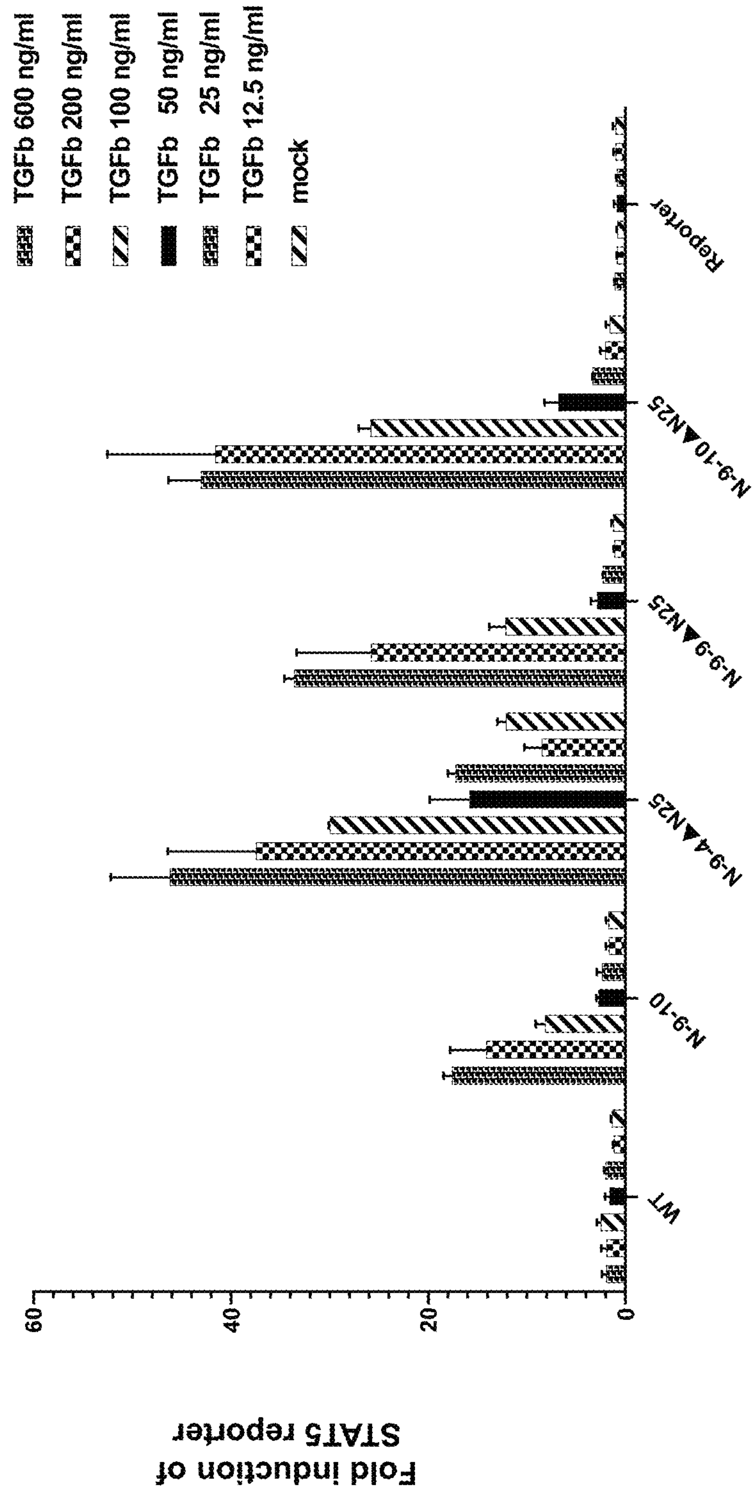
FIG. 10C shows the activation of chimeric cytokine receptors in the presence of TGF-β at various concentrations.

FIG. 10A shows additional design of inducible TGF-β-driven chimeric cytokine receptors. Constructs with further truncations in the transmembrane domain to decrease the flexibility between the ECD and intracellular signaling domain were made. FIG. 10B shows the inhibition of endogenous TGF-β signaling as determined by luciferase assay by the overexpression of TGF-β-driven chimeric cytokine receptors shown in FIG. 10A in 293 cells in the presence of different concentrations of TGF-β. Some of the constructs also carry the ΔN25 deletion in the ECD domain ("TGF-βR2ΔN25"). All TGF-β-driven chimeric cytokine receptors in FIG. 10B inhibited the endogenous TGF-β signaling, although clones with the ΔN25 deletion showed slightly decreased inhibition of the TGF-β signaling. The data in FIG. 10C show the activation of chimeric cytokine receptors in the presence of TGF-β at various concentrations. Chimeric receptors with the deletion in the transmembrane domain and ΔN25 deletion induced STAT5 signaling in the presence of TGF-β.

Figure 11A:
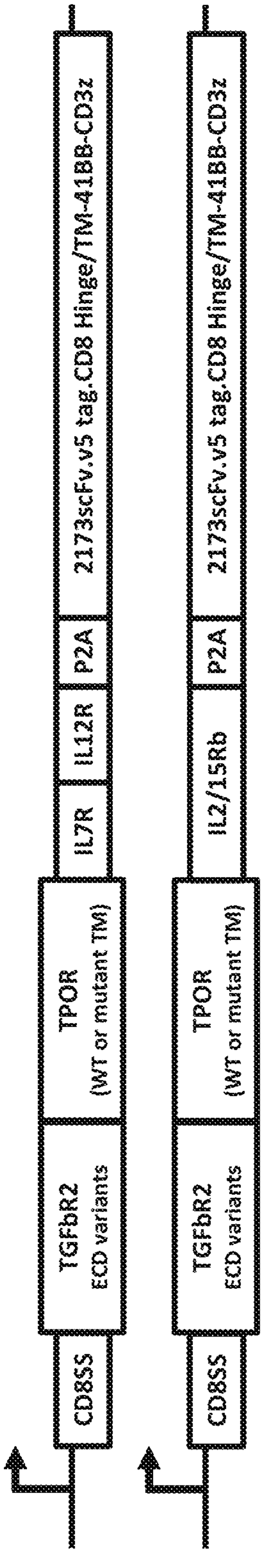
FIG. 11A shows schematics of chimeric cytokine receptor (CCR) CAR expression construct where the expression of the CCR and the EGFRvIII CAR are linked by a P2A peptide.
Figure 11B:
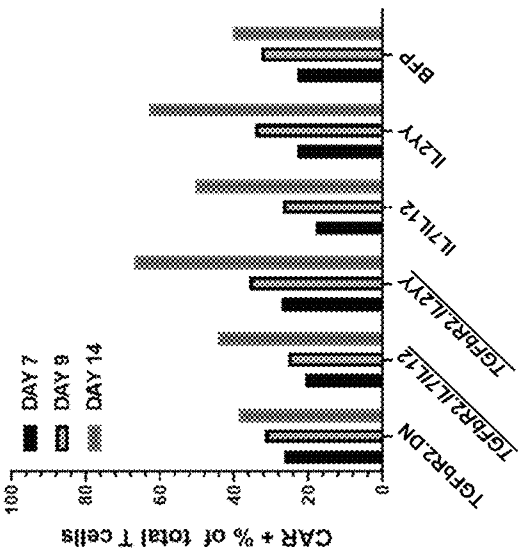
FIGS. 11B-11C are bar graphs depicting the yield of CAR+ T cells expressing various CCRs.
Figure 11C:
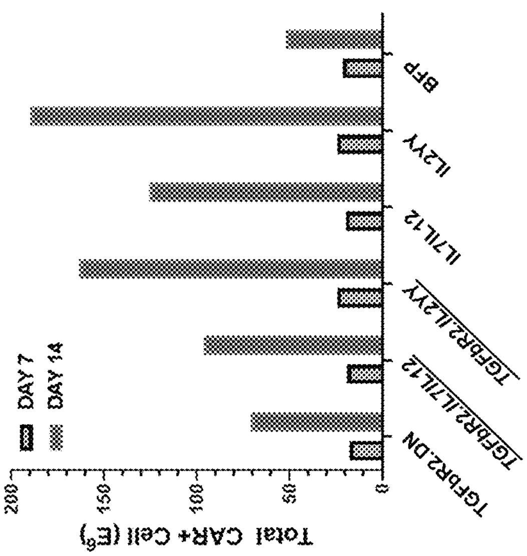

We next tested the constitutive chimeric receptors in CAR T cells. All constructs tested in FIGS. 11-16 contain the S505N and W515K substitutions in the TPOR/MPLR transmembrane domain. FIG. 11A shows schematics of the lentiviral vectors used to co-express in CAR T cells the TGF-βR2 chimeric cytokine receptors with the EGFRvIII-specific CAR (2173scFv). All chimeric cytokine receptors carry dimerization mutations in the transmembrane domain of TPOR/MPLR (S505N, W515K, see SEQ ID NO:60), and one or more cytokine receptor recruiting domains joined in tandem to mimic signaling from one or more cytokines. "IL2YY" refers to IL2Rb (393-433, 518-551), and "IL7IL12" refers to IL7R(316-459) and IL12Rb2(775-825) joined in tandem. As controls, CAR T cells were also produced, expressing a dominant negative truncation of TGF-βR2 ("TGF-βR2.DN"), constitutive chimeric cytokine receptor without the TGF-βR2 ECD ("IL7IL12", "IL2YY") or a BFP protein. The method to produced CAR T cells were as described in Sommer C, et al. Preclinical Evaluation of Allogeneic CAR T Cells Targeting BCMA for the Treatment of Multiple Myeloma. *Mol Ther.* 2019. doi:10.1016/j.ymthe.2019.04.001 and Sommer C, et al. Allogeneic FLT3 CAR T Cells with an Off-Switch Exhibit Potent Activity against AML and Can Be Depleted to Expedite Bone Marrow Recovery. *Mol Ther.* 2020. doi:10.1016/j.ymthe.2020.06.022. In brief, primary T cells from a healthy donor were transduced at MOI of 5, with lentiviruses expressing the CAR and each of the TGFβR2 chimeric cytokine receptors or controls. FIG. 11B shows the percentage of CAR+ T cells at day 7, 9 and 14 during CAR T cell production. CAR T cells with a constitutive chimeric cytokine receptor as indicated ("TGF-βR2.IL7IL12," "TGF-βR2.IL2YY," "IL7IL12," or "IL2YY") show higher proliferation and enrichment as compared to BFP alone over the production period. As the result, more EGFRvIII CAR+ T cells were obtained over time as compared to CAR T expressing BFP alone without a chimeric cytokine receptor (FIG. 11C).

Figure 11E:
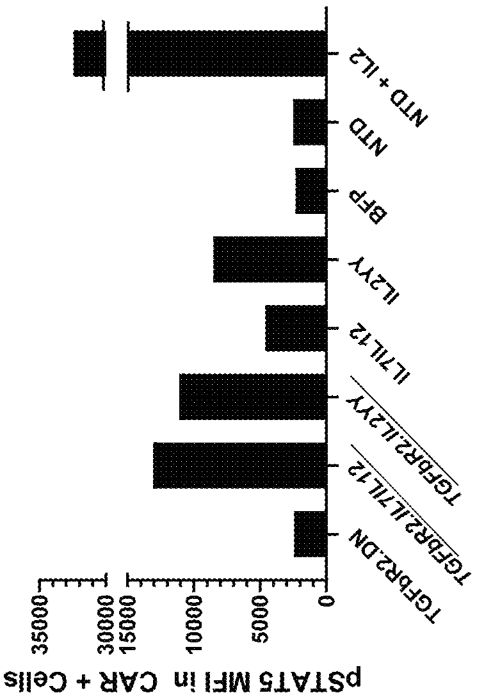
FIGS. 11D-11E show results of STAT5 phosphorylation in CAR T cells expressing various CCR or controls.
Figure 11D:
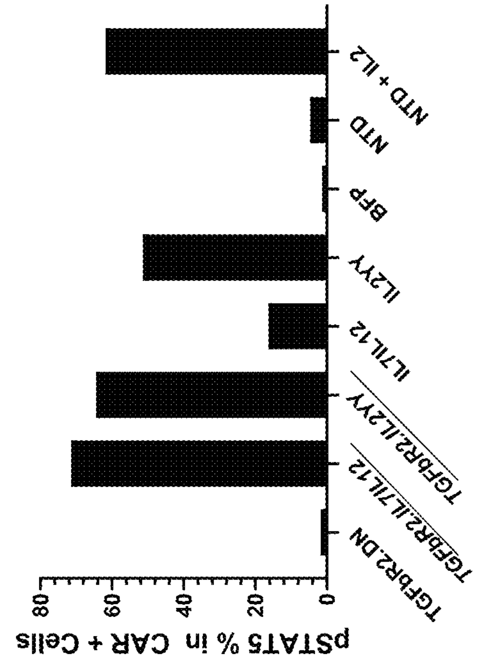

FIGS. 11D and 11E show results of assessing STAT 5 phosphorylation in the CAR T cells co-expressing either the various chimeric cytokine receptors or controls. The antibody used for detecting phosphorylated STAT5 was from BD Biosciences (BDB612599). CAR T cells with constitutive chimeric cytokine receptor with an TGF-βR2 ECD, i.e., TGF-βR2.IL7IL12 or TGF-βR2.IL2YY exhibited higher level of STAT5 phosphorylation, even in the absence of TGFβ, as compared to IL2YY and IL7IL12, i.e., constitutive chimeric cytokine receptors without a TGF-βR2 ECD, indicating stronger cytokine signaling with a TGF-βR2 ECD domain. The data suggest that the TGF-βR2 ECD improved the intercellular recruiting domain signaling in CAR T cells.

Figure 11F:
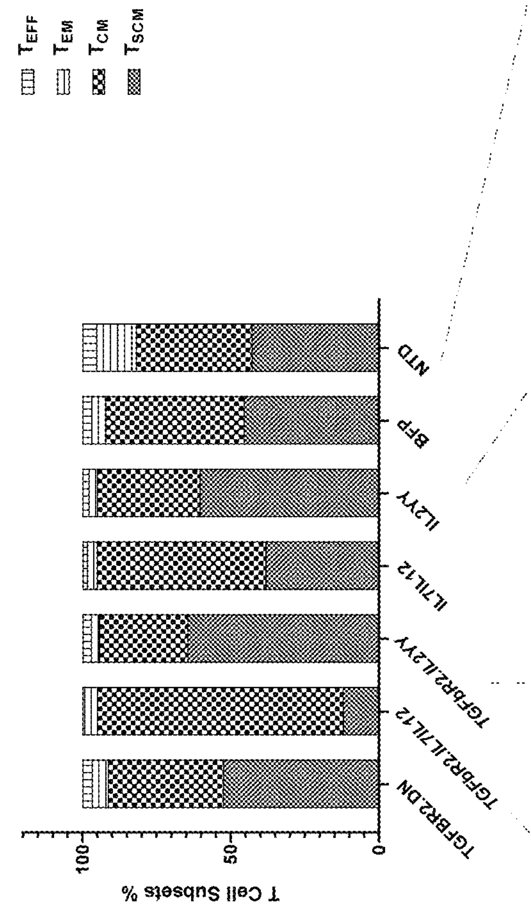
FIGS. 11F-11G depict CAR T cells phenotype at Day 14 of production.
Figure 11G:
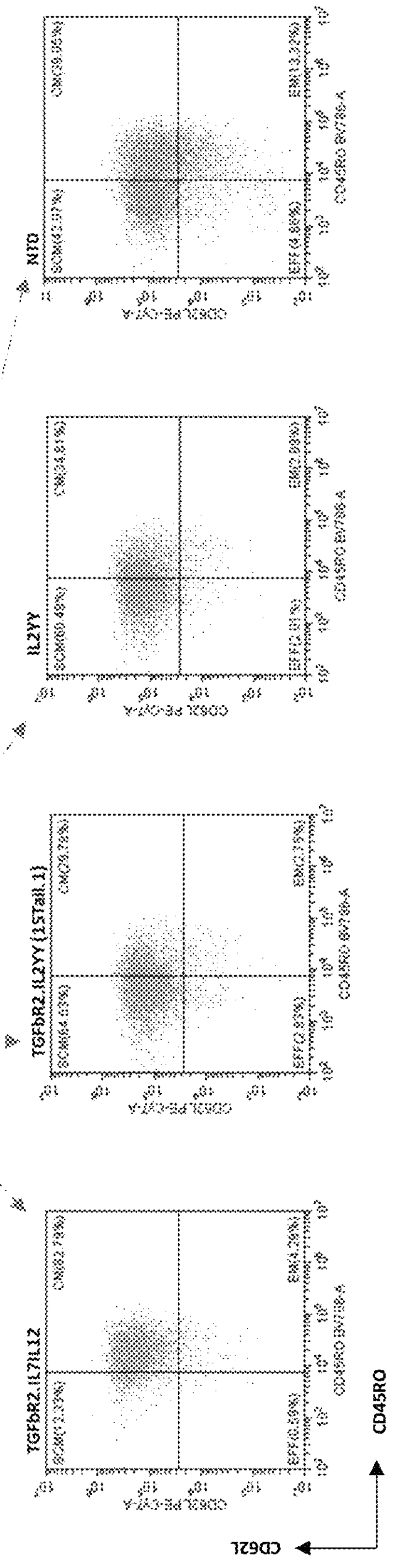

The data in FIGS. 11F and 11G show that the chimeric cytokine receptors regulated the differentiation of CAR T cells at Day 14 of CAR T production. CD62L and CD45RO staining was conducted using the antibodies from BioLegned (#304822) and BioLegand (#304234), respectively. Notably, CAR T cells expressing the TGF-βR2.IL7IL12 chimeric cytokine receptor largely differentiated into central memory T cells ($CD62L^{hi}CD45RO^{hi}$)—a result likely due to strong IL12Rb signaling, while CAR T cells expressing the TGFβR2.IL2YY or IL2YY chimeric cytokine receptor exhibited an enriched population of stem cell-like (stem) memory T cell ($CD62L^{hi}CD45RO^{low}$), a desirable T cell phenotype that has been associated with better clinical outcome.

Figure 11H:
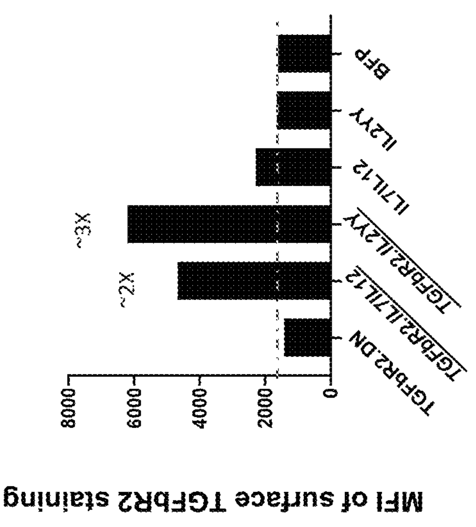
FIG. 11H shows results of total TGF-βR2 extracellular staining on CAR T cells.
Figure 11I:
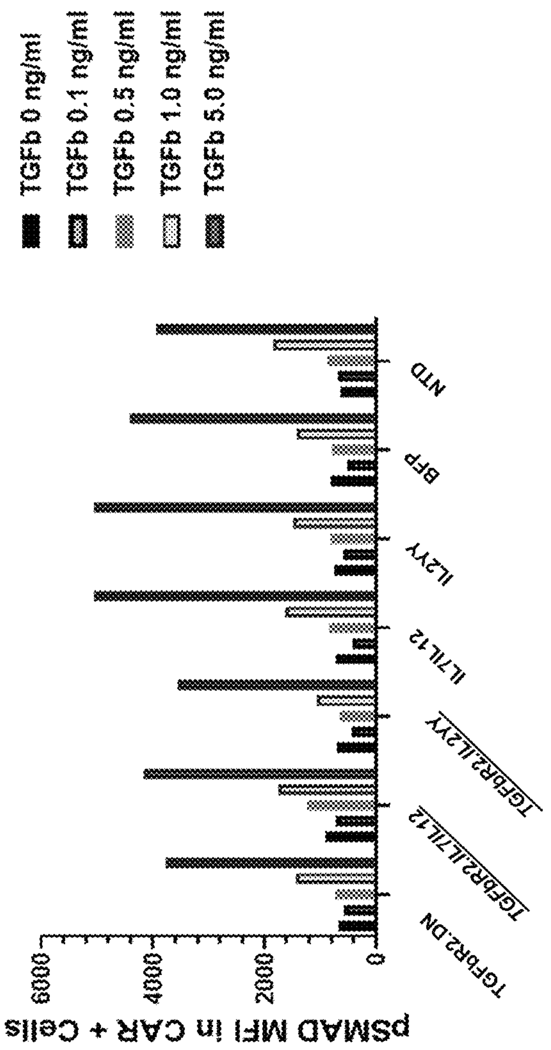
FIG. 11I depicts results of inhibition of TGF-βR2 signaling in CAR T cells expressing different CCRs in the presence of different concentrations of TGF-β.

Next, we compared the expression of TGF-βR2 chimeric cytokine receptor to the expression of endogenous TGF-βR2 by measuring total surface ECD by flow cytometry using an anti-human TGF-βR2 polyclonal antibody (R&D Systems, FAB2411A100). The results in FIG. 11H show an MFI of the ECD staining at about 1400-2300 resulting from the endogenous TGF-βR2 in the CAR T cells expressing the IL7IL12 or IL2YY chimeric cytokine receptor and CAR T cells expressing BFP. CAR T cells expressing a TGF-βR2 chimeric cytokine receptor (TGF-βR2.IL7IL12 and TGF-βR2.IL2YY) showed a 2-3 folds excessive MFI value, indicating a 2-3 folds higher levels of the TGF-βR2 ECD staining over the levels from endogenous TGF-βR2 receptor. FIG. 11I shows the level of SMAD phosphorylation within CAR T cells expressing different chimeric cytokine receptors or controls when exposed to various concentrations of TGFβ. The antibody used for detecting phosphorylated SMAD was from BD Biosciences (BDB562586). The results show that CAR T cells expressing the TGF-βR2.IL7IL12 and TGF-βR2.IL2YY chimeric cytokine receptors exhibited decreased SMAD phosphorylation as compared to the CAR T cells expressing the IL7IL12 and IL2YY chimeric cytokine receptors without the TGF-βR2 ectodomain, respectively.

Figure 12A:
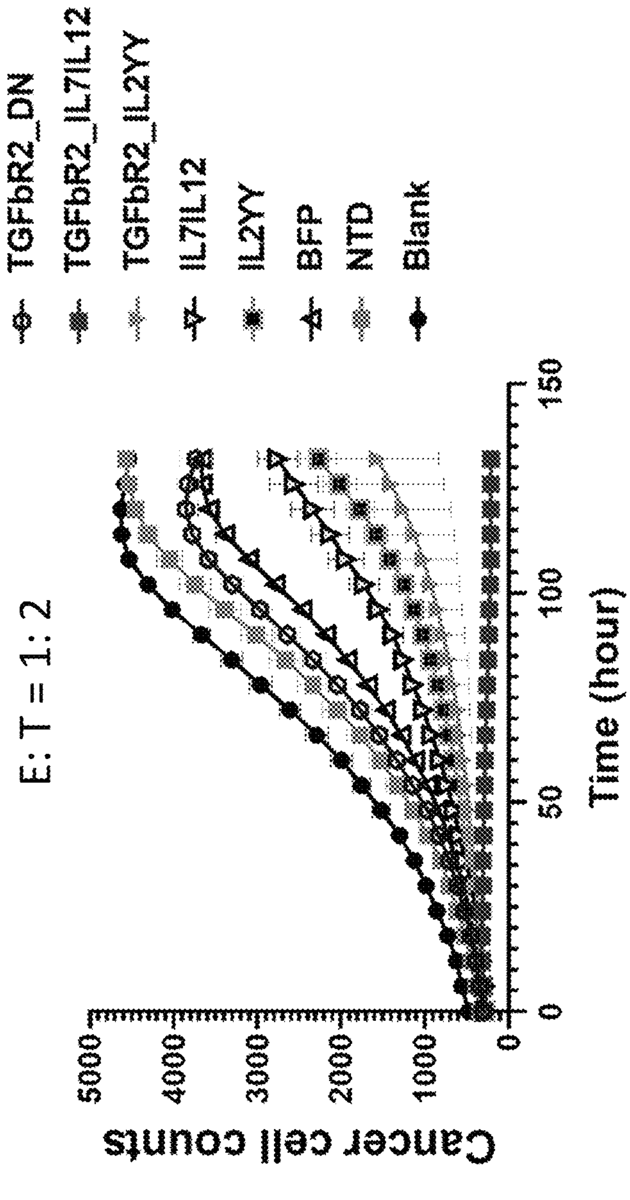
FIG. 12A exhibits results of cytotoxicity assay of CAR T cells expressing various CCRs against U87-EGFRvIII cells in the absence of exogenous TGFβ.
Figure 12B:
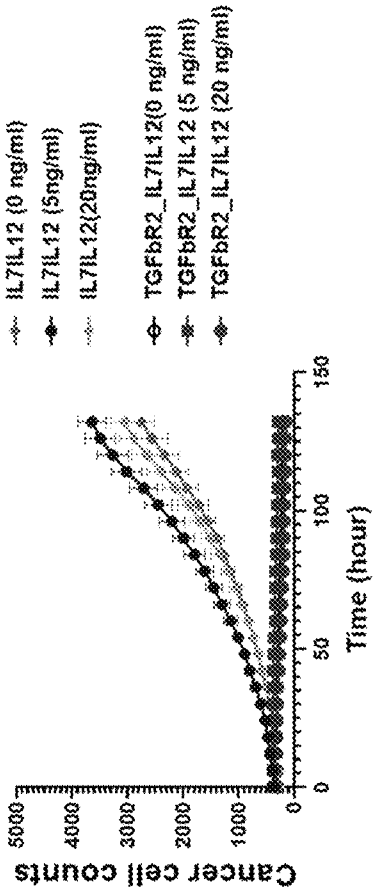
FIGS. 12B-12C show results of cytotoxicity assay of CAR T cells expressing various CCRs at different concentrations of TGFβ.
Figure 12C:
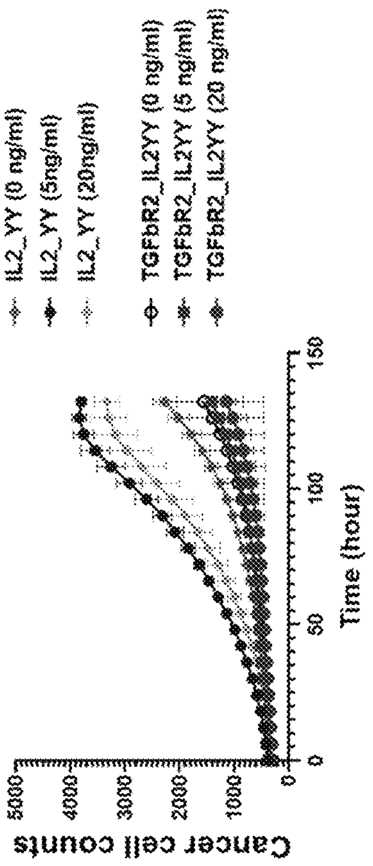

We next evaluated anti-tumor activities of the EGFRvIII CAR T cells expressing different chimeric cytokine receptors or controls against the target cells U87-EGFRvIII cells. In brief, CAR T cells were incubated with 10,000 target cells at E: T ratio of 1:2 in 200 ul of RPMI medium with 10% of FBS, and TGF-β at various concentrations of 0, 5, and 20 ng/ml. After one week of co-culture with target cells, the CAR T cells in 100 ul supernatant were transferred into new target cells (10,000) with the same TGFβ concentrations as the previous week. The cytotoxicity of the CAR T cells in the second week without added TGF-β was assessed and the results are shown in FIG. 12A. In the absence of exogenous TGFβ, CAR T cells expressing TGF-βR2 chimeric cytokine receptors (TGF-βR2.IL7IL12 and TGF-βR2.IL2YY) showed the most persistent cytotoxicity, with most of the target cells killed by the CAR T cells. CAR T cells expressing chimeric cytokine receptors without the TGF-βR2 ECD (IL7IL12 and IL2YY) also exhibited considerable cytotoxicity and inhibited the growth of the U87 cells till the second week. In comparison, CAR T cells with BFP or TGF-βR2.DN lost the activity and failed to inhibit the growth of the U87 cells (FIG. 12A). The data indicate that TGF-βR2 chimeric cytokine receptors enable more persistent cytotoxicity against the target cells. In the presence of TGFβ, the activity of CAR T cells without expressing a chimeric cytokine receptor with a TGFβR2 ECD was inhibited to various levels by TGF-β, likely the effect of signal transduction via the endogenous TGF-β receptors (FIGS. 12B-12C). In contrast, CAR T cells expressing TGF-βR2 chimeric cytokine receptors were resistant to TGF-β inhibition and were able to maintain strong cytotoxicity in conditions up to 20 ng/ml of TGF-β (FIGS. 12B, 12C).

Figure 13B:
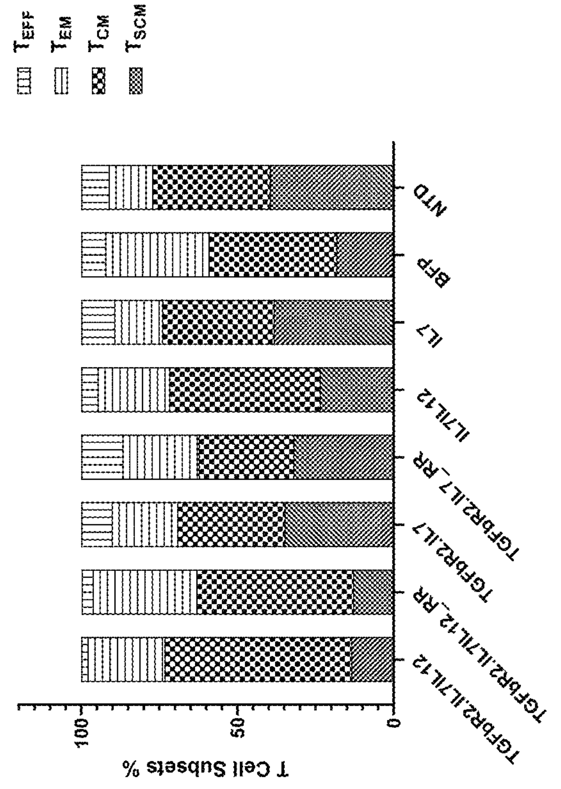
FIG. 13A shows STAT5 phosphorylation and FIG. 13B depicts the T cell phenotype of CAR T cells expressing CCRs with the S505N/W515K with or without the K553R/K573R substitutions in the TOPR/MPLR and JAK binding domain. All TGFbR2 chimeric cytokine receptor constructs tested in this experiment contain the S505N/W515K substitutions. The constructs labeled RR further contain the additional K553R/K573R substitutions.
Figure 13A:
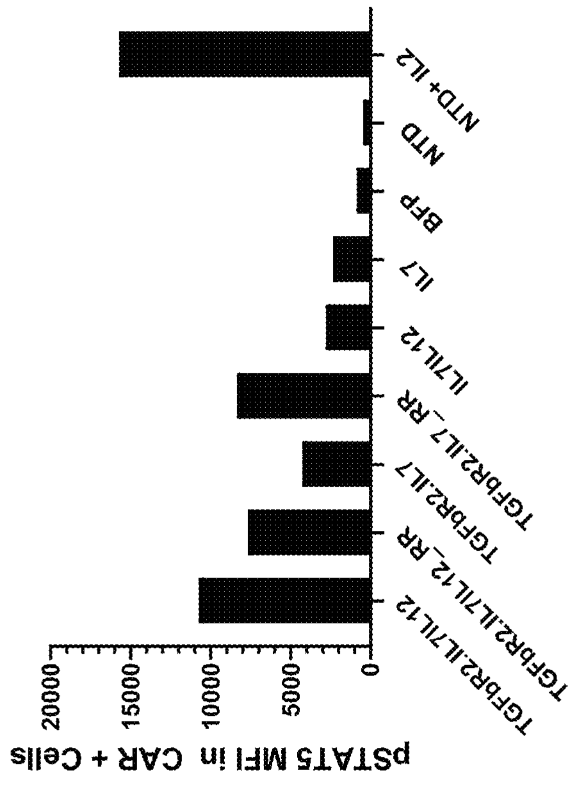

We next evaluated further modified constitutive TGF-βR2 chimeric cytokine receptor in CAR T cells. As shown above constitutive TGFβR2.IL7IL12 chimeric cytokine receptor having the S505N/W515K substitutions in the TPOR/MPLR transmembrane domain and the IL7Ra/IL12Rb recruiting domains (e.g., SEQ ID NO:163) increased STAT5 phosphorylation and led to substantial differentiation of central memory T cells. As the IL12 cytokine signaling has been implicated in the differentiation of memory T cells, we designed the TGF-βR2.IL7 chimeric cytokine receptor that eliminates the IL12 signaling. In addition, we introduced two mutations in the TpoR JAK-binding domain, K553R and K573R, (designated as "RR", e.g., SEQ ID NOS:165 and 170), to decrease ubiquitin-induced receptor degradation. See Saur S J, Sangkhae V, Geddis A E, Kaushansky K, Hitchcock IS. Ubiquitination and degradation of the thrombopoietin receptor c-Mpl. *Blood.* 2010. doi:10.1182/blood-2009-06-227033. CAR T cells expressing the chimeric cytokine receptor were produced and evaluated for STAT5 phosphorylation and T cell differentiation. Similar as before, these further modified TGF-βR2 chimeric cytokine receptors showed higher levels of STAT5 signaling as determined by STAT5 phosphorylation than the chimeric cytokine receptors without the TGF-βR2 ECD domain (both the IL7IL12 and IL7 chimeric cytokine receptor constructs contain the S505N/W515K substitutions) (FIG. 13A). In the assessment of T cell differentiation, CAR T cells expressing chimeric cytokine receptors without the IL12R recruiting domain (TGF-βR2.IL7, TGF-βR2.IL7_RR, and IL7) showed an increased proportion of stem memory T cell than their counterparts with the IL12R recruiting domain (FIG. 13B). These data demonstrate that by selecting different cytokine receptor motifs, we can modulate the TGF-βR2 chimeric cytokine receptors signaling and T cell differentiation.

To evaluate how the TGF-βR2 chimeric cytokine receptors affect T cell functions, CAR T cells were evaluated in long-term killing assay. In brief, CAR T cells expressing different chimeric cytokine receptor were mixed with 10,000 U87-EGFRvIII cancer cells at an E:T ratio of 1:1, in 200 ul RPMI medium with 10% FBS, with or without 5 ng/ml of TGFβ. Every two or three days, 100 ul of the supernatant with CAR T cells were transferred onto 10,000 fresh target cells to the final volume of 200 ul RPMI medium with 10% FBS and 5 ng/ml of TGFβ, and the survival of old target cells were quantified. The long-term cytotoxicity of CAR T cells with different TGF-βR2 chimeric cytokine receptors are summarized in FIGS. 14A-B. In the absence of exogenous TGFβ, TGF-βR2 chimeric cytokine receptors with various recruiting domains, for example, TGF-βR2.IL2YY, TGF-βR2.IL7, or TGF-βR2.IL2YYY(IL2Rb(339-379,393-

Figure 14A:
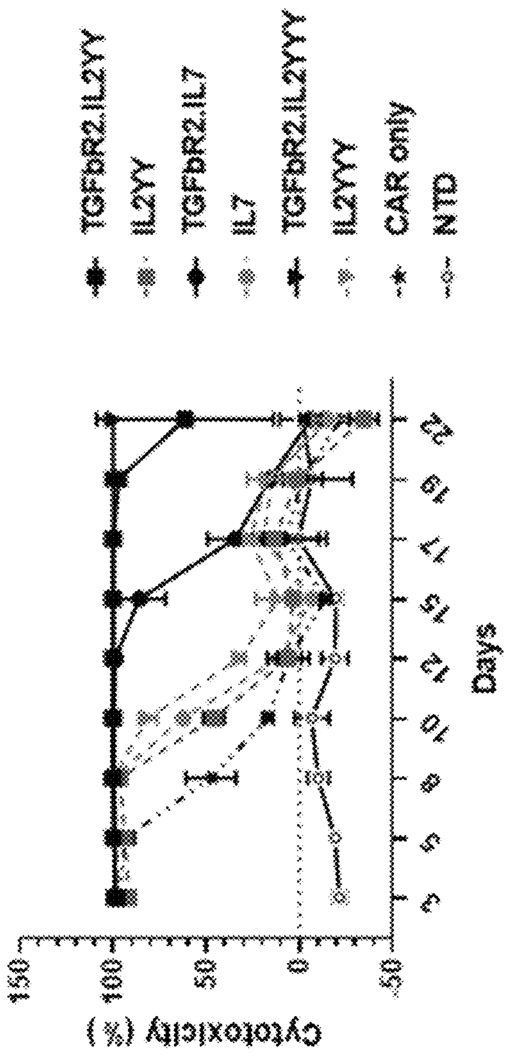
FIGS. 14A-14B show results of long-term cell killing assay of CAR T cells expressing various CCRs in the absence (FIG. 14A) or presence (FIG. 14B) of 5 ng/ml TGFβ.
Figure 14B:
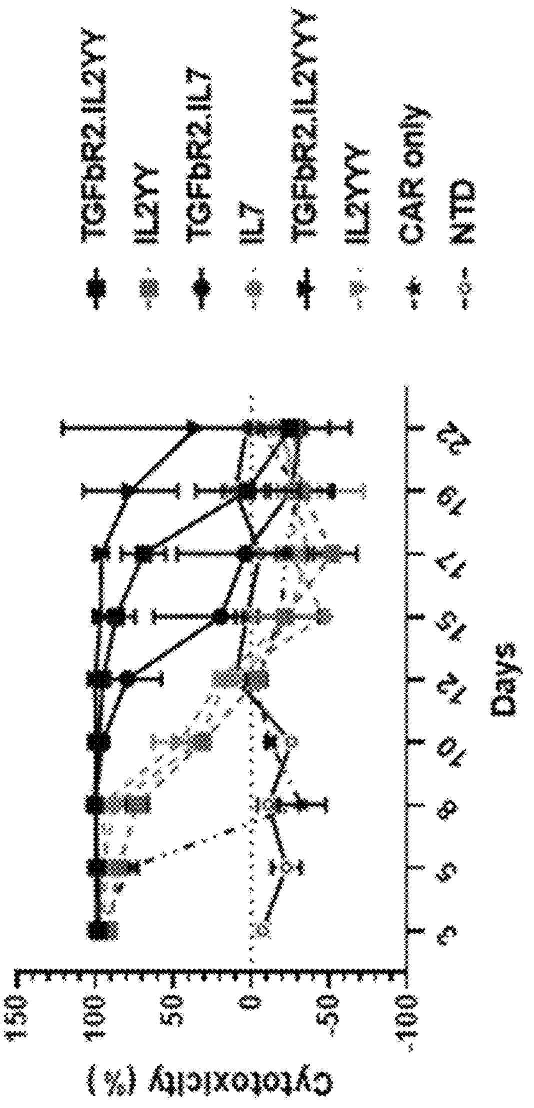

433,518-551)) all conferred more potent and durable cytotoxicity than CAR T cells expressing chimeric cytokine receptors without the TGF-βR2 ECD, confirming the previous observations that the TGF-βR2 ECD domain enhanced the chimeric cytokine receptor signaling (FIG. 14A). In the presence of 5 ng/ml TGFβ, CAR T cells expressing the TGF-βR2 chimeric cytokine receptor maintained more potent and persistent cytotoxicity than CAR T cells with or without expressing a chimeric cytokine receptor without a TGF-βR2 ECD (FIG. 14B). The chimeric cytokine receptors tested all contain the S505N/W515K substitutions, and the TGFβR2.IL2YYY and IL2YYY constructs have the additional H499L substitution in the TOPR/MPLR transmembrane domain.

Figure 15A:
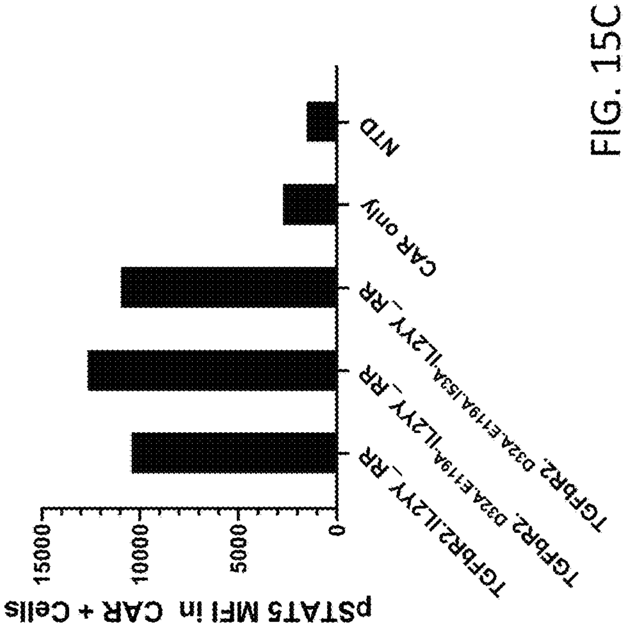
FIGS. 15A-15C show results of activation of STAT5 signaling (FIG. 15A), inhibition of TGFβ signaling (FIG. 15B), and long-term cell killing assay (FIG. 15C) of CAR T cells expressing various CCRs, some of which have reduced affinity for TGFβ (e.g., D32A, E119A and/or I53A substitutions in the ECD of TGFβR2).
Figure 15B:
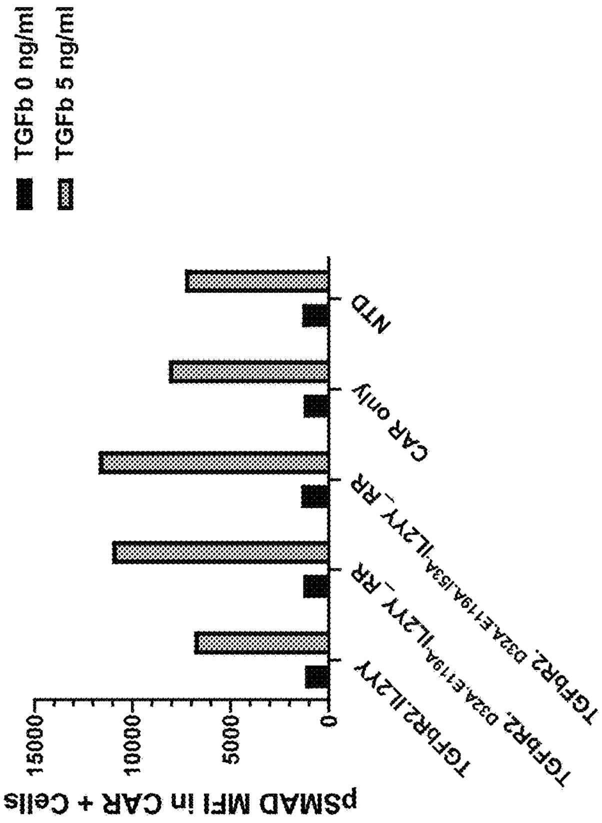

To further assess the inhibition on TGFβ signaling by a TGF-βR2 chimeric cytokine receptor and its influence on the functionality of CAR T cells, we analyzed the TGF-βR2.IL2YY_RR chimeric cytokine receptor (SEQ ID NO: 166), which carries the dimerization mutations in the TM region (S505N, W515K) and the degradation-resistant mutations (K553R and K573R) in the JAK-binding domain. We designed two additional variants bearing mutations in the TGF-βR2 ECD (D32A.E119A and D32A.E119A.I53A) that abolished the receptor's ability to bind the TGFβ ligand. CAR T cells expressing the designated chimeric cytokine receptors were produced and evaluated for cytokine signaling (pSTAT5), TGFβ signaling (pSMAD), and persistency of cytotoxicity against U87-EGFRvIII target cells. FIG. 15A shows the analysis of STAT5 signaling in the CAR T cells, in which all the TGF-βR2 chimeric cytokine receptors led to strong STAT5 phosphorylation in CAR T cells, comparing to the T cells expressing only the CAR. When the CAR T cells were exposed to 5 ng/ml of TGFβ ligand, various levels of SMAD phosphorylation were observed. Comparing to TGF-βR2 chimeric cytokine receptor with the loss-of-binding mutants, TGF-βR2.IL2YY_RR with the wildtype TGF β binding domain exhibited a decreased level of SMAD phosphorylation, indicating that the endogenous TGFβ signaling was successfully inhibited by the TGF-βR2 chimeric cytokine receptor with a wildtype, functional ligand binding domain (FIG. 15B).

Figure 15C:
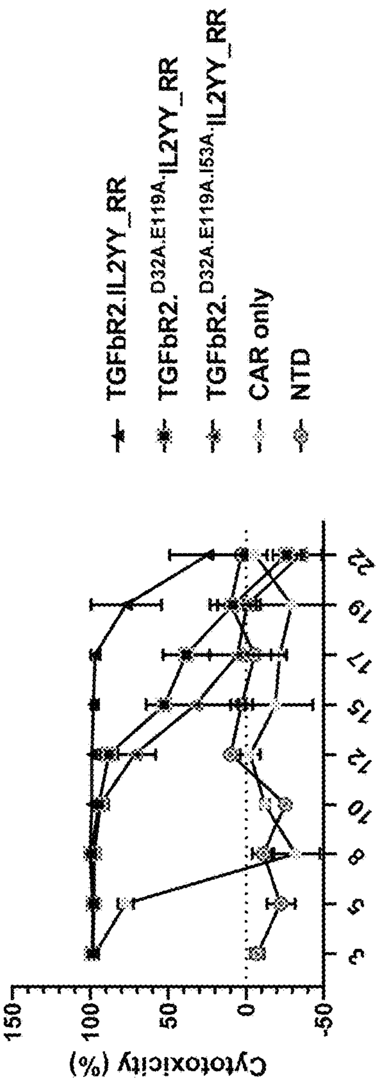

The long-term cytotoxicity of CAR T cells expressing different TGF-βR2 chimeric cytokine receptor against cancer cells in the presence of 5 ng/ml TGFβ was shown in FIG. 15C. Comparing to the control CAR T cells, which quickly lost the activity to kill target cells at day 8, CAR T cells with TGF-βR2 chimeric cytokine receptor conferred more durable activity. TGF-βR2 chimeric cytokine receptors with impaired ability to bind to TGFβ (D32A.E119A and D32A.E119A.I53A) also showed a faster decline in the cytotoxicity assay than CAR T cells expressing the TGF-βR2.IL2YY_RR chimeric cytokine receptor with a wildtype TGFβ binding ECD. These data demonstrate that both the cytokine signaling and the ability to inhibit endogenous TGFβ signaling are important for the long-term activity of CAR T cells.

Figure 16A:
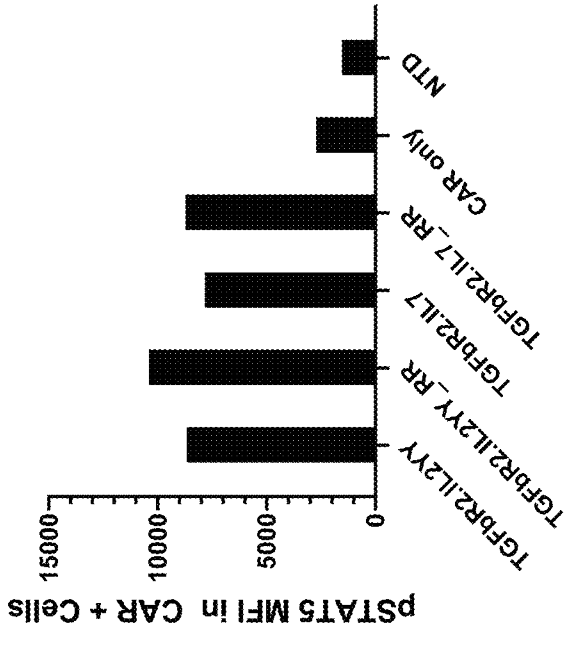
FIGS. 16A-16B compare the effects of TGFβR2 chimeric cytokine receptors with or without the degradation-resistant K533R/K573R substitutions on STAT5 signaling (FIG. 16A) and long-term cell killing (FIG. 16B).
Figure 16B:
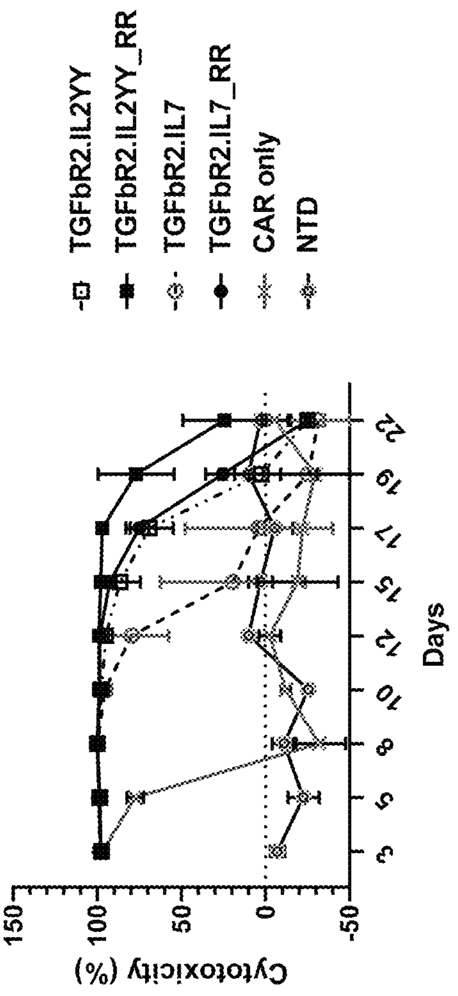

Results in FIGS. 16A-B show that the degradation-resistant mutations, K553R and K573R, can further improve the functionality of the constitutive TGF-βR2 chimeric cytokine receptors. In this experiment, CAR T cells expressing TGF-βR2 chimeric cytokine receptors with or without the degradation-resistant mutations (designated as "RR") were evaluated for the strength of the cytokine signaling as well as the long-term cytotoxicity assay against U87-EGFRvIII in the medium with 5 ng/ml of TGFβ ligand. The TGF-βR2 chimeric cytokine receptor with the K533R and K573R substitutions consistently display a stronger STAT5 phosphorylation (FIG. 16A) and a more durable capability to kill the target cells (FIG. 16B).

What is claimed is:

1. A chimeric cytokine receptor comprising:

a) a binding domain comprising an extracellular portion of a TGF-β receptor, or a TGF-β antigen binding domain;

b) a transmembrane domain;

c) an intracellular Janus Kinase (JAK)-binding domain; and d) an intracellular recruiting domain, wherein the transmembrane domain and the intracellular JAK-binding domain is a fragment of a variant of the full-length thrombopoietin receptor/myeloproliferative leukemia protein receptor (TPOR/MPLR) as shown in SEQ ID NO: 26, wherein the fragment is selected from the group consisting of SEQ ID NO: 30-71, 73-79, 160, and 217-234, and wherein the intracellular recruiting domain is not from TPOR/MPLR.

2. The chimeric cytokine receptor of claim 1, wherein the intracellular recruiting domain is a STAT-recruiting domain.

3. The chimeric cytokine receptor of claim 2, wherein the STAT-recruiting domain is from a receptor selected from BLNK, IL2RG, EGFR, EpoR, GHR, IFNAR1, IFNAR2, IFNAR1/2, IFNLR1, IL10R1, IL12Rb1, IL12Rb2, IL2Rb, IL2small, IL7R, IL7Ra, IL9R, IL15R, and IL21R.

4. The chimeric cytokine receptor of claim 3, wherein the recruiting domain comprises the STAT-recruiting domain from one or more receptors of IL7Ra, IL12Rb2, EGFR, IL21R, or IL2Rb.

5. The chimeric cytokine receptor of claim 2, wherein the STAT-recruiting domain comprises any one of the amino acid sequences of SEQ ID NO: 80-SEQ ID NO: 122 and SEQ ID NO: 161.

6. The chimeric cytokine receptor of claim 2, wherein the STAT-recruiting domain comprises SEQ ID NO: 80, SEQ ID NO: 112, SEQ ID NO: 111, SEQ ID NO: 101, SEQ ID NO: 120, SEQ ID NO: 99, or SEQ ID NO: 161.

7. The chimeric cytokine receptor of claim 1, wherein the chimeric cytokine receptor is a dimerized chimeric cytokine receptor comprising monomers that each comprise a) to d).

8. The chimeric cytokine receptor of claim 1, wherein the binding domain comprising an extracellular portion of a TGF-β receptor comprises an extracellular portion of a wild type TGF-β receptor sequence or one or more mutations to the extracellular portion of a wild type TGF-β receptor sequence.

9. The chimeric cytokine receptor of claim 8, wherein the binding domain comprising an extracellular portion of a TGF-β receptor comprises the extracellular portion of TGFBR2.

10. The chimeric cytokine receptor of claim 8, wherein the binding domain comprising an extracellular portion of a TGF-β receptor comprises the amino acid sequence of any one of SEQ ID NO: 2 to SEQ ID NO: 20 and SEQ ID NO: 159.

11. The chimeric cytokine receptor of claim 1, wherein the transmembrane domain and intracellular JAK-binding domain comprises an amino acid sequence selected from the group consisting of SEQ ID NO: 37-40, 53-56, 44-45, 64 and 70.

12. The chimeric cytokine receptor of claim 1, wherein the chimeric cytokine receptor is inducible.

13. The chimeric cytokine receptor of claim 12, wherein the chimeric cytokine receptor can be induced by a TGF-β ligand or an anti-TGFβR antibody.

14. The chimeric cytokine receptor of claim 13, wherein the TGF-B ligand is any one of TGFβ-1, TGF-μ2, or TGF-β3.

15. The chimeric cytokine receptor of claim 1, wherein the chimeric cytokine receptor is constitutively active.

16. The chimeric cytokine receptor of claim 15, wherein the chimeric cytokine receptor is constitutively active and can be further induced or exhibits further improved activities in the presence of TGF-β or an anti-TGFβR antibody.

17. The chimeric cytokine receptor of claim 1, wherein the chimeric cytokine receptor is capable of inhibiting TGFβR2-mediated signal transduction and/or enhancing STAT-mediated signal transduction when expressed in a cell.

18. The chimeric cytokine receptor of claim 17, wherein the cell is an immune cell.

19. A polynucleotide encoding the chimeric cytokine receptor of claim 1.

20. An expression vector comprising the polynucleotide of claim 19.

21. The expression vector of claim 20, further comprising a polynucleotide encoding a chimeric antigen receptor (CAR).

22. The expression vector of claim 21, wherein the CAR binds to any one or more of the targets selected from BCMA, EGFRVIII, Flt-3, WT-1, CD20, CD23, CD30, CD38, CD70, CD33, CD133, MHC-WT1, TSPAN10, MHC-PRAME, Liv1, ADAM10, CHRNA2, LeY, NKG2D, CS1, CD44v6, ROR1, CD19, Claudin-18.2, Claudin-18A2, Claudin18 isoform 2, Delta-like protein 3 (DLL3), Drosophila Delta homolog 3, Delta3, Mucin 17, Muc3, Fibroblast Activation Protein alpha (FAP alpha), Lymphocyte antigen 6 complex locus protein God (Ly6G6D), c6orf23, G6D, MEGT1, NG25, E3 ubiquitin-protein ligase RNF43, RING finger protein 43, ErbB2, carcinoembryonic antigen (CEA), epithelial cell adhesion molecule (EpCAM), epidermal growth factor receptor (EGFR), CD40, disialoganglioside GD2, GD3, C-type lectin-like molecule-1 (CLL-1), ductal-epithelial mucin, gp36, TAG-72, a glycosphingolipid, glioma-associated antigen, β-human chorionic gonadotropin, alphafetoprotein (AFP), lectin- reactive AFP, thyroglobulin, RAGE-1, MN-CA IX, human telomerase reverse transcriptase, RU1, RU2, intestinal carboxyl esterase, mut hsp70-2, M-CSF, prostase, prostase specific antigen (PSA), PAP, NY-ESO-1, LAGA-1a, p53, prostein, PSMA, survivin, telomerase, prostate-carcinoma tumor antigen-1 (PCTA-1), MAGE, ELF2M, neutrophil elastase, ephrin B2, CD22, insulin growth factor (IGF1)-1, IGF-II, IGFI receptor, mesothelin, a major histocompatibility complex (MHC) molecule presenting a tumor-specific peptide epitope, 5T4, O1, Nkp30, tumor stromal antigen, the extra domain A (EDA) of fibronectin, the extra domain B (EDB) of fibronectin, the AI domain of tenascin-C (TnC AI), fibroblast associated protein (fap), LRP6, melanoma-associated Chondroitin Sulfate Proteoglycan (MCSP), MARTI, MUC1, LMP2, Idiotype, NY-ESO-1, Ras mutant, gp100, proteinase 3, bcr-abl, tyrosinase, hTERT, EphA2, ML-TAP, ERG, NA17, PAX3, ALK, Androgen receptor, CD3, CD4, CD8, CD24, CD25, CD34, CD79, CD116, CD117, CD135, CD123, CD138, CTLA-4, B7-1, B7-2, endoglin, a major histocompatibility complex (MHC) molecule, MUC16, PSCA, Trop2, CD171, CA9, STEAP1, and VEGFR2.

23. An engineered immune cell comprising the vector of claim 20.

24. A method of preparing an engineered immune cell, the method comprising introducing the polynucleotide of claim 19 into an immune cell.

25. The method of claim 24, wherein the immune cell is selected from the group consisting of: T-cell, dendritic cell, killer dendritic cell, mast cell, NK-cell, macrophage, monocyte, B-cell and an immune cell derived from a stem cell.

26. An engineered immune cell expressing the chimeric cytokine receptor of claim 1.

27. The engineered immune cell of claim 26, further expressing at least one CAR.

28. The engineered immune cell of claim 27, wherein the CAR binds to any one or more of the targets selected from BCMA, EGFRVIII, Flt-3, WT-1, CD20, CD23, CD30, CD38, CD70, CD33, CD133, MHC-WT1, TSPAN10, MHC-PRAME, Livl, ADAM10, CHRNA2, LeY, NKG2D, CS1, CD44v6, ROR1, CD19, Claudin-18.2, Claudin-18A2, Claudin18 isoform 2, Delta-like protein 3 (DLL3), Drosophila Delta homolog 3, Delta3, Mucin 17, Muc3, Fibroblast Activation Protein alpha (FAP alpha), Lymphocyte antigen 6 complex locus protein God (Ly6G6D), c6orf23, G6D, MEGT1, NG25, E3 ubiquitin-protein ligase RNF43, RING finger protein 43, ErbB2, carcinoembryonic antigen (CEA), epithelial cell adhesion molecule (EpCAM), epidermal growth factor receptor (EGFR), CD40, disialoganglioside GD2, GD3, C-type lectin-like molecule-1 (CLL-1), ductal-epithelial mucin, gp36, TAG-72, a glycosphingolipid, glioma- associated antigen, β-human chorionic gonadotropin, alphafetoprotein (AFP), lectin-reactive AFP, thyroglobulin, RAGE-1, MN-CA IX, human telomerase reverse transcriptase, RU1, RU2, intestinal carboxyl esterase, mut hsp70-2, M-CSF, prostase, prostase specific antigen (PSA), PAP, NY-ESO-1, LAGA-1a, p53, prostein, PSMA, survivin, telomerase, prostate-carcinoma tumor antigen-1 (PCTA-1), MAGE, ELF2M, neutrophil elastase, ephrin B2, CD22, insulin growth factor (IGF1)-1, IGF-II, IGFI receptor, mesothelin, a major histocompatibility complex (MHC) molecule presenting a tumor-specific peptide epitope, 5T4, O1, Nkp30, tumor stromal antigen, the extra domain A (EDA) of fibronectin, the extra domain B (EDB) of fibronectin, the AI domain of tenascin-C (TnC AI), fibroblast associated protein (fap), LRP6, melanoma-associated Chondroitin Sulfate Proteoglycan (MCSP), MARTI, MUC1, LMP2, Idiotype, NY-ESO-1, Ras mutant, gp100, proteinase 3, bcr-abl, tyrosinase, hTERT, EphA2, ML-TAP, ERG, NA17, PAX3, ALK, Androgen receptor, CD3, CD4, CD8, CD24, CD25, CD34, CD79, CD116, CD117, CD135, CD123, CD138, CTLA-4, B7-1, B7-2, endoglin, a major histocompatibility complex (MHC) molecule, MUC16, PSCA, Trop2, CD171, CA9, STEAP1, and VEGFR2.

29. The engineered immune cell of claim 27, wherein the immune cell is an allogeneic immune cell or an autologous immune cell.

30. The engineered immune cell of claim 27, wherein the immune cell is selected from the group consisting of: T-cell, dendritic cell, killer dendritic cell, mast cell, NK-cell, macrophage, monocyte, B-cell and an immune cell derived from a stem cell.

31. The engineered immune cell of claim 27, wherein the immune cell exhibits reduced TGFβR-mediated signal transduction and/or enhanced STAT-mediated signal transduction as compared to an immune cell without expressing the chimeric cytokine receptor.

32. The engineered immune cell of claim 31, wherein the immune cell exhibits reduced TGFβR mediated signal transduction and/or enhanced STAT-mediated signal transduction when engaged with TGF-β or an anti-TGFβR antibody.

33. A pharmaceutical composition comprising the immune cells of claim 27.

34. A kit comprising the pharmaceutical composition of claim 33.

35. A method of treating a cancer, an autoimmune disorder, or an infection in a subject, comprising administering to the subject a therapeutically effective amount of the engineered immune cells of claim 27.

36. The method of claim 35, wherein the cancer comprises a solid tumor or a liquid tumor.

37. The method of claim 36, wherein the tumor is TGF-β positive tumor.

38. The method of claim 35, wherein the subject is treated with an anti-TGFβR-antibody.

39. A method of modulating an activity of the engineered immune cell of claim 32, comprising contacting the immune cell with a TGF-β ligand or with an anti-TGFβR antibody.

40. A chimeric cytokine receptor comprising the amino acid sequence selected from SEQ ID NOs: 124-151 and SEQ ID NOs: 163-216.

* * * * *

SEQUENCE LISTING

```
<160> NUMBER OF SEQ ID NOS: 275

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Ala Leu Pro Val Thr Ala Leu Leu Leu Pro Leu Ala Leu Leu Leu
1               5                   10                  15

His Ala Ala Arg Pro
            20


<210> SEQ ID NO 2
<211> LENGTH: 126
<212> TYPE: PRT
<213> ORGANISM: Homo sapiens

<400> SEQUENCE: 2

Met Glu Ala Ala Val Ala Ala Pro Arg Pro Arg Leu Leu Leu Leu Val
1               5                   10                  15

Leu Ala Ala Ala Ala Ala Ala Ala Ala Ala Leu Leu Pro Gly Ala Thr
            20                  25                  30

Ala Leu Gln Cys Phe Cys His Leu Cys Thr Lys Asp Asn Phe Thr Cys
        35                  40                  45
```

```
Val Thr Asp Gly Leu Cys Phe Val Ser Val Thr Glu Thr Thr Asp Lys
    50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Val Lys Ser Ser Pro Gly Leu Gly Pro Val Glu Leu
        115                 120                 125


<210> SEQ ID NO 3
<211> LENGTH: 166
<212> TYPE: PRT
<213> ORGANISM: Homo sapiens

<400> SEQUENCE: 3

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln
                165


<210> SEQ ID NO 4
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Leu Cys Lys Phe Cys Asp Val Arg Phe Ser Thr Cys Asp Asn Gln
1               5                   10                  15

Lys Ser Cys Met Ser Asn Cys Ser Ile Thr Ser Ile Cys Glu Lys Pro
            20                  25                  30

Gln Glu Val Cys Val Ala Val Trp Arg Lys Asn Asp Glu Asn Ile Thr
        35                  40                  45

Leu Glu Thr Val Cys His Asp Pro Lys Leu Pro Tyr His Asp Phe Ile
    50                  55                  60
```

Leu Glu Asp Ala Ala Ser Pro Lys Cys Ile Met Lys Glu Lys Lys Lys
65 70 75 80

Pro Gly Glu Thr Phe Phe Met Cys Ser Cys Ser Ser Asp Glu Cys Asn
85 90 95

Asp Asn Ile Ile Phe Ser Glu Glu Tyr Asn Thr Ser Asn Pro Asp Leu
100 105 110

Leu Leu Val Ile Phe Gln
115

<210> SEQ ID NO 5
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

Gln Leu Cys Lys Phe Cys Asp Val Arg Phe Ser Thr Cys Asp Asn Gln
1 5 10 15

Lys Ser Cys Met Ser Asn Cys Ser Ile Thr Ser Ile Cys Glu Lys Pro
20 25 30

Gln Glu Val Cys Val Ala Val Trp Arg Lys Asn Asp Glu Asn Ile Thr
35 40 45

Leu Glu Thr Val Cys His Asp Pro Lys Leu Pro Tyr His Asp Phe Ile
50 55 60

Leu Glu Asp Ala Ala Ser Pro Lys Cys Ile Met Lys Glu Lys Lys Lys
65 70 75 80

Pro Gly Glu Thr Phe Phe Met Cys Ser Cys Ser Ser Asp Glu Cys Asn
85 90 95

Asp Asn Ile Ile Phe Ser Glu Leu Leu Leu Val Ile Phe Gln
100 105 110

<210> SEQ ID NO 6
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

Gln Leu Cys Lys Phe Cys Asp Val Arg Phe Ser Thr Cys Asp Asn Gln
1 5 10 15

Lys Ser Cys Met Ser Asn Cys Ser Ile Thr Ser Ile Cys Glu Lys Pro
20 25 30

Gln Glu Val Cys Val Ala Val Trp Arg Lys Asn Asp Glu Asn Ile Thr
35 40 45

Leu Glu Thr Val Cys His Asp Pro Lys Leu Pro Tyr His Asp Phe Ile
50 55 60

Leu Glu Asp Ala Ala Ser Pro Lys Cys Ile Met Lys Glu Lys Lys Lys
65 70 75 80

Pro Gly Glu Thr Phe Phe Met Cys Ser Cys Ser Ser Asp Glu Cys Asn
85 90 95

Asp Asn Ile Ile Phe Ser Glu Pro Asp Leu Leu Leu Val Ile Phe Gln
100 105 110

<210> SEQ ID NO 7

<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 7

Gln Leu Cys Lys Phe Cys Asp Val Arg Phe Ser Thr Cys Asp Asn Gln
1 5 10 15

Lys Ser Cys Met Ser Asn Cys Ser Ile Thr Ser Ile Cys Glu Lys Pro
20 25 30

Gln Glu Val Cys Val Ala Val Trp Arg Lys Asn Asp Glu Asn Ile Thr
35 40 45

Leu Glu Thr Val Cys His Asp Pro Lys Leu Pro Tyr His Asp Phe Ile
50 55 60

Leu Glu Asp Ala Ala Ser Pro Lys Cys Ile Met Lys Glu Lys Lys Lys
65 70 75 80

Pro Gly Glu Thr Phe Phe Met Cys Ser Cys Ser Ser Asp Glu Cys Asn
85 90 95

Asp Asn Ile Ile Phe Ser Glu Glu Pro Asp Leu Leu Leu Val Ile Phe
100 105 110

Gln

<210> SEQ ID NO 8
<211> LENGTH: 114
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 8

Gln Leu Cys Lys Phe Cys Asp Val Arg Phe Ser Thr Cys Asp Asn Gln
1 5 10 15

Lys Ser Cys Met Ser Asn Cys Ser Ile Thr Ser Ile Cys Glu Lys Pro
20 25 30

Gln Glu Val Cys Val Ala Val Trp Arg Lys Asn Asp Glu Asn Ile Thr
35 40 45

Leu Glu Thr Val Cys His Asp Pro Lys Leu Pro Tyr His Asp Phe Ile
50 55 60

Leu Glu Asp Ala Ala Ser Pro Lys Cys Ile Met Lys Glu Lys Lys Lys
65 70 75 80

Pro Gly Glu Thr Phe Phe Met Cys Ser Cys Ser Ser Asp Glu Cys Asn
85 90 95

Asp Asn Ile Ile Phe Ser Glu Glu Tyr Pro Asp Leu Leu Leu Val Ile
100 105 110

Phe Gln

<210> SEQ ID NO 9
<211> LENGTH: 115
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 9

Gln Leu Cys Lys Phe Cys Asp Val Arg Phe Ser Thr Cys Asp Asn Gln
1 5 10 15

Lys Ser Cys Met Ser Asn Cys Ser Ile Thr Ser Ile Cys Glu Lys Pro
20 25 30

Gln Glu Val Cys Val Ala Val Trp Arg Lys Asn Asp Glu Asn Ile Thr
35 40 45

Leu Glu Thr Val Cys His Asp Pro Lys Leu Pro Tyr His Asp Phe Ile
50 55 60

Leu Glu Asp Ala Ala Ser Pro Lys Cys Ile Met Lys Glu Lys Lys Lys
65 70 75 80

Pro Gly Glu Thr Phe Phe Met Cys Ser Cys Ser Ser Asp Glu Cys Asn
85 90 95

Asp Asn Ile Ile Phe Ser Glu Glu Tyr Asn Pro Asp Leu Leu Leu Val
100 105 110

Ile Phe Gln
115

<210> SEQ ID NO 10
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

Gln Leu Cys Lys Phe Cys Asp Asn Arg Thr Ser Thr Cys Asp Asn Gln
1 5 10 15

Lys Ser Cys Met Ser Asn Cys Ser Ile Thr Ser Ile Cys Glu Lys Pro
20 25 30

Gln Glu Val Cys Val Ala Val Trp Arg Lys Asn Asp Glu Asn Ile Thr
35 40 45

Leu Glu Thr Val Cys His Asp Pro Lys Leu Pro Tyr His Asp Phe Ile
50 55 60

Leu Glu Asp Ala Ala Ser Pro Lys Cys Ile Met Lys Glu Lys Lys Lys
65 70 75 80

Pro Gly Glu Thr Phe Phe Met Cys Ser Cys Ser Ser Asp Glu Cys Asn
85 90 95

Asp Asn Ile Ile Phe Ser Glu Glu Tyr Asn Thr Ser Asn Pro Asp Leu
100 105 110

Leu Leu Val Ile Phe Gln
115

<210> SEQ ID NO 11
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

Gln Leu Cys Lys Phe Cys Asp Val Arg Phe Ser Thr Cys Asp Asn Gln
1 5 10 15

Thr Ser Cys Met Ser Asn Cys Ser Ile Thr Ser Ile Cys Glu Lys Pro
20 25 30

Gln Glu Val Cys Val Ala Val Trp Arg Lys Asn Asp Glu Asn Ile Thr
35 40 45

Leu Glu Thr Val Cys His Asp Pro Lys Leu Pro Tyr His Asp Phe Ile
50 55 60

Leu Glu Asp Ala Ala Ser Pro Lys Cys Ile Met Lys Glu Lys Lys Lys
65 70 75 80

Pro Gly Glu Thr Phe Phe Met Cys Ser Cys Ser Ser Asp Glu Cys Asn
85 90 95

Asp Asn Ile Ile Phe Ser Glu Glu Tyr Asn Thr Ser Asn Pro Asp Leu
100 105 110

Leu Leu Val Ile Phe Gln
115

<210> SEQ ID NO 12
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

Gln Leu Cys Lys Phe Cys Asp Val Arg Phe Ser Thr Cys Asp Asn Gln
1 5 10 15

Lys Ser Cys Met Ser Asn Cys Ser Ile Thr Ser Ile Cys Glu Asn Pro
20 25 30

Thr Glu Val Cys Val Ala Val Trp Arg Lys Asn Asp Glu Asn Ile Thr
35 40 45

Leu Glu Thr Val Cys His Asp Pro Lys Leu Pro Tyr His Asp Phe Ile
50 55 60

Leu Glu Asp Ala Ala Ser Pro Lys Cys Ile Met Lys Glu Lys Lys Lys
65 70 75 80

Pro Gly Glu Thr Phe Phe Met Cys Ser Cys Ser Ser Asp Glu Cys Asn
85 90 95

Asp Asn Ile Ile Phe Ser Glu Glu Tyr Asn Thr Ser Asn Pro Asp Leu
100 105 110

Leu Leu Val Ile Phe Gln
115

<210> SEQ ID NO 13
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

Gln Leu Cys Lys Phe Cys Asp Val Arg Phe Ser Thr Cys Asp Asn Gln
1 5 10 15

Lys Ser Cys Met Ser Asn Cys Ser Ile Thr Ser Ile Cys Glu Lys Pro
20 25 30

Asn Glu Thr Cys Val Ala Val Trp Arg Lys Asn Asp Glu Asn Ile Thr
35 40 45

Leu Glu Thr Val Cys His Asp Pro Lys Leu Pro Tyr His Asp Phe Ile
50 55 60

Leu Glu Asp Ala Ala Ser Pro Lys Cys Ile Met Lys Glu Lys Lys Lys
65 70 75 80

Pro Gly Glu Thr Phe Phe Met Cys Ser Cys Ser Ser Asp Glu Cys Asn
85 90 95

Asp Asn Ile Ile Phe Ser Glu Glu Tyr Asn Thr Ser Asn Pro Asp Leu
100 105 110

Leu Leu Val Ile Phe Gln
        115

<210> SEQ ID NO 14
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Leu Cys Lys Phe Cys Asp Lys Arg Phe Ser Thr Cys Asp Asn Gln
1               5                   10                  15

Lys Ser Cys Met Ser Asn Cys Ser Ile Thr Ser Ile Cys Glu Lys Pro
            20                  25                  30

Gln Glu Val Cys Val Ala Val Trp Arg Lys Asn Asp Glu Asn Ile Thr
        35                  40                  45

Leu Glu Thr Val Cys His Asp Pro Lys Leu Pro Tyr His Asp Phe Ile
    50                  55                  60

Leu Glu Asp Ala Ala Ser Pro Lys Cys Ile Met Lys Glu Lys Lys Lys
65                  70                  75                  80

Pro Gly Glu Thr Phe Phe Met Cys Ser Cys Ser Ser Asp Glu Cys Asn
                85                  90                  95

Asp Asn Ile Ile Phe Ser Glu Glu Tyr Asn Thr Ser Asn Pro Asp Leu
            100                 105                 110

Leu Leu Val Ile Phe Gln
        115

<210> SEQ ID NO 15
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Leu Cys Lys Phe Cys Asp Val Arg Phe Ser Thr Cys Asp Asn Gln
1               5                   10                  15

Lys Ser Cys Met Ser Asn Cys Ser Ile Thr Ser Ile Cys Glu Lys Pro
            20                  25                  30

Gln Glu Val Cys Val Ala Val Trp Arg Lys Asn Asp Lys Asn Ile Thr
        35                  40                  45

Leu Glu Thr Val Cys His Asp Pro Lys Leu Pro Tyr His Asp Phe Ile
    50                  55                  60

Leu Glu Asp Ala Ala Ser Pro Lys Cys Ile Met Lys Glu Lys Lys Lys
65                  70                  75                  80

Pro Gly Glu Thr Phe Phe Met Cys Ser Cys Ser Ser Asp Glu Cys Asn
                85                  90                  95

Asp Asn Ile Ile Phe Ser Glu Glu Tyr Asn Thr Ser Asn Pro Asp Leu
            100                 105                 110

Leu Leu Val Ile Phe Gln
        115

<210> SEQ ID NO 16
<211> LENGTH: 101
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 16

Gln Leu Cys Lys Phe Cys Asp Val Arg Phe Ser Thr Cys Asp Asn Gln
1 5 10 15

Lys Ser Cys Met Ser Asn Cys Ser Ile Thr Ser Ile Cys Glu Lys Pro
20 25 30

Gln Glu Val Cys Val Ala Val Trp Arg Lys Asn Asp Glu Asn Ile Thr
35 40 45

Leu Glu Thr Val Cys His Asp Pro Lys Leu Pro Tyr His Asn Phe Thr
50 55 60

Leu Glu Asp Ala Ala Ser Pro Lys Cys Ile Met Lys Glu Lys Lys Lys
65 70 75 80

Pro Gly Glu Thr Phe Phe Met Cys Ser Cys Ser Ser Asp Glu Cys Asn
85 90 95

Asp Asn Ile Ile Phe
100

<210> SEQ ID NO 17
<211> LENGTH: 101
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 17

Gln Leu Cys Lys Phe Cys Asp Val Arg Phe Ser Thr Cys Asp Asn Gln
1 5 10 15

Lys Ser Cys Met Ser Asn Cys Ser Ile Thr Ser Ile Cys Glu Lys Pro
20 25 30

Gln Glu Val Cys Val Ala Val Trp Arg Lys Asn Asp Glu Asn Ile Thr
35 40 45

Leu Glu Thr Val Cys His Asp Pro Lys Leu Pro Tyr His Asp Phe Asn
50 55 60

Leu Thr Asp Ala Ala Ser Pro Lys Cys Ile Met Lys Glu Lys Lys Lys
65 70 75 80

Pro Gly Glu Thr Phe Phe Met Cys Ser Cys Ser Ser Asp Glu Cys Asn
85 90 95

Asp Asn Ile Ile Phe
100

<210> SEQ ID NO 18
<211> LENGTH: 101
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 18

Gln Leu Cys Lys Phe Cys Asp Val Arg Phe Ser Thr Cys Asp Asn Gln
1 5 10 15

Lys Ser Cys Met Ser Asn Cys Ser Ile Thr Ser Ile Cys Glu Lys Pro
20 25 30

Gln Glu Val Cys Val Ala Val Trp Arg Lys Asn Asp Glu Asn Ile Thr
35 40 45

```
Leu Glu Thr Val Cys His Asp Pro Lys Leu Pro Tyr His Asp Phe Ile
    50                  55                  60

Leu Glu Asp Ala Ala Ser Pro Lys Cys Ile Met Lys Asn Lys Thr Lys
65                  70                  75                  80

Pro Gly Glu Thr Phe Phe Met Cys Ser Cys Ser Ser Asp Glu Cys Asn
                85                  90                  95

Asp Asn Ile Ile Phe
            100


<210> SEQ ID NO 19
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Leu Cys Lys Phe Cys Asp Val Arg Phe Ser Thr Cys Asp Asn Gln
1               5                   10                  15

Lys Ser Cys Met Ser Asn Cys Ser Ile Thr Ser Ile Cys Glu Lys Pro
            20                  25                  30

Gln Glu Val Cys Val Ala Val Trp Arg Lys Asn Asp Glu Asn Ile Thr
        35                  40                  45

Leu Glu Thr Val Cys His Asp Pro Lys Leu Pro Tyr His Asp Phe Ile
    50                  55                  60

Leu Glu Asp Ala Ala Ser Pro Lys Cys Ile Met Lys Glu Lys Lys Lys
65                  70                  75                  80

Pro Gly Glu Thr Phe Phe Met Cys Ser Cys Ser Ser Asp Glu Cys Asn
                85                  90                  95

Asp Asn Ile Thr Phe
            100


<210> SEQ ID NO 20
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Leu Cys Lys Phe Cys Asp Val Arg Phe Ser Thr Cys Asp Asn Gln
1               5                   10                  15

Lys Ser Cys Met Ser Asn Cys Ser Ile Thr Ser Ile Cys Glu Lys Pro
            20                  25                  30

Gln Glu Val Cys Val Ala Val Trp Arg Lys Asn Asp Glu Asn Ile Thr
        35                  40                  45

Leu Glu Thr Val Cys His Asp Pro Lys Leu Pro Tyr His Asp Phe Glu
    50                  55                  60

Leu Glu Asp Ala Ala Ser Pro Lys Cys Ile Met Lys Glu Lys Lys Lys
65                  70                  75                  80

Pro Gly Glu Thr Phe Phe Met Cys Ser Cys Ser Ser Asp Glu Cys Asn
                85                  90                  95

Asp Asn Ile Ile Phe
            100


<210> SEQ ID NO 21
<211> LENGTH: 508
```

```
<212> TYPE: PRT
<213> ORGANISM: Homo sapiens

<400> SEQUENCE: 21

Met Asp His Leu Gly Ala Ser Leu Trp Pro Gln Val Gly Ser Leu Cys
1               5                   10                  15

Leu Leu Leu Ala Gly Ala Ala Trp Ala Pro Pro Pro Asn Leu Pro Asp
            20                  25                  30

Pro Lys Phe Glu Ser Lys Ala Ala Leu Leu Ala Ala Arg Gly Pro Glu
        35                  40                  45

Glu Leu Leu Cys Phe Thr Glu Arg Leu Glu Asp Leu Val Cys Phe Trp
    50                  55                  60

Glu Glu Ala Ala Ser Ala Gly Val Gly Pro Gly Asn Tyr Ser Phe Ser
65                  70                  75                  80

Tyr Gln Leu Glu Asp Glu Pro Trp Lys Leu Cys Arg Leu His Gln Ala
                85                  90                  95

Pro Thr Ala Arg Gly Ala Val Arg Phe Trp Cys Ser Leu Pro Thr Ala
            100                 105                 110

Asp Thr Ser Ser Phe Val Pro Leu Glu Leu Arg Val Thr Ala Ala Ser
        115                 120                 125

Gly Ala Pro Arg Tyr His Arg Val Ile His Ile Asn Glu Val Val Leu
    130                 135                 140

Leu Asp Ala Pro Val Gly Leu Val Ala Arg Leu Ala Asp Glu Ser Gly
145                 150                 155                 160

His Val Val Leu Arg Trp Leu Pro Pro Pro Glu Thr Pro Met Thr Ser
                165                 170                 175

His Ile Arg Tyr Glu Val Asp Val Ser Ala Gly Asn Gly Ala Gly Ser
            180                 185                 190

Val Gln Arg Val Glu Ile Leu Glu Gly Arg Thr Glu Cys Val Leu Ser
        195                 200                 205

Asn Leu Arg Gly Arg Thr Arg Tyr Thr Phe Ala Val Arg Ala Arg Met
    210                 215                 220

Ala Glu Pro Ser Phe Gly Gly Phe Trp Ser Ala Trp Ser Glu Pro Val
225                 230                 235                 240

Ser Leu Leu Thr Pro Ser Asp Leu Asp Pro Leu Ile Leu Thr Leu Ser
                245                 250                 255

Leu Ile Leu Val Val Ile Leu Val Leu Leu Thr Val Leu Ala Leu Leu
            260                 265                 270

Ser His Arg Arg Ala Leu Lys Gln Lys Ile Trp Pro Gly Ile Pro Ser
        275                 280                 285

Pro Glu Ser Glu Phe Glu Gly Leu Phe Thr Thr His Lys Gly Asn Phe
    290                 295                 300

Gln Leu Trp Leu Tyr Gln Asn Asp Gly Cys Leu Trp Trp Ser Pro Cys
305                 310                 315                 320

Thr Pro Phe Thr Glu Asp Pro Pro Ala Ser Leu Glu Val Leu Ser Glu
                325                 330                 335

Arg Cys Trp Gly Thr Met Gln Ala Val Glu Pro Gly Thr Asp Asp Glu
            340                 345                 350

Gly Pro Leu Leu Glu Pro Val Gly Ser Glu His Ala Gln Asp Thr Tyr
        355                 360                 365

Leu Val Leu Asp Lys Trp Leu Leu Pro Arg Asn Pro Pro Ser Glu Asp
    370                 375                 380

Leu Pro Gly Pro Gly Gly Ser Val Asp Ile Val Ala Met Asp Glu Gly
385                 390                 395                 400
```

```
Ser Glu Ala Ser Ser Cys Ser Ser Ala Leu Ala Ser Lys Pro Ser Pro
                405                 410                 415

Glu Gly Ala Ser Ala Ala Ser Phe Glu Tyr Thr Ile Leu Asp Pro Ser
            420                 425                 430

Ser Gln Leu Leu Arg Pro Trp Thr Leu Cys Pro Glu Leu Pro Pro Thr
        435                 440                 445

Pro Pro His Leu Lys Tyr Leu Tyr Leu Val Val Ser Asp Ser Gly Ile
    450                 455                 460

Ser Thr Asp Tyr Ser Ser Gly Asp Ser Gln Gly Ala Gln Gly Gly Leu
465                 470                 475                 480

Ser Asp Gly Pro Tyr Ser Asn Pro Tyr Glu Asn Ser Leu Ile Pro Ala
                485                 490                 495

Ala Glu Pro Leu Pro Pro Ser Tyr Val Ala Cys Ser
            500                 505


<210> SEQ ID NO 22
<211> LENGTH: 918
<212> TYPE: PRT
<213> ORGANISM: Homo sapiens

<400> SEQUENCE: 22

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Arg Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255
```

```
Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
        355                 360                 365

Thr Leu Thr Arg Trp Lys Ser His Leu Gln Asn Tyr Thr Val Asn Ala
    370                 375                 380

Thr Lys Leu Thr Val Asn Leu Thr Asn Asp Arg Tyr Val Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
        435                 440                 445

Ser Val Lys Lys Tyr Ile Leu Glu Trp Cys Val Leu Ser Asp Lys Ala
    450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
        515                 520                 525

Lys Val Gly Lys Asn Glu Ala Val Leu Glu Trp Asp Gln Leu Pro Val
    530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
        595                 600                 605

Thr Thr Pro Lys Phe Ala Gln Gly Glu Ile Glu Ala Ile Val Val Pro
    610                 615                 620

Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
                645                 650                 655

Asp Pro Ser Lys Ser His Ile Ala Gln Trp Ser Pro His Thr Pro Pro
            660                 665                 670
```

```
Arg His Asn Phe Asn Ser Lys Asp Gln Met Tyr Ser Asp Gly Asn Phe
        675                 680                 685

Thr Asp Val Ser Val Val Glu Ile Glu Ala Asn Asp Lys Lys Pro Phe
    690                 695                 700

Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
                725                 730                 735

Ser Arg Pro Ser Ile Ser Ser Ser Asp Glu Asn Glu Ser Ser Gln Asn
            740                 745                 750

Thr Ser Ser Thr Val Gln Tyr Ser Thr Val Val His Ser Gly Tyr Arg
        755                 760                 765

His Gln Val Pro Ser Val Gln Val Phe Ser Arg Ser Glu Ser Thr Gln
    770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
                805                 810                 815

Gln Asn Cys Ser Gln His Glu Ser Ser Pro Asp Ile Ser His Phe Glu
            820                 825                 830

Arg Ser Lys Gln Val Ser Ser Val Asn Glu Glu Asp Phe Val Arg Leu
        835                 840                 845

Lys Gln Gln Ile Ser Asp His Ile Ser Gln Ser Cys Gly Ser Gly Gln
    850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
                885                 890                 895

Thr Asp Glu Gly Met Pro Lys Ser Tyr Leu Pro Gln Thr Val Arg Gln
            900                 905                 910

Gly Gly Tyr Met Pro Gln
        915


<210> SEQ ID NO 23
<211> LENGTH: 622
<212> TYPE: PRT
<213> ORGANISM: Homo sapiens

<400> SEQUENCE: 23

Met Lys Glu Asn Val Ala Ser Ala Thr Val Phe Thr Leu Leu Leu Phe
1               5                   10                  15

Leu Asn Thr Cys Leu Leu Asn Gly Gln Leu Pro Pro Gly Lys Pro Glu
            20                  25                  30

Ile Phe Lys Cys Arg Ser Pro Asn Lys Glu Thr Phe Thr Cys Trp Trp
        35                  40                  45

Arg Pro Gly Thr Asp Gly Gly Leu Pro Thr Asn Tyr Ser Leu Thr Tyr
    50                  55                  60

His Arg Glu Gly Glu Thr Leu Met His Glu Cys Pro Asp Tyr Ile Thr
65                  70                  75                  80

Gly Gly Pro Asn Ser Cys His Phe Gly Lys Gln Tyr Thr Ser Met Trp
                85                  90                  95

Arg Thr Tyr Ile Met Met Val Asn Ala Thr Asn Gln Met Gly Ser Ser
            100                 105                 110

Phe Ser Asp Glu Leu Tyr Val Asp Val Thr Tyr Ile Val Gln Pro Asp
        115                 120                 125
```

```
Pro Pro Leu Glu Leu Ala Val Glu Val Lys Gln Pro Glu Asp Arg Lys
    130                 135                 140

Pro Tyr Leu Trp Ile Lys Trp Ser Pro Pro Thr Leu Ile Asp Leu Lys
145                 150                 155                 160

Thr Gly Trp Phe Thr Leu Leu Tyr Glu Ile Arg Leu Lys Pro Glu Lys
                165                 170                 175

Ala Ala Glu Trp Glu Ile His Phe Ala Gly Gln Gln Thr Glu Phe Lys
            180                 185                 190

Ile Leu Ser Leu His Pro Gly Gln Lys Tyr Leu Val Gln Val Arg Cys
        195                 200                 205

Lys Pro Asp His Gly Tyr Trp Ser Ala Trp Ser Pro Ala Thr Phe Ile
    210                 215                 220

Gln Ile Pro Ser Asp Phe Thr Met Asn Asp Thr Thr Val Trp Ile Ser
225                 230                 235                 240

Val Ala Val Leu Ser Ala Val Ile Cys Leu Ile Ile Val Trp Ala Val
                245                 250                 255

Ala Leu Lys Gly Tyr Ser Met Val Thr Cys Ile Phe Pro Pro Val Pro
            260                 265                 270

Gly Pro Lys Ile Lys Gly Phe Asp Ala His Leu Leu Glu Lys Gly Lys
        275                 280                 285

Ser Glu Glu Leu Leu Ser Ala Leu Gly Cys Gln Asp Phe Pro Pro Thr
    290                 295                 300

Ser Asp Tyr Glu Asp Leu Leu Val Glu Tyr Leu Glu Val Asp Asp Ser
305                 310                 315                 320

Glu Asp Gln His Leu Met Ser Val His Ser Lys Glu His Pro Ser Gln
                325                 330                 335

Gly Met Lys Pro Thr Tyr Leu Asp Pro Asp Thr Asp Ser Gly Arg Gly
            340                 345                 350

Ser Cys Asp Ser Pro Ser Leu Leu Ser Glu Lys Cys Glu Glu Pro Gln
        355                 360                 365

Ala Asn Pro Ser Thr Phe Tyr Asp Pro Glu Val Ile Glu Lys Pro Glu
    370                 375                 380

Asn Pro Glu Thr Thr His Thr Trp Asp Pro Gln Cys Ile Ser Met Glu
385                 390                 395                 400

Gly Lys Ile Pro Tyr Phe His Ala Gly Gly Ser Lys Cys Ser Thr Trp
                405                 410                 415

Pro Leu Pro Gln Pro Ser Gln His Asn Pro Arg Ser Ser Tyr His Asn
            420                 425                 430

Ile Thr Asp Val Cys Glu Leu Ala Val Gly Pro Ala Gly Ala Pro Ala
        435                 440                 445

Thr Leu Leu Asn Glu Ala Gly Lys Asp Ala Leu Lys Ser Ser Gln Thr
    450                 455                 460

Ile Lys Ser Arg Glu Glu Gly Lys Ala Thr Gln Gln Arg Glu Val Glu
465                 470                 475                 480

Ser Phe His Ser Glu Thr Asp Gln Asp Thr Pro Trp Leu Leu Pro Gln
                485                 490                 495

Glu Lys Thr Pro Phe Gly Ser Ala Lys Pro Leu Asp Tyr Val Glu Ile
            500                 505                 510

His Lys Val Asn Lys Asp Gly Ala Leu Ser Leu Leu Pro Lys Gln Arg
        515                 520                 525

Glu Asn Ser Gly Lys Pro Lys Lys Pro Gly Thr Pro Glu Asn Asn Lys
    530                 535                 540
```

Glu Tyr Ala Lys Val Ser Gly Val Met Asp Asn Asn Ile Leu Val Leu
545 550 555 560

Val Pro Asp Pro His Ala Lys Asn Val Ala Cys Phe Glu Glu Ser Ala
565 570 575

Lys Glu Ala Pro Pro Ser Leu Glu Gln Asn Gln Ala Glu Lys Ala Leu
580 585 590

Ala Asn Phe Thr Ala Thr Ser Ser Lys Cys Arg Leu Gln Leu Gly Gly
595 600 605

Leu Asp Tyr Leu Asp Pro Ala Cys Phe Thr His Ser Phe His
610 615 620

<210> SEQ ID NO 24
<211> LENGTH: 638
<212> TYPE: PRT
<213> ORGANISM: Homo sapiens

<400> SEQUENCE: 24

Met Asp Leu Trp Gln Leu Leu Leu Thr Leu Ala Leu Ala Gly Ser Ser
1 5 10 15

Asp Ala Phe Ser Gly Ser Glu Ala Thr Ala Ala Ile Leu Ser Arg Ala
20 25 30

Pro Trp Ser Leu Gln Ser Val Asn Pro Gly Leu Lys Thr Asn Ser Ser
35 40 45

Lys Glu Pro Lys Phe Thr Lys Cys Arg Ser Pro Glu Arg Glu Thr Phe
50 55 60

Ser Cys His Trp Thr Asp Glu Val His His Gly Thr Lys Asn Leu Gly
65 70 75 80

Pro Ile Gln Leu Phe Tyr Thr Arg Arg Asn Thr Gln Glu Trp Thr Gln
85 90 95

Glu Trp Lys Glu Cys Pro Asp Tyr Val Ser Ala Gly Glu Asn Ser Cys
100 105 110

Tyr Phe Asn Ser Ser Phe Thr Ser Ile Trp Ile Pro Tyr Cys Ile Lys
115 120 125

Leu Thr Ser Asn Gly Gly Thr Val Asp Glu Lys Cys Phe Ser Val Asp
130 135 140

Glu Ile Val Gln Pro Asp Pro Pro Ile Ala Leu Asn Trp Thr Leu Leu
145 150 155 160

Asn Val Ser Leu Thr Gly Ile His Ala Asp Ile Gln Val Arg Trp Glu
165 170 175

Ala Pro Arg Asn Ala Asp Ile Gln Lys Gly Trp Met Val Leu Glu Tyr
180 185 190

Glu Leu Gln Tyr Lys Glu Val Asn Glu Thr Lys Trp Lys Met Met Asp
195 200 205

Pro Ile Leu Thr Thr Ser Val Pro Val Tyr Ser Leu Lys Val Asp Lys
210 215 220

Glu Tyr Glu Val Arg Val Arg Ser Lys Gln Arg Asn Ser Gly Asn Tyr
225 230 235 240

Gly Glu Phe Ser Glu Val Leu Tyr Val Thr Leu Pro Gln Met Ser Gln
245 250 255

Phe Thr Cys Glu Glu Asp Phe Tyr Phe Pro Trp Leu Leu Ile Ile Ile
260 265 270

Phe Gly Ile Phe Gly Leu Thr Val Met Leu Phe Val Phe Leu Phe Ser
275 280 285

Lys Gln Gln Arg Ile Lys Met Leu Ile Leu Pro Pro Val Pro Val Pro
290 295 300

```
Lys Ile Lys Gly Ile Asp Pro Asp Leu Leu Lys Glu Gly Lys Leu Glu
305                 310                 315                 320

Glu Val Asn Thr Ile Leu Ala Ile His Asp Ser Tyr Lys Pro Glu Phe
                325                 330                 335

His Ser Asp Asp Ser Trp Val Glu Phe Ile Glu Leu Asp Ile Asp Glu
            340                 345                 350

Pro Asp Glu Lys Thr Glu Glu Ser Asp Thr Asp Arg Leu Leu Ser Ser
        355                 360                 365

Asp His Glu Lys Ser His Ser Asn Leu Gly Val Lys Asp Gly Asp Ser
    370                 375                 380

Gly Arg Thr Ser Cys Cys Glu Pro Asp Ile Leu Glu Thr Asp Phe Asn
385                 390                 395                 400

Ala Asn Asp Ile His Glu Gly Thr Ser Glu Val Ala Gln Pro Gln Arg
                405                 410                 415

Leu Lys Gly Glu Ala Asp Leu Leu Cys Leu Asp Gln Lys Asn Gln Asn
            420                 425                 430

Asn Ser Pro Tyr His Asp Ala Cys Pro Ala Thr Gln Gln Pro Ser Val
        435                 440                 445

Ile Gln Ala Glu Lys Asn Lys Pro Gln Pro Leu Pro Thr Glu Gly Ala
    450                 455                 460

Glu Ser Thr His Gln Ala Ala His Ile Gln Leu Ser Asn Pro Ser Ser
465                 470                 475                 480

Leu Ser Asn Ile Asp Phe Tyr Ala Gln Val Ser Asp Ile Thr Pro Ala
                485                 490                 495

Gly Ser Val Val Leu Ser Pro Gly Gln Lys Asn Lys Ala Gly Met Ser
            500                 505                 510

Gln Cys Asp Met His Pro Glu Met Val Ser Leu Cys Gln Glu Asn Phe
        515                 520                 525

Leu Met Asp Asn Ala Tyr Phe Cys Glu Ala Asp Ala Lys Lys Cys Ile
    530                 535                 540

Pro Val Ala Pro His Ile Lys Val Glu Ser His Ile Gln Pro Ser Leu
545                 550                 555                 560

Asn Gln Glu Asp Ile Tyr Ile Thr Thr Glu Ser Leu Thr Thr Ala Ala
                565                 570                 575

Gly Arg Pro Gly Thr Gly Glu His Val Pro Gly Ser Glu Met Pro Val
            580                 585                 590

Pro Asp Tyr Thr Ser Ile His Ile Val Gln Ser Pro Gln Gly Leu Ile
        595                 600                 605

Leu Asn Ala Thr Ala Leu Pro Leu Pro Asp Lys Glu Phe Leu Ser Ser
    610                 615                 620

Cys Gly Tyr Val Ser Thr Asp Gln Leu Asn Lys Ile Met Pro
625                 630                 635
```

<210> SEQ ID NO 25
<211> LENGTH: 863
<212> TYPE: PRT
<213> ORGANISM: Homo sapiens

<400> SEQUENCE: 25

```
Met Ala Arg Leu Gly Asn Cys Ser Leu Thr Trp Ala Ala Leu Ile Ile
1               5                   10                  15

Leu Leu Leu Pro Gly Ser Leu Glu Glu Cys Gly His Ile Ser Val Ser
            20                  25                  30
```

```
Ala Pro Ile Val His Leu Gly Asp Pro Ile Thr Ala Ser Cys Ile Ile
        35                  40                  45

Lys Gln Asn Cys Ser His Leu Asp Pro Glu Pro Gln Ile Leu Trp Arg
    50                  55                  60

Leu Gly Ala Glu Leu Gln Pro Gly Gly Arg Gln Gln Arg Leu Ser Asp
65                  70                  75                  80

Gly Thr Gln Glu Ser Ile Ile Thr Leu Pro His Leu Asn His Thr Gln
                85                  90                  95

Ala Phe Leu Ser Cys Cys Leu Asn Trp Gly Asn Ser Leu Gln Ile Leu
            100                 105                 110

Asp Gln Val Glu Leu Arg Ala Gly Tyr Pro Pro Ala Ile Pro His Asn
        115                 120                 125

Leu Ser Cys Leu Met Asn Leu Thr Thr Ser Ser Leu Ile Cys Gln Trp
    130                 135                 140

Glu Pro Gly Pro Glu Thr His Leu Pro Thr Ser Phe Thr Leu Lys Ser
145                 150                 155                 160

Phe Lys Ser Arg Gly Asn Cys Gln Thr Gln Gly Asp Ser Ile Leu Asp
                165                 170                 175

Cys Val Pro Lys Asp Gly Gln Ser His Cys Cys Ile Pro Arg Lys His
            180                 185                 190

Leu Leu Leu Tyr Gln Asn Met Gly Ile Trp Val Gln Ala Glu Asn Ala
        195                 200                 205

Leu Gly Thr Ser Met Ser Pro Gln Leu Cys Leu Asp Pro Met Asp Val
    210                 215                 220

Val Lys Leu Glu Pro Pro Met Leu Arg Thr Met Asp Pro Ser Pro Glu
225                 230                 235                 240

Ala Ala Pro Pro Gln Ala Gly Cys Leu Gln Leu Cys Trp Glu Pro Trp
                245                 250                 255

Gln Pro Gly Leu His Ile Asn Gln Lys Cys Glu Leu Arg His Lys Pro
            260                 265                 270

Gln Arg Gly Glu Ala Ser Trp Ala Leu Val Gly Pro Leu Pro Leu Glu
        275                 280                 285

Ala Leu Gln Tyr Glu Leu Cys Gly Leu Leu Pro Ala Thr Ala Tyr Thr
    290                 295                 300

Leu Gln Ile Arg Cys Ile Arg Trp Pro Leu Pro Gly His Trp Ser Asp
305                 310                 315                 320

Trp Ser Pro Ser Leu Glu Leu Arg Thr Thr Glu Arg Ala Pro Thr Val
                325                 330                 335

Arg Leu Asp Thr Trp Trp Arg Gln Arg Gln Leu Asp Pro Arg Thr Val
            340                 345                 350

Gln Leu Phe Trp Lys Pro Val Pro Leu Glu Glu Asp Ser Gly Arg Ile
        355                 360                 365

Gln Gly Tyr Val Val Ser Trp Arg Pro Ser Gly Gln Ala Gly Ala Ile
    370                 375                 380

Leu Pro Leu Cys Asn Thr Thr Glu Leu Ser Cys Thr Phe His Leu Pro
385                 390                 395                 400

Ser Glu Ala Gln Glu Val Ala Leu Val Ala Tyr Asn Ser Ala Gly Thr
                405                 410                 415

Ser Arg Pro Thr Pro Val Val Phe Ser Glu Ser Arg Gly Pro Ala Leu
            420                 425                 430

Thr Arg Leu His Ala Met Ala Arg Asp Pro His Ser Leu Trp Val Gly
        435                 440                 445
```

```
Trp Glu Pro Pro Asn Pro Trp Pro Gln Gly Tyr Val Ile Glu Trp Gly
    450                 455                 460

Leu Gly Pro Pro Ser Ala Ser Asn Ser Asn Lys Thr Trp Arg Met Glu
465                 470                 475                 480

Gln Asn Gly Arg Ala Thr Gly Phe Leu Leu Lys Glu Asn Ile Arg Pro
                485                 490                 495

Phe Gln Leu Tyr Glu Ile Ile Val Thr Pro Leu Tyr Gln Asp Thr Met
            500                 505                 510

Gly Pro Ser Gln His Val Tyr Ala Tyr Ser Gln Glu Met Ala Pro Ser
        515                 520                 525

His Ala Pro Glu Leu His Leu Lys His Ile Gly Lys Thr Trp Ala Gln
    530                 535                 540

Leu Glu Trp Val Pro Glu Pro Pro Glu Leu Gly Lys Ser Pro Leu Thr
545                 550                 555                 560

His Tyr Thr Ile Phe Trp Thr Asn Ala Gln Asn Gln Ser Phe Ser Ala
                565                 570                 575

Ile Leu Asn Ala Ser Ser Arg Gly Phe Val Leu His Gly Leu Glu Pro
            580                 585                 590

Ala Ser Leu Tyr His Ile His Leu Met Ala Ala Ser Gln Ala Gly Ala
        595                 600                 605

Thr Asn Ser Thr Val Leu Thr Leu Met Thr Leu Thr Pro Glu Gly Ser
    610                 615                 620

Glu Leu His Ile Ile Leu Gly Leu Phe Gly Leu Leu Leu Leu Leu Thr
625                 630                 635                 640

Cys Leu Cys Gly Thr Ala Trp Leu Cys Cys Ser Pro Asn Arg Lys Asn
                645                 650                 655

Pro Leu Trp Pro Ser Val Pro Asp Pro Ala His Ser Ser Leu Gly Ser
            660                 665                 670

Trp Val Pro Thr Ile Met Glu Glu Leu Pro Gly Pro Arg Gln Gly Gln
        675                 680                 685

Trp Leu Gly Gln Thr Ser Glu Met Ser Arg Ala Leu Thr Pro His Pro
    690                 695                 700

Cys Val Gln Asp Ala Phe Gln Leu Pro Gly Leu Gly Thr Pro Pro Ile
705                 710                 715                 720

Thr Lys Leu Thr Val Leu Glu Glu Asp Glu Lys Lys Pro Val Pro Trp
                725                 730                 735

Glu Ser His Asn Ser Ser Glu Thr Cys Gly Leu Pro Thr Leu Val Gln
            740                 745                 750

Thr Tyr Val Leu Gln Gly Asp Pro Arg Ala Val Ser Thr Gln Pro Gln
        755                 760                 765

Ser Gln Ser Gly Thr Ser Asp Gln Val Leu Tyr Gly Gln Leu Leu Gly
    770                 775                 780

Ser Pro Thr Ser Pro Gly Pro Gly His Tyr Leu Arg Cys Asp Ser Thr
785                 790                 795                 800

Gln Pro Leu Leu Ala Gly Leu Thr Pro Ser Pro Lys Ser Tyr Glu Asn
                805                 810                 815

Leu Trp Phe Gln Ala Ser Pro Leu Gly Thr Leu Val Thr Pro Ala Pro
            820                 825                 830

Ser Gln Glu Asp Asp Cys Val Phe Gly Pro Leu Leu Asn Phe Pro Leu
        835                 840                 845

Leu Gln Gly Ile Arg Val His Gly Met Glu Ala Leu Gly Ser Phe
    850                 855                 860
```

<210> SEQ ID NO 26
<211> LENGTH: 635
<212> TYPE: PRT
<213> ORGANISM: Homo sapiens

<400> SEQUENCE: 26

Met Pro Ser Trp Ala Leu Phe Met Val Thr Ser Cys Leu Leu Leu Ala
1 5 10 15

Pro Gln Asn Leu Ala Gln Val Ser Ser Gln Asp Val Ser Leu Leu Ala
20 25 30

Ser Asp Ser Glu Pro Leu Lys Cys Phe Ser Arg Thr Phe Glu Asp Leu
35 40 45

Thr Cys Phe Trp Asp Glu Glu Glu Ala Ala Pro Ser Gly Thr Tyr Gln
50 55 60

Leu Leu Tyr Ala Tyr Pro Arg Glu Lys Pro Arg Ala Cys Pro Leu Ser
65 70 75 80

Ser Gln Ser Met Pro His Phe Gly Thr Arg Tyr Val Cys Gln Phe Pro
85 90 95

Asp Gln Glu Glu Val Arg Leu Phe Phe Pro Leu His Leu Trp Val Lys
100 105 110

Asn Val Phe Leu Asn Gln Thr Arg Thr Gln Arg Val Leu Phe Val Asp
115 120 125

Ser Val Gly Leu Pro Ala Pro Pro Ser Ile Ile Lys Ala Met Gly Gly
130 135 140

Ser Gln Pro Gly Glu Leu Gln Ile Ser Trp Glu Glu Pro Ala Pro Glu
145 150 155 160

Ile Ser Asp Phe Leu Arg Tyr Glu Leu Arg Tyr Gly Pro Arg Asp Pro
165 170 175

Lys Asn Ser Thr Gly Pro Thr Val Ile Gln Leu Ile Ala Thr Glu Thr
180 185 190

Cys Cys Pro Ala Leu Gln Arg Pro His Ser Ala Ser Ala Leu Asp Gln
195 200 205

Ser Pro Cys Ala Gln Pro Thr Met Pro Trp Gln Asp Gly Pro Lys Gln
210 215 220

Thr Ser Pro Ser Arg Glu Ala Ser Ala Leu Thr Ala Glu Gly Gly Ser
225 230 235 240

Cys Leu Ile Ser Gly Leu Gln Pro Gly Asn Ser Tyr Trp Leu Gln Leu
245 250 255

Arg Ser Glu Pro Asp Gly Ile Ser Leu Gly Gly Ser Trp Gly Ser Trp
260 265 270

Ser Leu Pro Val Thr Val Asp Leu Pro Gly Asp Ala Val Ala Leu Gly
275 280 285

Leu Gln Cys Phe Thr Leu Asp Leu Lys Asn Val Thr Cys Gln Trp Gln
290 295 300

Gln Gln Asp His Ala Ser Ser Gln Gly Phe Phe Tyr His Ser Arg Ala
305 310 315 320

Arg Cys Cys Pro Arg Asp Arg Tyr Pro Ile Trp Glu Asn Cys Glu Glu
325 330 335

Glu Glu Lys Thr Asn Pro Gly Leu Gln Thr Pro Gln Phe Ser Arg Cys
340 345 350

His Phe Lys Ser Arg Asn Asp Ser Ile Ile His Ile Leu Val Glu Val
355 360 365

Thr Thr Ala Pro Gly Thr Val His Ser Tyr Leu Gly Ser Pro Phe Trp
370 375 380

Ile His Gln Ala Val Arg Leu Pro Thr Pro Asn Leu His Trp Arg Glu
385 390 395 400

Ile Ser Ser Gly His Leu Glu Leu Glu Trp Gln His Pro Ser Ser Trp
405 410 415

Ala Ala Gln Glu Thr Cys Tyr Gln Leu Arg Tyr Thr Gly Glu Gly His
420 425 430

Gln Asp Trp Lys Val Leu Glu Pro Pro Leu Gly Ala Arg Gly Gly Thr
435 440 445

Leu Glu Leu Arg Pro Arg Ser Arg Tyr Arg Leu Gln Leu Arg Ala Arg
450 455 460

Leu Asn Gly Pro Thr Tyr Gln Gly Pro Trp Ser Ser Trp Ser Asp Pro
465 470 475 480

Thr Arg Val Glu Thr Ala Thr Glu Thr Ala Trp Ile Ser Leu Val Thr
485 490 495

Ala Leu His Leu Val Leu Gly Leu Ser Ala Val Leu Gly Leu Leu Leu
500 505 510

Leu Arg Trp Gln Phe Pro Ala His Tyr Arg Arg Leu Arg His Ala Leu
515 520 525

Trp Pro Ser Leu Pro Asp Leu His Arg Val Leu Gly Gln Tyr Leu Arg
530 535 540

Asp Thr Ala Ala Leu Ser Pro Pro Lys Ala Thr Val Ser Asp Thr Cys
545 550 555 560

Glu Glu Val Glu Pro Ser Leu Leu Glu Ile Leu Pro Lys Ser Ser Glu
565 570 575

Arg Thr Pro Leu Pro Leu Cys Ser Ser Gln Ala Gln Met Asp Tyr Arg
580 585 590

Arg Leu Gln Pro Ser Cys Leu Gly Thr Met Pro Leu Ser Val Cys Pro
595 600 605

Pro Met Ala Glu Ser Gly Ser Cys Cys Thr Thr His Ile Ala Asn His
610 615 620

Ser Tyr Leu Pro Leu Ser Tyr Trp Gln Gln Pro
625 630 635

<210> SEQ ID NO 27
<211> LENGTH: 97
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 27

Leu Thr Leu Met Thr Leu Thr Pro Glu Gly Ser Glu Leu His Ile Ile
1 5 10 15

Leu Gly Leu Phe Gly Leu Leu Leu Leu Leu Thr Cys Leu Cys Gly Thr
20 25 30

Ala Trp Leu Cys Cys Ser Pro Asn Arg Lys Asn Pro Leu Trp Pro Ser
35 40 45

Val Pro Asp Pro Ala His Ser Ser Leu Gly Ser Trp Val Pro Thr Ile
50 55 60

Met Glu Glu Asp Ala Phe Gln Leu Pro Gly Leu Gly Thr Pro Pro Ile
65 70 75 80

Thr Lys Leu Thr Val Leu Glu Glu Asp Glu Lys Lys Pro Val Pro Trp
85 90 95

Glu

<210> SEQ ID NO 28
<211> LENGTH: 92
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 28

```
Thr Thr Pro Lys Phe Ala Gln Gly Glu Ile Glu Ala Ile Val Val Pro
1               5                   10                  15

Val Cys Leu Ala Phe Leu Leu Thr Thr Leu Leu Gly Val Leu Phe Cys
            20                  25                  30

Phe Asn Lys Arg Asp Leu Ile Lys Lys His Ile Trp Pro Asn Val Pro
        35                  40                  45

Asp Pro Ser Lys Ser His Ile Ala Gln Trp Ser Pro His Thr Pro Pro
    50                  55                  60

Arg His Asn Phe Asn Ser Lys Asp Gln Met Tyr Ser Asp Gly Asn Phe
65                  70                  75                  80

Thr Asp Val Ser Val Val Glu Ile Glu Ala Asn Asp
                85                  90
```

<210> SEQ ID NO 29
<211> LENGTH: 105
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 29

```
Ser Asp Pro Thr Arg Val Glu Thr Ala Thr Glu Thr Ala Trp Ile Ser
1               5                   10                  15

Leu Val Thr Ala Leu His Leu Val Leu Gly Leu Ser Ala Val Leu Gly
            20                  25                  30

Leu Leu Leu Leu Arg Trp Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu
            100                 105
```

<210> SEQ ID NO 30
<211> LENGTH: 104
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 30

```
Ser Asp Pro Thr Arg Val Glu Thr Ala Thr Glu Thr Trp Ile Ser Leu
1               5                   10                  15

Val Thr Ala Leu His Leu Val Leu Gly Leu Ser Ala Val Leu Gly Leu
            20                  25                  30
```

Leu Leu Leu Arg Trp Gln Phe Pro Ala His Tyr Arg Arg Leu Arg His
35 40 45

Ala Leu Trp Pro Ser Leu Pro Asp Leu His Arg Val Leu Gly Gln Tyr
50 55 60

Leu Arg Asp Thr Ala Ala Leu Ser Pro Pro Lys Ala Thr Val Ser Asp
65 70 75 80

Thr Cys Glu Glu Val Glu Pro Ser Leu Leu Glu Ile Leu Pro Lys Ser
85 90 95

Ser Glu Arg Thr Pro Leu Pro Leu
100

<210> SEQ ID NO 31
<211> LENGTH: 103
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

Ser Asp Pro Thr Arg Val Glu Thr Ala Thr Glu Thr Ile Ser Leu Val
1 5 10 15

Thr Ala Leu His Leu Val Leu Gly Leu Ser Ala Val Leu Gly Leu Leu
20 25 30

Leu Leu Arg Trp Gln Phe Pro Ala His Tyr Arg Arg Leu Arg His Ala
35 40 45

Leu Trp Pro Ser Leu Pro Asp Leu His Arg Val Leu Gly Gln Tyr Leu
50 55 60

Arg Asp Thr Ala Ala Leu Ser Pro Pro Lys Ala Thr Val Ser Asp Thr
65 70 75 80

Cys Glu Glu Val Glu Pro Ser Leu Leu Glu Ile Leu Pro Lys Ser Ser
85 90 95

Glu Arg Thr Pro Leu Pro Leu
100

<210> SEQ ID NO 32
<211> LENGTH: 104
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

Ser Asp Pro Thr Arg Val Glu Thr Ala Thr Glu Thr Leu Ile Ser Leu
1 5 10 15

Val Thr Ala Leu His Leu Val Leu Gly Leu Ser Ala Val Leu Gly Leu
20 25 30

Leu Leu Leu Arg Trp Gln Phe Pro Ala His Tyr Arg Arg Leu Arg His
35 40 45

Ala Leu Trp Pro Ser Leu Pro Asp Leu His Arg Val Leu Gly Gln Tyr
50 55 60

Leu Arg Asp Thr Ala Ala Leu Ser Pro Pro Lys Ala Thr Val Ser Asp
65 70 75 80

Thr Cys Glu Glu Val Glu Pro Ser Leu Leu Glu Ile Leu Pro Lys Ser
85 90 95

Ser Glu Arg Thr Pro Leu Pro Leu
100

<210> SEQ ID NO 33
<211> LENGTH: 102
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 33

Ser Asp Pro Thr Arg Val Glu Thr Ala Thr Glu Thr Ser Leu Val Thr
1 5 10 15

Ala Leu His Leu Val Leu Gly Leu Ser Ala Val Leu Gly Leu Leu Leu
20 25 30

Leu Arg Trp Gln Phe Pro Ala His Tyr Arg Arg Leu Arg His Ala Leu
35 40 45

Trp Pro Ser Leu Pro Asp Leu His Arg Val Leu Gly Gln Tyr Leu Arg
50 55 60

Asp Thr Ala Ala Leu Ser Pro Pro Lys Ala Thr Val Ser Asp Thr Cys
65 70 75 80

Glu Glu Val Glu Pro Ser Leu Leu Glu Ile Leu Pro Lys Ser Ser Glu
85 90 95

Arg Thr Pro Leu Pro Leu
100

<210> SEQ ID NO 34
<211> LENGTH: 101
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 34

Ser Asp Pro Thr Arg Val Glu Thr Ala Thr Glu Thr Leu Val Thr Ala
1 5 10 15

Leu His Leu Val Leu Gly Leu Ser Ala Val Leu Gly Leu Leu Leu Leu
20 25 30

Arg Trp Gln Phe Pro Ala His Tyr Arg Arg Leu Arg His Ala Leu Trp
35 40 45

Pro Ser Leu Pro Asp Leu His Arg Val Leu Gly Gln Tyr Leu Arg Asp
50 55 60

Thr Ala Ala Leu Ser Pro Pro Lys Ala Thr Val Ser Asp Thr Cys Glu
65 70 75 80

Glu Val Glu Pro Ser Leu Leu Glu Ile Leu Pro Lys Ser Ser Glu Arg
85 90 95

Thr Pro Leu Pro Leu
100

<210> SEQ ID NO 35
<211> LENGTH: 102
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 35

Ser Asp Pro Thr Arg Val Glu Thr Ala Thr Glu Thr Ile Leu Val Thr
1 5 10 15

```
Ala Leu His Leu Val Leu Gly Leu Ser Ala Val Leu Gly Leu Leu Leu
            20                  25                  30

Leu Arg Trp Gln Phe Pro Ala His Tyr Arg Arg Leu Arg His Ala Leu
        35                  40                  45

Trp Pro Ser Leu Pro Asp Leu His Arg Val Leu Gly Gln Tyr Leu Arg
    50                  55                  60

Asp Thr Ala Ala Leu Ser Pro Pro Lys Ala Thr Val Ser Asp Thr Cys
65                  70                  75                  80

Glu Glu Val Glu Pro Ser Leu Leu Glu Ile Leu Pro Lys Ser Ser Glu
                85                  90                  95

Arg Thr Pro Leu Pro Leu
            100


<210> SEQ ID NO 36
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ser Asp Pro Thr Arg Val Glu Thr Ala Thr Glu Thr Val Thr Ala Leu
1               5                   10                  15

His Leu Val Leu Gly Leu Ser Ala Val Leu Gly Leu Leu Leu Leu Arg
            20                  25                  30

Trp Gln Phe Pro Ala His Tyr Arg Arg Leu Arg His Ala Leu Trp Pro
        35                  40                  45

Ser Leu Pro Asp Leu His Arg Val Leu Gly Gln Tyr Leu Arg Asp Thr
    50                  55                  60

Ala Ala Leu Ser Pro Pro Lys Ala Thr Val Ser Asp Thr Cys Glu Glu
65                  70                  75                  80

Val Glu Pro Ser Leu Leu Glu Ile Leu Pro Lys Ser Ser Glu Arg Thr
                85                  90                  95

Pro Leu Pro Leu
            100


<210> SEQ ID NO 37
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ser Asp Pro Thr Arg Val Glu Thr Ala Thr Glu Thr Thr Ala Leu His
1               5                   10                  15

Leu Val Leu Gly Leu Ser Ala Val Leu Gly Leu Leu Leu Leu Arg Trp
            20                  25                  30

Gln Phe Pro Ala His Tyr Arg Arg Leu Arg His Ala Leu Trp Pro Ser
        35                  40                  45

Leu Pro Asp Leu His Arg Val Leu Gly Gln Tyr Leu Arg Asp Thr Ala
    50                  55                  60

Ala Leu Ser Pro Pro Lys Ala Thr Val Ser Asp Thr Cys Glu Glu Val
65                  70                  75                  80

Glu Pro Ser Leu Leu Glu Ile Leu Pro Lys Ser Ser Glu Arg Thr Pro
                85                  90                  95
```

Leu Pro Leu

<210> SEQ ID NO 38
<211> LENGTH: 98
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 38

Ser Asp Pro Thr Arg Val Glu Thr Ala Thr Glu Thr Ala Leu His Leu
1 5 10 15

Val Leu Gly Leu Ser Ala Val Leu Gly Leu Leu Leu Leu Arg Trp Gln
20 25 30

Phe Pro Ala His Tyr Arg Arg Leu Arg His Ala Leu Trp Pro Ser Leu
35 40 45

Pro Asp Leu His Arg Val Leu Gly Gln Tyr Leu Arg Asp Thr Ala Ala
50 55 60

Leu Ser Pro Pro Lys Ala Thr Val Ser Asp Thr Cys Glu Glu Val Glu
65 70 75 80

Pro Ser Leu Leu Glu Ile Leu Pro Lys Ser Ser Glu Arg Thr Pro Leu
85 90 95

Pro Leu

<210> SEQ ID NO 39
<211> LENGTH: 97
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 39

Ser Asp Pro Thr Arg Val Glu Thr Ala Thr Glu Thr Leu His Leu Val
1 5 10 15

Leu Gly Leu Ser Ala Val Leu Gly Leu Leu Leu Leu Arg Trp Gln Phe
20 25 30

Pro Ala His Tyr Arg Arg Leu Arg His Ala Leu Trp Pro Ser Leu Pro
35 40 45

Asp Leu His Arg Val Leu Gly Gln Tyr Leu Arg Asp Thr Ala Ala Leu
50 55 60

Ser Pro Pro Lys Ala Thr Val Ser Asp Thr Cys Glu Glu Val Glu Pro
65 70 75 80

Ser Leu Leu Glu Ile Leu Pro Lys Ser Ser Glu Arg Thr Pro Leu Pro
85 90 95

Leu

<210> SEQ ID NO 40
<211> LENGTH: 96
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 40

Ser Asp Pro Thr Arg Val Glu Thr Ala Thr Glu Thr His Leu Val Leu
1 5 10 15

Gly Leu Ser Ala Val Leu Gly Leu Leu Leu Leu Arg Trp Gln Phe Pro
20 25 30

Ala His Tyr Arg Arg Leu Arg His Ala Leu Trp Pro Ser Leu Pro Asp
35 40 45

Leu His Arg Val Leu Gly Gln Tyr Leu Arg Asp Thr Ala Ala Leu Ser
50 55 60

Pro Pro Lys Ala Thr Val Ser Asp Thr Cys Glu Glu Val Glu Pro Ser
65 70 75 80

Leu Leu Glu Ile Leu Pro Lys Ser Ser Glu Arg Thr Pro Leu Pro Leu
85 90 95

<210> SEQ ID NO 41
<211> LENGTH: 95
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 41

Ser Asp Pro Thr Arg Val Glu Thr Ala Thr Glu Thr Leu Val Leu Gly
1 5 10 15

Leu Ser Ala Val Leu Gly Leu Leu Leu Leu Arg Trp Gln Phe Pro Ala
20 25 30

His Tyr Arg Arg Leu Arg His Ala Leu Trp Pro Ser Leu Pro Asp Leu
35 40 45

His Arg Val Leu Gly Gln Tyr Leu Arg Asp Thr Ala Ala Leu Ser Pro
50 55 60

Pro Lys Ala Thr Val Ser Asp Thr Cys Glu Glu Val Glu Pro Ser Leu
65 70 75 80

Leu Glu Ile Leu Pro Lys Ser Ser Glu Arg Thr Pro Leu Pro Leu
85 90 95

<210> SEQ ID NO 42
<211> LENGTH: 94
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

Ser Asp Pro Thr Arg Val Glu Thr Ala Thr Glu Thr Val Leu Gly Leu
1 5 10 15

Ser Ala Val Leu Gly Leu Leu Leu Leu Arg Trp Gln Phe Pro Ala His
20 25 30

Tyr Arg Arg Leu Arg His Ala Leu Trp Pro Ser Leu Pro Asp Leu His
35 40 45

Arg Val Leu Gly Gln Tyr Leu Arg Asp Thr Ala Ala Leu Ser Pro Pro
50 55 60

Lys Ala Thr Val Ser Asp Thr Cys Glu Glu Val Glu Pro Ser Leu Leu
65 70 75 80

Glu Ile Leu Pro Lys Ser Ser Glu Arg Thr Pro Leu Pro Leu
85 90

<210> SEQ ID NO 43
<211> LENGTH: 93
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 43

Ser Asp Pro Thr Arg Val Glu Thr Ala Thr Glu Thr Leu Gly Leu Ser
1 5 10 15

Ala Val Leu Gly Leu Leu Leu Leu Arg Trp Gln Phe Pro Ala His Tyr
20 25 30

Arg Arg Leu Arg His Ala Leu Trp Pro Ser Leu Pro Asp Leu His Arg
35 40 45

Val Leu Gly Gln Tyr Leu Arg Asp Thr Ala Ala Leu Ser Pro Pro Lys
50 55 60

Ala Thr Val Ser Asp Thr Cys Glu Glu Val Glu Pro Ser Leu Leu Glu
65 70 75 80

Ile Leu Pro Lys Ser Ser Glu Arg Thr Pro Leu Pro Leu
85 90

<210> SEQ ID NO 44
<211> LENGTH: 92
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 44

Ser Asp Pro Thr Arg Val Glu Thr Ala Thr Glu Thr Gly Leu Ser Ala
1 5 10 15

Val Leu Gly Leu Leu Leu Leu Arg Trp Gln Phe Pro Ala His Tyr Arg
20 25 30

Arg Leu Arg His Ala Leu Trp Pro Ser Leu Pro Asp Leu His Arg Val
35 40 45

Leu Gly Gln Tyr Leu Arg Asp Thr Ala Ala Leu Ser Pro Pro Lys Ala
50 55 60

Thr Val Ser Asp Thr Cys Glu Glu Val Glu Pro Ser Leu Leu Glu Ile
65 70 75 80

Leu Pro Lys Ser Ser Glu Arg Thr Pro Leu Pro Leu
85 90

<210> SEQ ID NO 45
<211> LENGTH: 91
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 45

Ser Asp Pro Thr Arg Val Glu Thr Ala Thr Glu Thr Leu Ser Ala Val
1 5 10 15

Leu Gly Leu Leu Leu Leu Arg Trp Gln Phe Pro Ala His Tyr Arg Arg
20 25 30

Leu Arg His Ala Leu Trp Pro Ser Leu Pro Asp Leu His Arg Val Leu
35 40 45

Gly Gln Tyr Leu Arg Asp Thr Ala Ala Leu Ser Pro Pro Lys Ala Thr
50 55 60

Val Ser Asp Thr Cys Glu Glu Val Glu Pro Ser Leu Leu Glu Ile Leu
65 70 75 80

Pro Lys Ser Ser Glu Arg Thr Pro Leu Pro Leu
85 90

<210> SEQ ID NO 46
<211> LENGTH: 90
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 46

Ser Asp Pro Thr Arg Val Glu Thr Ala Thr Glu Thr Ser Ala Val Leu
1 5 10 15

Gly Leu Leu Leu Leu Arg Trp Gln Phe Pro Ala His Tyr Arg Arg Leu
20 25 30

Arg His Ala Leu Trp Pro Ser Leu Pro Asp Leu His Arg Val Leu Gly
35 40 45

Gln Tyr Leu Arg Asp Thr Ala Ala Leu Ser Pro Pro Lys Ala Thr Val
50 55 60

Ser Asp Thr Cys Glu Glu Val Glu Pro Ser Leu Leu Glu Ile Leu Pro
65 70 75 80

Lys Ser Ser Glu Arg Thr Pro Leu Pro Leu
85 90

<210> SEQ ID NO 47
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

Ser Asp Pro Thr Arg Val Glu Thr Ala Thr Glu Thr Ala Val Leu Gly
1 5 10 15

Leu Leu Leu Leu Arg Trp Gln Phe Pro Ala His Tyr Arg Arg Leu Arg
20 25 30

His Ala Leu Trp Pro Ser Leu Pro Asp Leu His Arg Val Leu Gly Gln
35 40 45

Tyr Leu Arg Asp Thr Ala Ala Leu Ser Pro Pro Lys Ala Thr Val Ser
50 55 60

Asp Thr Cys Glu Glu Val Glu Pro Ser Leu Leu Glu Ile Leu Pro Lys
65 70 75 80

Ser Ser Glu Arg Thr Pro Leu Pro Leu
85

<210> SEQ ID NO 48
<211> LENGTH: 88
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 48

Ser Asp Pro Thr Arg Val Glu Thr Ala Thr Glu Thr Val Leu Gly Leu
1 5 10 15

Leu Leu Leu Arg Trp Gln Phe Pro Ala His Tyr Arg Arg Leu Arg His
20 25 30

Ala Leu Trp Pro Ser Leu Pro Asp Leu His Arg Val Leu Gly Gln Tyr
35 40 45

Leu Arg Asp Thr Ala Ala Leu Ser Pro Pro Lys Ala Thr Val Ser Asp
50 55 60

Thr Cys Glu Glu Val Glu Pro Ser Leu Leu Glu Ile Leu Pro Lys Ser
65 70 75 80

Ser Glu Arg Thr Pro Leu Pro Leu
85

<210> SEQ ID NO 49
<211> LENGTH: 87
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 49

Ser Asp Pro Thr Arg Val Glu Thr Ala Thr Glu Thr Leu Gly Leu Leu
1 5 10 15

Leu Leu Arg Trp Gln Phe Pro Ala His Tyr Arg Arg Leu Arg His Ala
20 25 30

Leu Trp Pro Ser Leu Pro Asp Leu His Arg Val Leu Gly Gln Tyr Leu
35 40 45

Arg Asp Thr Ala Ala Leu Ser Pro Pro Lys Ala Thr Val Ser Asp Thr
50 55 60

Cys Glu Glu Val Glu Pro Ser Leu Leu Glu Ile Leu Pro Lys Ser Ser
65 70 75 80

Glu Arg Thr Pro Leu Pro Leu
85

<210> SEQ ID NO 50
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

Ser Asp Pro Thr Arg Val Glu Thr Ala Thr Glu Thr Ala Trp Leu Ile
1 5 10 15

Ser Leu Val Thr Ala Leu His Leu Val Leu Gly Leu Ser Ala Val Leu
20 25 30

Gly Leu Leu Leu Leu Arg Trp Gln Phe Pro Ala His Tyr Arg Arg Leu
35 40 45

Arg His Ala Leu Trp Pro Ser Leu Pro Asp Leu His Arg Val Leu Gly
50 55 60

Gln Tyr Leu Arg Asp Thr Ala Ala Leu Ser Pro Pro Lys Ala Thr Val
65 70 75 80

Ser Asp Thr Cys Glu Glu Val Glu Pro Ser Leu Leu Glu Ile Leu Pro
85 90 95

Lys Ser Ser Glu Arg Thr Pro Leu Pro Leu
100 105

<210> SEQ ID NO 51
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 51

Ser Asp Pro Thr Arg Val Glu Thr Ala Thr Glu Thr Ala Trp Val Leu
1 5 10 15

Ile Ser Leu Val Thr Ala Leu His Leu Val Leu Gly Leu Ser Ala Val
20 25 30

Leu Gly Leu Leu Leu Leu Arg Trp Gln Phe Pro Ala His Tyr Arg Arg
35 40 45

Leu Arg His Ala Leu Trp Pro Ser Leu Pro Asp Leu His Arg Val Leu
50 55 60

Gly Gln Tyr Leu Arg Asp Thr Ala Ala Leu Ser Pro Pro Lys Ala Thr
65 70 75 80

Val Ser Asp Thr Cys Glu Glu Val Glu Pro Ser Leu Leu Glu Ile Leu
85 90 95

Pro Lys Ser Ser Glu Arg Thr Pro Leu Pro Leu
100 105

<210> SEQ ID NO 52
<211> LENGTH: 108
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 52

Ser Asp Pro Thr Arg Val Glu Thr Ala Thr Glu Thr Ala Trp Leu Val
1 5 10 15

Leu Ile Ser Leu Val Thr Ala Leu His Leu Val Leu Gly Leu Ser Ala
20 25 30

Val Leu Gly Leu Leu Leu Leu Arg Trp Gln Phe Pro Ala His Tyr Arg
35 40 45

Arg Leu Arg His Ala Leu Trp Pro Ser Leu Pro Asp Leu His Arg Val
50 55 60

Leu Gly Gln Tyr Leu Arg Asp Thr Ala Ala Leu Ser Pro Pro Lys Ala
65 70 75 80

Thr Val Ser Asp Thr Cys Glu Glu Val Glu Pro Ser Leu Leu Glu Ile
85 90 95

Leu Pro Lys Ser Ser Glu Arg Thr Pro Leu Pro Leu
100 105

<210> SEQ ID NO 53
<211> LENGTH: 109
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 53

Ser Asp Pro Thr Arg Val Glu Thr Ala Thr Glu Thr Ala Trp Ile Leu
1 5 10 15

Val Leu Ile Ser Leu Val Thr Ala Leu His Leu Val Leu Gly Leu Ser
20 25 30

Ala Val Leu Gly Leu Leu Leu Leu Arg Trp Gln Phe Pro Ala His Tyr
35 40 45

Arg Arg Leu Arg His Ala Leu Trp Pro Ser Leu Pro Asp Leu His Arg
50 55 60

Val Leu Gly Gln Tyr Leu Arg Asp Thr Ala Ala Leu Ser Pro Pro Lys
65 70 75 80

Ala Thr Val Ser Asp Thr Cys Glu Glu Val Glu Pro Ser Leu Leu Glu
85 90 95

Ile Leu Pro Lys Ser Ser Glu Arg Thr Pro Leu Pro Leu
100 105

<210> SEQ ID NO 54
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 54

Ser Asp Pro Thr Arg Val Glu Thr Ala Thr Glu Thr Ala Trp Leu Ile
1 5 10 15

Leu Val Leu Ile Ser Leu Val Thr Ala Leu His Leu Val Leu Gly Leu
20 25 30

Ser Ala Val Leu Gly Leu Leu Leu Leu Arg Trp Gln Phe Pro Ala His
35 40 45

Tyr Arg Arg Leu Arg His Ala Leu Trp Pro Ser Leu Pro Asp Leu His
50 55 60

Arg Val Leu Gly Gln Tyr Leu Arg Asp Thr Ala Ala Leu Ser Pro Pro
65 70 75 80

Lys Ala Thr Val Ser Asp Thr Cys Glu Glu Val Glu Pro Ser Leu Leu
85 90 95

Glu Ile Leu Pro Lys Ser Ser Glu Arg Thr Pro Leu Pro Leu
100 105 110

<210> SEQ ID NO 55
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

Ser Asp Pro Thr Arg Val Glu Thr Ala Thr Glu Thr Ala Trp Leu Leu
1 5 10 15

Ile Leu Val Leu Ile Ser Leu Val Thr Ala Leu His Leu Val Leu Gly
20 25 30

Leu Ser Ala Val Leu Gly Leu Leu Leu Leu Arg Trp Gln Phe Pro Ala
35 40 45

His Tyr Arg Arg Leu Arg His Ala Leu Trp Pro Ser Leu Pro Asp Leu
50 55 60

His Arg Val Leu Gly Gln Tyr Leu Arg Asp Thr Ala Ala Leu Ser Pro
65 70 75 80

Pro Lys Ala Thr Val Ser Asp Thr Cys Glu Glu Val Glu Pro Ser Leu
85 90 95

Leu Glu Ile Leu Pro Lys Ser Ser Glu Arg Thr Pro Leu Pro Leu
100 105 110

<210> SEQ ID NO 56
<211> LENGTH: 112

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 56

```
Ser Asp Pro Thr Arg Val Glu Thr Ala Thr Glu Thr Ala Trp Val Leu
1               5                   10                  15

Leu Ile Leu Val Leu Ile Ser Leu Val Thr Ala Leu His Leu Val Leu
            20                  25                  30

Gly Leu Ser Ala Val Leu Gly Leu Leu Leu Leu Arg Trp Gln Phe Pro
        35                  40                  45

Ala His Tyr Arg Arg Leu Arg His Ala Leu Trp Pro Ser Leu Pro Asp
    50                  55                  60

Leu His Arg Val Leu Gly Gln Tyr Leu Arg Asp Thr Ala Ala Leu Ser
65                  70                  75                  80

Pro Pro Lys Ala Thr Val Ser Asp Thr Cys Glu Glu Val Glu Pro Ser
                85                  90                  95

Leu Leu Glu Ile Leu Pro Lys Ser Ser Glu Arg Thr Pro Leu Pro Leu
            100                 105                 110
```

<210> SEQ ID NO 57
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 57

```
Ser Asp Pro Thr Arg Val Glu Thr Ala Thr Glu Thr Ala Trp Leu Val
1               5                   10                  15

Leu Leu Ile Leu Val Leu Ile Ser Leu Val Thr Ala Leu His Leu Val
            20                  25                  30

Leu Gly Leu Ser Ala Val Leu Gly Leu Leu Leu Leu Arg Trp Gln Phe
        35                  40                  45

Pro Ala His Tyr Arg Arg Leu Arg His Ala Leu Trp Pro Ser Leu Pro
    50                  55                  60

Asp Leu His Arg Val Leu Gly Gln Tyr Leu Arg Asp Thr Ala Ala Leu
65                  70                  75                  80

Ser Pro Pro Lys Ala Thr Val Ser Asp Thr Cys Glu Glu Val Glu Pro
                85                  90                  95

Ser Leu Leu Glu Ile Leu Pro Lys Ser Ser Glu Arg Thr Pro Leu Pro
            100                 105                 110

Leu
```

<210> SEQ ID NO 58
<211> LENGTH: 105
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 58

```
Ser Asp Pro Thr Arg Val Glu Thr Ala Thr Glu Thr Ala Trp Ile Ser
1               5                   10                  15

Leu Val Thr Ala Leu His Leu Val Leu Gly Leu Ser Ala Val Leu Gly
            20                  25                  30
```

```
Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu
            100                 105


<210> SEQ ID NO 59
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu
            100                 105


<210> SEQ ID NO 60
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Ser Asp Pro Thr Arg Val Glu Thr Ala Thr Glu Thr Ala Trp Ile Ser
1               5                   10                  15

Leu Val Thr Ala Leu His Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu
            100                 105
```

<210> SEQ ID NO 61
<211> LENGTH: 95
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 61

Ser Asp Pro Thr Arg Val Glu Thr Ala Thr Glu His Leu Val Leu Gly
1 5 10 15

Leu Ser Ala Val Leu Gly Leu Leu Leu Leu Arg Trp Gln Phe Pro Ala
20 25 30

His Tyr Arg Arg Leu Arg His Ala Leu Trp Pro Ser Leu Pro Asp Leu
35 40 45

His Arg Val Leu Gly Gln Tyr Leu Arg Asp Thr Ala Ala Leu Ser Pro
50 55 60

Pro Lys Ala Thr Val Ser Asp Thr Cys Glu Glu Val Glu Pro Ser Leu
65 70 75 80

Leu Glu Ile Leu Pro Lys Ser Ser Glu Arg Thr Pro Leu Pro Leu
85 90 95

<210> SEQ ID NO 62
<211> LENGTH: 94
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 62

Ser Asp Pro Thr Arg Val Glu Thr Ala Thr His Leu Val Leu Gly Leu
1 5 10 15

Ser Ala Val Leu Gly Leu Leu Leu Leu Arg Trp Gln Phe Pro Ala His
20 25 30

Tyr Arg Arg Leu Arg His Ala Leu Trp Pro Ser Leu Pro Asp Leu His
35 40 45

Arg Val Leu Gly Gln Tyr Leu Arg Asp Thr Ala Ala Leu Ser Pro Pro
50 55 60

Lys Ala Thr Val Ser Asp Thr Cys Glu Glu Val Glu Pro Ser Leu Leu
65 70 75 80

Glu Ile Leu Pro Lys Ser Ser Glu Arg Thr Pro Leu Pro Leu
85 90

<210> SEQ ID NO 63
<211> LENGTH: 93
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 63

Ser Asp Pro Thr Arg Val Glu Thr Ala His Leu Val Leu Gly Leu Ser
1 5 10 15

Ala Val Leu Gly Leu Leu Leu Leu Arg Trp Gln Phe Pro Ala His Tyr
20 25 30

Arg Arg Leu Arg His Ala Leu Trp Pro Ser Leu Pro Asp Leu His Arg
35 40 45

Val Leu Gly Gln Tyr Leu Arg Asp Thr Ala Ala Leu Ser Pro Pro Lys
50 55 60

Ala Thr Val Ser Asp Thr Cys Glu Glu Val Glu Pro Ser Leu Leu Glu
65 70 75 80

Ile Leu Pro Lys Ser Ser Glu Arg Thr Pro Leu Pro Leu
85 90

<210> SEQ ID NO 64
<211> LENGTH: 92
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 64

Ser Asp Pro Thr Arg Val Glu Thr His Leu Val Leu Gly Leu Ser Ala
1 5 10 15

Val Leu Gly Leu Leu Leu Leu Arg Trp Gln Phe Pro Ala His Tyr Arg
20 25 30

Arg Leu Arg His Ala Leu Trp Pro Ser Leu Pro Asp Leu His Arg Val
35 40 45

Leu Gly Gln Tyr Leu Arg Asp Thr Ala Ala Leu Ser Pro Pro Lys Ala
50 55 60

Thr Val Ser Asp Thr Cys Glu Glu Val Glu Pro Ser Leu Leu Glu Ile
65 70 75 80

Leu Pro Lys Ser Ser Glu Arg Thr Pro Leu Pro Leu
85 90

<210> SEQ ID NO 65
<211> LENGTH: 91
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 65

Ser Asp Pro Thr Arg Val Glu His Leu Val Leu Gly Leu Ser Ala Val
1 5 10 15

Leu Gly Leu Leu Leu Leu Arg Trp Gln Phe Pro Ala His Tyr Arg Arg
20 25 30

Leu Arg His Ala Leu Trp Pro Ser Leu Pro Asp Leu His Arg Val Leu
35 40 45

Gly Gln Tyr Leu Arg Asp Thr Ala Ala Leu Ser Pro Pro Lys Ala Thr
50 55 60

Val Ser Asp Thr Cys Glu Glu Val Glu Pro Ser Leu Leu Glu Ile Leu
65 70 75 80

Pro Lys Ser Ser Glu Arg Thr Pro Leu Pro Leu
85 90

<210> SEQ ID NO 66
<211> LENGTH: 90
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

Ser Asp Pro Thr Arg Val His Leu Val Leu Gly Leu Ser Ala Val Leu
1               5                   10                  15

Gly Leu Leu Leu Leu Arg Trp Gln Phe Pro Ala His Tyr Arg Arg Leu
            20                  25                  30

Arg His Ala Leu Trp Pro Ser Leu Pro Asp Leu His Arg Val Leu Gly
        35                  40                  45

Gln Tyr Leu Arg Asp Thr Ala Ala Leu Ser Pro Pro Lys Ala Thr Val
    50                  55                  60

Ser Asp Thr Cys Glu Glu Val Glu Pro Ser Leu Leu Glu Ile Leu Pro
65                  70                  75                  80

Lys Ser Ser Glu Arg Thr Pro Leu Pro Leu
                85                  90

<210> SEQ ID NO 67
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 67

Ser Asp Pro Thr Arg His Leu Val Leu Gly Leu Ser Ala Val Leu Gly
1               5                   10                  15

Leu Leu Leu Leu Arg Trp Gln Phe Pro Ala His Tyr Arg Arg Leu Arg
            20                  25                  30

His Ala Leu Trp Pro Ser Leu Pro Asp Leu His Arg Val Leu Gly Gln
        35                  40                  45

Tyr Leu Arg Asp Thr Ala Ala Leu Ser Pro Pro Lys Ala Thr Val Ser
    50                  55                  60

Asp Thr Cys Glu Glu Val Glu Pro Ser Leu Leu Glu Ile Leu Pro Lys
65                  70                  75                  80

Ser Ser Glu Arg Thr Pro Leu Pro Leu
                85

<210> SEQ ID NO 68
<211> LENGTH: 88
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 68

Ser Asp Pro Thr His Leu Val Leu Gly Leu Ser Ala Val Leu Gly Leu
1               5                   10                  15

Leu Leu Leu Arg Trp Gln Phe Pro Ala His Tyr Arg Arg Leu Arg His
            20                  25                  30

Ala Leu Trp Pro Ser Leu Pro Asp Leu His Arg Val Leu Gly Gln Tyr
        35                  40                  45

Leu Arg Asp Thr Ala Ala Leu Ser Pro Pro Lys Ala Thr Val Ser Asp
    50                  55                  60

Thr Cys Glu Glu Val Glu Pro Ser Leu Leu Glu Ile Leu Pro Lys Ser
65                  70                  75                  80

Ser Glu Arg Thr Pro Leu Pro Leu
                85

<210> SEQ ID NO 69
<211> LENGTH: 87
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 69

```
Ser Asp Pro His Leu Val Leu Gly Leu Ser Ala Val Leu Gly Leu Leu
1               5                   10                  15

Leu Leu Arg Trp Gln Phe Pro Ala His Tyr Arg Arg Leu Arg His Ala
            20                  25                  30

Leu Trp Pro Ser Leu Pro Asp Leu His Arg Val Leu Gly Gln Tyr Leu
        35                  40                  45

Arg Asp Thr Ala Ala Leu Ser Pro Pro Lys Ala Thr Val Ser Asp Thr
    50                  55                  60

Cys Glu Glu Val Glu Pro Ser Leu Leu Glu Ile Leu Pro Lys Ser Ser
65                  70                  75                  80

Glu Arg Thr Pro Leu Pro Leu
                85
```

<210> SEQ ID NO 70
<211> LENGTH: 86
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 70

```
Ser Asp His Leu Val Leu Gly Leu Ser Ala Val Leu Gly Leu Leu Leu
1               5                   10                  15

Leu Arg Trp Gln Phe Pro Ala His Tyr Arg Arg Leu Arg His Ala Leu
            20                  25                  30

Trp Pro Ser Leu Pro Asp Leu His Arg Val Leu Gly Gln Tyr Leu Arg
        35                  40                  45

Asp Thr Ala Ala Leu Ser Pro Pro Lys Ala Thr Val Ser Asp Thr Cys
    50                  55                  60

Glu Glu Val Glu Pro Ser Leu Leu Glu Ile Leu Pro Lys Ser Ser Glu
65                  70                  75                  80

Arg Thr Pro Leu Pro Leu
                85
```

<210> SEQ ID NO 71
<211> LENGTH: 85
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 71

```
Ser His Leu Val Leu Gly Leu Ser Ala Val Leu Gly Leu Leu Leu Leu
1               5                   10                  15

Arg Trp Gln Phe Pro Ala His Tyr Arg Arg Leu Arg His Ala Leu Trp
            20                  25                  30

Pro Ser Leu Pro Asp Leu His Arg Val Leu Gly Gln Tyr Leu Arg Asp
        35                  40                  45
```

Thr Ala Ala Leu Ser Pro Pro Lys Ala Thr Val Ser Asp Thr Cys Glu
    50                  55                  60

Glu Val Glu Pro Ser Leu Leu Glu Ile Leu Pro Lys Ser Ser Glu Arg
65                  70                  75                  80

Thr Pro Leu Pro Leu
                85

<210> SEQ ID NO 72
<211> LENGTH: 84
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

His Leu Val Leu Gly Leu Ser Ala Val Leu Gly Leu Leu Leu Leu Arg
1               5                   10                  15

Trp Gln Phe Pro Ala His Tyr Arg Arg Leu Arg His Ala Leu Trp Pro
            20                  25                  30

Ser Leu Pro Asp Leu His Arg Val Leu Gly Gln Tyr Leu Arg Asp Thr
        35                  40                  45

Ala Ala Leu Ser Pro Pro Lys Ala Thr Val Ser Asp Thr Cys Glu Glu
    50                  55                  60

Val Glu Pro Ser Leu Leu Glu Ile Leu Pro Lys Ser Ser Glu Arg Thr
65                  70                  75                  80

Pro Leu Pro Leu

<210> SEQ ID NO 73
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Ser Asp Pro Thr Arg Val Glu Thr Ala Thr Glu Thr Ala Trp Ile Ser
1               5                   10                  15

Leu Val His Leu Val Leu Gly Leu Ser Ala Val Leu Gly Leu Leu Leu
            20                  25                  30

Leu Arg Trp Gln Phe Pro Ala His Tyr Arg Arg Leu Arg His Ala Leu
        35                  40                  45

Trp Pro Ser Leu Pro Asp Leu His Arg Val Leu Gly Gln Tyr Leu Arg
    50                  55                  60

Asp Thr Ala Ala Leu Ser Pro Pro Lys Ala Thr Val Ser Asp Thr Cys
65                  70                  75                  80

Glu Glu Val Glu Pro Ser Leu Leu Glu Ile Leu Pro Lys Ser Ser Glu
                85                  90                  95

Arg Thr Pro Leu Pro Leu
            100

<210> SEQ ID NO 74
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Ser Asp Pro Thr Arg Val Glu Thr Ala Thr Glu Thr Ala Trp Ile Ser
1 5 10 15

His Leu Val Leu Gly Leu Ser Ala Val Leu Gly Leu Leu Leu Leu Arg
20 25 30

Trp Gln Phe Pro Ala His Tyr Arg Arg Leu Arg His Ala Leu Trp Pro
35 40 45

Ser Leu Pro Asp Leu His Arg Val Leu Gly Gln Tyr Leu Arg Asp Thr
50 55 60

Ala Ala Leu Ser Pro Pro Lys Ala Thr Val Ser Asp Thr Cys Glu Glu
65 70 75 80

Val Glu Pro Ser Leu Leu Glu Ile Leu Pro Lys Ser Ser Glu Arg Thr
85 90 95

Pro Leu Pro Leu
100

<210> SEQ ID NO 75
<211> LENGTH: 101
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 75

Ser Asp Pro Thr Arg Val Glu Thr Ala Thr Glu Thr Ala Trp Ile Ser
1 5 10 15

Pro His Leu Val Leu Gly Leu Ser Ala Val Leu Gly Leu Leu Leu Leu
20 25 30

Arg Trp Gln Phe Pro Ala His Tyr Arg Arg Leu Arg His Ala Leu Trp
35 40 45

Pro Ser Leu Pro Asp Leu His Arg Val Leu Gly Gln Tyr Leu Arg Asp
50 55 60

Thr Ala Ala Leu Ser Pro Pro Lys Ala Thr Val Ser Asp Thr Cys Glu
65 70 75 80

Glu Val Glu Pro Ser Leu Leu Glu Ile Leu Pro Lys Ser Ser Glu Arg
85 90 95

Thr Pro Leu Pro Leu
100

<210> SEQ ID NO 76
<211> LENGTH: 102
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 76

Ser Asp Pro Thr Arg Val Glu Thr Ala Thr Glu Thr Ala Trp Ile Ser
1 5 10 15

Pro Pro His Leu Val Leu Gly Leu Ser Ala Val Leu Gly Leu Leu Leu
20 25 30

Leu Arg Trp Gln Phe Pro Ala His Tyr Arg Arg Leu Arg His Ala Leu
35 40 45

Trp Pro Ser Leu Pro Asp Leu His Arg Val Leu Gly Gln Tyr Leu Arg
50 55 60

Asp Thr Ala Ala Leu Ser Pro Pro Lys Ala Thr Val Ser Asp Thr Cys
65 70 75 80

Glu Glu Val Glu Pro Ser Leu Leu Glu Ile Leu Pro Lys Ser Ser Glu
85 90 95

Arg Thr Pro Leu Pro Leu
100

<210> SEQ ID NO 77
<211> LENGTH: 99
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 77

Ser Asp Pro Thr Arg Val Glu Thr Ala Thr Glu Thr Ala Trp Ile His
1 5 10 15

Leu Val Leu Gly Leu Ser Ala Val Leu Gly Leu Leu Leu Leu Arg Trp
20 25 30

Gln Phe Pro Ala His Tyr Arg Arg Leu Arg His Ala Leu Trp Pro Ser
35 40 45

Leu Pro Asp Leu His Arg Val Leu Gly Gln Tyr Leu Arg Asp Thr Ala
50 55 60

Ala Leu Ser Pro Pro Lys Ala Thr Val Ser Asp Thr Cys Glu Glu Val
65 70 75 80

Glu Pro Ser Leu Leu Glu Ile Leu Pro Lys Ser Ser Glu Arg Thr Pro
85 90 95

Leu Pro Leu

<210> SEQ ID NO 78
<211> LENGTH: 100
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 78

Ser Asp Pro Thr Arg Val Glu Thr Ala Thr Glu Thr Ala Trp Ile Pro
1 5 10 15

His Leu Val Leu Gly Leu Ser Ala Val Leu Gly Leu Leu Leu Leu Arg
20 25 30

Trp Gln Phe Pro Ala His Tyr Arg Arg Leu Arg His Ala Leu Trp Pro
35 40 45

Ser Leu Pro Asp Leu His Arg Val Leu Gly Gln Tyr Leu Arg Asp Thr
50 55 60

Ala Ala Leu Ser Pro Pro Lys Ala Thr Val Ser Asp Thr Cys Glu Glu
65 70 75 80

Val Glu Pro Ser Leu Leu Glu Ile Leu Pro Lys Ser Ser Glu Arg Thr
85 90 95

Pro Leu Pro Leu
100

<210> SEQ ID NO 79
<211> LENGTH: 101
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 79

Ser Asp Pro Thr Arg Val Glu Thr Ala Thr Glu Thr Ala Trp Ile Pro
1 5 10 15

Pro His Leu Val Leu Gly Leu Ser Ala Val Leu Gly Leu Leu Leu Leu
20 25 30

Arg Trp Gln Phe Pro Ala His Tyr Arg Arg Leu Arg His Ala Leu Trp
35 40 45

Pro Ser Leu Pro Asp Leu His Arg Val Leu Gly Gln Tyr Leu Arg Asp
50 55 60

Thr Ala Ala Leu Ser Pro Pro Lys Ala Thr Val Ser Asp Thr Cys Glu
65 70 75 80

Glu Val Glu Pro Ser Leu Leu Glu Ile Leu Pro Lys Ser Ser Glu Arg
85 90 95

Thr Pro Leu Pro Leu
100

<210> SEQ ID NO 80
<211> LENGTH: 144
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 80

Ala Arg Asp Glu Val Glu Gly Phe Leu Gln Asp Thr Phe Pro Gln Gln
1 5 10 15

Leu Glu Glu Ser Glu Lys Gln Arg Leu Gly Gly Asp Val Gln Ser Pro
20 25 30

Asn Cys Pro Ser Glu Asp Val Val Ile Thr Pro Glu Ser Phe Gly Arg
35 40 45

Asp Ser Ser Leu Thr Cys Leu Ala Gly Asn Val Ser Ala Cys Asp Ala
50 55 60

Pro Ile Leu Ser Ser Ser Arg Ser Leu Asp Cys Arg Glu Ser Gly Lys
65 70 75 80

Asn Gly Pro His Val Tyr Gln Asp Leu Leu Leu Ser Leu Gly Thr Thr
85 90 95

Asn Ser Thr Leu Pro Pro Pro Phe Ser Leu Gln Ser Gly Ile Leu Thr
100 105 110

Leu Asn Pro Val Ala Gln Gly Gln Pro Ile Leu Thr Ser Leu Gly Ser
115 120 125

Asn Gln Glu Glu Ala Tyr Val Thr Met Ser Ser Phe Tyr Gln Asn Gln
130 135 140

<210> SEQ ID NO 81
<211> LENGTH: 219
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 81

Val Thr Gln Leu Leu Leu Gln Gln Asp Lys Val Pro Glu Pro Ala Ser
1 5 10 15

Leu Ser Ser Asn His Ser Leu Thr Ser Cys Phe Thr Asn Gln Gly Tyr
20 25 30

Phe Phe Phe His Leu Pro Asp Ala Leu Glu Ile Glu Ala Cys Gln Val
35 40 45

Tyr Phe Thr Tyr Asp Pro Tyr Ser Glu Glu Asp Pro Asp Glu Gly Val
50 55 60

Ala Gly Ala Pro Thr Gly Ser Ser Pro Gln Pro Leu Gln Pro Leu Ser
65 70 75 80

Gly Glu Asp Asp Ala Tyr Cys Thr Phe Pro Ser Arg Asp Asp Leu Leu
85 90 95

Leu Phe Ser Pro Ser Leu Leu Gly Gly Pro Ser Pro Pro Ser Thr Ala
100 105 110

Pro Gly Gly Ser Gly Ala Gly Glu Glu Arg Met Pro Pro Ser Leu Gln
115 120 125

Glu Arg Val Pro Arg Asp Trp Asp Pro Gln Pro Leu Gly Pro Pro Thr
130 135 140

Pro Gly Val Pro Asp Leu Val Asp Phe Gln Pro Pro Pro Glu Leu Val
145 150 155 160

Leu Arg Glu Ala Gly Glu Glu Val Pro Asp Ala Gly Pro Arg Glu Gly
165 170 175

Val Ser Phe Pro Trp Ser Arg Pro Pro Gly Gln Gly Glu Phe Arg Ala
180 185 190

Leu Asn Ala Arg Leu Pro Leu Asn Thr Asp Ala Tyr Leu Ser Leu Gln
195 200 205

Glu Leu Gln Gly Gln Asp Pro Thr His Leu Val
210 215

<210> SEQ ID NO 82
<211> LENGTH: 50
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 82

Ile Ser Thr Ile Ala Thr Val Glu Glu Thr Asn Gln Thr Asp Glu Asp
1 5 10 15

His Lys Lys Tyr Ser Ser Gln Thr Ser Gln Asp Ser Gly Asn Tyr Ser
20 25 30

Asn Glu Asp Glu Ser Glu Ser Lys Thr Ser Glu Glu Leu Gln Gln Asp
35 40 45

Phe Val
50

<210> SEQ ID NO 83
<211> LENGTH: 206
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 83

Lys Lys Lys Val Trp Asp Tyr Asn Tyr Asp Asp Glu Ser Asp Ser Asp
1 5 10 15

Thr Glu Ala Ala Pro Arg Thr Ser Gly Gly Gly Tyr Thr Met His Gly
20 25 30

Leu Thr Val Arg Pro Leu Gly Gln Ala Ser Ala Thr Ser Thr Glu Ser
35 40 45

Gln Leu Ile Asp Pro Glu Ser Glu Glu Glu Pro Asp Leu Pro Glu Val
50 55 60

Asp Val Glu Leu Pro Thr Met Pro Lys Asp Ser Pro Gln Gln Leu Glu
65 70 75 80

Leu Leu Ser Gly Pro Cys Glu Arg Arg Lys Ser Pro Leu Gln Asp Pro
85 90 95

Phe Pro Glu Glu Asp Tyr Ser Ser Thr Glu Gly Ser Gly Gly Arg Ile
100 105 110

Thr Phe Asn Val Asp Leu Asn Ser Val Phe Leu Arg Val Leu Asp Asp
115 120 125

Glu Asp Ser Asp Asp Leu Glu Ala Pro Leu Met Leu Ser Ser His Leu
130 135 140

Glu Glu Met Val Asp Pro Glu Asp Pro Asp Asn Val Gln Ser Asn His
145 150 155 160

Leu Leu Ala Ser Gly Glu Gly Thr Gln Pro Thr Phe Pro Ser Pro Ser
165 170 175

Ser Glu Gly Leu Trp Ser Glu Asp Ala Pro Ser Asp Gln Ser Asp Thr
180 185 190

Ser Glu Ser Asp Val Asp Leu Gly Asp Gly Tyr Ile Met Arg
195 200 205

<210> SEQ ID NO 84
<211> LENGTH: 256
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 84

Ile Ser Thr Ile Ala Thr Val Glu Glu Thr Asn Gln Thr Asp Glu Asp
1 5 10 15

His Lys Lys Tyr Ser Ser Gln Thr Ser Gln Asp Ser Gly Asn Tyr Ser
20 25 30

Asn Glu Asp Glu Ser Glu Ser Lys Thr Ser Glu Glu Leu Gln Gln Asp
35 40 45

Phe Val Lys Lys Lys Val Trp Asp Tyr Asn Tyr Asp Asp Glu Ser Asp
50 55 60

Ser Asp Thr Glu Ala Ala Pro Arg Thr Ser Gly Gly Gly Tyr Thr Met
65 70 75 80

His Gly Leu Thr Val Arg Pro Leu Gly Gln Ala Ser Ala Thr Ser Thr
85 90 95

Glu Ser Gln Leu Ile Asp Pro Glu Ser Glu Glu Glu Pro Asp Leu Pro
100 105 110

Glu Val Asp Val Glu Leu Pro Thr Met Pro Lys Asp Ser Pro Gln Gln
115 120 125

Leu Glu Leu Leu Ser Gly Pro Cys Glu Arg Arg Lys Ser Pro Leu Gln
130 135 140

Asp Pro Phe Pro Glu Glu Asp Tyr Ser Ser Thr Glu Gly Ser Gly Gly
145 150 155 160

Arg Ile Thr Phe Asn Val Asp Leu Asn Ser Val Phe Leu Arg Val Leu
165 170 175

```
Asp Asp Glu Asp Ser Asp Asp Leu Glu Ala Pro Leu Met Leu Ser Ser
            180                 185                 190

His Leu Glu Glu Met Val Asp Pro Glu Asp Pro Asp Asn Val Gln Ser
        195                 200                 205

Asn His Leu Leu Ala Ser Gly Glu Gly Thr Gln Pro Thr Phe Pro Ser
    210                 215                 220

Pro Ser Ser Glu Gly Leu Trp Ser Glu Asp Ala Pro Ser Asp Gln Ser
225                 230                 235                 240

Asp Thr Ser Glu Ser Asp Val Asp Leu Gly Asp Gly Tyr Ile Met Arg
                245                 250                 255


<210> SEQ ID NO 85
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Arg Gly Val Arg Pro Thr Pro Arg Val Arg Ala Pro Ala Thr Gln Gln
1               5                   10                  15

Thr Arg Trp Lys Lys Asp Leu Ala Glu Asp Glu Glu Glu Glu Asp Glu
            20                  25                  30

Glu Asp Thr Glu Asp Gly Val Ser Phe Gln Pro Tyr Ile Glu Pro Pro
        35                  40                  45

Ser Phe Leu Gly Gln Glu His Gln Ala Pro Gly His Ser Glu Ala Gly
    50                  55                  60

Gly Val Asp Ser Gly Arg Pro Arg Ala Pro Leu Val Pro Ser Glu Gly
65                  70                  75                  80

Ser Ser Ala Trp Asp Ser Ser Asp Arg Ser Trp Ala Ser Thr Val Asp
                85                  90                  95

Ser Ser Trp Asp Arg Ala Gly Ser Ser Gly Tyr Leu Ala Glu Lys Gly
            100                 105                 110

Pro Gly Gln Gly Pro Gly Gly Asp Gly His Gln Glu Ser Leu Pro Pro
        115                 120                 125

Pro Glu Phe Ser Lys Asp Ser Gly Phe Leu Glu Glu Leu Pro Glu Asp
    130                 135                 140

Asn Leu Ser Ser Trp Ala Thr Trp Gly Thr Leu Pro Pro Glu Pro Asn
145                 150                 155                 160

Leu Val Pro Gly Gly Pro Pro Val Ser Leu Gln Thr Leu Thr Phe Cys
                165                 170                 175

Trp Glu Ser Ser Pro Glu Glu Glu Glu Glu Ala Arg Glu Ser Glu Ile
            180                 185                 190

Glu Asp Ser Asp Ala Gly Ser Trp Gly Ala Glu Ser Thr Gln Arg Thr
        195                 200                 205

Glu Asp Arg Gly Arg Thr Leu Gly His Tyr Met Ala Arg
    210                 215                 220


<210> SEQ ID NO 86
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 86

Ile Pro Pro Lys Gly Gly Ala Leu Gly Glu Gly Pro Gly Ala Ser Pro
1 5 10 15

Cys Asn Gln His Ser Pro Tyr Trp Ala Pro Pro Cys Tyr Thr Leu Lys
20 25 30

Pro Glu Thr
35

<210> SEQ ID NO 87
<211> LENGTH: 166
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 87

Thr Ala Leu Leu Thr Cys Gly Pro Ala Arg Pro Trp Lys Ser Val Ala
1 5 10 15

Leu Glu Glu Glu Gln Glu Gly Pro Gly Thr Arg Leu Pro Gly Asn Leu
20 25 30

Ser Ser Glu Asp Val Leu Pro Ala Gly Cys Thr Glu Trp Arg Val Gln
35 40 45

Thr Leu Ala Tyr Leu Pro Gln Glu Asp Trp Ala Pro Thr Ser Leu Thr
50 55 60

Arg Pro Ala Pro Pro Asp Ser Glu Gly Ser Arg Ser Ser Ser Ser Ser
65 70 75 80

Ser Ser Ser Asn Asn Asn Asn Tyr Cys Ala Leu Gly Cys Tyr Gly Gly
85 90 95

Trp His Leu Ser Ala Leu Pro Gly Asn Thr Gln Ser Ser Gly Pro Ile
100 105 110

Pro Ala Leu Ala Cys Gly Leu Ser Cys Asp His Gln Gly Leu Glu Thr
115 120 125

Gln Gln Gly Val Ala Trp Val Leu Ala Gly His Cys Gln Arg Pro Gly
130 135 140

Leu His Glu Asp Leu Gln Gly Met Leu Leu Pro Ser Val Leu Ser Lys
145 150 155 160

Ala Arg Ser Trp Thr Phe
165

<210> SEQ ID NO 88
<211> LENGTH: 217
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 88

Pro Arg Ser Pro Ala Lys Arg Leu Gln Leu Thr Glu Leu Gln Glu Pro
1 5 10 15

Ala Glu Leu Val Glu Ser Asp Gly Val Pro Lys Pro Ser Phe Trp Pro
20 25 30

Thr Ala Gln Asn Ser Gly Gly Ser Ala Tyr Ser Glu Glu Arg Asp Arg
35 40 45

Pro Tyr Gly Leu Val Ser Ile Asp Thr Val Thr Val Leu Asp Ala Glu
50 55 60

Gly Pro Cys Thr Trp Pro Cys Ser Cys Glu Asp Asp Gly Tyr Pro Ala
65 70 75 80

Leu Asp Leu Asp Ala Gly Leu Glu Pro Ser Pro Gly Leu Glu Asp Pro
85 90 95

Leu Leu Asp Ala Gly Thr Thr Val Leu Ser Cys Gly Cys Val Ser Ala
100 105 110

Gly Ser Pro Gly Leu Gly Gly Pro Leu Gly Ser Leu Leu Asp Arg Leu
115 120 125

Lys Pro Pro Leu Ala Asp Gly Glu Asp Trp Ala Gly Gly Leu Pro Trp
130 135 140

Gly Gly Arg Ser Pro Gly Gly Val Ser Glu Ser Glu Ala Gly Ser Pro
145 150 155 160

Leu Ala Gly Leu Asp Met Asp Thr Phe Asp Ser Gly Phe Val Gly Ser
165 170 175

Asp Cys Ser Ser Pro Val Glu Cys Asp Phe Thr Ser Pro Gly Asp Glu
180 185 190

Gly Pro Pro Arg Ser Tyr Leu Arg Gln Trp Val Val Ile Pro Pro Pro
195 200 205

Leu Ser Ser Pro Gly Pro Gln Ala Ser
210 215

<210> SEQ ID NO 89
<211> LENGTH: 286
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 89

Pro Asp Glu Lys Thr Glu Glu Ser Asp Thr Asp Arg Leu Leu Ser Ser
1 5 10 15

Asp His Glu Lys Ser His Ser Asn Leu Gly Val Lys Asp Gly Asp Ser
20 25 30

Gly Arg Thr Ser Cys Cys Glu Pro Asp Ile Leu Glu Thr Asp Phe Asn
35 40 45

Ala Asn Asp Ile His Glu Gly Thr Ser Glu Val Ala Gln Pro Gln Arg
50 55 60

Leu Lys Gly Glu Ala Asp Leu Leu Cys Leu Asp Gln Lys Asn Gln Asn
65 70 75 80

Asn Ser Pro Tyr His Asp Ala Cys Pro Ala Thr Gln Gln Pro Ser Val
85 90 95

Ile Gln Ala Glu Lys Asn Lys Pro Gln Pro Leu Pro Thr Glu Gly Ala
100 105 110

Glu Ser Thr His Gln Ala Ala His Ile Gln Leu Ser Asn Pro Ser Ser
115 120 125

Leu Ser Asn Ile Asp Phe Tyr Ala Gln Val Ser Asp Ile Thr Pro Ala
130 135 140

Gly Ser Val Val Leu Ser Pro Gly Gln Lys Asn Lys Ala Gly Met Ser
145 150 155 160

Gln Cys Asp Met His Pro Glu Met Val Ser Leu Cys Gln Glu Asn Phe
165 170 175

Leu Met Asp Asn Ala Tyr Phe Cys Glu Ala Asp Ala Lys Lys Cys Ile
180 185 190

Pro Val Ala Pro His Ile Lys Val Glu Ser His Ile Gln Pro Ser Leu
195 200 205

Asn Gln Glu Asp Ile Tyr Ile Thr Thr Glu Ser Leu Thr Thr Ala Ala
    210                 215                 220

Gly Arg Pro Gly Thr Gly Glu His Val Pro Gly Ser Glu Met Pro Val
225                 230                 235                 240

Pro Asp Tyr Thr Ser Ile His Ile Val Gln Ser Pro Gln Gly Leu Ile
                245                 250                 255

Leu Asn Ala Thr Ala Leu Pro Leu Pro Asp Lys Glu Phe Leu Ser Ser
            260                 265                 270

Cys Gly Tyr Val Ser Thr Asp Gln Leu Asn Lys Ile Met Pro
        275                 280                 285

<210> SEQ ID NO 90
<211> LENGTH: 170
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Trp Gly Thr Met Gln Ala Val Glu Pro Gly Thr Asp Asp Glu Gly Pro
1               5                   10                  15

Leu Leu Glu Pro Val Gly Ser Glu His Ala Gln Asp Thr Tyr Leu Val
            20                  25                  30

Leu Asp Lys Trp Leu Leu Pro Arg Asn Pro Pro Ser Glu Asp Leu Pro
        35                  40                  45

Gly Pro Gly Gly Ser Val Asp Ile Val Ala Met Asp Glu Gly Ser Glu
    50                  55                  60

Ala Ser Ser Cys Ser Ser Ala Leu Ala Ser Lys Pro Ser Pro Glu Gly
65                  70                  75                  80

Ala Ser Ala Ala Ser Phe Glu Tyr Thr Ile Leu Asp Pro Ser Ser Gln
                85                  90                  95

Leu Leu Arg Pro Trp Thr Leu Cys Pro Glu Leu Pro Pro Thr Pro Pro
            100                 105                 110

His Leu Lys Tyr Leu Tyr Leu Val Val Ser Asp Ser Gly Ile Ser Thr
        115                 120                 125

Asp Tyr Ser Ser Gly Asp Ser Gln Gly Ala Gln Gly Gly Leu Ser Asp
    130                 135                 140

Gly Pro Tyr Ser Asn Pro Tyr Glu Asn Ser Leu Ile Pro Ala Ala Glu
145                 150                 155                 160

Pro Leu Pro Pro Ser Tyr Val Ala Cys Ser
                165                 170

<210> SEQ ID NO 91
<211> LENGTH: 203
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Ala Val Gln Leu Leu Leu Leu Gln Lys Asp Ser Ala Pro Leu Pro Ser
1               5                   10                  15

Pro Ser Gly His Ser Gln Ala Ser Cys Phe Thr Asn Gln Gly Tyr Phe
            20                  25                  30

Phe Phe His Leu Pro Asn Ala Leu Glu Ile Glu Ser Cys Gln Val Tyr
        35                  40                  45

```
Phe Thr Tyr Asp Pro Cys Val Glu Glu Glu Val Glu Glu Asp Gly Ser
    50                  55                  60

Arg Leu Pro Glu Gly Ser Pro His Pro Pro Leu Leu Pro Leu Ala Gly
65                  70                  75                  80

Glu Gln Asp Asp Tyr Cys Ala Phe Pro Pro Arg Asp Asp Leu Leu Leu
                85                  90                  95

Phe Ser Pro Ser Leu Ser Thr Pro Asn Thr Ala Tyr Gly Gly Ser Arg
            100                 105                 110

Ala Pro Glu Glu Arg Ser Pro Leu Ser Leu His Glu Gly Leu Pro Ser
        115                 120                 125

Leu Ala Ser Arg Asp Leu Met Gly Leu Gln Arg Pro Leu Glu Arg Met
    130                 135                 140

Pro Glu Gly Asp Gly Glu Gly Leu Ser Ala Asn Ser Ser Gly Glu Gln
145                 150                 155                 160

Ala Ser Val Pro Glu Gly Asn Leu His Gly Gln Asp Gln Asp Arg Gly
                165                 170                 175

Gln Gly Pro Ile Leu Thr Leu Asn Thr Asp Ala Tyr Leu Ser Leu Gln
            180                 185                 190

Glu Leu Gln Ala Gln Asp Ser Val His Leu Ile
        195                 200
```

<210> SEQ ID NO 92
<211> LENGTH: 144
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 92

```
Ala Arg Asp Glu Val Glu Ser Phe Leu Pro Asn Asp Leu Pro Ala Gln
1               5                   10                  15

Pro Glu Glu Leu Glu Thr Gln Gly His Arg Ala Ala Val His Ser Ala
            20                  25                  30

Asn Arg Ser Pro Glu Thr Ser Val Ser Pro Pro Glu Thr Val Arg Arg
        35                  40                  45

Glu Ser Pro Leu Arg Cys Leu Ala Arg Asn Leu Ser Thr Cys Asn Ala
    50                  55                  60

Pro Pro Leu Leu Ser Ser Arg Ser Pro Asp Tyr Arg Asp Gly Asp Arg
65                  70                  75                  80

Asn Arg Pro Pro Val Tyr Gln Asp Leu Leu Pro Asn Ser Gly Asn Thr
                85                  90                  95

Asn Val Pro Val Pro Val Pro Gln Pro Leu Pro Phe Gln Ser Gly Ile
            100                 105                 110

Leu Ile Pro Val Ser Gln Arg Gln Pro Ile Ser Thr Ser Ser Val Leu
        115                 120                 125

Asn Gln Glu Glu Ala Tyr Val Thr Met Ser Ser Phe Tyr Gln Asn Lys
    130                 135                 140
```

<210> SEQ ID NO 93
<211> LENGTH: 231
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 93

Val Ile Gln Gly Asp Glu Arg Met His Leu Pro Ser Pro Thr Asp Ser
1 5 10 15

Asn Phe Tyr Arg Ala Leu Met Asp Glu Glu Asp Met Asp Asp Val Val
20 25 30

Asp Ala Asp Glu Tyr Leu Ile Pro Gln Gln Gly Phe Phe Ser Ser Pro
35 40 45

Ser Thr Ser Arg Thr Pro Leu Leu Ser Ser Leu Ser Ala Thr Ser Asn
50 55 60

Asn Ser Thr Val Ala Cys Ile Asp Arg Asn Gly Leu Gln Ser Cys Pro
65 70 75 80

Ile Lys Glu Asp Ser Phe Leu Gln Arg Tyr Ser Ser Asp Pro Thr Gly
85 90 95

Ala Leu Thr Glu Asp Ser Ile Asp Asp Thr Phe Leu Pro Val Pro Glu
100 105 110

Tyr Ile Asn Gln Ser Val Pro Lys Arg Pro Ala Gly Ser Val Gln Asn
115 120 125

Pro Val Tyr His Asn Gln Pro Leu Asn Pro Ala Pro Ser Arg Asp Pro
130 135 140

His Tyr Gln Asp Pro His Ser Thr Ala Val Gly Asn Pro Glu Tyr Leu
145 150 155 160

Asn Thr Val Gln Pro Thr Cys Val Asn Ser Thr Phe Asp Ser Pro Ala
165 170 175

His Trp Ala Gln Lys Gly Ser His Gln Ile Ser Leu Asp Asn Pro Asp
180 185 190

Tyr Gln Gln Asp Phe Phe Pro Lys Glu Ala Lys Pro Asn Gly Ile Phe
195 200 205

Lys Gly Ser Thr Ala Glu Asn Ala Glu Tyr Leu Arg Val Ala Pro Gln
210 215 220

Ser Ser Glu Phe Ile Gly Ala
225 230

<210> SEQ ID NO 94
<211> LENGTH: 218
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 94

Val Ile Gln Gly Asp Glu Arg Met His Leu Pro Ser Pro Thr Asp Ser
1 5 10 15

Asn Phe Phe Arg Ala Leu Met Asp Glu Glu Asp Met Asp Asp Val Val
20 25 30

Asp Ala Asp Glu Tyr Leu Ile Pro Gln Gln Gly Phe Phe Ser Ser Pro
35 40 45

Ser Thr Ser Arg Thr Pro Leu Leu Ser Ser Leu Ser Ala Thr Ser Asn
50 55 60

Asn Ser Thr Val Ala Cys Ile Asp Arg Asn Gly Leu Gln Ser Cys Pro
65 70 75 80

Ile Lys Glu Asp Ser Phe Leu Gln Arg Ile Asp Asp Thr Phe Leu Pro
85 90 95

Val Pro Glu Tyr Ile Asn Gln Ser Val Pro Lys Arg Pro Ala Gly Ser
100 105 110

Val Gln Asn Pro Val Tyr His Asn Gln Pro Leu Asn Pro Ala Pro Ser
115 120 125

Arg Asp Pro His Tyr Gln Asp Pro His Ser Thr Ala Val Gly Asn Pro
130 135 140

Glu Tyr Leu Asn Thr Val Gln Pro Thr Cys Val Asn Ser Thr Phe Asp
145 150 155 160

Ser Pro Ala His Trp Ala Gln Lys Gly Ser His Gln Ile Ser Leu Asp
165 170 175

Asn Pro Asp Tyr Gln Gln Asp Phe Phe Pro Lys Glu Ala Lys Pro Asn
180 185 190

Gly Ile Phe Lys Gly Ser Thr Ala Glu Asn Ala Glu Tyr Leu Arg Val
195 200 205

Ala Pro Gln Ser Ser Glu Phe Ile Gly Ala
210 215

<210> SEQ ID NO 95
<211> LENGTH: 54
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 95

Val Ile Gln Gly Asp Glu Arg Met His Leu Pro Ser Pro Thr Asp Ser
1 5 10 15

Asn Phe Phe Arg Ala Leu Met Asp Glu Glu Asp Met Asp Asp Val Val
20 25 30

Asp Ala Asp Glu Tyr Leu Ile Pro Gln Gln Gly Phe Phe Ser Ser Pro
35 40 45

Ser Thr Ser Arg Thr Pro
50

<210> SEQ ID NO 96
<211> LENGTH: 54
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 96

Asn Asn Ser Thr Val Ala Cys Ile Asp Arg Asn Gly Leu Gln Ser Cys
1 5 10 15

Pro Ile Lys Glu Asp Ser Phe Leu Gln Arg Ile Asp Asp Thr Phe Leu
20 25 30

Pro Val Pro Glu Tyr Ile Asn Gln Ser Val Pro Lys Arg Pro Ala Gly
35 40 45

Ser Val Gln Asn Pro Val
50

<210> SEQ ID NO 97
<211> LENGTH: 54
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 97

Lys Glu Asp Ser Phe Leu Gln Arg Ile Asp Asp Thr Phe Leu Pro Val
1 5 10 15

Pro Glu Phe Ile Asn Gln Ser Val Pro Lys Arg Pro Ala Gly Ser Val
20 25 30

Gln Asn Pro Val Tyr His Asn Gln Pro Leu Asn Pro Ala Pro Ser Arg
35 40 45

Asp Pro His Phe Gln Asp
50

<210> SEQ ID NO 98
<211> LENGTH: 54
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 98

Val Pro Glu Phe Ile Asn Gln Ser Val Pro Lys Arg Pro Ala Gly Ser
1 5 10 15

Val Gln Asn Pro Val Phe His Asn Gln Pro Leu Asn Pro Ala Pro Ser
20 25 30

Arg Asp Pro His Tyr Gln Asp Pro His Ser Thr Ala Val Gly Asn Pro
35 40 45

Glu Tyr Leu Asn Thr Val
50

<210> SEQ ID NO 99
<211> LENGTH: 54
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 99

Pro Glu Tyr Leu Asn Thr Val Gln Pro Thr Cys Val Asn Ser Thr Phe
1 5 10 15

Asp Ser Pro Ala His Trp Ala Gln Lys Gly Ser His Gln Ile Ser Leu
20 25 30

Asp Asn Pro Asp Tyr Gln Gln Asp Phe Phe Pro Lys Glu Ala Lys Pro
35 40 45

Asn Gly Ile Phe Lys Gly
50

<210> SEQ ID NO 100
<211> LENGTH: 54
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 100

Trp Ala Gln Lys Gly Ser His Gln Ile Ser Leu Asp Asn Pro Asp Phe
1 5 10 15

Gln Gln Asp Phe Phe Pro Lys Glu Ala Lys Pro Asn Gly Ile Phe Lys
20 25 30

Gly Ser Thr Ala Glu Asn Ala Glu Tyr Leu Arg Val Ala Pro Gln Ser
35 40 45

Ser Glu Phe Ile Gly Ala
50

<210> SEQ ID NO 101
<211> LENGTH: 51
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 101

Ser Asp Pro Lys Pro Glu Asn Pro Ala Cys Pro Trp Thr Val Leu Pro
1 5 10 15

Ala Gly Asp Leu Pro Thr His Asp Gly Tyr Leu Pro Ser Asn Ile Asp
20 25 30

Asp Leu Pro Ser His Glu Ala Pro Leu Ala Asp Ser Leu Glu Glu Leu
35 40 45

Glu Pro Gln
50

<210> SEQ ID NO 102
<211> LENGTH: 41
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 102

Ala Cys Asp Ala Pro Ile Leu Ser Ser Ser Arg Ser Leu Asp Cys Arg
1 5 10 15

Glu Ser Gly Lys Asn Gly Pro His Val Tyr Gln Asp Leu Leu Leu Ser
20 25 30

Leu Gly Thr Thr Asn Ser Thr Leu Pro
35 40

<210> SEQ ID NO 103
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 103

Gly Ile Leu Thr Leu Asn Pro Val Ala Gln Gly Gln Pro Ile Leu Thr
1 5 10 15

Ser Leu Gly Ser Asn Gln Glu Glu Ala Tyr Val Thr Met Ser Ser Phe
20 25 30

Tyr Gln Asn Gln
35

<210> SEQ ID NO 104
<211> LENGTH: 68
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 104

```
Ala Cys Asp Ala Pro Ile Leu Ser Ser Ser Arg Ser Leu Asp Cys Arg
1               5                   10                  15

Glu Ser Gly Lys Asn Gly Pro His Val Tyr Gln Asp Leu Leu Leu Ser
            20                  25                  30

Leu Gly Thr Thr Asn Ser Thr Leu Pro Gln Gly Gln Pro Ile Leu Thr
        35                  40                  45

Ser Leu Gly Ser Asn Gln Glu Glu Ala Tyr Val Thr Met Ser Ser Phe
    50                  55                  60

Tyr Gln Asn Gln
65
```

<210> SEQ ID NO 105
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 105

```
Gly Ile Leu Thr Leu Asn Pro Val Ala Gln Gly Gln Pro Ile Leu Thr
1               5                   10                  15

Ser Leu Gly Ser Asn Gln Glu Glu Ala Tyr Val Thr Met Ser Ser Phe
            20                  25                  30

Phe Gln Asn Gln
        35
```

<210> SEQ ID NO 106
<211> LENGTH: 68
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 106

```
Ala Cys Asp Ala Pro Ile Leu Ser Ser Ser Arg Ser Leu Asp Cys Arg
1               5                   10                  15

Glu Ser Gly Lys Asn Gly Pro His Val Tyr Gln Asp Leu Leu Leu Ser
            20                  25                  30

Leu Gly Thr Thr Asn Ser Thr Leu Pro Gln Gly Gln Pro Ile Leu Thr
        35                  40                  45

Ser Leu Gly Ser Asn Gln Glu Glu Ala Tyr Val Thr Met Ser Ser Phe
    50                  55                  60

Phe Gln Asn Gln
65
```

<210> SEQ ID NO 107
<211> LENGTH: 41
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 107

```
Asp Glu Gly Val Ala Gly Ala Pro Thr Gly Ser Ser Pro Gln Pro Leu
1               5                   10                  15

Gln Pro Leu Ser Gly Glu Asp Asp Ala Tyr Cys Thr Phe Pro Ser Arg
            20                  25                  30
```

Asp Asp Leu Leu Leu Phe Ser Pro Ser
35 40

<210> SEQ ID NO 108
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 108

Gly Gln Gly Glu Phe Arg Ala Leu Asn Ala Arg Leu Pro Leu Asn Thr
1 5 10 15

Asp Ala Tyr Leu Ser Leu Gln Glu Leu Gln Gly Gln Asp Pro Thr His
20 25 30

Leu Val

<210> SEQ ID NO 109
<211> LENGTH: 82
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 109

Gln Gln Asp Lys Val Pro Glu Pro Ala Ser Leu Ser Ser Asn His Ser
1 5 10 15

Leu Thr Ser Cys Phe Thr Asn Gln Gly Tyr Phe Phe Phe His Leu Pro
20 25 30

Asp Ala Leu Glu Ile Glu Ala Cys Gln Asp Glu Gly Val Ala Gly Ala
35 40 45

Pro Thr Gly Ser Ser Pro Gln Pro Leu Gln Pro Leu Ser Gly Glu Asp
50 55 60

Asp Ala Tyr Cys Thr Phe Pro Ser Arg Asp Asp Leu Leu Leu Phe Ser
65 70 75 80

Pro Ser

<210> SEQ ID NO 110
<211> LENGTH: 75
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 110

Gln Gln Asp Lys Val Pro Glu Pro Ala Ser Leu Ser Ser Asn His Ser
1 5 10 15

Leu Thr Ser Cys Phe Thr Asn Gln Gly Tyr Phe Phe Phe His Leu Pro
20 25 30

Asp Ala Leu Glu Ile Glu Ala Cys Gln Gly Gln Gly Glu Phe Arg Ala
35 40 45

Leu Asn Ala Arg Leu Pro Leu Asn Thr Asp Ala Tyr Leu Ser Leu Gln
50 55 60

Glu Leu Gln Gly Gln Asp Pro Thr His Leu Val
65 70 75

<210> SEQ ID NO 111

<211> LENGTH: 75
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 111

Asp Glu Gly Val Ala Gly Ala Pro Thr Gly Ser Ser Pro Gln Pro Leu
1 5 10 15

Gln Pro Leu Ser Gly Glu Asp Asp Ala Tyr Cys Thr Phe Pro Ser Arg
20 25 30

Asp Asp Leu Leu Leu Phe Ser Pro Ser Gly Gln Gly Glu Phe Arg Ala
35 40 45

Leu Asn Ala Arg Leu Pro Leu Asn Thr Asp Ala Tyr Leu Ser Leu Gln
50 55 60

Glu Leu Gln Gly Gln Asp Pro Thr His Leu Val
65 70 75

<210> SEQ ID NO 112
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 112

Gln Gln Asp Lys Val Pro Glu Pro Ala Ser Leu Ser Ser Asn His Ser
1 5 10 15

Leu Thr Ser Cys Phe Thr Asn Gln Gly Tyr Phe Phe Phe His Leu Pro
20 25 30

Asp Ala Leu Glu Ile Glu Ala Cys Gln Asp Glu Gly Val Ala Gly Ala
35 40 45

Pro Thr Gly Ser Ser Pro Gln Pro Leu Gln Pro Leu Ser Gly Glu Asp
50 55 60

Asp Ala Tyr Cys Thr Phe Pro Ser Arg Asp Asp Leu Leu Leu Phe Ser
65 70 75 80

Pro Ser Gly Gln Gly Glu Phe Arg Ala Leu Asn Ala Arg Leu Pro Leu
85 90 95

Asn Thr Asp Ala Tyr Leu Ser Leu Gln Glu Leu Gln Gly Gln Asp Pro
100 105 110

Thr His Leu Val
115

<210> SEQ ID NO 113
<211> LENGTH: 43
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 113

Lys Lys Lys Val Trp Asp Tyr Asn Tyr Asp Asp Glu Ser Asp Ser Asp
1 5 10 15

Thr Glu Ala Ala Pro Arg Thr Ser Gly Gly Gly Tyr Thr Met His Gly
20 25 30

Leu Thr Val Arg Pro Leu Gly Gln Ala Ser Ala
35 40

<210> SEQ ID NO 114
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 114

Glu Gly Leu Trp Ser Glu Asp Ala Pro Ser Asp Gln Ser Asp Thr Ser
1 5 10 15

Glu Ser Asp Val Asp Leu Gly Asp Gly Tyr Ile Met Arg
20 25

<210> SEQ ID NO 115
<211> LENGTH: 72
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 115

Lys Lys Lys Val Trp Asp Tyr Asn Tyr Asp Asp Glu Ser Asp Ser Asp
1 5 10 15

Thr Glu Ala Ala Pro Arg Thr Ser Gly Gly Gly Tyr Thr Met His Gly
20 25 30

Leu Thr Val Arg Pro Leu Gly Gln Ala Ser Ala Glu Gly Leu Trp Ser
35 40 45

Glu Asp Ala Pro Ser Asp Gln Ser Asp Thr Ser Glu Ser Asp Val Asp
50 55 60

Leu Gly Asp Gly Tyr Ile Met Arg
65 70

<210> SEQ ID NO 116
<211> LENGTH: 156
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 116

Ala Ser Glu Ser Pro Ala Asp Glu Glu Glu Gln Trp Ser Asp Asp Phe
1 5 10 15

Asp Ser Asp Tyr Glu Asn Pro Asp Glu His Ser Asp Ser Glu Met Tyr
20 25 30

Val Met Pro Ala Glu Glu Asn Ala Asp Asp Ser Tyr Glu Pro Pro Pro
35 40 45

Val Glu Gln Glu Thr Arg Pro Val His Pro Ala Leu Pro Phe Ala Arg
50 55 60

Gly Glu Tyr Ile Asp Asn Arg Ser Ser Gln Arg His Ser Pro Pro Phe
65 70 75 80

Ser Lys Thr Leu Pro Ser Lys Pro Ser Trp Pro Ser Glu Lys Ala Arg
85 90 95

Leu Thr Ser Thr Leu Pro Ala Leu Thr Ala Leu Gln Lys Pro Gln Val
100 105 110

Pro Pro Lys Pro Lys Gly Leu Leu Glu Asp Glu Ala Asp Tyr Val Val
115 120 125

```
Pro Val Glu Asp Asn Asp Glu Asn Tyr Ile His Pro Thr Glu Ser Ser
    130                 135                 140

Ser Pro Pro Pro Glu Lys Ala Pro Met Val Asn Arg
145                 150                 155


<210> SEQ ID NO 117
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Ala Ser Glu Ser Pro Ala Asp Glu Glu Glu Gln Trp Ser Asp Asp Phe
1               5                   10                  15

Asp Ser Asp Phe Glu Asn Pro Asp Glu His Ser Asp Ser Glu Met Tyr
            20                  25                  30

Val Met Pro Ala Glu Glu Asn Ala Asp Asp Ser Tyr Glu Pro Pro Pro
        35                  40                  45

Val Glu Gln Glu Thr Arg Pro Val His Pro Ala Leu Pro Phe Ala Arg
    50                  55                  60

Gly Glu Tyr Ile Asp Asn Arg Ser Ser Gln Arg His Ser Pro Pro Phe
65                  70                  75                  80

Ser Lys Thr Leu Pro Ser Lys Pro Ser Trp Pro Ser Glu Lys Ala Arg
                85                  90                  95

Leu Thr Ser Thr Leu Pro Ala Leu Thr Ala Leu Gln Lys Pro Gln Val
            100                 105                 110

Pro Pro Lys Pro Lys Gly Leu Leu Glu Asp Glu Ala Asp Tyr Val Val
        115                 120                 125

Pro Val Glu Asp Asn Asp Glu Asn Tyr Ile His Pro Thr Glu Ser Ser
    130                 135                 140

Ser Pro Pro Pro Glu Lys Ala Pro Met Val Asn Arg
145                 150                 155


<210> SEQ ID NO 118
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Ala Ser Glu Ser Pro Ala Asp Glu Glu Glu Gln Trp Ser Asp Asp Phe
1               5                   10                  15

Asp Ser Asp Phe Glu Asn Pro Asp Glu His Ser Asp Ser Glu Met Tyr
            20                  25                  30

Val Met Pro Ala Glu Glu Asn Ala Asp Asp Ser Phe Glu Pro Pro Pro
        35                  40                  45

Val Glu Gln Glu Thr Arg Pro Val His Pro Ala Leu Pro Phe Ala Arg
    50                  55                  60

Gly Glu Tyr Ile Asp Asn Arg Ser Ser Gln Arg His Ser Pro Pro Phe
65                  70                  75                  80

Ser Lys Thr Leu Pro Ser Lys Pro Ser Trp Pro Ser Glu Lys Ala Arg
                85                  90                  95

Leu Thr Ser Thr Leu Pro Ala Leu Thr Ala Leu Gln Lys Pro Gln Val
            100                 105                 110
```

Pro Pro Lys Pro Lys Gly Leu Leu Glu Asp Glu Ala Asp Tyr Val Val
115 120 125

Pro Val Glu Asp Asn Asp Glu Asn Tyr Ile His Pro Thr Glu Ser Ser
130 135 140

Ser Pro Pro Pro Glu Lys Ala Pro Met Val Asn Arg
145 150 155

<210> SEQ ID NO 119
<211> LENGTH: 170
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 119

Trp Gly Thr Met Gln Ala Val Glu Pro Gly Thr Asp Asp Glu Gly Pro
1 5 10 15

Leu Leu Glu Pro Val Gly Ser Glu His Ala Gln Asp Thr Tyr Leu Val
20 25 30

Leu Asp Lys Trp Leu Leu Pro Arg Asn Pro Pro Ser Glu Asp Leu Pro
35 40 45

Gly Pro Gly Gly Ser Val Asp Ile Val Ala Met Asp Glu Gly Ser Glu
50 55 60

Ala Ser Ser Cys Ser Ser Ala Leu Ala Ser Lys Pro Ser Pro Glu Gly
65 70 75 80

Ala Ser Ala Ala Ser Phe Glu Tyr Thr Ile Leu Asp Pro Ser Ser Gln
85 90 95

Leu Leu Arg Pro Trp Thr Leu Cys Pro Glu Leu Pro Pro Thr Pro Pro
100 105 110

His Leu Lys Tyr Leu Tyr Leu Val Val Ser Asp Ser Gly Ile Ser Thr
115 120 125

Asp Tyr Ser Ser Gly Asp Ser Gln Gly Ala Gln Gly Gly Leu Ser Asp
130 135 140

Gly Pro Tyr Ser Asn Pro Tyr Glu Asn Ser Leu Ile Pro Ala Ala Glu
145 150 155 160

Pro Leu Pro Pro Ser Tyr Val Ala Cys Ser
165 170

<210> SEQ ID NO 120
<211> LENGTH: 149
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 120

Val Thr Pro Val Phe Arg His Pro Pro Cys Ser Asn Trp Pro Gln Arg
1 5 10 15

Glu Lys Gly Ile Gln Gly His Gln Ala Ser Glu Lys Asp Met Met His
20 25 30

Ser Ala Ser Ser Pro Pro Pro Pro Arg Ala Leu Gln Ala Glu Ser Arg
35 40 45

Gln Leu Val Asp Leu Tyr Lys Val Leu Glu Ser Arg Gly Ser Asp Pro
50 55 60

Lys Pro Glu Asn Pro Ala Cys Pro Trp Thr Val Leu Pro Ala Gly Asp
65 70 75 80

Leu Pro Thr His Asp Gly Tyr Leu Pro Ser Asn Ile Asp Asp Leu Pro
85 90 95

Ser His Glu Ala Pro Leu Ala Asp Ser Leu Glu Glu Leu Glu Pro Gln
100 105 110

His Ile Ser Leu Ser Val Phe Pro Ser Ser Ser Leu His Pro Leu Thr
115 120 125

Phe Ser Cys Gly Asp Lys Leu Thr Leu Asp Gln Leu Lys Met Arg Cys
130 135 140

Asp Ser Leu Met Leu
145

<210> SEQ ID NO 121
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 121

Trp Asp Lys Gly Glu Arg Thr Glu Pro Leu Glu Lys Thr Glu Leu Pro
1 5 10 15

Glu Gly Ala Pro Glu Leu Ala Leu Asp Thr Glu Leu Ser Leu Glu Asp
20 25 30

Gly Asp Arg Cys Lys Ala Lys Met
35 40

<210> SEQ ID NO 122
<211> LENGTH: 275
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 122

Val Ser Pro Glu Leu Lys Asn Leu Asp Leu His Gly Ser Thr Asp Ser
1 5 10 15

Gly Phe Gly Ser Thr Lys Pro Ser Leu Gln Thr Glu Glu Pro Gln Phe
20 25 30

Leu Leu Pro Asp Pro His Pro Gln Ala Asp Arg Thr Leu Gly Asn Arg
35 40 45

Glu Pro Pro Val Leu Gly Asp Ser Cys Ser Ser Gly Ser Ser Asn Ser
50 55 60

Thr Asp Ser Gly Ile Cys Leu Gln Glu Pro Ser Leu Ser Pro Ser Thr
65 70 75 80

Gly Pro Thr Trp Glu Gln Gln Val Gly Ser Asn Ser Arg Gly Gln Asp
85 90 95

Asp Ser Gly Ile Asp Leu Val Gln Asn Ser Glu Gly Arg Ala Gly Asp
100 105 110

Thr Gln Gly Gly Ser Ala Leu Gly His His Ser Pro Pro Glu Pro Glu
115 120 125

Val Pro Gly Glu Glu Asp Pro Ala Ala Val Ala Phe Gln Gly Tyr Leu
130 135 140

Arg Gln Thr Arg Cys Ala Glu Glu Lys Ala Thr Lys Thr Gly Cys Leu
145 150 155 160

Glu Glu Glu Ser Pro Leu Thr Asp Gly Leu Gly Pro Lys Phe Gly Arg
165 170 175

Cys Leu Val Asp Glu Ala Gly Leu His Pro Pro Ala Leu Ala Lys Gly
180 185 190

Tyr Leu Lys Gln Asp Pro Leu Glu Met Thr Leu Ala Ser Ser Gly Ala
195 200 205

Pro Thr Gly Gln Trp Asn Gln Pro Thr Glu Glu Trp Ser Leu Leu Ala
210 215 220

Leu Ser Ser Cys Ser Asp Leu Gly Ile Ser Asp Trp Ser Phe Ala His
225 230 235 240

Asp Leu Ala Pro Leu Gly Cys Val Ala Ala Pro Gly Gly Leu Leu Gly
245 250 255

Ser Phe Asn Ser Asp Leu Val Thr Leu Pro Leu Ile Ser Ser Leu Gln
260 265 270

Ser Ser Glu
275

<210> SEQ ID NO 123
<211> LENGTH: 487
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 123

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

Asp Glu Asn Ile Thr Leu Glu Thr Val Cys His Asp Pro Lys Leu Pro
115 120 125

Tyr His Asp Phe Ile Leu Glu Asp Ala Ala Ser Pro Lys Cys Ile Met
130 135 140

Lys Glu Lys Lys Lys Pro Gly Glu Thr Phe Phe Met Cys Ser Cys Ser
145 150 155 160

Ser Asp Glu Cys Asn Asp Asn Ile Ile Phe Ser Glu Glu Tyr Asn Thr
165 170 175

Ser Asn Pro Asp Leu Leu Leu Val Ile Phe Gln Ser Asp Pro Thr Arg
180 185 190

Val Glu Thr Ala Thr Glu Thr Ala Trp Ile Ser Leu Val Thr Ala Leu
195 200 205

His Leu Val Leu Gly Leu Ser Ala Val Leu Gly Leu Leu Leu Leu Arg
210 215 220

Trp Gln Phe Pro Ala His Tyr Arg Arg Leu Arg His Ala Leu Trp Pro
225 230 235 240

```
Ser Leu Pro Asp Leu His Arg Val Leu Gly Gln Tyr Leu Arg Asp Thr
                245                 250                 255

Ala Ala Leu Ser Pro Pro Lys Ala Thr Val Ser Asp Thr Cys Glu Glu
            260                 265                 270

Val Glu Pro Ser Leu Leu Glu Ile Leu Pro Lys Ser Ser Glu Arg Thr
        275                 280                 285

Pro Leu Pro Leu Ala Arg Asp Glu Val Glu Gly Phe Leu Gln Asp Thr
    290                 295                 300

Phe Pro Gln Gln Leu Glu Glu Ser Glu Lys Gln Arg Leu Gly Gly Asp
305                 310                 315                 320

Val Gln Ser Pro Asn Cys Pro Ser Glu Asp Val Val Ile Thr Pro Glu
                325                 330                 335

Ser Phe Gly Arg Asp Ser Ser Leu Thr Cys Leu Ala Gly Asn Val Ser
            340                 345                 350

Ala Cys Asp Ala Pro Ile Leu Ser Ser Ser Arg Ser Leu Asp Cys Arg
        355                 360                 365

Glu Ser Gly Lys Asn Gly Pro His Val Tyr Gln Asp Leu Leu Leu Ser
    370                 375                 380

Leu Gly Thr Thr Asn Ser Thr Leu Pro Pro Pro Phe Ser Leu Gln Ser
385                 390                 395                 400

Gly Ile Leu Thr Leu Asn Pro Val Ala Gln Gly Gln Pro Ile Leu Thr
                405                 410                 415

Ser Leu Gly Ser Asn Gln Glu Glu Ala Tyr Val Thr Met Ser Ser Phe
            420                 425                 430

Tyr Gln Asn Gln Ser Asp Pro Lys Pro Glu Asn Pro Ala Cys Pro Trp
        435                 440                 445

Thr Val Leu Pro Ala Gly Asp Leu Pro Thr His Asp Gly Tyr Leu Pro
    450                 455                 460

Ser Asn Ile Asp Asp Leu Pro Ser His Glu Ala Pro Leu Ala Asp Ser
465                 470                 475                 480

Leu Glu Glu Leu Glu Pro Gln
                485
```

<210> SEQ ID NO 124
<211> LENGTH: 486
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 124

```
Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95
```

```
Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Trp Ile Ser Leu Val Thr Ala Leu His
        195                 200                 205

Leu Val Leu Gly Leu Ser Ala Val Leu Gly Leu Leu Leu Leu Arg Trp
    210                 215                 220

Gln Phe Pro Ala His Tyr Arg Arg Leu Arg His Ala Leu Trp Pro Ser
225                 230                 235                 240

Leu Pro Asp Leu His Arg Val Leu Gly Gln Tyr Leu Arg Asp Thr Ala
                245                 250                 255

Ala Leu Ser Pro Pro Lys Ala Thr Val Ser Asp Thr Cys Glu Glu Val
            260                 265                 270

Glu Pro Ser Leu Leu Glu Ile Leu Pro Lys Ser Ser Glu Arg Thr Pro
        275                 280                 285

Leu Pro Leu Ala Arg Asp Glu Val Glu Gly Phe Leu Gln Asp Thr Phe
    290                 295                 300

Pro Gln Gln Leu Glu Glu Ser Glu Lys Gln Arg Leu Gly Gly Asp Val
305                 310                 315                 320

Gln Ser Pro Asn Cys Pro Ser Glu Asp Val Val Ile Thr Pro Glu Ser
                325                 330                 335

Phe Gly Arg Asp Ser Ser Leu Thr Cys Leu Ala Gly Asn Val Ser Ala
            340                 345                 350

Cys Asp Ala Pro Ile Leu Ser Ser Ser Arg Ser Leu Asp Cys Arg Glu
        355                 360                 365

Ser Gly Lys Asn Gly Pro His Val Tyr Gln Asp Leu Leu Leu Ser Leu
    370                 375                 380

Gly Thr Thr Asn Ser Thr Leu Pro Pro Pro Phe Ser Leu Gln Ser Gly
385                 390                 395                 400

Ile Leu Thr Leu Asn Pro Val Ala Gln Gly Gln Pro Ile Leu Thr Ser
                405                 410                 415

Leu Gly Ser Asn Gln Glu Glu Ala Tyr Val Thr Met Ser Ser Phe Tyr
            420                 425                 430

Gln Asn Gln Ser Asp Pro Lys Pro Glu Asn Pro Ala Cys Pro Trp Thr
        435                 440                 445

Val Leu Pro Ala Gly Asp Leu Pro Thr His Asp Gly Tyr Leu Pro Ser
    450                 455                 460

Asn Ile Asp Asp Leu Pro Ser His Glu Ala Pro Leu Ala Asp Ser Leu
465                 470                 475                 480

Glu Glu Leu Glu Pro Gln
                485
```

<210> SEQ ID NO 125
<211> LENGTH: 485

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 125

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

Asp Glu Asn Ile Thr Leu Glu Thr Val Cys His Asp Pro Lys Leu Pro
115 120 125

Tyr His Asp Phe Ile Leu Glu Asp Ala Ala Ser Pro Lys Cys Ile Met
130 135 140

Lys Glu Lys Lys Lys Pro Gly Glu Thr Phe Phe Met Cys Ser Cys Ser
145 150 155 160

Ser Asp Glu Cys Asn Asp Asn Ile Ile Phe Ser Glu Glu Tyr Asn Thr
165 170 175

Ser Asn Pro Asp Leu Leu Leu Val Ile Phe Gln Ser Asp Pro Thr Arg
180 185 190

Val Glu Thr Ala Thr Glu Thr Ile Ser Leu Val Thr Ala Leu His Leu
195 200 205

Val Leu Gly Leu Ser Ala Val Leu Gly Leu Leu Leu Leu Arg Trp Gln
210 215 220

Phe Pro Ala His Tyr Arg Arg Leu Arg His Ala Leu Trp Pro Ser Leu
225 230 235 240

Pro Asp Leu His Arg Val Leu Gly Gln Tyr Leu Arg Asp Thr Ala Ala
245 250 255

Leu Ser Pro Pro Lys Ala Thr Val Ser Asp Thr Cys Glu Glu Val Glu
260 265 270

Pro Ser Leu Leu Glu Ile Leu Pro Lys Ser Ser Glu Arg Thr Pro Leu
275 280 285

Pro Leu Ala Arg Asp Glu Val Glu Gly Phe Leu Gln Asp Thr Phe Pro
290 295 300

Gln Gln Leu Glu Glu Ser Glu Lys Gln Arg Leu Gly Gly Asp Val Gln
305 310 315 320

Ser Pro Asn Cys Pro Ser Glu Asp Val Val Ile Thr Pro Glu Ser Phe
325 330 335

Gly Arg Asp Ser Ser Leu Thr Cys Leu Ala Gly Asn Val Ser Ala Cys
340 345 350

Asp Ala Pro Ile Leu Ser Ser Ser Arg Ser Leu Asp Cys Arg Glu Ser
355 360 365

Gly Lys Asn Gly Pro His Val Tyr Gln Asp Leu Leu Leu Ser Leu Gly
370 375 380

Thr Thr Asn Ser Thr Leu Pro Pro Pro Phe Ser Leu Gln Ser Gly Ile
385 390 395 400

Leu Thr Leu Asn Pro Val Ala Gln Gly Gln Pro Ile Leu Thr Ser Leu
405 410 415

Gly Ser Asn Gln Glu Glu Ala Tyr Val Thr Met Ser Ser Phe Tyr Gln
420 425 430

Asn Gln Ser Asp Pro Lys Pro Glu Asn Pro Ala Cys Pro Trp Thr Val
435 440 445

Leu Pro Ala Gly Asp Leu Pro Thr His Asp Gly Tyr Leu Pro Ser Asn
450 455 460

Ile Asp Asp Leu Pro Ser His Glu Ala Pro Leu Ala Asp Ser Leu Glu
465 470 475 480

Glu Leu Glu Pro Gln
485

<210> SEQ ID NO 126
<211> LENGTH: 486
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 126

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

Asp Glu Asn Ile Thr Leu Glu Thr Val Cys His Asp Pro Lys Leu Pro
115 120 125

Tyr His Asp Phe Ile Leu Glu Asp Ala Ala Ser Pro Lys Cys Ile Met
130 135 140

Lys Glu Lys Lys Lys Pro Gly Glu Thr Phe Phe Met Cys Ser Cys Ser
145 150 155 160

Ser Asp Glu Cys Asn Asp Asn Ile Ile Phe Ser Glu Glu Tyr Asn Thr
165 170 175

Ser Asn Pro Asp Leu Leu Leu Val Ile Phe Gln Ser Asp Pro Thr Arg
180 185 190

Val Glu Thr Ala Thr Glu Thr Leu Ile Ser Leu Val Thr Ala Leu His
195 200 205

Leu Val Leu Gly Leu Ser Ala Val Leu Gly Leu Leu Leu Leu Arg Trp
210 215 220

Gln Phe Pro Ala His Tyr Arg Arg Leu Arg His Ala Leu Trp Pro Ser
225 230 235 240

Leu Pro Asp Leu His Arg Val Leu Gly Gln Tyr Leu Arg Asp Thr Ala
245 250 255

Ala Leu Ser Pro Pro Lys Ala Thr Val Ser Asp Thr Cys Glu Glu Val
260 265 270

Glu Pro Ser Leu Leu Glu Ile Leu Pro Lys Ser Ser Glu Arg Thr Pro
275 280 285

Leu Pro Leu Ala Arg Asp Glu Val Glu Gly Phe Leu Gln Asp Thr Phe
290 295 300

Pro Gln Gln Leu Glu Glu Ser Glu Lys Gln Arg Leu Gly Gly Asp Val
305 310 315 320

Gln Ser Pro Asn Cys Pro Ser Glu Asp Val Val Ile Thr Pro Glu Ser
325 330 335

Phe Gly Arg Asp Ser Ser Leu Thr Cys Leu Ala Gly Asn Val Ser Ala
340 345 350

Cys Asp Ala Pro Ile Leu Ser Ser Ser Arg Ser Leu Asp Cys Arg Glu
355 360 365

Ser Gly Lys Asn Gly Pro His Val Tyr Gln Asp Leu Leu Leu Ser Leu
370 375 380

Gly Thr Thr Asn Ser Thr Leu Pro Pro Pro Phe Ser Leu Gln Ser Gly
385 390 395 400

Ile Leu Thr Leu Asn Pro Val Ala Gln Gly Gln Pro Ile Leu Thr Ser
405 410 415

Leu Gly Ser Asn Gln Glu Glu Ala Tyr Val Thr Met Ser Ser Phe Tyr
420 425 430

Gln Asn Gln Ser Asp Pro Lys Pro Glu Asn Pro Ala Cys Pro Trp Thr
435 440 445

Val Leu Pro Ala Gly Asp Leu Pro Thr His Asp Gly Tyr Leu Pro Ser
450 455 460

Asn Ile Asp Asp Leu Pro Ser His Glu Ala Pro Leu Ala Asp Ser Leu
465 470 475 480

Glu Glu Leu Glu Pro Gln
485

<210> SEQ ID NO 127
<211> LENGTH: 484
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 127

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

```
Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Ser Leu Val Thr Ala Leu His Leu Val
        195                 200                 205

Leu Gly Leu Ser Ala Val Leu Gly Leu Leu Leu Leu Arg Trp Gln Phe
    210                 215                 220

Pro Ala His Tyr Arg Arg Leu Arg His Ala Leu Trp Pro Ser Leu Pro
225                 230                 235                 240

Asp Leu His Arg Val Leu Gly Gln Tyr Leu Arg Asp Thr Ala Ala Leu
                245                 250                 255

Ser Pro Pro Lys Ala Thr Val Ser Asp Thr Cys Glu Glu Val Glu Pro
            260                 265                 270

Ser Leu Leu Glu Ile Leu Pro Lys Ser Ser Glu Arg Thr Pro Leu Pro
        275                 280                 285

Leu Ala Arg Asp Glu Val Glu Gly Phe Leu Gln Asp Thr Phe Pro Gln
    290                 295                 300

Gln Leu Glu Glu Ser Glu Lys Gln Arg Leu Gly Gly Asp Val Gln Ser
305                 310                 315                 320

Pro Asn Cys Pro Ser Glu Asp Val Val Ile Thr Pro Glu Ser Phe Gly
                325                 330                 335

Arg Asp Ser Ser Leu Thr Cys Leu Ala Gly Asn Val Ser Ala Cys Asp
            340                 345                 350

Ala Pro Ile Leu Ser Ser Ser Arg Ser Leu Asp Cys Arg Glu Ser Gly
        355                 360                 365

Lys Asn Gly Pro His Val Tyr Gln Asp Leu Leu Leu Ser Leu Gly Thr
    370                 375                 380

Thr Asn Ser Thr Leu Pro Pro Pro Phe Ser Leu Gln Ser Gly Ile Leu
385                 390                 395                 400

Thr Leu Asn Pro Val Ala Gln Gly Gln Pro Ile Leu Thr Ser Leu Gly
                405                 410                 415

Ser Asn Gln Glu Glu Ala Tyr Val Thr Met Ser Ser Phe Tyr Gln Asn
            420                 425                 430

Gln Ser Asp Pro Lys Pro Glu Asn Pro Ala Cys Pro Trp Thr Val Leu
        435                 440                 445

Pro Ala Gly Asp Leu Pro Thr His Asp Gly Tyr Leu Pro Ser Asn Ile
    450                 455                 460

Asp Asp Leu Pro Ser His Glu Ala Pro Leu Ala Asp Ser Leu Glu Glu
465                 470                 475                 480

Leu Glu Pro Gln
```

<210> SEQ ID NO 128
<211> LENGTH: 483
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 128

Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Leu Val Thr Ala Leu His Leu Val Leu
        195                 200                 205

Gly Leu Ser Ala Val Leu Gly Leu Leu Leu Leu Arg Trp Gln Phe Pro
    210                 215                 220

Ala His Tyr Arg Arg Leu Arg His Ala Leu Trp Pro Ser Leu Pro Asp
225                 230                 235                 240

Leu His Arg Val Leu Gly Gln Tyr Leu Arg Asp Thr Ala Ala Leu Ser
                245                 250                 255

Pro Pro Lys Ala Thr Val Ser Asp Thr Cys Glu Glu Val Glu Pro Ser
            260                 265                 270

Leu Leu Glu Ile Leu Pro Lys Ser Ser Glu Arg Thr Pro Leu Pro Leu
        275                 280                 285

Ala Arg Asp Glu Val Glu Gly Phe Leu Gln Asp Thr Phe Pro Gln Gln
    290                 295                 300

Leu Glu Glu Ser Glu Lys Gln Arg Leu Gly Gly Asp Val Gln Ser Pro
305                 310                 315                 320

Asn Cys Pro Ser Glu Asp Val Val Ile Thr Pro Glu Ser Phe Gly Arg
                325                 330                 335

Asp Ser Ser Leu Thr Cys Leu Ala Gly Asn Val Ser Ala Cys Asp Ala
            340                 345                 350

Pro Ile Leu Ser Ser Ser Arg Ser Leu Asp Cys Arg Glu Ser Gly Lys
        355                 360                 365

Asn Gly Pro His Val Tyr Gln Asp Leu Leu Leu Ser Leu Gly Thr Thr
    370                 375                 380
```

Asn Ser Thr Leu Pro Pro Pro Phe Ser Leu Gln Ser Gly Ile Leu Thr
385 390 395 400

Leu Asn Pro Val Ala Gln Gly Gln Pro Ile Leu Thr Ser Leu Gly Ser
405 410 415

Asn Gln Glu Glu Ala Tyr Val Thr Met Ser Ser Phe Tyr Gln Asn Gln
420 425 430

Ser Asp Pro Lys Pro Glu Asn Pro Ala Cys Pro Trp Thr Val Leu Pro
435 440 445

Ala Gly Asp Leu Pro Thr His Asp Gly Tyr Leu Pro Ser Asn Ile Asp
450 455 460

Asp Leu Pro Ser His Glu Ala Pro Leu Ala Asp Ser Leu Glu Glu Leu
465 470 475 480

Glu Pro Gln

<210> SEQ ID NO 129
<211> LENGTH: 484
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 129

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

Asp Glu Asn Ile Thr Leu Glu Thr Val Cys His Asp Pro Lys Leu Pro
115 120 125

Tyr His Asp Phe Ile Leu Glu Asp Ala Ala Ser Pro Lys Cys Ile Met
130 135 140

Lys Glu Lys Lys Lys Pro Gly Glu Thr Phe Phe Met Cys Ser Cys Ser
145 150 155 160

Ser Asp Glu Cys Asn Asp Asn Ile Ile Phe Ser Glu Glu Tyr Asn Thr
165 170 175

Ser Asn Pro Asp Leu Leu Leu Val Ile Phe Gln Ser Asp Pro Thr Arg
180 185 190

Val Glu Thr Ala Thr Glu Thr Ile Leu Val Thr Ala Leu His Leu Val
195 200 205

Leu Gly Leu Ser Ala Val Leu Gly Leu Leu Leu Leu Arg Trp Gln Phe
210 215 220

Pro Ala His Tyr Arg Arg Leu Arg His Ala Leu Trp Pro Ser Leu Pro
225 230 235 240

Asp Leu His Arg Val Leu Gly Gln Tyr Leu Arg Asp Thr Ala Ala Leu
245 250 255

```
Ser Pro Pro Lys Ala Thr Val Ser Asp Thr Cys Glu Glu Val Glu Pro
            260                 265                 270

Ser Leu Leu Glu Ile Leu Pro Lys Ser Ser Glu Arg Thr Pro Leu Pro
        275                 280                 285

Leu Ala Arg Asp Glu Val Glu Gly Phe Leu Gln Asp Thr Phe Pro Gln
    290                 295                 300

Gln Leu Glu Glu Ser Glu Lys Gln Arg Leu Gly Gly Asp Val Gln Ser
305                 310                 315                 320

Pro Asn Cys Pro Ser Glu Asp Val Val Ile Thr Pro Glu Ser Phe Gly
                325                 330                 335

Arg Asp Ser Ser Leu Thr Cys Leu Ala Gly Asn Val Ser Ala Cys Asp
            340                 345                 350

Ala Pro Ile Leu Ser Ser Ser Arg Ser Leu Asp Cys Arg Glu Ser Gly
        355                 360                 365

Lys Asn Gly Pro His Val Tyr Gln Asp Leu Leu Leu Ser Leu Gly Thr
    370                 375                 380

Thr Asn Ser Thr Leu Pro Pro Pro Phe Ser Leu Gln Ser Gly Ile Leu
385                 390                 395                 400

Thr Leu Asn Pro Val Ala Gln Gly Gln Pro Ile Leu Thr Ser Leu Gly
                405                 410                 415

Ser Asn Gln Glu Glu Ala Tyr Val Thr Met Ser Ser Phe Tyr Gln Asn
            420                 425                 430

Gln Ser Asp Pro Lys Pro Glu Asn Pro Ala Cys Pro Trp Thr Val Leu
        435                 440                 445

Pro Ala Gly Asp Leu Pro Thr His Asp Gly Tyr Leu Pro Ser Asn Ile
    450                 455                 460

Asp Asp Leu Pro Ser His Glu Ala Pro Leu Ala Asp Ser Leu Glu Glu
465                 470                 475                 480

Leu Glu Pro Gln
```

<210> SEQ ID NO 130
<211> LENGTH: 482
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 130

```
Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125
```

```
Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Val Thr Ala Leu His Leu Val Leu Gly
        195                 200                 205

Leu Ser Ala Val Leu Gly Leu Leu Leu Leu Arg Trp Gln Phe Pro Ala
    210                 215                 220

His Tyr Arg Arg Leu Arg His Ala Leu Trp Pro Ser Leu Pro Asp Leu
225                 230                 235                 240

His Arg Val Leu Gly Gln Tyr Leu Arg Asp Thr Ala Ala Leu Ser Pro
                245                 250                 255

Pro Lys Ala Thr Val Ser Asp Thr Cys Glu Glu Val Glu Pro Ser Leu
            260                 265                 270

Leu Glu Ile Leu Pro Lys Ser Ser Glu Arg Thr Pro Leu Pro Leu Ala
        275                 280                 285

Arg Asp Glu Val Glu Gly Phe Leu Gln Asp Thr Phe Pro Gln Gln Leu
    290                 295                 300

Glu Glu Ser Glu Lys Gln Arg Leu Gly Gly Asp Val Gln Ser Pro Asn
305                 310                 315                 320

Cys Pro Ser Glu Asp Val Val Ile Thr Pro Glu Ser Phe Gly Arg Asp
                325                 330                 335

Ser Ser Leu Thr Cys Leu Ala Gly Asn Val Ser Ala Cys Asp Ala Pro
            340                 345                 350

Ile Leu Ser Ser Ser Arg Ser Leu Asp Cys Arg Glu Ser Gly Lys Asn
        355                 360                 365

Gly Pro His Val Tyr Gln Asp Leu Leu Leu Ser Leu Gly Thr Thr Asn
    370                 375                 380

Ser Thr Leu Pro Pro Pro Phe Ser Leu Gln Ser Gly Ile Leu Thr Leu
385                 390                 395                 400

Asn Pro Val Ala Gln Gly Gln Pro Ile Leu Thr Ser Leu Gly Ser Asn
                405                 410                 415

Gln Glu Glu Ala Tyr Val Thr Met Ser Ser Phe Tyr Gln Asn Gln Ser
            420                 425                 430

Asp Pro Lys Pro Glu Asn Pro Ala Cys Pro Trp Thr Val Leu Pro Ala
        435                 440                 445

Gly Asp Leu Pro Thr His Asp Gly Tyr Leu Pro Ser Asn Ile Asp Asp
    450                 455                 460

Leu Pro Ser His Glu Ala Pro Leu Ala Asp Ser Leu Glu Glu Leu Glu
465                 470                 475                 480

Pro Gln


<210> SEQ ID NO 131
<211> LENGTH: 481
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 131

Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Thr Ala Leu His Leu Val Leu Gly Leu
        195                 200                 205

Ser Ala Val Leu Gly Leu Leu Leu Leu Arg Trp Gln Phe Pro Ala His
    210                 215                 220

Tyr Arg Arg Leu Arg His Ala Leu Trp Pro Ser Leu Pro Asp Leu His
225                 230                 235                 240

Arg Val Leu Gly Gln Tyr Leu Arg Asp Thr Ala Ala Leu Ser Pro Pro
                245                 250                 255

Lys Ala Thr Val Ser Asp Thr Cys Glu Glu Val Glu Pro Ser Leu Leu
            260                 265                 270

Glu Ile Leu Pro Lys Ser Ser Glu Arg Thr Pro Leu Pro Leu Ala Arg
        275                 280                 285

Asp Glu Val Glu Gly Phe Leu Gln Asp Thr Phe Pro Gln Gln Leu Glu
    290                 295                 300

Glu Ser Glu Lys Gln Arg Leu Gly Gly Asp Val Gln Ser Pro Asn Cys
305                 310                 315                 320

Pro Ser Glu Asp Val Val Ile Thr Pro Glu Ser Phe Gly Arg Asp Ser
                325                 330                 335

Ser Leu Thr Cys Leu Ala Gly Asn Val Ser Ala Cys Asp Ala Pro Ile
            340                 345                 350

Leu Ser Ser Ser Arg Ser Leu Asp Cys Arg Glu Ser Gly Lys Asn Gly
        355                 360                 365

Pro His Val Tyr Gln Asp Leu Leu Leu Ser Leu Gly Thr Thr Asn Ser
    370                 375                 380

Thr Leu Pro Pro Pro Phe Ser Leu Gln Ser Gly Ile Leu Thr Leu Asn
385                 390                 395                 400

Pro Val Ala Gln Gly Gln Pro Ile Leu Thr Ser Leu Gly Ser Asn Gln
405 410 415

Glu Glu Ala Tyr Val Thr Met Ser Ser Phe Tyr Gln Asn Gln Ser Asp
420 425 430

Pro Lys Pro Glu Asn Pro Ala Cys Pro Trp Thr Val Leu Pro Ala Gly
435 440 445

Asp Leu Pro Thr His Asp Gly Tyr Leu Pro Ser Asn Ile Asp Asp Leu
450 455 460

Pro Ser His Glu Ala Pro Leu Ala Asp Ser Leu Glu Glu Leu Glu Pro
465 470 475 480

Gln

<210> SEQ ID NO 132
<211> LENGTH: 480
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 132

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

Asp Glu Asn Ile Thr Leu Glu Thr Val Cys His Asp Pro Lys Leu Pro
115 120 125

Tyr His Asp Phe Ile Leu Glu Asp Ala Ala Ser Pro Lys Cys Ile Met
130 135 140

Lys Glu Lys Lys Lys Pro Gly Glu Thr Phe Phe Met Cys Ser Cys Ser
145 150 155 160

Ser Asp Glu Cys Asn Asp Asn Ile Ile Phe Ser Glu Glu Tyr Asn Thr
165 170 175

Ser Asn Pro Asp Leu Leu Leu Val Ile Phe Gln Ser Asp Pro Thr Arg
180 185 190

Val Glu Thr Ala Thr Glu Thr Ala Leu His Leu Val Leu Gly Leu Ser
195 200 205

Ala Val Leu Gly Leu Leu Leu Leu Arg Trp Gln Phe Pro Ala His Tyr
210 215 220

Arg Arg Leu Arg His Ala Leu Trp Pro Ser Leu Pro Asp Leu His Arg
225 230 235 240

Val Leu Gly Gln Tyr Leu Arg Asp Thr Ala Ala Leu Ser Pro Pro Lys
245 250 255

Ala Thr Val Ser Asp Thr Cys Glu Glu Val Glu Pro Ser Leu Leu Glu
260 265 270

```
Ile Leu Pro Lys Ser Ser Glu Arg Thr Pro Leu Pro Leu Ala Arg Asp
        275                 280                 285

Glu Val Glu Gly Phe Leu Gln Asp Thr Phe Pro Gln Gln Leu Glu Glu
    290                 295                 300

Ser Glu Lys Gln Arg Leu Gly Gly Asp Val Gln Ser Pro Asn Cys Pro
305                 310                 315                 320

Ser Glu Asp Val Val Ile Thr Pro Glu Ser Phe Gly Arg Asp Ser Ser
                325                 330                 335

Leu Thr Cys Leu Ala Gly Asn Val Ser Ala Cys Asp Ala Pro Ile Leu
            340                 345                 350

Ser Ser Ser Arg Ser Leu Asp Cys Arg Glu Ser Gly Lys Asn Gly Pro
        355                 360                 365

His Val Tyr Gln Asp Leu Leu Leu Ser Leu Gly Thr Thr Asn Ser Thr
    370                 375                 380

Leu Pro Pro Pro Phe Ser Leu Gln Ser Gly Ile Leu Thr Leu Asn Pro
385                 390                 395                 400

Val Ala Gln Gly Gln Pro Ile Leu Thr Ser Leu Gly Ser Asn Gln Glu
                405                 410                 415

Glu Ala Tyr Val Thr Met Ser Ser Phe Tyr Gln Asn Gln Ser Asp Pro
            420                 425                 430

Lys Pro Glu Asn Pro Ala Cys Pro Trp Thr Val Leu Pro Ala Gly Asp
        435                 440                 445

Leu Pro Thr His Asp Gly Tyr Leu Pro Ser Asn Ile Asp Asp Leu Pro
    450                 455                 460

Ser His Glu Ala Pro Leu Ala Asp Ser Leu Glu Glu Leu Glu Pro Gln
465                 470                 475                 480
```

<210> SEQ ID NO 133
<211> LENGTH: 479
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 133

```
Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140
```

Lys Glu Lys Lys Lys Pro Gly Glu Thr Phe Phe Met Cys Ser Cys Ser
145 150 155 160

Ser Asp Glu Cys Asn Asp Asn Ile Ile Phe Ser Glu Glu Tyr Asn Thr
165 170 175

Ser Asn Pro Asp Leu Leu Leu Val Ile Phe Gln Ser Asp Pro Thr Arg
180 185 190

Val Glu Thr Ala Thr Glu Thr Leu His Leu Val Leu Gly Leu Ser Ala
195 200 205

Val Leu Gly Leu Leu Leu Leu Arg Trp Gln Phe Pro Ala His Tyr Arg
210 215 220

Arg Leu Arg His Ala Leu Trp Pro Ser Leu Pro Asp Leu His Arg Val
225 230 235 240

Leu Gly Gln Tyr Leu Arg Asp Thr Ala Ala Leu Ser Pro Pro Lys Ala
245 250 255

Thr Val Ser Asp Thr Cys Glu Glu Val Glu Pro Ser Leu Leu Glu Ile
260 265 270

Leu Pro Lys Ser Ser Glu Arg Thr Pro Leu Pro Leu Ala Arg Asp Glu
275 280 285

Val Glu Gly Phe Leu Gln Asp Thr Phe Pro Gln Gln Leu Glu Glu Ser
290 295 300

Glu Lys Gln Arg Leu Gly Gly Asp Val Gln Ser Pro Asn Cys Pro Ser
305 310 315 320

Glu Asp Val Val Ile Thr Pro Glu Ser Phe Gly Arg Asp Ser Ser Leu
325 330 335

Thr Cys Leu Ala Gly Asn Val Ser Ala Cys Asp Ala Pro Ile Leu Ser
340 345 350

Ser Ser Arg Ser Leu Asp Cys Arg Glu Ser Gly Lys Asn Gly Pro His
355 360 365

Val Tyr Gln Asp Leu Leu Leu Ser Leu Gly Thr Thr Asn Ser Thr Leu
370 375 380

Pro Pro Pro Phe Ser Leu Gln Ser Gly Ile Leu Thr Leu Asn Pro Val
385 390 395 400

Ala Gln Gly Gln Pro Ile Leu Thr Ser Leu Gly Ser Asn Gln Glu Glu
405 410 415

Ala Tyr Val Thr Met Ser Ser Phe Tyr Gln Asn Gln Ser Asp Pro Lys
420 425 430

Pro Glu Asn Pro Ala Cys Pro Trp Thr Val Leu Pro Ala Gly Asp Leu
435 440 445

Pro Thr His Asp Gly Tyr Leu Pro Ser Asn Ile Asp Asp Leu Pro Ser
450 455 460

His Glu Ala Pro Leu Ala Asp Ser Leu Glu Glu Leu Glu Pro Gln
465 470 475

<210> SEQ ID NO 134
<211> LENGTH: 478
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 134

Met Ala Leu Pro Val Thr Ala Leu Leu Leu Pro Leu Ala Leu Leu Leu
1 5 10 15

```
His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr His Leu Val Leu Gly Leu Ser Ala Val
        195                 200                 205

Leu Gly Leu Leu Leu Leu Arg Trp Gln Phe Pro Ala His Tyr Arg Arg
    210                 215                 220

Leu Arg His Ala Leu Trp Pro Ser Leu Pro Asp Leu His Arg Val Leu
225                 230                 235                 240

Gly Gln Tyr Leu Arg Asp Thr Ala Ala Leu Ser Pro Pro Lys Ala Thr
                245                 250                 255

Val Ser Asp Thr Cys Glu Glu Val Glu Pro Ser Leu Leu Glu Ile Leu
            260                 265                 270

Pro Lys Ser Ser Glu Arg Thr Pro Leu Pro Leu Ala Arg Asp Glu Val
        275                 280                 285

Glu Gly Phe Leu Gln Asp Thr Phe Pro Gln Gln Leu Glu Glu Ser Glu
    290                 295                 300

Lys Gln Arg Leu Gly Gly Asp Val Gln Ser Pro Asn Cys Pro Ser Glu
305                 310                 315                 320

Asp Val Val Ile Thr Pro Glu Ser Phe Gly Arg Asp Ser Ser Leu Thr
                325                 330                 335

Cys Leu Ala Gly Asn Val Ser Ala Cys Asp Ala Pro Ile Leu Ser Ser
            340                 345                 350

Ser Arg Ser Leu Asp Cys Arg Glu Ser Gly Lys Asn Gly Pro His Val
        355                 360                 365

Tyr Gln Asp Leu Leu Leu Ser Leu Gly Thr Thr Asn Ser Thr Leu Pro
    370                 375                 380

Pro Pro Phe Ser Leu Gln Ser Gly Ile Leu Thr Leu Asn Pro Val Ala
385                 390                 395                 400

Gln Gly Gln Pro Ile Leu Thr Ser Leu Gly Ser Asn Gln Glu Glu Ala
                405                 410                 415

Tyr Val Thr Met Ser Ser Phe Tyr Gln Asn Gln Ser Asp Pro Lys Pro
            420                 425                 430
```

Glu Asn Pro Ala Cys Pro Trp Thr Val Leu Pro Ala Gly Asp Leu Pro
435 440 445

Thr His Asp Gly Tyr Leu Pro Ser Asn Ile Asp Asp Leu Pro Ser His
450 455 460

Glu Ala Pro Leu Ala Asp Ser Leu Glu Glu Leu Glu Pro Gln
465 470 475

<210> SEQ ID NO 135
<211> LENGTH: 477
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 135

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

Asp Glu Asn Ile Thr Leu Glu Thr Val Cys His Asp Pro Lys Leu Pro
115 120 125

Tyr His Asp Phe Ile Leu Glu Asp Ala Ala Ser Pro Lys Cys Ile Met
130 135 140

Lys Glu Lys Lys Lys Pro Gly Glu Thr Phe Phe Met Cys Ser Cys Ser
145 150 155 160

Ser Asp Glu Cys Asn Asp Asn Ile Ile Phe Ser Glu Glu Tyr Asn Thr
165 170 175

Ser Asn Pro Asp Leu Leu Leu Val Ile Phe Gln Ser Asp Pro Thr Arg
180 185 190

Val Glu Thr Ala Thr Glu Thr Leu Val Leu Gly Leu Ser Ala Val Leu
195 200 205

Gly Leu Leu Leu Leu Arg Trp Gln Phe Pro Ala His Tyr Arg Arg Leu
210 215 220

Arg His Ala Leu Trp Pro Ser Leu Pro Asp Leu His Arg Val Leu Gly
225 230 235 240

Gln Tyr Leu Arg Asp Thr Ala Ala Leu Ser Pro Pro Lys Ala Thr Val
245 250 255

Ser Asp Thr Cys Glu Glu Val Glu Pro Ser Leu Leu Glu Ile Leu Pro
260 265 270

Lys Ser Ser Glu Arg Thr Pro Leu Pro Leu Ala Arg Asp Glu Val Glu
275 280 285

Gly Phe Leu Gln Asp Thr Phe Pro Gln Gln Leu Glu Glu Ser Glu Lys
290 295 300

Gln Arg Leu Gly Gly Asp Val Gln Ser Pro Asn Cys Pro Ser Glu Asp
305 310 315 320

Val Val Ile Thr Pro Glu Ser Phe Gly Arg Asp Ser Ser Leu Thr Cys
325 330 335

Leu Ala Gly Asn Val Ser Ala Cys Asp Ala Pro Ile Leu Ser Ser Ser
340 345 350

Arg Ser Leu Asp Cys Arg Glu Ser Gly Lys Asn Gly Pro His Val Tyr
355 360 365

Gln Asp Leu Leu Leu Ser Leu Gly Thr Thr Asn Ser Thr Leu Pro Pro
370 375 380

Pro Phe Ser Leu Gln Ser Gly Ile Leu Thr Leu Asn Pro Val Ala Gln
385 390 395 400

Gly Gln Pro Ile Leu Thr Ser Leu Gly Ser Asn Gln Glu Glu Ala Tyr
405 410 415

Val Thr Met Ser Ser Phe Tyr Gln Asn Gln Ser Asp Pro Lys Pro Glu
420 425 430

Asn Pro Ala Cys Pro Trp Thr Val Leu Pro Ala Gly Asp Leu Pro Thr
435 440 445

His Asp Gly Tyr Leu Pro Ser Asn Ile Asp Asp Leu Pro Ser His Glu
450 455 460

Ala Pro Leu Ala Asp Ser Leu Glu Glu Leu Glu Pro Gln
465 470 475

<210> SEQ ID NO 136
<211> LENGTH: 476
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 136

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

Asp Glu Asn Ile Thr Leu Glu Thr Val Cys His Asp Pro Lys Leu Pro
115 120 125

Tyr His Asp Phe Ile Leu Glu Asp Ala Ala Ser Pro Lys Cys Ile Met
130 135 140

Lys Glu Lys Lys Lys Pro Gly Glu Thr Phe Phe Met Cys Ser Cys Ser
145 150 155 160

Ser Asp Glu Cys Asn Asp Asn Ile Ile Phe Ser Glu Glu Tyr Asn Thr
165 170 175

Ser Asn Pro Asp Leu Leu Leu Val Ile Phe Gln Ser Asp Pro Thr Arg
180 185 190

Val Glu Thr Ala Thr Glu Thr Val Leu Gly Leu Ser Ala Val Leu Gly
195 200 205

Leu Leu Leu Leu Arg Trp Gln Phe Pro Ala His Tyr Arg Arg Leu Arg
210 215 220

His Ala Leu Trp Pro Ser Leu Pro Asp Leu His Arg Val Leu Gly Gln
225 230 235 240

Tyr Leu Arg Asp Thr Ala Ala Leu Ser Pro Pro Lys Ala Thr Val Ser
245 250 255

Asp Thr Cys Glu Glu Val Glu Pro Ser Leu Leu Glu Ile Leu Pro Lys
260 265 270

Ser Ser Glu Arg Thr Pro Leu Pro Leu Ala Arg Asp Glu Val Glu Gly
275 280 285

Phe Leu Gln Asp Thr Phe Pro Gln Gln Leu Glu Glu Ser Glu Lys Gln
290 295 300

Arg Leu Gly Gly Asp Val Gln Ser Pro Asn Cys Pro Ser Glu Asp Val
305 310 315 320

Val Ile Thr Pro Glu Ser Phe Gly Arg Asp Ser Ser Leu Thr Cys Leu
325 330 335

Ala Gly Asn Val Ser Ala Cys Asp Ala Pro Ile Leu Ser Ser Ser Arg
340 345 350

Ser Leu Asp Cys Arg Glu Ser Gly Lys Asn Gly Pro His Val Tyr Gln
355 360 365

Asp Leu Leu Leu Ser Leu Gly Thr Thr Asn Ser Thr Leu Pro Pro Pro
370 375 380

Phe Ser Leu Gln Ser Gly Ile Leu Thr Leu Asn Pro Val Ala Gln Gly
385 390 395 400

Gln Pro Ile Leu Thr Ser Leu Gly Ser Asn Gln Glu Glu Ala Tyr Val
405 410 415

Thr Met Ser Ser Phe Tyr Gln Asn Gln Ser Asp Pro Lys Pro Glu Asn
420 425 430

Pro Ala Cys Pro Trp Thr Val Leu Pro Ala Gly Asp Leu Pro Thr His
435 440 445

Asp Gly Tyr Leu Pro Ser Asn Ile Asp Asp Leu Pro Ser His Glu Ala
450 455 460

Pro Leu Ala Asp Ser Leu Glu Glu Leu Glu Pro Gln
465 470 475

<210> SEQ ID NO 137
<211> LENGTH: 475
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 137

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

```
Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Leu Gly Leu Ser Ala Val Leu Gly Leu
        195                 200                 205

Leu Leu Leu Arg Trp Gln Phe Pro Ala His Tyr Arg Arg Leu Arg His
    210                 215                 220

Ala Leu Trp Pro Ser Leu Pro Asp Leu His Arg Val Leu Gly Gln Tyr
225                 230                 235                 240

Leu Arg Asp Thr Ala Ala Leu Ser Pro Pro Lys Ala Thr Val Ser Asp
                245                 250                 255

Thr Cys Glu Glu Val Glu Pro Ser Leu Leu Glu Ile Leu Pro Lys Ser
            260                 265                 270

Ser Glu Arg Thr Pro Leu Pro Leu Ala Arg Asp Glu Val Glu Gly Phe
        275                 280                 285

Leu Gln Asp Thr Phe Pro Gln Gln Leu Glu Glu Ser Glu Lys Gln Arg
    290                 295                 300

Leu Gly Gly Asp Val Gln Ser Pro Asn Cys Pro Ser Glu Asp Val Val
305                 310                 315                 320

Ile Thr Pro Glu Ser Phe Gly Arg Asp Ser Ser Leu Thr Cys Leu Ala
                325                 330                 335

Gly Asn Val Ser Ala Cys Asp Ala Pro Ile Leu Ser Ser Ser Arg Ser
            340                 345                 350

Leu Asp Cys Arg Glu Ser Gly Lys Asn Gly Pro His Val Tyr Gln Asp
        355                 360                 365

Leu Leu Leu Ser Leu Gly Thr Thr Asn Ser Thr Leu Pro Pro Pro Phe
    370                 375                 380

Ser Leu Gln Ser Gly Ile Leu Thr Leu Asn Pro Val Ala Gln Gly Gln
385                 390                 395                 400

Pro Ile Leu Thr Ser Leu Gly Ser Asn Gln Glu Glu Ala Tyr Val Thr
                405                 410                 415

Met Ser Ser Phe Tyr Gln Asn Gln Ser Asp Pro Lys Pro Glu Asn Pro
            420                 425                 430

Ala Cys Pro Trp Thr Val Leu Pro Ala Gly Asp Leu Pro Thr His Asp
        435                 440                 445

Gly Tyr Leu Pro Ser Asn Ile Asp Asp Leu Pro Ser His Glu Ala Pro
    450                 455                 460

Leu Ala Asp Ser Leu Glu Glu Leu Glu Pro Gln
465                 470                 475
```

<210> SEQ ID NO 138
<211> LENGTH: 474
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 138

Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Gly Leu Ser Ala Val Leu Gly Leu Leu
        195                 200                 205

Leu Leu Arg Trp Gln Phe Pro Ala His Tyr Arg Arg Leu Arg His Ala
    210                 215                 220

Leu Trp Pro Ser Leu Pro Asp Leu His Arg Val Leu Gly Gln Tyr Leu
225                 230                 235                 240

Arg Asp Thr Ala Ala Leu Ser Pro Pro Lys Ala Thr Val Ser Asp Thr
                245                 250                 255

Cys Glu Glu Val Glu Pro Ser Leu Leu Glu Ile Leu Pro Lys Ser Ser
            260                 265                 270

Glu Arg Thr Pro Leu Pro Leu Ala Arg Asp Glu Val Glu Gly Phe Leu
        275                 280                 285

Gln Asp Thr Phe Pro Gln Gln Leu Glu Glu Ser Glu Lys Gln Arg Leu
    290                 295                 300

Gly Gly Asp Val Gln Ser Pro Asn Cys Pro Ser Glu Asp Val Val Ile
305                 310                 315                 320

Thr Pro Glu Ser Phe Gly Arg Asp Ser Ser Leu Thr Cys Leu Ala Gly
                325                 330                 335

Asn Val Ser Ala Cys Asp Ala Pro Ile Leu Ser Ser Ser Arg Ser Leu
            340                 345                 350

Asp Cys Arg Glu Ser Gly Lys Asn Gly Pro His Val Tyr Gln Asp Leu
        355                 360                 365

Leu Leu Ser Leu Gly Thr Thr Asn Ser Thr Leu Pro Pro Pro Phe Ser
    370                 375                 380

Leu Gln Ser Gly Ile Leu Thr Leu Asn Pro Val Ala Gln Gly Gln Pro
385                 390                 395                 400

Ile Leu Thr Ser Leu Gly Ser Asn Gln Glu Glu Ala Tyr Val Thr Met
                405                 410                 415

Ser Ser Phe Tyr Gln Asn Gln Ser Asp Pro Lys Pro Glu Asn Pro Ala
            420                 425                 430

Cys Pro Trp Thr Val Leu Pro Ala Gly Asp Leu Pro Thr His Asp Gly
        435                 440                 445

Tyr Leu Pro Ser Asn Ile Asp Asp Leu Pro Ser His Glu Ala Pro Leu
    450                 455                 460

Ala Asp Ser Leu Glu Glu Leu Glu Pro Gln
465                 470

<210> SEQ ID NO 139
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Leu Ser Ala Val Leu Gly Leu Leu Leu
        195                 200                 205

Leu Arg Trp Gln Phe Pro Ala His Tyr Arg Arg Leu Arg His Ala Leu
    210                 215                 220

Trp Pro Ser Leu Pro Asp Leu His Arg Val Leu Gly Gln Tyr Leu Arg
225                 230                 235                 240

```
Asp Thr Ala Ala Leu Ser Pro Pro Lys Ala Thr Val Ser Asp Thr Cys
                245                 250                 255

Glu Glu Val Glu Pro Ser Leu Leu Glu Ile Leu Pro Lys Ser Ser Glu
            260                 265                 270

Arg Thr Pro Leu Pro Leu Ala Arg Asp Glu Val Glu Gly Phe Leu Gln
        275                 280                 285

Asp Thr Phe Pro Gln Gln Leu Glu Glu Ser Glu Lys Gln Arg Leu Gly
    290                 295                 300

Gly Asp Val Gln Ser Pro Asn Cys Pro Ser Glu Asp Val Val Ile Thr
305                 310                 315                 320

Pro Glu Ser Phe Gly Arg Asp Ser Ser Leu Thr Cys Leu Ala Gly Asn
                325                 330                 335

Val Ser Ala Cys Asp Ala Pro Ile Leu Ser Ser Ser Arg Ser Leu Asp
            340                 345                 350

Cys Arg Glu Ser Gly Lys Asn Gly Pro His Val Tyr Gln Asp Leu Leu
        355                 360                 365

Leu Ser Leu Gly Thr Thr Asn Ser Thr Leu Pro Pro Pro Phe Ser Leu
    370                 375                 380

Gln Ser Gly Ile Leu Thr Leu Asn Pro Val Ala Gln Gly Gln Pro Ile
385                 390                 395                 400

Leu Thr Ser Leu Gly Ser Asn Gln Glu Glu Ala Tyr Val Thr Met Ser
                405                 410                 415

Ser Phe Tyr Gln Asn Gln Ser Asp Pro Lys Pro Glu Asn Pro Ala Cys
            420                 425                 430

Pro Trp Thr Val Leu Pro Ala Gly Asp Leu Pro Thr His Asp Gly Tyr
        435                 440                 445

Leu Pro Ser Asn Ile Asp Asp Leu Pro Ser His Glu Ala Pro Leu Ala
    450                 455                 460

Asp Ser Leu Glu Glu Leu Glu Pro Gln
465                 470
```

<210> SEQ ID NO 140
<211> LENGTH: 472
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 140

```
Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110
```

```
Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Ser Ala Val Leu Gly Leu Leu Leu Leu
        195                 200                 205

Arg Trp Gln Phe Pro Ala His Tyr Arg Arg Leu Arg His Ala Leu Trp
    210                 215                 220

Pro Ser Leu Pro Asp Leu His Arg Val Leu Gly Gln Tyr Leu Arg Asp
225                 230                 235                 240

Thr Ala Ala Leu Ser Pro Pro Lys Ala Thr Val Ser Asp Thr Cys Glu
                245                 250                 255

Glu Val Glu Pro Ser Leu Leu Glu Ile Leu Pro Lys Ser Ser Glu Arg
            260                 265                 270

Thr Pro Leu Pro Leu Ala Arg Asp Glu Val Glu Gly Phe Leu Gln Asp
        275                 280                 285

Thr Phe Pro Gln Gln Leu Glu Glu Ser Glu Lys Gln Arg Leu Gly Gly
    290                 295                 300

Asp Val Gln Ser Pro Asn Cys Pro Ser Glu Asp Val Val Ile Thr Pro
305                 310                 315                 320

Glu Ser Phe Gly Arg Asp Ser Ser Leu Thr Cys Leu Ala Gly Asn Val
                325                 330                 335

Ser Ala Cys Asp Ala Pro Ile Leu Ser Ser Ser Arg Ser Leu Asp Cys
            340                 345                 350

Arg Glu Ser Gly Lys Asn Gly Pro His Val Tyr Gln Asp Leu Leu Leu
        355                 360                 365

Ser Leu Gly Thr Thr Asn Ser Thr Leu Pro Pro Pro Phe Ser Leu Gln
    370                 375                 380

Ser Gly Ile Leu Thr Leu Asn Pro Val Ala Gln Gly Gln Pro Ile Leu
385                 390                 395                 400

Thr Ser Leu Gly Ser Asn Gln Glu Glu Ala Tyr Val Thr Met Ser Ser
                405                 410                 415

Phe Tyr Gln Asn Gln Ser Asp Pro Lys Pro Glu Asn Pro Ala Cys Pro
            420                 425                 430

Trp Thr Val Leu Pro Ala Gly Asp Leu Pro Thr His Asp Gly Tyr Leu
        435                 440                 445

Pro Ser Asn Ile Asp Asp Leu Pro Ser His Glu Ala Pro Leu Ala Asp
    450                 455                 460

Ser Leu Glu Glu Leu Glu Pro Gln
465                 470
```

<210> SEQ ID NO 141
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

```
Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Ala Val Leu Gly Leu Leu Leu Leu Arg
        195                 200                 205

Trp Gln Phe Pro Ala His Tyr Arg Arg Leu Arg His Ala Leu Trp Pro
    210                 215                 220

Ser Leu Pro Asp Leu His Arg Val Leu Gly Gln Tyr Leu Arg Asp Thr
225                 230                 235                 240

Ala Ala Leu Ser Pro Pro Lys Ala Thr Val Ser Asp Thr Cys Glu Glu
                245                 250                 255

Val Glu Pro Ser Leu Leu Glu Ile Leu Pro Lys Ser Ser Glu Arg Thr
            260                 265                 270

Pro Leu Pro Leu Ala Arg Asp Glu Val Glu Gly Phe Leu Gln Asp Thr
        275                 280                 285

Phe Pro Gln Gln Leu Glu Glu Ser Glu Lys Gln Arg Leu Gly Gly Asp
    290                 295                 300

Val Gln Ser Pro Asn Cys Pro Ser Glu Asp Val Val Ile Thr Pro Glu
305                 310                 315                 320

Ser Phe Gly Arg Asp Ser Ser Leu Thr Cys Leu Ala Gly Asn Val Ser
                325                 330                 335

Ala Cys Asp Ala Pro Ile Leu Ser Ser Ser Arg Ser Leu Asp Cys Arg
            340                 345                 350

Glu Ser Gly Lys Asn Gly Pro His Val Tyr Gln Asp Leu Leu Leu Ser
        355                 360                 365

Leu Gly Thr Thr Asn Ser Thr Leu Pro Pro Pro Phe Ser Leu Gln Ser
    370                 375                 380

Gly Ile Leu Thr Leu Asn Pro Val Ala Gln Gly Gln Pro Ile Leu Thr
385                 390                 395                 400

Ser Leu Gly Ser Asn Gln Glu Glu Ala Tyr Val Thr Met Ser Ser Phe
                405                 410                 415
```

```
Tyr Gln Asn Gln Ser Asp Pro Lys Pro Glu Asn Pro Ala Cys Pro Trp
            420                 425                 430

Thr Val Leu Pro Ala Gly Asp Leu Pro Thr His Asp Gly Tyr Leu Pro
        435                 440                 445

Ser Asn Ile Asp Asp Leu Pro Ser His Glu Ala Pro Leu Ala Asp Ser
    450                 455                 460

Leu Glu Glu Leu Glu Pro Gln
465                 470


<210> SEQ ID NO 142
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Val Leu Gly Leu Leu Leu Leu Arg Trp
        195                 200                 205

Gln Phe Pro Ala His Tyr Arg Arg Leu Arg His Ala Leu Trp Pro Ser
    210                 215                 220

Leu Pro Asp Leu His Arg Val Leu Gly Gln Tyr Leu Arg Asp Thr Ala
225                 230                 235                 240

Ala Leu Ser Pro Pro Lys Ala Thr Val Ser Asp Thr Cys Glu Glu Val
                245                 250                 255

Glu Pro Ser Leu Leu Glu Ile Leu Pro Lys Ser Ser Glu Arg Thr Pro
            260                 265                 270

Leu Pro Leu Ala Arg Asp Glu Val Glu Gly Phe Leu Gln Asp Thr Phe
        275                 280                 285
```

Pro Gln Gln Leu Glu Glu Ser Glu Lys Gln Arg Leu Gly Gly Asp Val
    290                 295                 300

Gln Ser Pro Asn Cys Pro Ser Glu Asp Val Val Ile Thr Pro Glu Ser
305                 310                 315                 320

Phe Gly Arg Asp Ser Ser Leu Thr Cys Leu Ala Gly Asn Val Ser Ala
                325                 330                 335

Cys Asp Ala Pro Ile Leu Ser Ser Ser Arg Ser Leu Asp Cys Arg Glu
            340                 345                 350

Ser Gly Lys Asn Gly Pro His Val Tyr Gln Asp Leu Leu Leu Ser Leu
        355                 360                 365

Gly Thr Thr Asn Ser Thr Leu Pro Pro Pro Phe Ser Leu Gln Ser Gly
    370                 375                 380

Ile Leu Thr Leu Asn Pro Val Ala Gln Gly Gln Pro Ile Leu Thr Ser
385                 390                 395                 400

Leu Gly Ser Asn Gln Glu Glu Ala Tyr Val Thr Met Ser Ser Phe Tyr
                405                 410                 415

Gln Asn Gln Ser Asp Pro Lys Pro Glu Asn Pro Ala Cys Pro Trp Thr
            420                 425                 430

Val Leu Pro Ala Gly Asp Leu Pro Thr His Asp Gly Tyr Leu Pro Ser
        435                 440                 445

Asn Ile Asp Asp Leu Pro Ser His Glu Ala Pro Leu Ala Asp Ser Leu
    450                 455                 460

Glu Glu Leu Glu Pro Gln
465                 470

<210> SEQ ID NO 143
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
165 170 175

Ser Asn Pro Asp Leu Leu Leu Val Ile Phe Gln Ser Asp Pro Thr Arg
180 185 190

Val Glu Thr Ala Thr Glu Thr Leu Gly Leu Leu Leu Leu Arg Trp Gln
195 200 205

Phe Pro Ala His Tyr Arg Arg Leu Arg His Ala Leu Trp Pro Ser Leu
210 215 220

Pro Asp Leu His Arg Val Leu Gly Gln Tyr Leu Arg Asp Thr Ala Ala
225 230 235 240

Leu Ser Pro Pro Lys Ala Thr Val Ser Asp Thr Cys Glu Glu Val Glu
245 250 255

Pro Ser Leu Leu Glu Ile Leu Pro Lys Ser Ser Glu Arg Thr Pro Leu
260 265 270

Pro Leu Ala Arg Asp Glu Val Glu Gly Phe Leu Gln Asp Thr Phe Pro
275 280 285

Gln Gln Leu Glu Glu Ser Glu Lys Gln Arg Leu Gly Gly Asp Val Gln
290 295 300

Ser Pro Asn Cys Pro Ser Glu Asp Val Val Ile Thr Pro Glu Ser Phe
305 310 315 320

Gly Arg Asp Ser Ser Leu Thr Cys Leu Ala Gly Asn Val Ser Ala Cys
325 330 335

Asp Ala Pro Ile Leu Ser Ser Ser Arg Ser Leu Asp Cys Arg Glu Ser
340 345 350

Gly Lys Asn Gly Pro His Val Tyr Gln Asp Leu Leu Leu Ser Leu Gly
355 360 365

Thr Thr Asn Ser Thr Leu Pro Pro Pro Phe Ser Leu Gln Ser Gly Ile
370 375 380

Leu Thr Leu Asn Pro Val Ala Gln Gly Gln Pro Ile Leu Thr Ser Leu
385 390 395 400

Gly Ser Asn Gln Glu Glu Ala Tyr Val Thr Met Ser Ser Phe Tyr Gln
405 410 415

Asn Gln Ser Asp Pro Lys Pro Glu Asn Pro Ala Cys Pro Trp Thr Val
420 425 430

Leu Pro Ala Gly Asp Leu Pro Thr His Asp Gly Tyr Leu Pro Ser Asn
435 440 445

Ile Asp Asp Leu Pro Ser His Glu Ala Pro Leu Ala Asp Ser Leu Glu
450 455 460

Glu Leu Glu Pro Gln
465

<210> SEQ ID NO 144
<211> LENGTH: 488
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 144

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

```
Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Ala Trp Leu Ile Ser Leu Val Thr Ala
        195                 200                 205

Leu His Leu Val Leu Gly Leu Ser Ala Val Leu Gly Leu Leu Leu Leu
    210                 215                 220

Arg Trp Gln Phe Pro Ala His Tyr Arg Arg Leu Arg His Ala Leu Trp
225                 230                 235                 240

Pro Ser Leu Pro Asp Leu His Arg Val Leu Gly Gln Tyr Leu Arg Asp
                245                 250                 255

Thr Ala Ala Leu Ser Pro Pro Lys Ala Thr Val Ser Asp Thr Cys Glu
            260                 265                 270

Glu Val Glu Pro Ser Leu Leu Glu Ile Leu Pro Lys Ser Ser Glu Arg
        275                 280                 285

Thr Pro Leu Pro Leu Ala Arg Asp Glu Val Glu Gly Phe Leu Gln Asp
    290                 295                 300

Thr Phe Pro Gln Gln Leu Glu Glu Ser Glu Lys Gln Arg Leu Gly Gly
305                 310                 315                 320

Asp Val Gln Ser Pro Asn Cys Pro Ser Glu Asp Val Val Ile Thr Pro
                325                 330                 335

Glu Ser Phe Gly Arg Asp Ser Ser Leu Thr Cys Leu Ala Gly Asn Val
            340                 345                 350

Ser Ala Cys Asp Ala Pro Ile Leu Ser Ser Ser Arg Ser Leu Asp Cys
        355                 360                 365

Arg Glu Ser Gly Lys Asn Gly Pro His Val Tyr Gln Asp Leu Leu Leu
    370                 375                 380

Ser Leu Gly Thr Thr Asn Ser Thr Leu Pro Pro Pro Phe Ser Leu Gln
385                 390                 395                 400

Ser Gly Ile Leu Thr Leu Asn Pro Val Ala Gln Gly Gln Pro Ile Leu
                405                 410                 415

Thr Ser Leu Gly Ser Asn Gln Glu Glu Ala Tyr Val Thr Met Ser Ser
            420                 425                 430

Phe Tyr Gln Asn Gln Ser Asp Pro Lys Pro Glu Asn Pro Ala Cys Pro
        435                 440                 445
```

-continued

Trp Thr Val Leu Pro Ala Gly Asp Leu Pro Thr His Asp Gly Tyr Leu
    450                 455                 460

Pro Ser Asn Ile Asp Asp Leu Pro Ser His Glu Ala Pro Leu Ala Asp
465                 470                 475                 480

Ser Leu Glu Glu Leu Glu Pro Gln
                485

<210> SEQ ID NO 145
<211> LENGTH: 489
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Ala Trp Val Leu Ile Ser Leu Val Thr
        195                 200                 205

Ala Leu His Leu Val Leu Gly Leu Ser Ala Val Leu Gly Leu Leu Leu
    210                 215                 220

Leu Arg Trp Gln Phe Pro Ala His Tyr Arg Arg Leu Arg His Ala Leu
225                 230                 235                 240

Trp Pro Ser Leu Pro Asp Leu His Arg Val Leu Gly Gln Tyr Leu Arg
                245                 250                 255

Asp Thr Ala Ala Leu Ser Pro Pro Lys Ala Thr Val Ser Asp Thr Cys
            260                 265                 270

Glu Glu Val Glu Pro Ser Leu Leu Glu Ile Leu Pro Lys Ser Ser Glu
        275                 280                 285

Arg Thr Pro Leu Pro Leu Ala Arg Asp Glu Val Glu Gly Phe Leu Gln
    290                 295                 300

Asp Thr Phe Pro Gln Gln Leu Glu Glu Ser Glu Lys Gln Arg Leu Gly
305                 310                 315                 320

Gly Asp Val Gln Ser Pro Asn Cys Pro Ser Glu Asp Val Val Ile Thr
325 330 335

Pro Glu Ser Phe Gly Arg Asp Ser Ser Leu Thr Cys Leu Ala Gly Asn
340 345 350

Val Ser Ala Cys Asp Ala Pro Ile Leu Ser Ser Ser Arg Ser Leu Asp
355 360 365

Cys Arg Glu Ser Gly Lys Asn Gly Pro His Val Tyr Gln Asp Leu Leu
370 375 380

Leu Ser Leu Gly Thr Thr Asn Ser Thr Leu Pro Pro Pro Phe Ser Leu
385 390 395 400

Gln Ser Gly Ile Leu Thr Leu Asn Pro Val Ala Gln Gly Gln Pro Ile
405 410 415

Leu Thr Ser Leu Gly Ser Asn Gln Glu Glu Ala Tyr Val Thr Met Ser
420 425 430

Ser Phe Tyr Gln Asn Gln Ser Asp Pro Lys Pro Glu Asn Pro Ala Cys
435 440 445

Pro Trp Thr Val Leu Pro Ala Gly Asp Leu Pro Thr His Asp Gly Tyr
450 455 460

Leu Pro Ser Asn Ile Asp Asp Leu Pro Ser His Glu Ala Pro Leu Ala
465 470 475 480

Asp Ser Leu Glu Glu Leu Glu Pro Gln
485

<210> SEQ ID NO 146
<211> LENGTH: 490
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 146

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

Asp Glu Asn Ile Thr Leu Glu Thr Val Cys His Asp Pro Lys Leu Pro
115 120 125

Tyr His Asp Phe Ile Leu Glu Asp Ala Ala Ser Pro Lys Cys Ile Met
130 135 140

Lys Glu Lys Lys Lys Pro Gly Glu Thr Phe Phe Met Cys Ser Cys Ser
145 150 155 160

Ser Asp Glu Cys Asn Asp Asn Ile Ile Phe Ser Glu Glu Tyr Asn Thr
165 170 175

Ser Asn Pro Asp Leu Leu Leu Val Ile Phe Gln Ser Asp Pro Thr Arg
180 185 190

Val Glu Thr Ala Thr Glu Thr Ala Trp Leu Val Leu Ile Ser Leu Val
195 200 205

Thr Ala Leu His Leu Val Leu Gly Leu Ser Ala Val Leu Gly Leu Leu
210 215 220

Leu Leu Arg Trp Gln Phe Pro Ala His Tyr Arg Arg Leu Arg His Ala
225 230 235 240

Leu Trp Pro Ser Leu Pro Asp Leu His Arg Val Leu Gly Gln Tyr Leu
245 250 255

Arg Asp Thr Ala Ala Leu Ser Pro Pro Lys Ala Thr Val Ser Asp Thr
260 265 270

Cys Glu Glu Val Glu Pro Ser Leu Leu Glu Ile Leu Pro Lys Ser Ser
275 280 285

Glu Arg Thr Pro Leu Pro Leu Ala Arg Asp Glu Val Glu Gly Phe Leu
290 295 300

Gln Asp Thr Phe Pro Gln Gln Leu Glu Glu Ser Glu Lys Gln Arg Leu
305 310 315 320

Gly Gly Asp Val Gln Ser Pro Asn Cys Pro Ser Glu Asp Val Val Ile
325 330 335

Thr Pro Glu Ser Phe Gly Arg Asp Ser Ser Leu Thr Cys Leu Ala Gly
340 345 350

Asn Val Ser Ala Cys Asp Ala Pro Ile Leu Ser Ser Ser Arg Ser Leu
355 360 365

Asp Cys Arg Glu Ser Gly Lys Asn Gly Pro His Val Tyr Gln Asp Leu
370 375 380

Leu Leu Ser Leu Gly Thr Thr Asn Ser Thr Leu Pro Pro Pro Phe Ser
385 390 395 400

Leu Gln Ser Gly Ile Leu Thr Leu Asn Pro Val Ala Gln Gly Gln Pro
405 410 415

Ile Leu Thr Ser Leu Gly Ser Asn Gln Glu Glu Ala Tyr Val Thr Met
420 425 430

Ser Ser Phe Tyr Gln Asn Gln Ser Asp Pro Lys Pro Glu Asn Pro Ala
435 440 445

Cys Pro Trp Thr Val Leu Pro Ala Gly Asp Leu Pro Thr His Asp Gly
450 455 460

Tyr Leu Pro Ser Asn Ile Asp Asp Leu Pro Ser His Glu Ala Pro Leu
465 470 475 480

Ala Asp Ser Leu Glu Glu Leu Glu Pro Gln
485 490

<210> SEQ ID NO 147
<211> LENGTH: 491
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 147

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

```
Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Ala Trp Ile Leu Val Leu Ile Ser Leu
        195                 200                 205

Val Thr Ala Leu His Leu Val Leu Gly Leu Ser Ala Val Leu Gly Leu
    210                 215                 220

Leu Leu Leu Arg Trp Gln Phe Pro Ala His Tyr Arg Arg Leu Arg His
225                 230                 235                 240

Ala Leu Trp Pro Ser Leu Pro Asp Leu His Arg Val Leu Gly Gln Tyr
                245                 250                 255

Leu Arg Asp Thr Ala Ala Leu Ser Pro Pro Lys Ala Thr Val Ser Asp
            260                 265                 270

Thr Cys Glu Glu Val Glu Pro Ser Leu Leu Glu Ile Leu Pro Lys Ser
        275                 280                 285

Ser Glu Arg Thr Pro Leu Pro Leu Ala Arg Asp Glu Val Glu Gly Phe
    290                 295                 300

Leu Gln Asp Thr Phe Pro Gln Gln Leu Glu Glu Ser Glu Lys Gln Arg
305                 310                 315                 320

Leu Gly Gly Asp Val Gln Ser Pro Asn Cys Pro Ser Glu Asp Val Val
                325                 330                 335

Ile Thr Pro Glu Ser Phe Gly Arg Asp Ser Ser Leu Thr Cys Leu Ala
            340                 345                 350

Gly Asn Val Ser Ala Cys Asp Ala Pro Ile Leu Ser Ser Ser Arg Ser
        355                 360                 365

Leu Asp Cys Arg Glu Ser Gly Lys Asn Gly Pro His Val Tyr Gln Asp
    370                 375                 380

Leu Leu Leu Ser Leu Gly Thr Thr Asn Ser Thr Leu Pro Pro Pro Phe
385                 390                 395                 400

Ser Leu Gln Ser Gly Ile Leu Thr Leu Asn Pro Val Ala Gln Gly Gln
                405                 410                 415

Pro Ile Leu Thr Ser Leu Gly Ser Asn Gln Glu Glu Ala Tyr Val Thr
            420                 425                 430

Met Ser Ser Phe Tyr Gln Asn Gln Ser Asp Pro Lys Pro Glu Asn Pro
        435                 440                 445
```

Ala Cys Pro Trp Thr Val Leu Pro Ala Gly Asp Leu Pro Thr His Asp
450 455 460

Gly Tyr Leu Pro Ser Asn Ile Asp Asp Leu Pro Ser His Glu Ala Pro
465 470 475 480

Leu Ala Asp Ser Leu Glu Glu Leu Glu Pro Gln
485 490

<210> SEQ ID NO 148
<211> LENGTH: 492
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 148

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

Asp Glu Asn Ile Thr Leu Glu Thr Val Cys His Asp Pro Lys Leu Pro
115 120 125

Tyr His Asp Phe Ile Leu Glu Asp Ala Ala Ser Pro Lys Cys Ile Met
130 135 140

Lys Glu Lys Lys Lys Pro Gly Glu Thr Phe Phe Met Cys Ser Cys Ser
145 150 155 160

Ser Asp Glu Cys Asn Asp Asn Ile Ile Phe Ser Glu Glu Tyr Asn Thr
165 170 175

Ser Asn Pro Asp Leu Leu Leu Val Ile Phe Gln Ser Asp Pro Thr Arg
180 185 190

Val Glu Thr Ala Thr Glu Thr Ala Trp Leu Ile Leu Val Leu Ile Ser
195 200 205

Leu Val Thr Ala Leu His Leu Val Leu Gly Leu Ser Ala Val Leu Gly
210 215 220

Leu Leu Leu Leu Arg Trp Gln Phe Pro Ala His Tyr Arg Arg Leu Arg
225 230 235 240

His Ala Leu Trp Pro Ser Leu Pro Asp Leu His Arg Val Leu Gly Gln
245 250 255

Tyr Leu Arg Asp Thr Ala Ala Leu Ser Pro Pro Lys Ala Thr Val Ser
260 265 270

Asp Thr Cys Glu Glu Val Glu Pro Ser Leu Leu Glu Ile Leu Pro Lys
275 280 285

Ser Ser Glu Arg Thr Pro Leu Pro Leu Ala Arg Asp Glu Val Glu Gly
290 295 300

Phe Leu Gln Asp Thr Phe Pro Gln Gln Leu Glu Glu Ser Glu Lys Gln
305 310 315 320

Arg Leu Gly Gly Asp Val Gln Ser Pro Asn Cys Pro Ser Glu Asp Val
                325                 330                 335

Val Ile Thr Pro Glu Ser Phe Gly Arg Asp Ser Ser Leu Thr Cys Leu
            340                 345                 350

Ala Gly Asn Val Ser Ala Cys Asp Ala Pro Ile Leu Ser Ser Ser Arg
        355                 360                 365

Ser Leu Asp Cys Arg Glu Ser Gly Lys Asn Gly Pro His Val Tyr Gln
    370                 375                 380

Asp Leu Leu Leu Ser Leu Gly Thr Thr Asn Ser Thr Leu Pro Pro Pro
385                 390                 395                 400

Phe Ser Leu Gln Ser Gly Ile Leu Thr Leu Asn Pro Val Ala Gln Gly
                405                 410                 415

Gln Pro Ile Leu Thr Ser Leu Gly Ser Asn Gln Glu Glu Ala Tyr Val
            420                 425                 430

Thr Met Ser Ser Phe Tyr Gln Asn Gln Ser Asp Pro Lys Pro Glu Asn
        435                 440                 445

Pro Ala Cys Pro Trp Thr Val Leu Pro Ala Gly Asp Leu Pro Thr His
    450                 455                 460

Asp Gly Tyr Leu Pro Ser Asn Ile Asp Asp Leu Pro Ser His Glu Ala
465                 470                 475                 480

Pro Leu Ala Asp Ser Leu Glu Glu Leu Glu Pro Gln
                485                 490

<210> SEQ ID NO 149
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
180 185 190

Val Glu Thr Ala Thr Glu Thr Ala Trp Leu Leu Ile Leu Val Leu Ile
195 200 205

Ser Leu Val Thr Ala Leu His Leu Val Leu Gly Leu Ser Ala Val Leu
210 215 220

Gly Leu Leu Leu Leu Arg Trp Gln Phe Pro Ala His Tyr Arg Arg Leu
225 230 235 240

Arg His Ala Leu Trp Pro Ser Leu Pro Asp Leu His Arg Val Leu Gly
245 250 255

Gln Tyr Leu Arg Asp Thr Ala Ala Leu Ser Pro Pro Lys Ala Thr Val
260 265 270

Ser Asp Thr Cys Glu Glu Val Glu Pro Ser Leu Leu Glu Ile Leu Pro
275 280 285

Lys Ser Ser Glu Arg Thr Pro Leu Pro Leu Ala Arg Asp Glu Val Glu
290 295 300

Gly Phe Leu Gln Asp Thr Phe Pro Gln Gln Leu Glu Glu Ser Glu Lys
305 310 315 320

Gln Arg Leu Gly Gly Asp Val Gln Ser Pro Asn Cys Pro Ser Glu Asp
325 330 335

Val Val Ile Thr Pro Glu Ser Phe Gly Arg Asp Ser Ser Leu Thr Cys
340 345 350

Leu Ala Gly Asn Val Ser Ala Cys Asp Ala Pro Ile Leu Ser Ser Ser
355 360 365

Arg Ser Leu Asp Cys Arg Glu Ser Gly Lys Asn Gly Pro His Val Tyr
370 375 380

Gln Asp Leu Leu Leu Ser Leu Gly Thr Thr Asn Ser Thr Leu Pro Pro
385 390 395 400

Pro Phe Ser Leu Gln Ser Gly Ile Leu Thr Leu Asn Pro Val Ala Gln
405 410 415

Gly Gln Pro Ile Leu Thr Ser Leu Gly Ser Asn Gln Glu Glu Ala Tyr
420 425 430

Val Thr Met Ser Ser Phe Tyr Gln Asn Gln Ser Asp Pro Lys Pro Glu
435 440 445

Asn Pro Ala Cys Pro Trp Thr Val Leu Pro Ala Gly Asp Leu Pro Thr
450 455 460

His Asp Gly Tyr Leu Pro Ser Asn Ile Asp Asp Leu Pro Ser His Glu
465 470 475 480

Ala Pro Leu Ala Asp Ser Leu Glu Glu Leu Glu Pro Gln
485 490

<210> SEQ ID NO 150
<211> LENGTH: 494
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 150

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

```
Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Ala Trp Val Leu Leu Ile Leu Val Leu
        195                 200                 205

Ile Ser Leu Val Thr Ala Leu His Leu Val Leu Gly Leu Ser Ala Val
    210                 215                 220

Leu Gly Leu Leu Leu Leu Arg Trp Gln Phe Pro Ala His Tyr Arg Arg
225                 230                 235                 240

Leu Arg His Ala Leu Trp Pro Ser Leu Pro Asp Leu His Arg Val Leu
                245                 250                 255

Gly Gln Tyr Leu Arg Asp Thr Ala Ala Leu Ser Pro Pro Lys Ala Thr
            260                 265                 270

Val Ser Asp Thr Cys Glu Glu Val Glu Pro Ser Leu Leu Glu Ile Leu
        275                 280                 285

Pro Lys Ser Ser Glu Arg Thr Pro Leu Pro Leu Ala Arg Asp Glu Val
    290                 295                 300

Glu Gly Phe Leu Gln Asp Thr Phe Pro Gln Gln Leu Glu Glu Ser Glu
305                 310                 315                 320

Lys Gln Arg Leu Gly Gly Asp Val Gln Ser Pro Asn Cys Pro Ser Glu
                325                 330                 335

Asp Val Val Ile Thr Pro Glu Ser Phe Gly Arg Asp Ser Ser Leu Thr
            340                 345                 350

Cys Leu Ala Gly Asn Val Ser Ala Cys Asp Ala Pro Ile Leu Ser Ser
        355                 360                 365

Ser Arg Ser Leu Asp Cys Arg Glu Ser Gly Lys Asn Gly Pro His Val
    370                 375                 380

Tyr Gln Asp Leu Leu Leu Ser Leu Gly Thr Thr Asn Ser Thr Leu Pro
385                 390                 395                 400

Pro Pro Phe Ser Leu Gln Ser Gly Ile Leu Thr Leu Asn Pro Val Ala
                405                 410                 415

Gln Gly Gln Pro Ile Leu Thr Ser Leu Gly Ser Asn Gln Glu Glu Ala
            420                 425                 430

Tyr Val Thr Met Ser Ser Phe Tyr Gln Asn Gln Ser Asp Pro Lys Pro
        435                 440                 445
```

```
Glu Asn Pro Ala Cys Pro Trp Thr Val Leu Pro Ala Gly Asp Leu Pro
    450                 455                 460

Thr His Asp Gly Tyr Leu Pro Ser Asn Ile Asp Asp Leu Pro Ser His
465                 470                 475                 480

Glu Ala Pro Leu Ala Asp Ser Leu Glu Glu Leu Glu Pro Gln
                485                 490


<210> SEQ ID NO 151
<211> LENGTH: 495
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Ala Trp Leu Val Leu Leu Ile Leu Val
        195                 200                 205

Leu Ile Ser Leu Val Thr Ala Leu His Leu Val Leu Gly Leu Ser Ala
    210                 215                 220

Val Leu Gly Leu Leu Leu Leu Arg Trp Gln Phe Pro Ala His Tyr Arg
225                 230                 235                 240

Arg Leu Arg His Ala Leu Trp Pro Ser Leu Pro Asp Leu His Arg Val
                245                 250                 255

Leu Gly Gln Tyr Leu Arg Asp Thr Ala Ala Leu Ser Pro Pro Lys Ala
            260                 265                 270

Thr Val Ser Asp Thr Cys Glu Glu Val Glu Pro Ser Leu Leu Glu Ile
        275                 280                 285

Leu Pro Lys Ser Ser Glu Arg Thr Pro Leu Pro Leu Ala Arg Asp Glu
    290                 295                 300

Val Glu Gly Phe Leu Gln Asp Thr Phe Pro Gln Gln Leu Glu Glu Ser
305                 310                 315                 320
```

Glu Lys Gln Arg Leu Gly Gly Asp Val Gln Ser Pro Asn Cys Pro Ser
325 330 335

Glu Asp Val Val Ile Thr Pro Glu Ser Phe Gly Arg Asp Ser Ser Leu
340 345 350

Thr Cys Leu Ala Gly Asn Val Ser Ala Cys Asp Ala Pro Ile Leu Ser
355 360 365

Ser Ser Arg Ser Leu Asp Cys Arg Glu Ser Gly Lys Asn Gly Pro His
370 375 380

Val Tyr Gln Asp Leu Leu Leu Ser Leu Gly Thr Thr Asn Ser Thr Leu
385 390 395 400

Pro Pro Pro Phe Ser Leu Gln Ser Gly Ile Leu Thr Leu Asn Pro Val
405 410 415

Ala Gln Gly Gln Pro Ile Leu Thr Ser Leu Gly Ser Asn Gln Glu Glu
420 425 430

Ala Tyr Val Thr Met Ser Ser Phe Tyr Gln Asn Gln Ser Asp Pro Lys
435 440 445

Pro Glu Asn Pro Ala Cys Pro Trp Thr Val Leu Pro Ala Gly Asp Leu
450 455 460

Pro Thr His Asp Gly Tyr Leu Pro Ser Asn Ile Asp Asp Leu Pro Ser
465 470 475 480

His Glu Ala Pro Leu Ala Asp Ser Leu Glu Glu Leu Glu Pro Gln
485 490 495

<210> SEQ ID NO 152
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 152

Lys Pro Ile Pro Asn Pro Leu Leu Gly Leu Asp Ser Thr
1 5 10

<210> SEQ ID NO 153
<211> LENGTH: 246
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 153

Glu Ile Gln Leu Val Gln Ser Gly Ala Glu Val Lys Lys Pro Gly Glu
1 5 10 15

Ser Leu Arg Ile Ser Cys Lys Gly Ser Gly Phe Asn Ile Glu Asp Tyr
20 25 30

Tyr Ile His Trp Val Arg Gln Met Pro Gly Lys Gly Leu Glu Trp Met
35 40 45

Gly Arg Ile Asp Pro Glu Asn Asp Glu Thr Lys Tyr Gly Pro Ile Phe
50 55 60

Gln Gly His Val Thr Ile Ser Ala Asp Thr Ser Ile Asn Thr Val Tyr
65 70 75 80

Leu Gln Trp Ser Ser Leu Lys Ala Ser Asp Thr Ala Met Tyr Tyr Cys
85 90 95

Ala Phe Arg Gly Gly Val Tyr Trp Gly Gln Gly Thr Thr Val Thr Val
100 105 110

```
Ser Ser Gly Gly Gly Gly Ser Gly Gly Gly Gly Ser Gly Gly Gly Gly
        115                 120                 125

Ser Gly Gly Gly Gly Ser Asp Val Val Met Thr Gln Ser Pro Asp Ser
    130                 135                 140

Leu Ala Val Ser Leu Gly Glu Arg Ala Thr Ile Asn Cys Lys Ser Ser
145                 150                 155                 160

Gln Ser Leu Leu Asp Ser Asp Gly Lys Thr Tyr Leu Asn Trp Leu Gln
                165                 170                 175

Gln Lys Pro Gly Gln Pro Pro Lys Arg Leu Ile Ser Leu Val Ser Lys
            180                 185                 190

Leu Asp Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Trp Gln Gly Thr His Phe Pro Gly Thr Phe Gly Gly Gly
225                 230                 235                 240

Thr Lys Val Glu Ile Lys
                245


<210> SEQ ID NO 154
<211> LENGTH: 69
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65


<210> SEQ ID NO 155
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 156
<211> LENGTH: 112
<212> TYPE: PRT
<213> ORGANISM: Artificial Sequence
```

<220> FEATURE:
<223> OTHER INFORMATION: Description of Artificial Sequence: Synthetic
polypeptide

<400> SEQUENCE: 156

Arg Val Lys Phe Ser Arg Ser Ala Asp Ala Pro Ala Tyr Gln Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 157
<211> LENGTH: 233
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 157

Met Ser Glu Leu Ile Lys Glu Asn Met His Met Lys Leu Tyr Met Glu
1 5 10 15

Gly Thr Val Asp Asn His His Phe Lys Cys Thr Ser Glu Gly Glu Gly
20 25 30

Lys Pro Tyr Glu Gly Thr Gln Thr Met Arg Ile Lys Val Val Glu Gly
35 40 45

Gly Pro Leu Pro Phe Ala Phe Asp Ile Leu Ala Thr Ser Phe Leu Tyr
50 55 60

Gly Ser Lys Thr Phe Ile Asn His Thr Gln Gly Ile Pro Asp Phe Phe
65 70 75 80

Lys Gln Ser Phe Pro Glu Gly Phe Thr Trp Glu Arg Val Thr Thr Tyr
85 90 95

Glu Asp Gly Gly Val Leu Thr Ala Thr Gln Asp Thr Ser Leu Gln Asp
100 105 110

Gly Cys Leu Ile Tyr Asn Val Lys Ile Arg Gly Val Asn Phe Thr Ser
115 120 125

Asn Gly Pro Val Met Gln Lys Lys Thr Leu Gly Trp Glu Ala Phe Thr
130 135 140

Glu Thr Leu Tyr Pro Ala Asp Gly Gly Leu Glu Gly Arg Asn Asp Met
145 150 155 160

Ala Leu Lys Leu Val Gly Gly Ser His Leu Ile Ala Asn Ile Lys Thr
165 170 175

Thr Tyr Arg Ser Lys Lys Pro Ala Lys Asn Leu Lys Met Pro Gly Val
180 185 190

Tyr Tyr Val Asp Tyr Arg Leu Glu Arg Ile Lys Glu Ala Asn Asn Glu
195 200 205

Thr Tyr Val Glu Gln His Glu Val Ala Val Ala Arg Tyr Cys Asp Leu
210 215 220

Pro Ser Lys Leu Gly His Lys Leu Asn
225 230

<210> SEQ ID NO 158
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 158

Gly Ser Gly Ala Thr Asn Phe Ser Leu Leu Lys Gln Ala Gly Asp Val
1 5 10 15

Glu Glu Asn Pro Gly Pro
20

<210> SEQ ID NO 159
<211> LENGTH: 143
<212> TYPE: PRT
<213> ORGANISM: Homo sapiens

<400> SEQUENCE: 159

Ile Pro Pro His Val Gln Lys Ser Val Asn Asn Asp Met Ile Val Thr
1 5 10 15

Asp Asn Asn Gly Ala Val Lys Phe Pro Gln Leu Cys Lys Phe Cys Asp
20 25 30

Val Arg Phe Ser Thr Cys Asp Asn Gln Lys Ser Cys Met Ser Asn Cys
35 40 45

Ser Ile Thr Ser Ile Cys Glu Lys Pro Gln Glu Val Cys Val Ala Val
50 55 60

Trp Arg Lys Asn Asp Glu Asn Ile Thr Leu Glu Thr Val Cys His Asp
65 70 75 80

Pro Lys Leu Pro Tyr His Asp Phe Ile Leu Glu Asp Ala Ala Ser Pro
85 90 95

Lys Cys Ile Met Lys Glu Lys Lys Lys Pro Gly Glu Thr Phe Phe Met
100 105 110

Cys Ser Cys Ser Ser Asp Glu Cys Asn Asp Asn Ile Ile Phe Ser Glu
115 120 125

Glu Tyr Asn Thr Ser Asn Pro Asp Leu Leu Leu Val Ile Phe Gln
130 135 140

<210> SEQ ID NO 160
<211> LENGTH: 105
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 160

Ser Asp Pro Thr Arg Val Glu Thr Ala Thr Glu Thr Ala Trp Ile Ser
1 5 10 15

Leu Val Thr Ala Leu His Leu Val Leu Gly Leu Asn Ala Val Leu Gly
20 25 30

Leu Leu Leu Leu Arg Lys Gln Phe Pro Ala His Tyr Arg Arg Leu Arg
35 40 45

His Ala Leu Trp Pro Ser Leu Pro Asp Leu His Arg Val Leu Gly Gln
50 55 60

```
Tyr Leu Arg Asp Thr Ala Ala Leu Ser Pro Pro Arg Ala Thr Val Ser
65                  70                  75                  80

Asp Thr Cys Glu Glu Val Glu Pro Ser Leu Leu Glu Ile Leu Pro Arg
                85                  90                  95

Ser Ser Glu Arg Thr Pro Leu Pro Leu
            100                 105


<210> SEQ ID NO 161
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Ala Arg Asp Glu Val Glu Gly Phe Leu Gln Asp Thr Phe Pro Gln Gln
1               5                   10                  15

Leu Glu Glu Ser Glu Lys Gln Arg Leu Gly Gly Asp Val Gln Ser Pro
            20                  25                  30

Asn Cys Pro Ser Glu Asp Val Val Ile Thr Pro Glu Ser Phe Gly Arg
        35                  40                  45

Asp Ser Ser Leu Thr Cys Leu Ala Gly Asn Val Ser Ala Cys Asp Ala
    50                  55                  60

Pro Ile Leu Ser Ser Ser Arg Ser Leu Asp Cys Arg Glu Ser Gly Lys
65                  70                  75                  80

Asn Gly Pro His Val Tyr Gln Asp Leu Leu Leu Ser Leu Gly Thr Thr
                85                  90                  95

Asn Ser Thr Leu Pro Pro Pro Phe Ser Leu Gln Ser Gly Ile Leu Thr
            100                 105                 110

Leu Asn Pro Val Ala Gln Gly Gln Pro Ile Leu Thr Ser Leu Gly Ser
        115                 120                 125

Asn Gln Glu Glu Ala Tyr Val Thr Met Ser Ser Phe Tyr Gln Asn Gln
    130                 135                 140

Ser Arg Ser Asp Pro Lys Pro Glu Asn Pro Ala Cys Pro Trp Thr Val
145                 150                 155                 160

Leu Pro Ala Gly Asp Leu Pro Thr His Asp Gly Tyr Leu Pro Ser Asn
                165                 170                 175

Ile Asp Asp Leu Pro Ser His Glu Ala Pro Leu Ala Asp Ser Leu Glu
            180                 185                 190

Glu Leu Glu Pro Gln
        195


<210> SEQ ID NO 162
<211> LENGTH: 491
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45
```

```
Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Ala Trp Ile Ser Leu Val Thr Ala Leu
        195                 200                 205

His Leu Val Leu Gly Leu Ser Ala Val Leu Gly Leu Leu Leu Leu Arg
    210                 215                 220

Trp Gln Phe Pro Ala His Tyr Arg Arg Leu Arg His Ala Leu Trp Pro
225                 230                 235                 240

Ser Leu Pro Asp Leu His Arg Val Leu Gly Gln Tyr Leu Arg Asp Thr
                245                 250                 255

Ala Ala Leu Ser Pro Pro Lys Ala Thr Val Ser Asp Thr Cys Glu Glu
            260                 265                 270

Val Glu Pro Ser Leu Leu Glu Ile Leu Pro Lys Ser Ser Glu Arg Thr
        275                 280                 285

Pro Leu Pro Leu Leu Glu Ala Arg Asp Glu Val Glu Gly Phe Leu Gln
    290                 295                 300

Asp Thr Phe Pro Gln Gln Leu Glu Glu Ser Glu Lys Gln Arg Leu Gly
305                 310                 315                 320

Gly Asp Val Gln Ser Pro Asn Cys Pro Ser Glu Asp Val Val Ile Thr
                325                 330                 335

Pro Glu Ser Phe Gly Arg Asp Ser Ser Leu Thr Cys Leu Ala Gly Asn
            340                 345                 350

Val Ser Ala Cys Asp Ala Pro Ile Leu Ser Ser Ser Arg Ser Leu Asp
        355                 360                 365

Cys Arg Glu Ser Gly Lys Asn Gly Pro His Val Tyr Gln Asp Leu Leu
    370                 375                 380

Leu Ser Leu Gly Thr Thr Asn Ser Thr Leu Pro Pro Pro Phe Ser Leu
385                 390                 395                 400

Gln Ser Gly Ile Leu Thr Leu Asn Pro Val Ala Gln Gly Gln Pro Ile
                405                 410                 415

Leu Thr Ser Leu Gly Ser Asn Gln Glu Glu Ala Tyr Val Thr Met Ser
            420                 425                 430

Ser Phe Tyr Gln Asn Gln Ser Arg Ser Asp Pro Lys Pro Glu Asn Pro
        435                 440                 445

Ala Cys Pro Trp Thr Val Leu Pro Ala Gly Asp Leu Pro Thr His Asp
    450                 455                 460
```

Gly Tyr Leu Pro Ser Asn Ile Asp Asp Leu Pro Ser His Glu Ala Pro
465 470 475 480

Leu Ala Asp Ser Leu Glu Glu Leu Glu Pro Gln
485 490

<210> SEQ ID NO 163
<211> LENGTH: 491
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 163

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

Asp Glu Asn Ile Thr Leu Glu Thr Val Cys His Asp Pro Lys Leu Pro
115 120 125

Tyr His Asp Phe Ile Leu Glu Asp Ala Ala Ser Pro Lys Cys Ile Met
130 135 140

Lys Glu Lys Lys Lys Pro Gly Glu Thr Phe Phe Met Cys Ser Cys Ser
145 150 155 160

Ser Asp Glu Cys Asn Asp Asn Ile Ile Phe Ser Glu Glu Tyr Asn Thr
165 170 175

Ser Asn Pro Asp Leu Leu Leu Val Ile Phe Gln Ser Asp Pro Thr Arg
180 185 190

Val Glu Thr Ala Thr Glu Thr Ala Trp Ile Ser Leu Val Thr Ala Leu
195 200 205

His Leu Val Leu Gly Leu Asn Ala Val Leu Gly Leu Leu Leu Leu Arg
210 215 220

Lys Gln Phe Pro Ala His Tyr Arg Arg Leu Arg His Ala Leu Trp Pro
225 230 235 240

Ser Leu Pro Asp Leu His Arg Val Leu Gly Gln Tyr Leu Arg Asp Thr
245 250 255

Ala Ala Leu Ser Pro Pro Lys Ala Thr Val Ser Asp Thr Cys Glu Glu
260 265 270

Val Glu Pro Ser Leu Leu Glu Ile Leu Pro Lys Ser Ser Glu Arg Thr
275 280 285

Pro Leu Pro Leu Leu Glu Ala Arg Asp Glu Val Glu Gly Phe Leu Gln
290 295 300

Asp Thr Phe Pro Gln Gln Leu Glu Glu Ser Glu Lys Gln Arg Leu Gly
305 310 315 320

Gly Asp Val Gln Ser Pro Asn Cys Pro Ser Glu Asp Val Val Ile Thr
325 330 335

Pro Glu Ser Phe Gly Arg Asp Ser Ser Leu Thr Cys Leu Ala Gly Asn
340 345 350

Val Ser Ala Cys Asp Ala Pro Ile Leu Ser Ser Ser Arg Ser Leu Asp
355 360 365

Cys Arg Glu Ser Gly Lys Asn Gly Pro His Val Tyr Gln Asp Leu Leu
370 375 380

Leu Ser Leu Gly Thr Thr Asn Ser Thr Leu Pro Pro Pro Phe Ser Leu
385 390 395 400

Gln Ser Gly Ile Leu Thr Leu Asn Pro Val Ala Gln Gly Gln Pro Ile
405 410 415

Leu Thr Ser Leu Gly Ser Asn Gln Glu Glu Ala Tyr Val Thr Met Ser
420 425 430

Ser Phe Tyr Gln Asn Gln Ser Arg Ser Asp Pro Lys Pro Glu Asn Pro
435 440 445

Ala Cys Pro Trp Thr Val Leu Pro Ala Gly Asp Leu Pro Thr His Asp
450 455 460

Gly Tyr Leu Pro Ser Asn Ile Asp Asp Leu Pro Ser His Glu Ala Pro
465 470 475 480

Leu Ala Asp Ser Leu Glu Glu Leu Glu Pro Gln
485 490

<210> SEQ ID NO 164
<211> LENGTH: 369
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 164

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

Asp Glu Asn Ile Thr Leu Glu Thr Val Cys His Asp Pro Lys Leu Pro
115 120 125

Tyr His Asp Phe Ile Leu Glu Asp Ala Ala Ser Pro Lys Cys Ile Met
130 135 140

Lys Glu Lys Lys Lys Pro Gly Glu Thr Phe Phe Met Cys Ser Cys Ser
145 150 155 160

Ser Asp Glu Cys Asn Asp Asn Ile Ile Phe Ser Glu Glu Tyr Asn Thr
165 170 175

Ser Asn Pro Asp Leu Leu Leu Val Ile Phe Gln Ser Asp Pro Thr Arg
180 185 190

Val Glu Thr Ala Thr Glu Thr Ala Trp Ile Ser Leu Val Thr Ala Leu
195 200 205

His Leu Val Leu Gly Leu Asn Ala Val Leu Gly Leu Leu Leu Leu Arg
210 215 220

Lys Gln Phe Pro Ala His Tyr Arg Arg Leu Arg His Ala Leu Trp Pro
225 230 235 240

Ser Leu Pro Asp Leu His Arg Val Leu Gly Gln Tyr Leu Arg Asp Thr
245 250 255

Ala Ala Leu Ser Pro Pro Lys Ala Thr Val Ser Asp Thr Cys Glu Glu
260 265 270

Val Glu Pro Ser Leu Leu Glu Ile Leu Pro Lys Ser Ser Glu Arg Thr
275 280 285

Pro Leu Pro Leu Leu Glu Asp Glu Gly Val Ala Gly Ala Pro Thr Gly
290 295 300

Ser Ser Pro Gln Pro Leu Gln Pro Leu Ser Gly Glu Asp Asp Ala Tyr
305 310 315 320

Cys Thr Phe Pro Ser Arg Asp Asp Leu Leu Leu Phe Ser Pro Ser Gly
325 330 335

Gln Gly Glu Phe Arg Ala Leu Asn Ala Arg Leu Pro Leu Asn Thr Asp
340 345 350

Ala Tyr Leu Ser Leu Gln Glu Leu Gln Gly Gln Asp Pro Thr His Leu
355 360 365

Val

<210> SEQ ID NO 165
<211> LENGTH: 491
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 165

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

Asp Glu Asn Ile Thr Leu Glu Thr Val Cys His Asp Pro Lys Leu Pro
115 120 125

Tyr His Asp Phe Ile Leu Glu Asp Ala Ala Ser Pro Lys Cys Ile Met
130 135 140

Lys Glu Lys Lys Lys Pro Gly Glu Thr Phe Phe Met Cys Ser Cys Ser
145 150 155 160

```
Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Ala Trp Ile Ser Leu Val Thr Ala Leu
        195                 200                 205

His Leu Val Leu Gly Leu Asn Ala Val Leu Gly Leu Leu Leu Leu Arg
    210                 215                 220

Lys Gln Phe Pro Ala His Tyr Arg Arg Leu Arg His Ala Leu Trp Pro
225                 230                 235                 240

Ser Leu Pro Asp Leu His Arg Val Leu Gly Gln Tyr Leu Arg Asp Thr
                245                 250                 255

Ala Ala Leu Ser Pro Pro Arg Ala Thr Val Ser Asp Thr Cys Glu Glu
            260                 265                 270

Val Glu Pro Ser Leu Leu Glu Ile Leu Pro Arg Ser Ser Glu Arg Thr
        275                 280                 285

Pro Leu Pro Leu Leu Glu Ala Arg Asp Glu Val Glu Gly Phe Leu Gln
    290                 295                 300

Asp Thr Phe Pro Gln Gln Leu Glu Glu Ser Glu Lys Gln Arg Leu Gly
305                 310                 315                 320

Gly Asp Val Gln Ser Pro Asn Cys Pro Ser Glu Asp Val Val Ile Thr
                325                 330                 335

Pro Glu Ser Phe Gly Arg Asp Ser Ser Leu Thr Cys Leu Ala Gly Asn
            340                 345                 350

Val Ser Ala Cys Asp Ala Pro Ile Leu Ser Ser Ser Arg Ser Leu Asp
        355                 360                 365

Cys Arg Glu Ser Gly Lys Asn Gly Pro His Val Tyr Gln Asp Leu Leu
    370                 375                 380

Leu Ser Leu Gly Thr Thr Asn Ser Thr Leu Pro Pro Pro Phe Ser Leu
385                 390                 395                 400

Gln Ser Gly Ile Leu Thr Leu Asn Pro Val Ala Gln Gly Gln Pro Ile
                405                 410                 415

Leu Thr Ser Leu Gly Ser Asn Gln Glu Glu Ala Tyr Val Thr Met Ser
            420                 425                 430

Ser Phe Tyr Gln Asn Gln Ser Arg Ser Asp Pro Lys Pro Glu Asn Pro
        435                 440                 445

Ala Cys Pro Trp Thr Val Leu Pro Ala Gly Asp Leu Pro Thr His Asp
    450                 455                 460

Gly Tyr Leu Pro Ser Asn Ile Asp Asp Leu Pro Ser His Glu Ala Pro
465                 470                 475                 480

Leu Ala Asp Ser Leu Glu Glu Leu Glu Pro Gln
                485                 490


<210> SEQ ID NO 166
<211> LENGTH: 369
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Met Ala Leu Pro Val Thr Ala Leu Leu Leu Pro Leu Ala Leu Leu Leu
1               5                   10                  15
```

```
His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Ala Trp Ile Ser Leu Val Thr Ala Leu
        195                 200                 205

His Leu Val Leu Gly Leu Asn Ala Val Leu Gly Leu Leu Leu Leu Arg
    210                 215                 220

Lys Gln Phe Pro Ala His Tyr Arg Arg Leu Arg His Ala Leu Trp Pro
225                 230                 235                 240

Ser Leu Pro Asp Leu His Arg Val Leu Gly Gln Tyr Leu Arg Asp Thr
                245                 250                 255

Ala Ala Leu Ser Pro Pro Arg Ala Thr Val Ser Asp Thr Cys Glu Glu
            260                 265                 270

Val Glu Pro Ser Leu Leu Glu Ile Leu Pro Arg Ser Ser Glu Arg Thr
        275                 280                 285

Pro Leu Pro Leu Leu Glu Asp Glu Gly Val Ala Gly Ala Pro Thr Gly
    290                 295                 300

Ser Ser Pro Gln Pro Leu Gln Pro Leu Ser Gly Glu Asp Asp Ala Tyr
305                 310                 315                 320

Cys Thr Phe Pro Ser Arg Asp Asp Leu Leu Leu Phe Ser Pro Ser Gly
                325                 330                 335

Gln Gly Glu Phe Arg Ala Leu Asn Ala Arg Leu Pro Leu Asn Thr Asp
            340                 345                 350

Ala Tyr Leu Ser Leu Gln Glu Leu Gln Gly Gln Asp Pro Thr His Leu
        355                 360                 365

Val
```

<210> SEQ ID NO 167
<211> LENGTH: 348
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Ser Asp Pro Thr Arg Val Glu Thr Ala Thr
                165                 170                 175

Glu Thr Ala Trp Ile Ser Leu Val Thr Ala Leu His Leu Val Leu Gly
            180                 185                 190

Leu Asn Ala Val Leu Gly Leu Leu Leu Leu Arg Lys Gln Phe Pro Ala
        195                 200                 205

His Tyr Arg Arg Leu Arg His Ala Leu Trp Pro Ser Leu Pro Asp Leu
    210                 215                 220

His Arg Val Leu Gly Gln Tyr Leu Arg Asp Thr Ala Ala Leu Ser Pro
225                 230                 235                 240

Pro Lys Ala Thr Val Ser Asp Thr Cys Glu Glu Val Glu Pro Ser Leu
                245                 250                 255

Leu Glu Ile Leu Pro Lys Ser Ser Glu Arg Thr Pro Leu Pro Leu Leu
            260                 265                 270

Glu Asp Glu Gly Val Ala Gly Ala Pro Thr Gly Ser Ser Pro Gln Pro
        275                 280                 285

Leu Gln Pro Leu Ser Gly Glu Asp Asp Ala Tyr Cys Thr Phe Pro Ser
    290                 295                 300

Arg Asp Asp Leu Leu Leu Phe Ser Pro Ser Gly Gln Gly Glu Phe Arg
305                 310                 315                 320

Ala Leu Asn Ala Arg Leu Pro Leu Asn Thr Asp Ala Tyr Leu Ser Leu
                325                 330                 335

Gln Glu Leu Gln Gly Gln Asp Pro Thr His Leu Val
            340                 345

<210> SEQ ID NO 168
<211> LENGTH: 348
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Ser Asp Pro Thr Arg Val Glu Thr Ala Thr
                165                 170                 175

Glu Thr Ala Trp Ile Ser Leu Val Thr Ala Leu His Leu Val Leu Gly
            180                 185                 190

Leu Asn Ala Val Leu Gly Leu Leu Leu Leu Arg Lys Gln Phe Pro Ala
        195                 200                 205

His Tyr Arg Arg Leu Arg His Ala Leu Trp Pro Ser Leu Pro Asp Leu
    210                 215                 220

His Arg Val Leu Gly Gln Tyr Leu Arg Asp Thr Ala Ala Leu Ser Pro
225                 230                 235                 240

Pro Arg Ala Thr Val Ser Asp Thr Cys Glu Glu Val Glu Pro Ser Leu
                245                 250                 255

Leu Glu Ile Leu Pro Arg Ser Ser Glu Arg Thr Pro Leu Pro Leu Leu
            260                 265                 270

Glu Asp Glu Gly Val Ala Gly Ala Pro Thr Gly Ser Ser Pro Gln Pro
        275                 280                 285

Leu Gln Pro Leu Ser Gly Glu Asp Asp Ala Tyr Cys Thr Phe Pro Ser
    290                 295                 300

Arg Asp Asp Leu Leu Leu Phe Ser Pro Ser Gly Gln Gly Glu Phe Arg
305                 310                 315                 320

Ala Leu Asn Ala Arg Leu Pro Leu Asn Thr Asp Ala Tyr Leu Ser Leu
                325                 330                 335

Gln Glu Leu Gln Gly Gln Asp Pro Thr His Leu Val
            340                 345

<210> SEQ ID NO 169
<211> LENGTH: 438
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

```
Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Ala Trp Ile Ser Leu Val Thr Ala Leu
        195                 200                 205

His Leu Val Leu Gly Leu Asn Ala Val Leu Gly Leu Leu Leu Leu Arg
    210                 215                 220

Lys Gln Phe Pro Ala His Tyr Arg Arg Leu Arg His Ala Leu Trp Pro
225                 230                 235                 240

Ser Leu Pro Asp Leu His Arg Val Leu Gly Gln Tyr Leu Arg Asp Thr
                245                 250                 255

Ala Ala Leu Ser Pro Pro Lys Ala Thr Val Ser Asp Thr Cys Glu Glu
            260                 265                 270

Val Glu Pro Ser Leu Leu Glu Ile Leu Pro Lys Ser Ser Glu Arg Thr
        275                 280                 285

Pro Leu Pro Leu Leu Glu Ala Arg Asp Glu Val Glu Gly Phe Leu Gln
    290                 295                 300

Asp Thr Phe Pro Gln Gln Leu Glu Glu Ser Glu Lys Gln Arg Leu Gly
305                 310                 315                 320

Gly Asp Val Gln Ser Pro Asn Cys Pro Ser Glu Asp Val Val Ile Thr
                325                 330                 335

Pro Glu Ser Phe Gly Arg Asp Ser Ser Leu Thr Cys Leu Ala Gly Asn
            340                 345                 350

Val Ser Ala Cys Asp Ala Pro Ile Leu Ser Ser Ser Arg Ser Leu Asp
        355                 360                 365

Cys Arg Glu Ser Gly Lys Asn Gly Pro His Val Tyr Gln Asp Leu Leu
    370                 375                 380

Leu Ser Leu Gly Thr Thr Asn Ser Thr Leu Pro Pro Pro Phe Ser Leu
385                 390                 395                 400
```

Gln Ser Gly Ile Leu Thr Leu Asn Pro Val Ala Gln Gly Gln Pro Ile
405 410 415

Leu Thr Ser Leu Gly Ser Asn Gln Glu Glu Ala Tyr Val Thr Met Ser
420 425 430

Ser Phe Tyr Gln Asn Gln
435

<210> SEQ ID NO 170
<211> LENGTH: 438
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 170

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

Asp Glu Asn Ile Thr Leu Glu Thr Val Cys His Asp Pro Lys Leu Pro
115 120 125

Tyr His Asp Phe Ile Leu Glu Asp Ala Ala Ser Pro Lys Cys Ile Met
130 135 140

Lys Glu Lys Lys Lys Pro Gly Glu Thr Phe Phe Met Cys Ser Cys Ser
145 150 155 160

Ser Asp Glu Cys Asn Asp Asn Ile Ile Phe Ser Glu Glu Tyr Asn Thr
165 170 175

Ser Asn Pro Asp Leu Leu Leu Val Ile Phe Gln Ser Asp Pro Thr Arg
180 185 190

Val Glu Thr Ala Thr Glu Thr Ala Trp Ile Ser Leu Val Thr Ala Leu
195 200 205

His Leu Val Leu Gly Leu Asn Ala Val Leu Gly Leu Leu Leu Leu Arg
210 215 220

Lys Gln Phe Pro Ala His Tyr Arg Arg Leu Arg His Ala Leu Trp Pro
225 230 235 240

Ser Leu Pro Asp Leu His Arg Val Leu Gly Gln Tyr Leu Arg Asp Thr
245 250 255

Ala Ala Leu Ser Pro Pro Arg Ala Thr Val Ser Asp Thr Cys Glu Glu
260 265 270

Val Glu Pro Ser Leu Leu Glu Ile Leu Pro Arg Ser Ser Glu Arg Thr
275 280 285

Pro Leu Pro Leu Leu Glu Ala Arg Asp Glu Val Glu Gly Phe Leu Gln
290 295 300

```
Asp Thr Phe Pro Gln Gln Leu Glu Glu Ser Glu Lys Gln Arg Leu Gly
305                 310                 315                 320

Gly Asp Val Gln Ser Pro Asn Cys Pro Ser Glu Asp Val Val Ile Thr
                325                 330                 335

Pro Glu Ser Phe Gly Arg Asp Ser Ser Leu Thr Cys Leu Ala Gly Asn
            340                 345                 350

Val Ser Ala Cys Asp Ala Pro Ile Leu Ser Ser Ser Arg Ser Leu Asp
        355                 360                 365

Cys Arg Glu Ser Gly Lys Asn Gly Pro His Val Tyr Gln Asp Leu Leu
    370                 375                 380

Leu Ser Leu Gly Thr Thr Asn Ser Thr Leu Pro Pro Pro Phe Ser Leu
385                 390                 395                 400

Gln Ser Gly Ile Leu Thr Leu Asn Pro Val Ala Gln Gly Gln Pro Ile
                405                 410                 415

Leu Thr Ser Leu Gly Ser Asn Gln Glu Glu Ala Tyr Val Thr Met Ser
            420                 425                 430

Ser Phe Tyr Gln Asn Gln
        435
```

<210> SEQ ID NO 171
<211> LENGTH: 410
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 171

```
Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Ala Trp Ile Ser Leu Val Thr Ala Leu
        195                 200                 205
```

Leu Leu Val Leu Gly Leu Asn Ala Val Leu Gly Leu Leu Leu Leu Arg
    210                 215                 220

Lys Gln Phe Pro Ala His Tyr Arg Arg Leu Arg His Ala Leu Trp Pro
225                 230                 235                 240

Ser Leu Pro Asp Leu His Arg Val Leu Gly Gln Tyr Leu Arg Asp Thr
                245                 250                 255

Ala Ala Leu Ser Pro Pro Lys Ala Thr Val Ser Asp Thr Cys Glu Glu
            260                 265                 270

Val Glu Pro Ser Leu Leu Glu Ile Leu Pro Lys Ser Ser Glu Arg Thr
        275                 280                 285

Pro Leu Pro Leu Leu Glu Gln Gln Asp Lys Val Pro Glu Pro Ala Ser
    290                 295                 300

Leu Ser Ser Asn His Ser Leu Thr Ser Cys Phe Thr Asn Gln Gly Tyr
305                 310                 315                 320

Phe Phe Phe His Leu Pro Asp Ala Leu Glu Ile Glu Ala Cys Gln Asp
                325                 330                 335

Glu Gly Val Ala Gly Ala Pro Thr Gly Ser Ser Pro Gln Pro Leu Gln
            340                 345                 350

Pro Leu Ser Gly Glu Asp Asp Ala Tyr Cys Thr Phe Pro Ser Arg Asp
        355                 360                 365

Asp Leu Leu Leu Phe Ser Pro Ser Gly Gln Gly Glu Phe Arg Ala Leu
    370                 375                 380

Asn Ala Arg Leu Pro Leu Asn Thr Asp Ala Tyr Leu Ser Leu Gln Glu
385                 390                 395                 400

Leu Gln Gly Gln Asp Pro Thr His Leu Val
                405                 410

<210> SEQ ID NO 172
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

```
Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Trp Ile Ser Leu Val Thr Ala Leu His
        195                 200                 205

Leu Val Leu Gly Leu Ser Ala Val Leu Gly Leu Leu Leu Leu Arg Trp
    210                 215                 220

Gln Phe Pro Ala His Tyr Arg Arg Leu Arg His Ala Leu Trp Pro Ser
225                 230                 235                 240

Leu Pro Asp Leu His Arg Val Leu Gly Gln Tyr Leu Arg Asp Thr Ala
                245                 250                 255

Ala Leu Ser Pro Pro Lys Ala Thr Val Ser Asp Thr Cys Glu Glu Val
            260                 265                 270

Glu Pro Ser Leu Leu Glu Ile Leu Pro Lys Ser Ser Glu Arg Thr Pro
        275                 280                 285

Leu Pro Leu Leu Glu Ala Arg Asp Glu Val Glu Gly Phe Leu Gln Asp
    290                 295                 300

Thr Phe Pro Gln Gln Leu Glu Glu Ser Glu Lys Gln Arg Leu Gly Gly
305                 310                 315                 320

Asp Val Gln Ser Pro Asn Cys Pro Ser Glu Asp Val Val Ile Thr Pro
                325                 330                 335

Glu Ser Phe Gly Arg Asp Ser Ser Leu Thr Cys Leu Ala Gly Asn Val
            340                 345                 350

Ser Ala Cys Asp Ala Pro Ile Leu Ser Ser Ser Arg Ser Leu Asp Cys
        355                 360                 365

Arg Glu Ser Gly Lys Asn Gly Pro His Val Tyr Gln Asp Leu Leu Leu
    370                 375                 380

Ser Leu Gly Thr Thr Asn Ser Thr Leu Pro Pro Pro Phe Ser Leu Gln
385                 390                 395                 400

Ser Gly Ile Leu Thr Leu Asn Pro Val Ala Gln Gly Gln Pro Ile Leu
                405                 410                 415

Thr Ser Leu Gly Ser Asn Gln Glu Glu Ala Tyr Val Thr Met Ser Ser
            420                 425                 430

Phe Tyr Gln Asn Gln Ser Arg Ser Asp Pro Lys Pro Glu Asn Pro Ala
        435                 440                 445

Cys Pro Trp Thr Val Leu Pro Ala Gly Asp Leu Pro Thr His Asp Gly
    450                 455                 460

Tyr Leu Pro Ser Asn Ile Asp Asp Leu Pro Ser His Glu Ala Pro Leu
465                 470                 475                 480

Ala Asp Ser Leu Glu Glu Leu Glu Pro Gln
                485                 490
```

<210> SEQ ID NO 173
<211> LENGTH: 489
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 173

```
Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Ile Ser Leu Val Thr Ala Leu His Leu
        195                 200                 205

Val Leu Gly Leu Ser Ala Val Leu Gly Leu Leu Leu Leu Arg Trp Gln
    210                 215                 220

Phe Pro Ala His Tyr Arg Arg Leu Arg His Ala Leu Trp Pro Ser Leu
225                 230                 235                 240

Pro Asp Leu His Arg Val Leu Gly Gln Tyr Leu Arg Asp Thr Ala Ala
                245                 250                 255

Leu Ser Pro Pro Lys Ala Thr Val Ser Asp Thr Cys Glu Glu Val Glu
            260                 265                 270

Pro Ser Leu Leu Glu Ile Leu Pro Lys Ser Ser Glu Arg Thr Pro Leu
        275                 280                 285

Pro Leu Leu Glu Ala Arg Asp Glu Val Glu Gly Phe Leu Gln Asp Thr
    290                 295                 300

Phe Pro Gln Gln Leu Glu Glu Ser Glu Lys Gln Arg Leu Gly Gly Asp
305                 310                 315                 320

Val Gln Ser Pro Asn Cys Pro Ser Glu Asp Val Val Ile Thr Pro Glu
                325                 330                 335

Ser Phe Gly Arg Asp Ser Ser Leu Thr Cys Leu Ala Gly Asn Val Ser
            340                 345                 350

Ala Cys Asp Ala Pro Ile Leu Ser Ser Ser Arg Ser Leu Asp Cys Arg
        355                 360                 365

Glu Ser Gly Lys Asn Gly Pro His Val Tyr Gln Asp Leu Leu Leu Ser
    370                 375                 380

Leu Gly Thr Thr Asn Ser Thr Leu Pro Pro Pro Phe Ser Leu Gln Ser
385                 390                 395                 400
```

```
Gly Ile Leu Thr Leu Asn Pro Val Ala Gln Gly Gln Pro Ile Leu Thr
                405                 410                 415

Ser Leu Gly Ser Asn Gln Glu Glu Ala Tyr Val Thr Met Ser Ser Phe
            420                 425                 430

Tyr Gln Asn Gln Ser Arg Ser Asp Pro Lys Pro Glu Asn Pro Ala Cys
        435                 440                 445

Pro Trp Thr Val Leu Pro Ala Gly Asp Leu Pro Thr His Asp Gly Tyr
    450                 455                 460

Leu Pro Ser Asn Ile Asp Asp Leu Pro Ser His Glu Ala Pro Leu Ala
465                 470                 475                 480

Asp Ser Leu Glu Glu Leu Glu Pro Gln
                485


<210> SEQ ID NO 174
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Leu Ile Ser Leu Val Thr Ala Leu His
        195                 200                 205

Leu Val Leu Gly Leu Ser Ala Val Leu Gly Leu Leu Leu Leu Arg Trp
    210                 215                 220

Gln Phe Pro Ala His Tyr Arg Arg Leu Arg His Ala Leu Trp Pro Ser
225                 230                 235                 240

Leu Pro Asp Leu His Arg Val Leu Gly Gln Tyr Leu Arg Asp Thr Ala
                245                 250                 255
```

Ala Leu Ser Pro Pro Lys Ala Thr Val Ser Asp Thr Cys Glu Glu Val
260 265 270

Glu Pro Ser Leu Leu Glu Ile Leu Pro Lys Ser Ser Glu Arg Thr Pro
275 280 285

Leu Pro Leu Leu Glu Ala Arg Asp Glu Val Glu Gly Phe Leu Gln Asp
290 295 300

Thr Phe Pro Gln Gln Leu Glu Glu Ser Glu Lys Gln Arg Leu Gly Gly
305 310 315 320

Asp Val Gln Ser Pro Asn Cys Pro Ser Glu Asp Val Val Ile Thr Pro
325 330 335

Glu Ser Phe Gly Arg Asp Ser Ser Leu Thr Cys Leu Ala Gly Asn Val
340 345 350

Ser Ala Cys Asp Ala Pro Ile Leu Ser Ser Ser Arg Ser Leu Asp Cys
355 360 365

Arg Glu Ser Gly Lys Asn Gly Pro His Val Tyr Gln Asp Leu Leu Leu
370 375 380

Ser Leu Gly Thr Thr Asn Ser Thr Leu Pro Pro Pro Phe Ser Leu Gln
385 390 395 400

Ser Gly Ile Leu Thr Leu Asn Pro Val Ala Gln Gly Gln Pro Ile Leu
405 410 415

Thr Ser Leu Gly Ser Asn Gln Glu Glu Ala Tyr Val Thr Met Ser Ser
420 425 430

Phe Tyr Gln Asn Gln Ser Arg Ser Asp Pro Lys Pro Glu Asn Pro Ala
435 440 445

Cys Pro Trp Thr Val Leu Pro Ala Gly Asp Leu Pro Thr His Asp Gly
450 455 460

Tyr Leu Pro Ser Asn Ile Asp Asp Leu Pro Ser His Glu Ala Pro Leu
465 470 475 480

Ala Asp Ser Leu Glu Glu Leu Glu Pro Gln
485 490

<210> SEQ ID NO 175
<211> LENGTH: 488
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 175

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

```
Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Ser Leu Val Thr Ala Leu His Leu Val
        195                 200                 205

Leu Gly Leu Ser Ala Val Leu Gly Leu Leu Leu Leu Arg Trp Gln Phe
    210                 215                 220

Pro Ala His Tyr Arg Arg Leu Arg His Ala Leu Trp Pro Ser Leu Pro
225                 230                 235                 240

Asp Leu His Arg Val Leu Gly Gln Tyr Leu Arg Asp Thr Ala Ala Leu
                245                 250                 255

Ser Pro Pro Lys Ala Thr Val Ser Asp Thr Cys Glu Glu Val Glu Pro
            260                 265                 270

Ser Leu Leu Glu Ile Leu Pro Lys Ser Ser Glu Arg Thr Pro Leu Pro
        275                 280                 285

Leu Leu Glu Ala Arg Asp Glu Val Glu Gly Phe Leu Gln Asp Thr Phe
    290                 295                 300

Pro Gln Gln Leu Glu Glu Ser Glu Lys Gln Arg Leu Gly Gly Asp Val
305                 310                 315                 320

Gln Ser Pro Asn Cys Pro Ser Glu Asp Val Val Ile Thr Pro Glu Ser
                325                 330                 335

Phe Gly Arg Asp Ser Ser Leu Thr Cys Leu Ala Gly Asn Val Ser Ala
            340                 345                 350

Cys Asp Ala Pro Ile Leu Ser Ser Ser Arg Ser Leu Asp Cys Arg Glu
        355                 360                 365

Ser Gly Lys Asn Gly Pro His Val Tyr Gln Asp Leu Leu Leu Ser Leu
    370                 375                 380

Gly Thr Thr Asn Ser Thr Leu Pro Pro Pro Phe Ser Leu Gln Ser Gly
385                 390                 395                 400

Ile Leu Thr Leu Asn Pro Val Ala Gln Gly Gln Pro Ile Leu Thr Ser
                405                 410                 415

Leu Gly Ser Asn Gln Glu Glu Ala Tyr Val Thr Met Ser Ser Phe Tyr
            420                 425                 430

Gln Asn Gln Ser Arg Ser Asp Pro Lys Pro Glu Asn Pro Ala Cys Pro
        435                 440                 445

Trp Thr Val Leu Pro Ala Gly Asp Leu Pro Thr His Asp Gly Tyr Leu
    450                 455                 460

Pro Ser Asn Ile Asp Asp Leu Pro Ser His Glu Ala Pro Leu Ala Asp
465                 470                 475                 480

Ser Leu Glu Glu Leu Glu Pro Gln
                485
```

<210> SEQ ID NO 176
<211> LENGTH: 487
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 176

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

Asp Glu Asn Ile Thr Leu Glu Thr Val Cys His Asp Pro Lys Leu Pro
115 120 125

Tyr His Asp Phe Ile Leu Glu Asp Ala Ala Ser Pro Lys Cys Ile Met
130 135 140

Lys Glu Lys Lys Lys Pro Gly Glu Thr Phe Phe Met Cys Ser Cys Ser
145 150 155 160

Ser Asp Glu Cys Asn Asp Asn Ile Ile Phe Ser Glu Glu Tyr Asn Thr
165 170 175

Ser Asn Pro Asp Leu Leu Leu Val Ile Phe Gln Ser Asp Pro Thr Arg
180 185 190

Val Glu Thr Ala Thr Glu Thr Leu Val Thr Ala Leu His Leu Val Leu
195 200 205

Gly Leu Ser Ala Val Leu Gly Leu Leu Leu Leu Arg Trp Gln Phe Pro
210 215 220

Ala His Tyr Arg Arg Leu Arg His Ala Leu Trp Pro Ser Leu Pro Asp
225 230 235 240

Leu His Arg Val Leu Gly Gln Tyr Leu Arg Asp Thr Ala Ala Leu Ser
245 250 255

Pro Pro Lys Ala Thr Val Ser Asp Thr Cys Glu Glu Val Glu Pro Ser
260 265 270

Leu Leu Glu Ile Leu Pro Lys Ser Ser Glu Arg Thr Pro Leu Pro Leu
275 280 285

Leu Glu Ala Arg Asp Glu Val Glu Gly Phe Leu Gln Asp Thr Phe Pro
290 295 300

Gln Gln Leu Glu Glu Ser Glu Lys Gln Arg Leu Gly Gly Asp Val Gln
305 310 315 320

Ser Pro Asn Cys Pro Ser Glu Asp Val Val Ile Thr Pro Glu Ser Phe
325 330 335

Gly Arg Asp Ser Ser Leu Thr Cys Leu Ala Gly Asn Val Ser Ala Cys
340 345 350

Asp Ala Pro Ile Leu Ser Ser Ser Arg Ser Leu Asp Cys Arg Glu Ser
355 360 365

Gly Lys Asn Gly Pro His Val Tyr Gln Asp Leu Leu Leu Ser Leu Gly
370 375 380

Thr Thr Asn Ser Thr Leu Pro Pro Pro Phe Ser Leu Gln Ser Gly Ile
385 390 395 400

```
Leu Thr Leu Asn Pro Val Ala Gln Gly Gln Pro Ile Leu Thr Ser Leu
                405                 410                 415

Gly Ser Asn Gln Glu Glu Ala Tyr Val Thr Met Ser Ser Phe Tyr Gln
            420                 425                 430

Asn Gln Ser Arg Ser Asp Pro Lys Pro Glu Asn Pro Ala Cys Pro Trp
        435                 440                 445

Thr Val Leu Pro Ala Gly Asp Leu Pro Thr His Asp Gly Tyr Leu Pro
    450                 455                 460

Ser Asn Ile Asp Asp Leu Pro Ser His Glu Ala Pro Leu Ala Asp Ser
465                 470                 475                 480

Leu Glu Glu Leu Glu Pro Gln
                485


<210> SEQ ID NO 177
<211> LENGTH: 488
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Ile Leu Val Thr Ala Leu His Leu Val
        195                 200                 205

Leu Gly Leu Ser Ala Val Leu Gly Leu Leu Leu Leu Arg Trp Gln Phe
    210                 215                 220

Pro Ala His Tyr Arg Arg Leu Arg His Ala Leu Trp Pro Ser Leu Pro
225                 230                 235                 240

Asp Leu His Arg Val Leu Gly Gln Tyr Leu Arg Asp Thr Ala Ala Leu
                245                 250                 255
```

Ser Pro Pro Lys Ala Thr Val Ser Asp Thr Cys Glu Glu Val Glu Pro
260 265 270

Ser Leu Leu Glu Ile Leu Pro Lys Ser Ser Glu Arg Thr Pro Leu Pro
275 280 285

Leu Leu Glu Ala Arg Asp Glu Val Glu Gly Phe Leu Gln Asp Thr Phe
290 295 300

Pro Gln Gln Leu Glu Glu Ser Glu Lys Gln Arg Leu Gly Gly Asp Val
305 310 315 320

Gln Ser Pro Asn Cys Pro Ser Glu Asp Val Val Ile Thr Pro Glu Ser
325 330 335

Phe Gly Arg Asp Ser Ser Leu Thr Cys Leu Ala Gly Asn Val Ser Ala
340 345 350

Cys Asp Ala Pro Ile Leu Ser Ser Ser Arg Ser Leu Asp Cys Arg Glu
355 360 365

Ser Gly Lys Asn Gly Pro His Val Tyr Gln Asp Leu Leu Leu Ser Leu
370 375 380

Gly Thr Thr Asn Ser Thr Leu Pro Pro Pro Phe Ser Leu Gln Ser Gly
385 390 395 400

Ile Leu Thr Leu Asn Pro Val Ala Gln Gly Gln Pro Ile Leu Thr Ser
405 410 415

Leu Gly Ser Asn Gln Glu Glu Ala Tyr Val Thr Met Ser Ser Phe Tyr
420 425 430

Gln Asn Gln Ser Arg Ser Asp Pro Lys Pro Glu Asn Pro Ala Cys Pro
435 440 445

Trp Thr Val Leu Pro Ala Gly Asp Leu Pro Thr His Asp Gly Tyr Leu
450 455 460

Pro Ser Asn Ile Asp Asp Leu Pro Ser His Glu Ala Pro Leu Ala Asp
465 470 475 480

Ser Leu Glu Glu Leu Glu Pro Gln
485

<210> SEQ ID NO 178
<211> LENGTH: 486
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 178

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

```
Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Val Thr Ala Leu His Leu Val Leu Gly
        195                 200                 205

Leu Ser Ala Val Leu Gly Leu Leu Leu Leu Arg Trp Gln Phe Pro Ala
    210                 215                 220

His Tyr Arg Arg Leu Arg His Ala Leu Trp Pro Ser Leu Pro Asp Leu
225                 230                 235                 240

His Arg Val Leu Gly Gln Tyr Leu Arg Asp Thr Ala Ala Leu Ser Pro
                245                 250                 255

Pro Lys Ala Thr Val Ser Asp Thr Cys Glu Glu Val Glu Pro Ser Leu
            260                 265                 270

Leu Glu Ile Leu Pro Lys Ser Ser Glu Arg Thr Pro Leu Pro Leu Leu
        275                 280                 285

Glu Ala Arg Asp Glu Val Glu Gly Phe Leu Gln Asp Thr Phe Pro Gln
    290                 295                 300

Gln Leu Glu Glu Ser Glu Lys Gln Arg Leu Gly Gly Asp Val Gln Ser
305                 310                 315                 320

Pro Asn Cys Pro Ser Glu Asp Val Val Ile Thr Pro Glu Ser Phe Gly
                325                 330                 335

Arg Asp Ser Ser Leu Thr Cys Leu Ala Gly Asn Val Ser Ala Cys Asp
            340                 345                 350

Ala Pro Ile Leu Ser Ser Ser Arg Ser Leu Asp Cys Arg Glu Ser Gly
        355                 360                 365

Lys Asn Gly Pro His Val Tyr Gln Asp Leu Leu Leu Ser Leu Gly Thr
    370                 375                 380

Thr Asn Ser Thr Leu Pro Pro Pro Phe Ser Leu Gln Ser Gly Ile Leu
385                 390                 395                 400

Thr Leu Asn Pro Val Ala Gln Gly Gln Pro Ile Leu Thr Ser Leu Gly
                405                 410                 415

Ser Asn Gln Glu Glu Ala Tyr Val Thr Met Ser Ser Phe Tyr Gln Asn
            420                 425                 430

Gln Ser Arg Ser Asp Pro Lys Pro Glu Asn Pro Ala Cys Pro Trp Thr
        435                 440                 445

Val Leu Pro Ala Gly Asp Leu Pro Thr His Asp Gly Tyr Leu Pro Ser
    450                 455                 460

Asn Ile Asp Asp Leu Pro Ser His Glu Ala Pro Leu Ala Asp Ser Leu
465                 470                 475                 480

Glu Glu Leu Glu Pro Gln
                485
```

<210> SEQ ID NO 179
<211> LENGTH: 485
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 179

```
Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Thr Ala Leu His Leu Val Leu Gly Leu
        195                 200                 205

Ser Ala Val Leu Gly Leu Leu Leu Leu Arg Trp Gln Phe Pro Ala His
    210                 215                 220

Tyr Arg Arg Leu Arg His Ala Leu Trp Pro Ser Leu Pro Asp Leu His
225                 230                 235                 240

Arg Val Leu Gly Gln Tyr Leu Arg Asp Thr Ala Ala Leu Ser Pro Pro
                245                 250                 255

Lys Ala Thr Val Ser Asp Thr Cys Glu Glu Val Glu Pro Ser Leu Leu
            260                 265                 270

Glu Ile Leu Pro Lys Ser Ser Glu Arg Thr Pro Leu Pro Leu Leu Glu
        275                 280                 285

Ala Arg Asp Glu Val Glu Gly Phe Leu Gln Asp Thr Phe Pro Gln Gln
    290                 295                 300

Leu Glu Glu Ser Glu Lys Gln Arg Leu Gly Gly Asp Val Gln Ser Pro
305                 310                 315                 320

Asn Cys Pro Ser Glu Asp Val Val Ile Thr Pro Glu Ser Phe Gly Arg
                325                 330                 335

Asp Ser Ser Leu Thr Cys Leu Ala Gly Asn Val Ser Ala Cys Asp Ala
            340                 345                 350

Pro Ile Leu Ser Ser Ser Arg Ser Leu Asp Cys Arg Glu Ser Gly Lys
        355                 360                 365

Asn Gly Pro His Val Tyr Gln Asp Leu Leu Leu Ser Leu Gly Thr Thr
    370                 375                 380

Asn Ser Thr Leu Pro Pro Pro Phe Ser Leu Gln Ser Gly Ile Leu Thr
385                 390                 395                 400
```

Leu Asn Pro Val Ala Gln Gly Gln Pro Ile Leu Thr Ser Leu Gly Ser
405 410 415

Asn Gln Glu Glu Ala Tyr Val Thr Met Ser Ser Phe Tyr Gln Asn Gln
420 425 430

Ser Arg Ser Asp Pro Lys Pro Glu Asn Pro Ala Cys Pro Trp Thr Val
435 440 445

Leu Pro Ala Gly Asp Leu Pro Thr His Asp Gly Tyr Leu Pro Ser Asn
450 455 460

Ile Asp Asp Leu Pro Ser His Glu Ala Pro Leu Ala Asp Ser Leu Glu
465 470 475 480

Glu Leu Glu Pro Gln
485

<210> SEQ ID NO 180
<211> LENGTH: 484
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 180

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

Asp Glu Asn Ile Thr Leu Glu Thr Val Cys His Asp Pro Lys Leu Pro
115 120 125

Tyr His Asp Phe Ile Leu Glu Asp Ala Ala Ser Pro Lys Cys Ile Met
130 135 140

Lys Glu Lys Lys Lys Pro Gly Glu Thr Phe Phe Met Cys Ser Cys Ser
145 150 155 160

Ser Asp Glu Cys Asn Asp Asn Ile Ile Phe Ser Glu Glu Tyr Asn Thr
165 170 175

Ser Asn Pro Asp Leu Leu Leu Val Ile Phe Gln Ser Asp Pro Thr Arg
180 185 190

Val Glu Thr Ala Thr Glu Thr Ala Leu His Leu Val Leu Gly Leu Ser
195 200 205

Ala Val Leu Gly Leu Leu Leu Leu Arg Trp Gln Phe Pro Ala His Tyr
210 215 220

Arg Arg Leu Arg His Ala Leu Trp Pro Ser Leu Pro Asp Leu His Arg
225 230 235 240

Val Leu Gly Gln Tyr Leu Arg Asp Thr Ala Ala Leu Ser Pro Pro Lys
245 250 255

Ala Thr Val Ser Asp Thr Cys Glu Glu Val Glu Pro Ser Leu Leu Glu
260 265 270

Ile Leu Pro Lys Ser Ser Glu Arg Thr Pro Leu Pro Leu Leu Glu Ala
275 280 285

Arg Asp Glu Val Glu Gly Phe Leu Gln Asp Thr Phe Pro Gln Gln Leu
290 295 300

Glu Glu Ser Glu Lys Gln Arg Leu Gly Gly Asp Val Gln Ser Pro Asn
305 310 315 320

Cys Pro Ser Glu Asp Val Val Ile Thr Pro Glu Ser Phe Gly Arg Asp
325 330 335

Ser Ser Leu Thr Cys Leu Ala Gly Asn Val Ser Ala Cys Asp Ala Pro
340 345 350

Ile Leu Ser Ser Ser Arg Ser Leu Asp Cys Arg Glu Ser Gly Lys Asn
355 360 365

Gly Pro His Val Tyr Gln Asp Leu Leu Leu Ser Leu Gly Thr Thr Asn
370 375 380

Ser Thr Leu Pro Pro Pro Phe Ser Leu Gln Ser Gly Ile Leu Thr Leu
385 390 395 400

Asn Pro Val Ala Gln Gly Gln Pro Ile Leu Thr Ser Leu Gly Ser Asn
405 410 415

Gln Glu Glu Ala Tyr Val Thr Met Ser Ser Phe Tyr Gln Asn Gln Ser
420 425 430

Arg Ser Asp Pro Lys Pro Glu Asn Pro Ala Cys Pro Trp Thr Val Leu
435 440 445

Pro Ala Gly Asp Leu Pro Thr His Asp Gly Tyr Leu Pro Ser Asn Ile
450 455 460

Asp Asp Leu Pro Ser His Glu Ala Pro Leu Ala Asp Ser Leu Glu Glu
465 470 475 480

Leu Glu Pro Gln

<210> SEQ ID NO 181
<211> LENGTH: 483
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 181

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

Asp Glu Asn Ile Thr Leu Glu Thr Val Cys His Asp Pro Lys Leu Pro
115 120 125

```
Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Leu His Leu Val Leu Gly Leu Ser Ala
        195                 200                 205

Val Leu Gly Leu Leu Leu Leu Arg Trp Gln Phe Pro Ala His Tyr Arg
    210                 215                 220

Arg Leu Arg His Ala Leu Trp Pro Ser Leu Pro Asp Leu His Arg Val
225                 230                 235                 240

Leu Gly Gln Tyr Leu Arg Asp Thr Ala Ala Leu Ser Pro Pro Lys Ala
                245                 250                 255

Thr Val Ser Asp Thr Cys Glu Glu Val Glu Pro Ser Leu Leu Glu Ile
            260                 265                 270

Leu Pro Lys Ser Ser Glu Arg Thr Pro Leu Pro Leu Leu Glu Ala Arg
        275                 280                 285

Asp Glu Val Glu Gly Phe Leu Gln Asp Thr Phe Pro Gln Gln Leu Glu
    290                 295                 300

Glu Ser Glu Lys Gln Arg Leu Gly Gly Asp Val Gln Ser Pro Asn Cys
305                 310                 315                 320

Pro Ser Glu Asp Val Val Ile Thr Pro Glu Ser Phe Gly Arg Asp Ser
                325                 330                 335

Ser Leu Thr Cys Leu Ala Gly Asn Val Ser Ala Cys Asp Ala Pro Ile
            340                 345                 350

Leu Ser Ser Ser Arg Ser Leu Asp Cys Arg Glu Ser Gly Lys Asn Gly
        355                 360                 365

Pro His Val Tyr Gln Asp Leu Leu Leu Ser Leu Gly Thr Thr Asn Ser
    370                 375                 380

Thr Leu Pro Pro Pro Phe Ser Leu Gln Ser Gly Ile Leu Thr Leu Asn
385                 390                 395                 400

Pro Val Ala Gln Gly Gln Pro Ile Leu Thr Ser Leu Gly Ser Asn Gln
                405                 410                 415

Glu Glu Ala Tyr Val Thr Met Ser Ser Phe Tyr Gln Asn Gln Ser Arg
            420                 425                 430

Ser Asp Pro Lys Pro Glu Asn Pro Ala Cys Pro Trp Thr Val Leu Pro
        435                 440                 445

Ala Gly Asp Leu Pro Thr His Asp Gly Tyr Leu Pro Ser Asn Ile Asp
    450                 455                 460

Asp Leu Pro Ser His Glu Ala Pro Leu Ala Asp Ser Leu Glu Glu Leu
465                 470                 475                 480

Glu Pro Gln
```

<210> SEQ ID NO 182
<211> LENGTH: 482
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 182

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

Asp Glu Asn Ile Thr Leu Glu Thr Val Cys His Asp Pro Lys Leu Pro
115 120 125

Tyr His Asp Phe Ile Leu Glu Asp Ala Ala Ser Pro Lys Cys Ile Met
130 135 140

Lys Glu Lys Lys Lys Pro Gly Glu Thr Phe Phe Met Cys Ser Cys Ser
145 150 155 160

Ser Asp Glu Cys Asn Asp Asn Ile Ile Phe Ser Glu Glu Tyr Asn Thr
165 170 175

Ser Asn Pro Asp Leu Leu Leu Val Ile Phe Gln Ser Asp Pro Thr Arg
180 185 190

Val Glu Thr Ala Thr Glu Thr His Leu Val Leu Gly Leu Ser Ala Val
195 200 205

Leu Gly Leu Leu Leu Leu Arg Trp Gln Phe Pro Ala His Tyr Arg Arg
210 215 220

Leu Arg His Ala Leu Trp Pro Ser Leu Pro Asp Leu His Arg Val Leu
225 230 235 240

Gly Gln Tyr Leu Arg Asp Thr Ala Ala Leu Ser Pro Pro Lys Ala Thr
245 250 255

Val Ser Asp Thr Cys Glu Glu Val Glu Pro Ser Leu Leu Glu Ile Leu
260 265 270

Pro Lys Ser Ser Glu Arg Thr Pro Leu Pro Leu Leu Glu Ala Arg Asp
275 280 285

Glu Val Glu Gly Phe Leu Gln Asp Thr Phe Pro Gln Gln Leu Glu Glu
290 295 300

Ser Glu Lys Gln Arg Leu Gly Gly Asp Val Gln Ser Pro Asn Cys Pro
305 310 315 320

Ser Glu Asp Val Val Ile Thr Pro Glu Ser Phe Gly Arg Asp Ser Ser
325 330 335

Leu Thr Cys Leu Ala Gly Asn Val Ser Ala Cys Asp Ala Pro Ile Leu
340 345 350

Ser Ser Ser Arg Ser Leu Asp Cys Arg Glu Ser Gly Lys Asn Gly Pro
355 360 365

His Val Tyr Gln Asp Leu Leu Leu Ser Leu Gly Thr Thr Asn Ser Thr
370 375 380

Leu Pro Pro Pro Phe Ser Leu Gln Ser Gly Ile Leu Thr Leu Asn Pro
385 390 395 400

Val Ala Gln Gly Gln Pro Ile Leu Thr Ser Leu Gly Ser Asn Gln Glu
405 410 415

Glu Ala Tyr Val Thr Met Ser Ser Phe Tyr Gln Asn Gln Ser Arg Ser
420 425 430

Asp Pro Lys Pro Glu Asn Pro Ala Cys Pro Trp Thr Val Leu Pro Ala
435 440 445

Gly Asp Leu Pro Thr His Asp Gly Tyr Leu Pro Ser Asn Ile Asp Asp
450 455 460

Leu Pro Ser His Glu Ala Pro Leu Ala Asp Ser Leu Glu Glu Leu Glu
465 470 475 480

Pro Gln

<210> SEQ ID NO 183
<211> LENGTH: 481
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 183

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

Asp Glu Asn Ile Thr Leu Glu Thr Val Cys His Asp Pro Lys Leu Pro
115 120 125

Tyr His Asp Phe Ile Leu Glu Asp Ala Ala Ser Pro Lys Cys Ile Met
130 135 140

Lys Glu Lys Lys Lys Pro Gly Glu Thr Phe Phe Met Cys Ser Cys Ser
145 150 155 160

Ser Asp Glu Cys Asn Asp Asn Ile Ile Phe Ser Glu Glu Tyr Asn Thr
165 170 175

Ser Asn Pro Asp Leu Leu Leu Val Ile Phe Gln Ser Asp Pro Thr Arg
180 185 190

Val Glu Thr Ala Thr Glu Thr Leu Val Leu Gly Leu Ser Ala Val Leu
195 200 205

Gly Leu Leu Leu Leu Arg Trp Gln Phe Pro Ala His Tyr Arg Arg Leu
210 215 220

Arg His Ala Leu Trp Pro Ser Leu Pro Asp Leu His Arg Val Leu Gly
225 230 235 240

Gln Tyr Leu Arg Asp Thr Ala Ala Leu Ser Pro Pro Lys Ala Thr Val
245 250 255

Ser Asp Thr Cys Glu Glu Val Glu Pro Ser Leu Leu Glu Ile Leu Pro
260 265 270

```
Lys Ser Ser Glu Arg Thr Pro Leu Pro Leu Leu Glu Ala Arg Asp Glu
        275                 280                 285

Val Glu Gly Phe Leu Gln Asp Thr Phe Pro Gln Gln Leu Glu Glu Ser
    290                 295                 300

Glu Lys Gln Arg Leu Gly Gly Asp Val Gln Ser Pro Asn Cys Pro Ser
305                 310                 315                 320

Glu Asp Val Val Ile Thr Pro Glu Ser Phe Gly Arg Asp Ser Ser Leu
                325                 330                 335

Thr Cys Leu Ala Gly Asn Val Ser Ala Cys Asp Ala Pro Ile Leu Ser
            340                 345                 350

Ser Ser Arg Ser Leu Asp Cys Arg Glu Ser Gly Lys Asn Gly Pro His
        355                 360                 365

Val Tyr Gln Asp Leu Leu Leu Ser Leu Gly Thr Thr Asn Ser Thr Leu
    370                 375                 380

Pro Pro Pro Phe Ser Leu Gln Ser Gly Ile Leu Thr Leu Asn Pro Val
385                 390                 395                 400

Ala Gln Gly Gln Pro Ile Leu Thr Ser Leu Gly Ser Asn Gln Glu Glu
                405                 410                 415

Ala Tyr Val Thr Met Ser Ser Phe Tyr Gln Asn Gln Ser Arg Ser Asp
            420                 425                 430

Pro Lys Pro Glu Asn Pro Ala Cys Pro Trp Thr Val Leu Pro Ala Gly
        435                 440                 445

Asp Leu Pro Thr His Asp Gly Tyr Leu Pro Ser Asn Ile Asp Asp Leu
    450                 455                 460

Pro Ser His Glu Ala Pro Leu Ala Asp Ser Leu Glu Glu Leu Glu Pro
465                 470                 475                 480

Gln


<210> SEQ ID NO 184
<211> LENGTH: 480
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140
```

Lys Glu Lys Lys Lys Pro Gly Glu Thr Phe Phe Met Cys Ser Cys Ser
145 150 155 160

Ser Asp Glu Cys Asn Asp Asn Ile Ile Phe Ser Glu Glu Tyr Asn Thr
165 170 175

Ser Asn Pro Asp Leu Leu Leu Val Ile Phe Gln Ser Asp Pro Thr Arg
180 185 190

Val Glu Thr Ala Thr Glu Thr Val Leu Gly Leu Ser Ala Val Leu Gly
195 200 205

Leu Leu Leu Leu Arg Trp Gln Phe Pro Ala His Tyr Arg Arg Leu Arg
210 215 220

His Ala Leu Trp Pro Ser Leu Pro Asp Leu His Arg Val Leu Gly Gln
225 230 235 240

Tyr Leu Arg Asp Thr Ala Ala Leu Ser Pro Pro Lys Ala Thr Val Ser
245 250 255

Asp Thr Cys Glu Glu Val Glu Pro Ser Leu Leu Glu Ile Leu Pro Lys
260 265 270

Ser Ser Glu Arg Thr Pro Leu Pro Leu Leu Glu Ala Arg Asp Glu Val
275 280 285

Glu Gly Phe Leu Gln Asp Thr Phe Pro Gln Gln Leu Glu Glu Ser Glu
290 295 300

Lys Gln Arg Leu Gly Gly Asp Val Gln Ser Pro Asn Cys Pro Ser Glu
305 310 315 320

Asp Val Val Ile Thr Pro Glu Ser Phe Gly Arg Asp Ser Ser Leu Thr
325 330 335

Cys Leu Ala Gly Asn Val Ser Ala Cys Asp Ala Pro Ile Leu Ser Ser
340 345 350

Ser Arg Ser Leu Asp Cys Arg Glu Ser Gly Lys Asn Gly Pro His Val
355 360 365

Tyr Gln Asp Leu Leu Leu Ser Leu Gly Thr Thr Asn Ser Thr Leu Pro
370 375 380

Pro Pro Phe Ser Leu Gln Ser Gly Ile Leu Thr Leu Asn Pro Val Ala
385 390 395 400

Gln Gly Gln Pro Ile Leu Thr Ser Leu Gly Ser Asn Gln Glu Glu Ala
405 410 415

Tyr Val Thr Met Ser Ser Phe Tyr Gln Asn Gln Ser Arg Ser Asp Pro
420 425 430

Lys Pro Glu Asn Pro Ala Cys Pro Trp Thr Val Leu Pro Ala Gly Asp
435 440 445

Leu Pro Thr His Asp Gly Tyr Leu Pro Ser Asn Ile Asp Asp Leu Pro
450 455 460

Ser His Glu Ala Pro Leu Ala Asp Ser Leu Glu Glu Leu Glu Pro Gln
465 470 475 480

<210> SEQ ID NO 185
<211> LENGTH: 479
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 185

Met Ala Leu Pro Val Thr Ala Leu Leu Leu Pro Leu Ala Leu Leu Leu
1 5 10 15

```
His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Leu Gly Leu Ser Ala Val Leu Gly Leu
        195                 200                 205

Leu Leu Leu Arg Trp Gln Phe Pro Ala His Tyr Arg Arg Leu Arg His
    210                 215                 220

Ala Leu Trp Pro Ser Leu Pro Asp Leu His Arg Val Leu Gly Gln Tyr
225                 230                 235                 240

Leu Arg Asp Thr Ala Ala Leu Ser Pro Pro Lys Ala Thr Val Ser Asp
                245                 250                 255

Thr Cys Glu Glu Val Glu Pro Ser Leu Leu Glu Ile Leu Pro Lys Ser
            260                 265                 270

Ser Glu Arg Thr Pro Leu Pro Leu Leu Glu Ala Arg Asp Glu Val Glu
        275                 280                 285

Gly Phe Leu Gln Asp Thr Phe Pro Gln Gln Leu Glu Glu Ser Glu Lys
    290                 295                 300

Gln Arg Leu Gly Gly Asp Val Gln Ser Pro Asn Cys Pro Ser Glu Asp
305                 310                 315                 320

Val Val Ile Thr Pro Glu Ser Phe Gly Arg Asp Ser Ser Leu Thr Cys
                325                 330                 335

Leu Ala Gly Asn Val Ser Ala Cys Asp Ala Pro Ile Leu Ser Ser Ser
            340                 345                 350

Arg Ser Leu Asp Cys Arg Glu Ser Gly Lys Asn Gly Pro His Val Tyr
        355                 360                 365

Gln Asp Leu Leu Leu Ser Leu Gly Thr Thr Asn Ser Thr Leu Pro Pro
    370                 375                 380

Pro Phe Ser Leu Gln Ser Gly Ile Leu Thr Leu Asn Pro Val Ala Gln
385                 390                 395                 400

Gly Gln Pro Ile Leu Thr Ser Leu Gly Ser Asn Gln Glu Glu Ala Tyr
                405                 410                 415

Val Thr Met Ser Ser Phe Tyr Gln Asn Gln Ser Arg Ser Asp Pro Lys
            420                 425                 430
```

```
Pro Glu Asn Pro Ala Cys Pro Trp Thr Val Leu Pro Ala Gly Asp Leu
        435                 440                 445

Pro Thr His Asp Gly Tyr Leu Pro Ser Asn Ile Asp Asp Leu Pro Ser
    450                 455                 460

His Glu Ala Pro Leu Ala Asp Ser Leu Glu Glu Leu Glu Pro Gln
465                 470                 475


<210> SEQ ID NO 186
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Gly Leu Ser Ala Val Leu Gly Leu Leu
        195                 200                 205

Leu Leu Arg Trp Gln Phe Pro Ala His Tyr Arg Arg Leu Arg His Ala
    210                 215                 220

Leu Trp Pro Ser Leu Pro Asp Leu His Arg Val Leu Gly Gln Tyr Leu
225                 230                 235                 240

Arg Asp Thr Ala Ala Leu Ser Pro Pro Lys Ala Thr Val Ser Asp Thr
                245                 250                 255

Cys Glu Glu Val Glu Pro Ser Leu Leu Glu Ile Leu Pro Lys Ser Ser
            260                 265                 270

Glu Arg Thr Pro Leu Pro Leu Leu Glu Ala Arg Asp Glu Val Glu Gly
        275                 280                 285

Phe Leu Gln Asp Thr Phe Pro Gln Gln Leu Glu Glu Ser Glu Lys Gln
    290                 295                 300

Arg Leu Gly Gly Asp Val Gln Ser Pro Asn Cys Pro Ser Glu Asp Val
305                 310                 315                 320
```

Val Ile Thr Pro Glu Ser Phe Gly Arg Asp Ser Ser Leu Thr Cys Leu
325 330 335

Ala Gly Asn Val Ser Ala Cys Asp Ala Pro Ile Leu Ser Ser Ser Arg
340 345 350

Ser Leu Asp Cys Arg Glu Ser Gly Lys Asn Gly Pro His Val Tyr Gln
355 360 365

Asp Leu Leu Leu Ser Leu Gly Thr Thr Asn Ser Thr Leu Pro Pro Pro
370 375 380

Phe Ser Leu Gln Ser Gly Ile Leu Thr Leu Asn Pro Val Ala Gln Gly
385 390 395 400

Gln Pro Ile Leu Thr Ser Leu Gly Ser Asn Gln Glu Glu Ala Tyr Val
405 410 415

Thr Met Ser Ser Phe Tyr Gln Asn Gln Ser Arg Ser Asp Pro Lys Pro
420 425 430

Glu Asn Pro Ala Cys Pro Trp Thr Val Leu Pro Ala Gly Asp Leu Pro
435 440 445

Thr His Asp Gly Tyr Leu Pro Ser Asn Ile Asp Asp Leu Pro Ser His
450 455 460

Glu Ala Pro Leu Ala Asp Ser Leu Glu Glu Leu Glu Pro Gln
465 470 475

<210> SEQ ID NO 187
<211> LENGTH: 477
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 187

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

Asp Glu Asn Ile Thr Leu Glu Thr Val Cys His Asp Pro Lys Leu Pro
115 120 125

Tyr His Asp Phe Ile Leu Glu Asp Ala Ala Ser Pro Lys Cys Ile Met
130 135 140

Lys Glu Lys Lys Lys Pro Gly Glu Thr Phe Phe Met Cys Ser Cys Ser
145 150 155 160

Ser Asp Glu Cys Asn Asp Asn Ile Ile Phe Ser Glu Glu Tyr Asn Thr
165 170 175

Ser Asn Pro Asp Leu Leu Leu Val Ile Phe Gln Ser Asp Pro Thr Arg
180 185 190

Val Glu Thr Ala Thr Glu Thr Leu Ser Ala Val Leu Gly Leu Leu Leu
195 200 205

Leu Arg Trp Gln Phe Pro Ala His Tyr Arg Arg Leu Arg His Ala Leu
210 215 220

Trp Pro Ser Leu Pro Asp Leu His Arg Val Leu Gly Gln Tyr Leu Arg
225 230 235 240

Asp Thr Ala Ala Leu Ser Pro Pro Lys Ala Thr Val Ser Asp Thr Cys
245 250 255

Glu Glu Val Glu Pro Ser Leu Leu Glu Ile Leu Pro Lys Ser Ser Glu
260 265 270

Arg Thr Pro Leu Pro Leu Leu Glu Ala Arg Asp Glu Val Glu Gly Phe
275 280 285

Leu Gln Asp Thr Phe Pro Gln Gln Leu Glu Glu Ser Glu Lys Gln Arg
290 295 300

Leu Gly Gly Asp Val Gln Ser Pro Asn Cys Pro Ser Glu Asp Val Val
305 310 315 320

Ile Thr Pro Glu Ser Phe Gly Arg Asp Ser Ser Leu Thr Cys Leu Ala
325 330 335

Gly Asn Val Ser Ala Cys Asp Ala Pro Ile Leu Ser Ser Ser Arg Ser
340 345 350

Leu Asp Cys Arg Glu Ser Gly Lys Asn Gly Pro His Val Tyr Gln Asp
355 360 365

Leu Leu Leu Ser Leu Gly Thr Thr Asn Ser Thr Leu Pro Pro Pro Phe
370 375 380

Ser Leu Gln Ser Gly Ile Leu Thr Leu Asn Pro Val Ala Gln Gly Gln
385 390 395 400

Pro Ile Leu Thr Ser Leu Gly Ser Asn Gln Glu Glu Ala Tyr Val Thr
405 410 415

Met Ser Ser Phe Tyr Gln Asn Gln Ser Arg Ser Asp Pro Lys Pro Glu
420 425 430

Asn Pro Ala Cys Pro Trp Thr Val Leu Pro Ala Gly Asp Leu Pro Thr
435 440 445

His Asp Gly Tyr Leu Pro Ser Asn Ile Asp Asp Leu Pro Ser His Glu
450 455 460

Ala Pro Leu Ala Asp Ser Leu Glu Glu Leu Glu Pro Gln
465 470 475

<210> SEQ ID NO 188
<211> LENGTH: 476
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 188

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

```
Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Ser Ala Val Leu Gly Leu Leu Leu Leu
        195                 200                 205

Arg Trp Gln Phe Pro Ala His Tyr Arg Arg Leu Arg His Ala Leu Trp
    210                 215                 220

Pro Ser Leu Pro Asp Leu His Arg Val Leu Gly Gln Tyr Leu Arg Asp
225                 230                 235                 240

Thr Ala Ala Leu Ser Pro Pro Lys Ala Thr Val Ser Asp Thr Cys Glu
                245                 250                 255

Glu Val Glu Pro Ser Leu Leu Glu Ile Leu Pro Lys Ser Ser Glu Arg
            260                 265                 270

Thr Pro Leu Pro Leu Leu Glu Ala Arg Asp Glu Val Glu Gly Phe Leu
        275                 280                 285

Gln Asp Thr Phe Pro Gln Gln Leu Glu Glu Ser Glu Lys Gln Arg Leu
    290                 295                 300

Gly Gly Asp Val Gln Ser Pro Asn Cys Pro Ser Glu Asp Val Val Ile
305                 310                 315                 320

Thr Pro Glu Ser Phe Gly Arg Asp Ser Ser Leu Thr Cys Leu Ala Gly
                325                 330                 335

Asn Val Ser Ala Cys Asp Ala Pro Ile Leu Ser Ser Ser Arg Ser Leu
            340                 345                 350

Asp Cys Arg Glu Ser Gly Lys Asn Gly Pro His Val Tyr Gln Asp Leu
        355                 360                 365

Leu Leu Ser Leu Gly Thr Thr Asn Ser Thr Leu Pro Pro Pro Phe Ser
    370                 375                 380

Leu Gln Ser Gly Ile Leu Thr Leu Asn Pro Val Ala Gln Gly Gln Pro
385                 390                 395                 400

Ile Leu Thr Ser Leu Gly Ser Asn Gln Glu Glu Ala Tyr Val Thr Met
                405                 410                 415

Ser Ser Phe Tyr Gln Asn Gln Ser Arg Ser Asp Pro Lys Pro Glu Asn
            420                 425                 430

Pro Ala Cys Pro Trp Thr Val Leu Pro Ala Gly Asp Leu Pro Thr His
        435                 440                 445

Asp Gly Tyr Leu Pro Ser Asn Ile Asp Asp Leu Pro Ser His Glu Ala
    450                 455                 460

Pro Leu Ala Asp Ser Leu Glu Glu Leu Glu Pro Gln
465                 470                 475
```

<210> SEQ ID NO 189
<211> LENGTH: 475
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 189

```
Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Ala Val Leu Gly Leu Leu Leu Leu Arg
        195                 200                 205

Trp Gln Phe Pro Ala His Tyr Arg Arg Leu Arg His Ala Leu Trp Pro
    210                 215                 220

Ser Leu Pro Asp Leu His Arg Val Leu Gly Gln Tyr Leu Arg Asp Thr
225                 230                 235                 240

Ala Ala Leu Ser Pro Pro Lys Ala Thr Val Ser Asp Thr Cys Glu Glu
                245                 250                 255

Val Glu Pro Ser Leu Leu Glu Ile Leu Pro Lys Ser Ser Glu Arg Thr
            260                 265                 270

Pro Leu Pro Leu Leu Glu Ala Arg Asp Glu Val Glu Gly Phe Leu Gln
        275                 280                 285

Asp Thr Phe Pro Gln Gln Leu Glu Glu Ser Glu Lys Gln Arg Leu Gly
    290                 295                 300

Gly Asp Val Gln Ser Pro Asn Cys Pro Ser Glu Asp Val Val Ile Thr
305                 310                 315                 320

Pro Glu Ser Phe Gly Arg Asp Ser Ser Leu Thr Cys Leu Ala Gly Asn
                325                 330                 335

Val Ser Ala Cys Asp Ala Pro Ile Leu Ser Ser Ser Arg Ser Leu Asp
            340                 345                 350

Cys Arg Glu Ser Gly Lys Asn Gly Pro His Val Tyr Gln Asp Leu Leu
        355                 360                 365
```

```
Leu Ser Leu Gly Thr Thr Asn Ser Thr Leu Pro Pro Pro Phe Ser Leu
    370                 375                 380

Gln Ser Gly Ile Leu Thr Leu Asn Pro Val Ala Gln Gly Gln Pro Ile
385                 390                 395                 400

Leu Thr Ser Leu Gly Ser Asn Gln Glu Glu Ala Tyr Val Thr Met Ser
                405                 410                 415

Ser Phe Tyr Gln Asn Gln Ser Arg Ser Asp Pro Lys Pro Glu Asn Pro
            420                 425                 430

Ala Cys Pro Trp Thr Val Leu Pro Ala Gly Asp Leu Pro Thr His Asp
        435                 440                 445

Gly Tyr Leu Pro Ser Asn Ile Asp Asp Leu Pro Ser His Glu Ala Pro
    450                 455                 460

Leu Ala Asp Ser Leu Glu Glu Leu Glu Pro Gln
465                 470                 475


<210> SEQ ID NO 190
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Val Leu Gly Leu Leu Leu Leu Arg Trp
        195                 200                 205

Gln Phe Pro Ala His Tyr Arg Arg Leu Arg His Ala Leu Trp Pro Ser
    210                 215                 220

Leu Pro Asp Leu His Arg Val Leu Gly Gln Tyr Leu Arg Asp Thr Ala
225                 230                 235                 240
```

Ala Leu Ser Pro Pro Lys Ala Thr Val Ser Asp Thr Cys Glu Glu Val
245 250 255

Glu Pro Ser Leu Leu Glu Ile Leu Pro Lys Ser Ser Glu Arg Thr Pro
260 265 270

Leu Pro Leu Leu Glu Ala Arg Asp Glu Val Glu Gly Phe Leu Gln Asp
275 280 285

Thr Phe Pro Gln Gln Leu Glu Glu Ser Glu Lys Gln Arg Leu Gly Gly
290 295 300

Asp Val Gln Ser Pro Asn Cys Pro Ser Glu Asp Val Val Ile Thr Pro
305 310 315 320

Glu Ser Phe Gly Arg Asp Ser Ser Leu Thr Cys Leu Ala Gly Asn Val
325 330 335

Ser Ala Cys Asp Ala Pro Ile Leu Ser Ser Ser Arg Ser Leu Asp Cys
340 345 350

Arg Glu Ser Gly Lys Asn Gly Pro His Val Tyr Gln Asp Leu Leu Leu
355 360 365

Ser Leu Gly Thr Thr Asn Ser Thr Leu Pro Pro Pro Phe Ser Leu Gln
370 375 380

Ser Gly Ile Leu Thr Leu Asn Pro Val Ala Gln Gly Gln Pro Ile Leu
385 390 395 400

Thr Ser Leu Gly Ser Asn Gln Glu Glu Ala Tyr Val Thr Met Ser Ser
405 410 415

Phe Tyr Gln Asn Gln Ser Arg Ser Asp Pro Lys Pro Glu Asn Pro Ala
420 425 430

Cys Pro Trp Thr Val Leu Pro Ala Gly Asp Leu Pro Thr His Asp Gly
435 440 445

Tyr Leu Pro Ser Asn Ile Asp Asp Leu Pro Ser His Glu Ala Pro Leu
450 455 460

Ala Asp Ser Leu Glu Glu Leu Glu Pro Gln
465 470

<210> SEQ ID NO 191
<211> LENGTH: 473
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 191

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

```
Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Leu Gly Leu Leu Leu Leu Arg Trp Gln
        195                 200                 205

Phe Pro Ala His Tyr Arg Arg Leu Arg His Ala Leu Trp Pro Ser Leu
    210                 215                 220

Pro Asp Leu His Arg Val Leu Gly Gln Tyr Leu Arg Asp Thr Ala Ala
225                 230                 235                 240

Leu Ser Pro Pro Lys Ala Thr Val Ser Asp Thr Cys Glu Glu Val Glu
                245                 250                 255

Pro Ser Leu Leu Glu Ile Leu Pro Lys Ser Ser Glu Arg Thr Pro Leu
            260                 265                 270

Pro Leu Leu Glu Ala Arg Asp Glu Val Glu Gly Phe Leu Gln Asp Thr
        275                 280                 285

Phe Pro Gln Gln Leu Glu Glu Ser Glu Lys Gln Arg Leu Gly Gly Asp
    290                 295                 300

Val Gln Ser Pro Asn Cys Pro Ser Glu Asp Val Val Ile Thr Pro Glu
305                 310                 315                 320

Ser Phe Gly Arg Asp Ser Ser Leu Thr Cys Leu Ala Gly Asn Val Ser
                325                 330                 335

Ala Cys Asp Ala Pro Ile Leu Ser Ser Ser Arg Ser Leu Asp Cys Arg
            340                 345                 350

Glu Ser Gly Lys Asn Gly Pro His Val Tyr Gln Asp Leu Leu Leu Ser
        355                 360                 365

Leu Gly Thr Thr Asn Ser Thr Leu Pro Pro Pro Phe Ser Leu Gln Ser
    370                 375                 380

Gly Ile Leu Thr Leu Asn Pro Val Ala Gln Gly Gln Pro Ile Leu Thr
385                 390                 395                 400

Ser Leu Gly Ser Asn Gln Glu Glu Ala Tyr Val Thr Met Ser Ser Phe
                405                 410                 415

Tyr Gln Asn Gln Ser Arg Ser Asp Pro Lys Pro Glu Asn Pro Ala Cys
            420                 425                 430

Pro Trp Thr Val Leu Pro Ala Gly Asp Leu Pro Thr His Asp Gly Tyr
        435                 440                 445

Leu Pro Ser Asn Ile Asp Asp Leu Pro Ser His Glu Ala Pro Leu Ala
    450                 455                 460

Asp Ser Leu Glu Glu Leu Glu Pro Gln
465                 470
```

<210> SEQ ID NO 192
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

```
Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Ala Trp Leu Ile Ser Leu Val Thr Ala
        195                 200                 205

Leu His Leu Val Leu Gly Leu Ser Ala Val Leu Gly Leu Leu Leu Leu
    210                 215                 220

Arg Trp Gln Phe Pro Ala His Tyr Arg Arg Leu Arg His Ala Leu Trp
225                 230                 235                 240

Pro Ser Leu Pro Asp Leu His Arg Val Leu Gly Gln Tyr Leu Arg Asp
                245                 250                 255

Thr Ala Ala Leu Ser Pro Pro Lys Ala Thr Val Ser Asp Thr Cys Glu
            260                 265                 270

Glu Val Glu Pro Ser Leu Leu Glu Ile Leu Pro Lys Ser Ser Glu Arg
        275                 280                 285

Thr Pro Leu Pro Leu Leu Glu Ala Arg Asp Glu Val Glu Gly Phe Leu
    290                 295                 300

Gln Asp Thr Phe Pro Gln Gln Leu Glu Glu Ser Glu Lys Gln Arg Leu
305                 310                 315                 320

Gly Gly Asp Val Gln Ser Pro Asn Cys Pro Ser Glu Asp Val Val Ile
                325                 330                 335

Thr Pro Glu Ser Phe Gly Arg Asp Ser Ser Leu Thr Cys Leu Ala Gly
            340                 345                 350

Asn Val Ser Ala Cys Asp Ala Pro Ile Leu Ser Ser Ser Arg Ser Leu
        355                 360                 365

Asp Cys Arg Glu Ser Gly Lys Asn Gly Pro His Val Tyr Gln Asp Leu
    370                 375                 380

Leu Leu Ser Leu Gly Thr Thr Asn Ser Thr Leu Pro Pro Pro Phe Ser
385                 390                 395                 400

Leu Gln Ser Gly Ile Leu Thr Leu Asn Pro Val Ala Gln Gly Gln Pro
                405                 410                 415
```

```
Ile Leu Thr Ser Leu Gly Ser Asn Gln Glu Glu Ala Tyr Val Thr Met
            420                 425                 430

Ser Ser Phe Tyr Gln Asn Gln Ser Arg Ser Asp Pro Lys Pro Glu Asn
        435                 440                 445

Pro Ala Cys Pro Trp Thr Val Leu Pro Ala Gly Asp Leu Pro Thr His
    450                 455                 460

Asp Gly Tyr Leu Pro Ser Asn Ile Asp Asp Leu Pro Ser His Glu Ala
465                 470                 475                 480

Pro Leu Ala Asp Ser Leu Glu Glu Leu Glu Pro Gln
                485                 490


<210> SEQ ID NO 193
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Ala Trp Val Leu Ile Ser Leu Val Thr
        195                 200                 205

Ala Leu His Leu Val Leu Gly Leu Ser Ala Val Leu Gly Leu Leu Leu
    210                 215                 220

Leu Arg Trp Gln Phe Pro Ala His Tyr Arg Arg Leu Arg His Ala Leu
225                 230                 235                 240

Trp Pro Ser Leu Pro Asp Leu His Arg Val Leu Gly Gln Tyr Leu Arg
                245                 250                 255

Asp Thr Ala Ala Leu Ser Pro Pro Lys Ala Thr Val Ser Asp Thr Cys
            260                 265                 270
```

Glu Glu Val Glu Pro Ser Leu Leu Glu Ile Leu Pro Lys Ser Ser Glu
275 280 285

Arg Thr Pro Leu Pro Leu Leu Glu Ala Arg Asp Glu Val Glu Gly Phe
290 295 300

Leu Gln Asp Thr Phe Pro Gln Gln Leu Glu Glu Ser Glu Lys Gln Arg
305 310 315 320

Leu Gly Gly Asp Val Gln Ser Pro Asn Cys Pro Ser Glu Asp Val Val
325 330 335

Ile Thr Pro Glu Ser Phe Gly Arg Asp Ser Ser Leu Thr Cys Leu Ala
340 345 350

Gly Asn Val Ser Ala Cys Asp Ala Pro Ile Leu Ser Ser Ser Arg Ser
355 360 365

Leu Asp Cys Arg Glu Ser Gly Lys Asn Gly Pro His Val Tyr Gln Asp
370 375 380

Leu Leu Leu Ser Leu Gly Thr Thr Asn Ser Thr Leu Pro Pro Pro Phe
385 390 395 400

Ser Leu Gln Ser Gly Ile Leu Thr Leu Asn Pro Val Ala Gln Gly Gln
405 410 415

Pro Ile Leu Thr Ser Leu Gly Ser Asn Gln Glu Glu Ala Tyr Val Thr
420 425 430

Met Ser Ser Phe Tyr Gln Asn Gln Ser Arg Ser Asp Pro Lys Pro Glu
435 440 445

Asn Pro Ala Cys Pro Trp Thr Val Leu Pro Ala Gly Asp Leu Pro Thr
450 455 460

His Asp Gly Tyr Leu Pro Ser Asn Ile Asp Asp Leu Pro Ser His Glu
465 470 475 480

Ala Pro Leu Ala Asp Ser Leu Glu Glu Leu Glu Pro Gln
485 490

<210> SEQ ID NO 194
<211> LENGTH: 494
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 194

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

Asp Glu Asn Ile Thr Leu Glu Thr Val Cys His Asp Pro Lys Leu Pro
115 120 125

```
Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Ala Trp Leu Val Leu Ile Ser Leu Val
        195                 200                 205

Thr Ala Leu His Leu Val Leu Gly Leu Ser Ala Val Leu Gly Leu Leu
    210                 215                 220

Leu Leu Arg Trp Gln Phe Pro Ala His Tyr Arg Arg Leu Arg His Ala
225                 230                 235                 240

Leu Trp Pro Ser Leu Pro Asp Leu His Arg Val Leu Gly Gln Tyr Leu
                245                 250                 255

Arg Asp Thr Ala Ala Leu Ser Pro Pro Lys Ala Thr Val Ser Asp Thr
            260                 265                 270

Cys Glu Glu Val Glu Pro Ser Leu Leu Glu Ile Leu Pro Lys Ser Ser
        275                 280                 285

Glu Arg Thr Pro Leu Pro Leu Leu Glu Ala Arg Asp Glu Val Glu Gly
    290                 295                 300

Phe Leu Gln Asp Thr Phe Pro Gln Gln Leu Glu Glu Ser Glu Lys Gln
305                 310                 315                 320

Arg Leu Gly Gly Asp Val Gln Ser Pro Asn Cys Pro Ser Glu Asp Val
                325                 330                 335

Val Ile Thr Pro Glu Ser Phe Gly Arg Asp Ser Ser Leu Thr Cys Leu
            340                 345                 350

Ala Gly Asn Val Ser Ala Cys Asp Ala Pro Ile Leu Ser Ser Ser Arg
        355                 360                 365

Ser Leu Asp Cys Arg Glu Ser Gly Lys Asn Gly Pro His Val Tyr Gln
    370                 375                 380

Asp Leu Leu Leu Ser Leu Gly Thr Thr Asn Ser Thr Leu Pro Pro Pro
385                 390                 395                 400

Phe Ser Leu Gln Ser Gly Ile Leu Thr Leu Asn Pro Val Ala Gln Gly
                405                 410                 415

Gln Pro Ile Leu Thr Ser Leu Gly Ser Asn Gln Glu Glu Ala Tyr Val
            420                 425                 430

Thr Met Ser Ser Phe Tyr Gln Asn Gln Ser Arg Ser Asp Pro Lys Pro
        435                 440                 445

Glu Asn Pro Ala Cys Pro Trp Thr Val Leu Pro Ala Gly Asp Leu Pro
    450                 455                 460

Thr His Asp Gly Tyr Leu Pro Ser Asn Ile Asp Asp Leu Pro Ser His
465                 470                 475                 480

Glu Ala Pro Leu Ala Asp Ser Leu Glu Glu Leu Glu Pro Gln
                485                 490
```

<210> SEQ ID NO 195
<211> LENGTH: 495
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Ala Trp Ile Leu Val Leu Ile Ser Leu
        195                 200                 205

Val Thr Ala Leu His Leu Val Leu Gly Leu Ser Ala Val Leu Gly Leu
    210                 215                 220

Leu Leu Leu Arg Trp Gln Phe Pro Ala His Tyr Arg Arg Leu Arg His
225                 230                 235                 240

Ala Leu Trp Pro Ser Leu Pro Asp Leu His Arg Val Leu Gly Gln Tyr
                245                 250                 255

Leu Arg Asp Thr Ala Ala Leu Ser Pro Pro Lys Ala Thr Val Ser Asp
            260                 265                 270

Thr Cys Glu Glu Val Glu Pro Ser Leu Leu Glu Ile Leu Pro Lys Ser
        275                 280                 285

Ser Glu Arg Thr Pro Leu Pro Leu Leu Glu Ala Arg Asp Glu Val Glu
    290                 295                 300

Gly Phe Leu Gln Asp Thr Phe Pro Gln Gln Leu Glu Glu Ser Glu Lys
305                 310                 315                 320

Gln Arg Leu Gly Gly Asp Val Gln Ser Pro Asn Cys Pro Ser Glu Asp
                325                 330                 335

Val Val Ile Thr Pro Glu Ser Phe Gly Arg Asp Ser Ser Leu Thr Cys
            340                 345                 350

Leu Ala Gly Asn Val Ser Ala Cys Asp Ala Pro Ile Leu Ser Ser Ser
        355                 360                 365

Arg Ser Leu Asp Cys Arg Glu Ser Gly Lys Asn Gly Pro His Val Tyr
    370                 375                 380

Gln Asp Leu Leu Leu Ser Leu Gly Thr Thr Asn Ser Thr Leu Pro Pro
385                 390                 395                 400

Pro Phe Ser Leu Gln Ser Gly Ile Leu Thr Leu Asn Pro Val Ala Gln
                405                 410                 415

Gly Gln Pro Ile Leu Thr Ser Leu Gly Ser Asn Gln Glu Glu Ala Tyr
420 425 430

Val Thr Met Ser Ser Phe Tyr Gln Asn Gln Ser Arg Ser Asp Pro Lys
435 440 445

Pro Glu Asn Pro Ala Cys Pro Trp Thr Val Leu Pro Ala Gly Asp Leu
450 455 460

Pro Thr His Asp Gly Tyr Leu Pro Ser Asn Ile Asp Asp Leu Pro Ser
465 470 475 480

His Glu Ala Pro Leu Ala Asp Ser Leu Glu Glu Leu Glu Pro Gln
485 490 495

<210> SEQ ID NO 196
<211> LENGTH: 496
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 196

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

Asp Glu Asn Ile Thr Leu Glu Thr Val Cys His Asp Pro Lys Leu Pro
115 120 125

Tyr His Asp Phe Ile Leu Glu Asp Ala Ala Ser Pro Lys Cys Ile Met
130 135 140

Lys Glu Lys Lys Lys Pro Gly Glu Thr Phe Phe Met Cys Ser Cys Ser
145 150 155 160

Ser Asp Glu Cys Asn Asp Asn Ile Ile Phe Ser Glu Glu Tyr Asn Thr
165 170 175

Ser Asn Pro Asp Leu Leu Leu Val Ile Phe Gln Ser Asp Pro Thr Arg
180 185 190

Val Glu Thr Ala Thr Glu Thr Ala Trp Leu Ile Leu Val Leu Ile Ser
195 200 205

Leu Val Thr Ala Leu His Leu Val Leu Gly Leu Ser Ala Val Leu Gly
210 215 220

Leu Leu Leu Leu Arg Trp Gln Phe Pro Ala His Tyr Arg Arg Leu Arg
225 230 235 240

His Ala Leu Trp Pro Ser Leu Pro Asp Leu His Arg Val Leu Gly Gln
245 250 255

Tyr Leu Arg Asp Thr Ala Ala Leu Ser Pro Pro Lys Ala Thr Val Ser
260 265 270

Asp Thr Cys Glu Glu Val Glu Pro Ser Leu Leu Glu Ile Leu Pro Lys
275 280 285

Ser Ser Glu Arg Thr Pro Leu Pro Leu Leu Glu Ala Arg Asp Glu Val
290 295 300

Glu Gly Phe Leu Gln Asp Thr Phe Pro Gln Gln Leu Glu Glu Ser Glu
305 310 315 320

Lys Gln Arg Leu Gly Gly Asp Val Gln Ser Pro Asn Cys Pro Ser Glu
325 330 335

Asp Val Val Ile Thr Pro Glu Ser Phe Gly Arg Asp Ser Ser Leu Thr
340 345 350

Cys Leu Ala Gly Asn Val Ser Ala Cys Asp Ala Pro Ile Leu Ser Ser
355 360 365

Ser Arg Ser Leu Asp Cys Arg Glu Ser Gly Lys Asn Gly Pro His Val
370 375 380

Tyr Gln Asp Leu Leu Leu Ser Leu Gly Thr Thr Asn Ser Thr Leu Pro
385 390 395 400

Pro Pro Phe Ser Leu Gln Ser Gly Ile Leu Thr Leu Asn Pro Val Ala
405 410 415

Gln Gly Gln Pro Ile Leu Thr Ser Leu Gly Ser Asn Gln Glu Glu Ala
420 425 430

Tyr Val Thr Met Ser Ser Phe Tyr Gln Asn Gln Ser Arg Ser Asp Pro
435 440 445

Lys Pro Glu Asn Pro Ala Cys Pro Trp Thr Val Leu Pro Ala Gly Asp
450 455 460

Leu Pro Thr His Asp Gly Tyr Leu Pro Ser Asn Ile Asp Asp Leu Pro
465 470 475 480

Ser His Glu Ala Pro Leu Ala Asp Ser Leu Glu Glu Leu Glu Pro Gln
485 490 495

<210> SEQ ID NO 197
<211> LENGTH: 497
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 197

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

Asp Glu Asn Ile Thr Leu Glu Thr Val Cys His Asp Pro Lys Leu Pro
115 120 125

```
Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Ala Trp Leu Leu Ile Leu Val Leu Ile
        195                 200                 205

Ser Leu Val Thr Ala Leu His Leu Val Leu Gly Leu Ser Ala Val Leu
    210                 215                 220

Gly Leu Leu Leu Leu Arg Trp Gln Phe Pro Ala His Tyr Arg Arg Leu
225                 230                 235                 240

Arg His Ala Leu Trp Pro Ser Leu Pro Asp Leu His Arg Val Leu Gly
                245                 250                 255

Gln Tyr Leu Arg Asp Thr Ala Ala Leu Ser Pro Pro Lys Ala Thr Val
            260                 265                 270

Ser Asp Thr Cys Glu Glu Val Glu Pro Ser Leu Leu Glu Ile Leu Pro
        275                 280                 285

Lys Ser Ser Glu Arg Thr Pro Leu Pro Leu Leu Glu Ala Arg Asp Glu
    290                 295                 300

Val Glu Gly Phe Leu Gln Asp Thr Phe Pro Gln Gln Leu Glu Glu Ser
305                 310                 315                 320

Glu Lys Gln Arg Leu Gly Gly Asp Val Gln Ser Pro Asn Cys Pro Ser
                325                 330                 335

Glu Asp Val Val Ile Thr Pro Glu Ser Phe Gly Arg Asp Ser Ser Leu
            340                 345                 350

Thr Cys Leu Ala Gly Asn Val Ser Ala Cys Asp Ala Pro Ile Leu Ser
        355                 360                 365

Ser Ser Arg Ser Leu Asp Cys Arg Glu Ser Gly Lys Asn Gly Pro His
    370                 375                 380

Val Tyr Gln Asp Leu Leu Leu Ser Leu Gly Thr Thr Asn Ser Thr Leu
385                 390                 395                 400

Pro Pro Pro Phe Ser Leu Gln Ser Gly Ile Leu Thr Leu Asn Pro Val
                405                 410                 415

Ala Gln Gly Gln Pro Ile Leu Thr Ser Leu Gly Ser Asn Gln Glu Glu
            420                 425                 430

Ala Tyr Val Thr Met Ser Ser Phe Tyr Gln Asn Gln Ser Arg Ser Asp
        435                 440                 445

Pro Lys Pro Glu Asn Pro Ala Cys Pro Trp Thr Val Leu Pro Ala Gly
    450                 455                 460

Asp Leu Pro Thr His Asp Gly Tyr Leu Pro Ser Asn Ile Asp Asp Leu
465                 470                 475                 480

Pro Ser His Glu Ala Pro Leu Ala Asp Ser Leu Glu Glu Leu Glu Pro
                485                 490                 495

Gln
```

```
<210> SEQ ID NO 198
<211> LENGTH: 498
<212> TYPE: PRT
<213> ORGANISM: Artificial Sequence
<220> FEATURE:
```

<223> OTHER INFORMATION: Description of Artificial Sequence: Synthetic polypeptide

<400> SEQUENCE: 198

Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu Thr Ala Trp Val Leu Leu Ile Leu Val Leu
        195                 200                 205

Ile Ser Leu Val Thr Ala Leu His Leu Val Leu Gly Leu Ser Ala Val
    210                 215                 220

Leu Gly Leu Leu Leu Leu Arg Trp Gln Phe Pro Ala His Tyr Arg Arg
225                 230                 235                 240

Leu Arg His Ala Leu Trp Pro Ser Leu Pro Asp Leu His Arg Val Leu
                245                 250                 255

Gly Gln Tyr Leu Arg Asp Thr Ala Ala Leu Ser Pro Pro Lys Ala Thr
            260                 265                 270

Val Ser Asp Thr Cys Glu Glu Val Glu Pro Ser Leu Leu Glu Ile Leu
        275                 280                 285

Pro Lys Ser Ser Glu Arg Thr Pro Leu Pro Leu Leu Glu Ala Arg Asp
    290                 295                 300

Glu Val Glu Gly Phe Leu Gln Asp Thr Phe Pro Gln Gln Leu Glu Glu
305                 310                 315                 320

Ser Glu Lys Gln Arg Leu Gly Gly Asp Val Gln Ser Pro Asn Cys Pro
                325                 330                 335

Ser Glu Asp Val Val Ile Thr Pro Glu Ser Phe Gly Arg Asp Ser Ser
            340                 345                 350

Leu Thr Cys Leu Ala Gly Asn Val Ser Ala Cys Asp Ala Pro Ile Leu
        355                 360                 365

Ser Ser Ser Arg Ser Leu Asp Cys Arg Glu Ser Gly Lys Asn Gly Pro
    370                 375                 380

His Val Tyr Gln Asp Leu Leu Leu Ser Leu Gly Thr Thr Asn Ser Thr
385                 390                 395                 400

Leu Pro Pro Pro Phe Ser Leu Gln Ser Gly Ile Leu Thr Leu Asn Pro
405 410 415

Val Ala Gln Gly Gln Pro Ile Leu Thr Ser Leu Gly Ser Asn Gln Glu
420 425 430

Glu Ala Tyr Val Thr Met Ser Ser Phe Tyr Gln Asn Gln Ser Arg Ser
435 440 445

Asp Pro Lys Pro Glu Asn Pro Ala Cys Pro Trp Thr Val Leu Pro Ala
450 455 460

Gly Asp Leu Pro Thr His Asp Gly Tyr Leu Pro Ser Asn Ile Asp Asp
465 470 475 480

Leu Pro Ser His Glu Ala Pro Leu Ala Asp Ser Leu Glu Glu Leu Glu
485 490 495

Pro Gln

<210> SEQ ID NO 199
<211> LENGTH: 499
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 199

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

Asp Glu Asn Ile Thr Leu Glu Thr Val Cys His Asp Pro Lys Leu Pro
115 120 125

Tyr His Asp Phe Ile Leu Glu Asp Ala Ala Ser Pro Lys Cys Ile Met
130 135 140

Lys Glu Lys Lys Lys Pro Gly Glu Thr Phe Phe Met Cys Ser Cys Ser
145 150 155 160

Ser Asp Glu Cys Asn Asp Asn Ile Ile Phe Ser Glu Glu Tyr Asn Thr
165 170 175

Ser Asn Pro Asp Leu Leu Leu Val Ile Phe Gln Ser Asp Pro Thr Arg
180 185 190

Val Glu Thr Ala Thr Glu Thr Ala Trp Leu Val Leu Leu Ile Leu Val
195 200 205

Leu Ile Ser Leu Val Thr Ala Leu His Leu Val Leu Gly Leu Ser Ala
210 215 220

Val Leu Gly Leu Leu Leu Leu Arg Trp Gln Phe Pro Ala His Tyr Arg
225 230 235 240

Arg Leu Arg His Ala Leu Trp Pro Ser Leu Pro Asp Leu His Arg Val
245 250 255

Leu Gly Gln Tyr Leu Arg Asp Thr Ala Ala Leu Ser Pro Pro Lys Ala
260 265 270

Thr Val Ser Asp Thr Cys Glu Glu Val Glu Pro Ser Leu Leu Glu Ile
275 280 285

Leu Pro Lys Ser Ser Glu Arg Thr Pro Leu Pro Leu Leu Glu Ala Arg
290 295 300

Asp Glu Val Glu Gly Phe Leu Gln Asp Thr Phe Pro Gln Gln Leu Glu
305 310 315 320

Glu Ser Glu Lys Gln Arg Leu Gly Gly Asp Val Gln Ser Pro Asn Cys
325 330 335

Pro Ser Glu Asp Val Val Ile Thr Pro Glu Ser Phe Gly Arg Asp Ser
340 345 350

Ser Leu Thr Cys Leu Ala Gly Asn Val Ser Ala Cys Asp Ala Pro Ile
355 360 365

Leu Ser Ser Ser Arg Ser Leu Asp Cys Arg Glu Ser Gly Lys Asn Gly
370 375 380

Pro His Val Tyr Gln Asp Leu Leu Leu Ser Leu Gly Thr Thr Asn Ser
385 390 395 400

Thr Leu Pro Pro Pro Phe Ser Leu Gln Ser Gly Ile Leu Thr Leu Asn
405 410 415

Pro Val Ala Gln Gly Gln Pro Ile Leu Thr Ser Leu Gly Ser Asn Gln
420 425 430

Glu Glu Ala Tyr Val Thr Met Ser Ser Phe Tyr Gln Asn Gln Ser Arg
435 440 445

Ser Asp Pro Lys Pro Glu Asn Pro Ala Cys Pro Trp Thr Val Leu Pro
450 455 460

Ala Gly Asp Leu Pro Thr His Asp Gly Tyr Leu Pro Ser Asn Ile Asp
465 470 475 480

Asp Leu Pro Ser His Glu Ala Pro Leu Ala Asp Ser Leu Glu Glu Leu
485 490 495

Glu Pro Gln

<210> SEQ ID NO 200
<211> LENGTH: 481
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 200

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

```
Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr Glu His Leu Val Leu Gly Leu Ser Ala Val Leu
        195                 200                 205

Gly Leu Leu Leu Leu Arg Trp Gln Phe Pro Ala His Tyr Arg Arg Leu
    210                 215                 220

Arg His Ala Leu Trp Pro Ser Leu Pro Asp Leu His Arg Val Leu Gly
225                 230                 235                 240

Gln Tyr Leu Arg Asp Thr Ala Ala Leu Ser Pro Pro Lys Ala Thr Val
                245                 250                 255

Ser Asp Thr Cys Glu Glu Val Glu Pro Ser Leu Leu Glu Ile Leu Pro
            260                 265                 270

Lys Ser Ser Glu Arg Thr Pro Leu Pro Leu Leu Glu Ala Arg Asp Glu
        275                 280                 285

Val Glu Gly Phe Leu Gln Asp Thr Phe Pro Gln Gln Leu Glu Glu Ser
    290                 295                 300

Glu Lys Gln Arg Leu Gly Gly Asp Val Gln Ser Pro Asn Cys Pro Ser
305                 310                 315                 320

Glu Asp Val Val Ile Thr Pro Glu Ser Phe Gly Arg Asp Ser Ser Leu
                325                 330                 335

Thr Cys Leu Ala Gly Asn Val Ser Ala Cys Asp Ala Pro Ile Leu Ser
            340                 345                 350

Ser Ser Arg Ser Leu Asp Cys Arg Glu Ser Gly Lys Asn Gly Pro His
        355                 360                 365

Val Tyr Gln Asp Leu Leu Leu Ser Leu Gly Thr Thr Asn Ser Thr Leu
    370                 375                 380

Pro Pro Pro Phe Ser Leu Gln Ser Gly Ile Leu Thr Leu Asn Pro Val
385                 390                 395                 400

Ala Gln Gly Gln Pro Ile Leu Thr Ser Leu Gly Ser Asn Gln Glu Glu
                405                 410                 415

Ala Tyr Val Thr Met Ser Ser Phe Tyr Gln Asn Gln Ser Arg Ser Asp
            420                 425                 430

Pro Lys Pro Glu Asn Pro Ala Cys Pro Trp Thr Val Leu Pro Ala Gly
        435                 440                 445

Asp Leu Pro Thr His Asp Gly Tyr Leu Pro Ser Asn Ile Asp Asp Leu
    450                 455                 460

Pro Ser His Glu Ala Pro Leu Ala Asp Ser Leu Glu Glu Leu Glu Pro
465                 470                 475                 480

Gln
```

<210> SEQ ID NO 201
<211> LENGTH: 480
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 201

```
Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala Thr His Leu Val Leu Gly Leu Ser Ala Val Leu Gly
        195                 200                 205

Leu Leu Leu Leu Arg Trp Gln Phe Pro Ala His Tyr Arg Arg Leu Arg
    210                 215                 220

His Ala Leu Trp Pro Ser Leu Pro Asp Leu His Arg Val Leu Gly Gln
225                 230                 235                 240

Tyr Leu Arg Asp Thr Ala Ala Leu Ser Pro Pro Lys Ala Thr Val Ser
                245                 250                 255

Asp Thr Cys Glu Glu Val Glu Pro Ser Leu Leu Glu Ile Leu Pro Lys
            260                 265                 270

Ser Ser Glu Arg Thr Pro Leu Pro Leu Leu Glu Ala Arg Asp Glu Val
        275                 280                 285

Glu Gly Phe Leu Gln Asp Thr Phe Pro Gln Gln Leu Glu Glu Ser Glu
    290                 295                 300

Lys Gln Arg Leu Gly Gly Asp Val Gln Ser Pro Asn Cys Pro Ser Glu
305                 310                 315                 320

Asp Val Val Ile Thr Pro Glu Ser Phe Gly Arg Asp Ser Ser Leu Thr
                325                 330                 335

Cys Leu Ala Gly Asn Val Ser Ala Cys Asp Ala Pro Ile Leu Ser Ser
            340                 345                 350

Ser Arg Ser Leu Asp Cys Arg Glu Ser Gly Lys Asn Gly Pro His Val
        355                 360                 365

Tyr Gln Asp Leu Leu Leu Ser Leu Gly Thr Thr Asn Ser Thr Leu Pro
    370                 375                 380
```

```
Pro Pro Phe Ser Leu Gln Ser Gly Ile Leu Thr Leu Asn Pro Val Ala
385                 390                 395                 400

Gln Gly Gln Pro Ile Leu Thr Ser Leu Gly Ser Asn Gln Glu Glu Ala
                405                 410                 415

Tyr Val Thr Met Ser Ser Phe Tyr Gln Asn Gln Ser Arg Ser Asp Pro
            420                 425                 430

Lys Pro Glu Asn Pro Ala Cys Pro Trp Thr Val Leu Pro Ala Gly Asp
        435                 440                 445

Leu Pro Thr His Asp Gly Tyr Leu Pro Ser Asn Ile Asp Asp Leu Pro
    450                 455                 460

Ser His Glu Ala Pro Leu Ala Asp Ser Leu Glu Glu Leu Glu Pro Gln
465                 470                 475                 480


<210> SEQ ID NO 202
<211> LENGTH: 479
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr Ala His Leu Val Leu Gly Leu Ser Ala Val Leu Gly Leu
        195                 200                 205

Leu Leu Leu Arg Trp Gln Phe Pro Ala His Tyr Arg Arg Leu Arg His
    210                 215                 220

Ala Leu Trp Pro Ser Leu Pro Asp Leu His Arg Val Leu Gly Gln Tyr
225                 230                 235                 240

Leu Arg Asp Thr Ala Ala Leu Ser Pro Pro Lys Ala Thr Val Ser Asp
                245                 250                 255
```

Thr Cys Glu Glu Val Glu Pro Ser Leu Leu Glu Ile Leu Pro Lys Ser
260 265 270

Ser Glu Arg Thr Pro Leu Pro Leu Leu Glu Ala Arg Asp Glu Val Glu
275 280 285

Gly Phe Leu Gln Asp Thr Phe Pro Gln Gln Leu Glu Glu Ser Glu Lys
290 295 300

Gln Arg Leu Gly Gly Asp Val Gln Ser Pro Asn Cys Pro Ser Glu Asp
305 310 315 320

Val Val Ile Thr Pro Glu Ser Phe Gly Arg Asp Ser Ser Leu Thr Cys
325 330 335

Leu Ala Gly Asn Val Ser Ala Cys Asp Ala Pro Ile Leu Ser Ser Ser
340 345 350

Arg Ser Leu Asp Cys Arg Glu Ser Gly Lys Asn Gly Pro His Val Tyr
355 360 365

Gln Asp Leu Leu Leu Ser Leu Gly Thr Thr Asn Ser Thr Leu Pro Pro
370 375 380

Pro Phe Ser Leu Gln Ser Gly Ile Leu Thr Leu Asn Pro Val Ala Gln
385 390 395 400

Gly Gln Pro Ile Leu Thr Ser Leu Gly Ser Asn Gln Glu Glu Ala Tyr
405 410 415

Val Thr Met Ser Ser Phe Tyr Gln Asn Gln Ser Arg Ser Asp Pro Lys
420 425 430

Pro Glu Asn Pro Ala Cys Pro Trp Thr Val Leu Pro Ala Gly Asp Leu
435 440 445

Pro Thr His Asp Gly Tyr Leu Pro Ser Asn Ile Asp Asp Leu Pro Ser
450 455 460

His Glu Ala Pro Leu Ala Asp Ser Leu Glu Glu Leu Glu Pro Gln
465 470 475

<210> SEQ ID NO 203
<211> LENGTH: 478
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 203

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

Asp Glu Asn Ile Thr Leu Glu Thr Val Cys His Asp Pro Lys Leu Pro
115 120 125

```
Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu Thr His Leu Val Leu Gly Leu Ser Ala Val Leu Gly Leu Leu
        195                 200                 205

Leu Leu Arg Trp Gln Phe Pro Ala His Tyr Arg Arg Leu Arg His Ala
    210                 215                 220

Leu Trp Pro Ser Leu Pro Asp Leu His Arg Val Leu Gly Gln Tyr Leu
225                 230                 235                 240

Arg Asp Thr Ala Ala Leu Ser Pro Pro Lys Ala Thr Val Ser Asp Thr
                245                 250                 255

Cys Glu Glu Val Glu Pro Ser Leu Leu Glu Ile Leu Pro Lys Ser Ser
            260                 265                 270

Glu Arg Thr Pro Leu Pro Leu Leu Glu Ala Arg Asp Glu Val Glu Gly
        275                 280                 285

Phe Leu Gln Asp Thr Phe Pro Gln Gln Leu Glu Glu Ser Glu Lys Gln
    290                 295                 300

Arg Leu Gly Gly Asp Val Gln Ser Pro Asn Cys Pro Ser Glu Asp Val
305                 310                 315                 320

Val Ile Thr Pro Glu Ser Phe Gly Arg Asp Ser Ser Leu Thr Cys Leu
                325                 330                 335

Ala Gly Asn Val Ser Ala Cys Asp Ala Pro Ile Leu Ser Ser Ser Arg
            340                 345                 350

Ser Leu Asp Cys Arg Glu Ser Gly Lys Asn Gly Pro His Val Tyr Gln
        355                 360                 365

Asp Leu Leu Leu Ser Leu Gly Thr Thr Asn Ser Thr Leu Pro Pro Pro
    370                 375                 380

Phe Ser Leu Gln Ser Gly Ile Leu Thr Leu Asn Pro Val Ala Gln Gly
385                 390                 395                 400

Gln Pro Ile Leu Thr Ser Leu Gly Ser Asn Gln Glu Glu Ala Tyr Val
                405                 410                 415

Thr Met Ser Ser Phe Tyr Gln Asn Gln Ser Arg Ser Asp Pro Lys Pro
            420                 425                 430

Glu Asn Pro Ala Cys Pro Trp Thr Val Leu Pro Ala Gly Asp Leu Pro
        435                 440                 445

Thr His Asp Gly Tyr Leu Pro Ser Asn Ile Asp Asp Leu Pro Ser His
    450                 455                 460

Glu Ala Pro Leu Ala Asp Ser Leu Glu Glu Leu Glu Pro Gln
465                 470                 475
```

<210> SEQ ID NO 204
<211> LENGTH: 477
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 204

```
Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro Thr Arg
            180                 185                 190

Val Glu His Leu Val Leu Gly Leu Ser Ala Val Leu Gly Leu Leu Leu
        195                 200                 205

Leu Arg Trp Gln Phe Pro Ala His Tyr Arg Arg Leu Arg His Ala Leu
    210                 215                 220

Trp Pro Ser Leu Pro Asp Leu His Arg Val Leu Gly Gln Tyr Leu Arg
225                 230                 235                 240

Asp Thr Ala Ala Leu Ser Pro Pro Lys Ala Thr Val Ser Asp Thr Cys
                245                 250                 255

Glu Glu Val Glu Pro Ser Leu Leu Glu Ile Leu Pro Lys Ser Ser Glu
            260                 265                 270

Arg Thr Pro Leu Pro Leu Leu Glu Ala Arg Asp Glu Val Glu Gly Phe
        275                 280                 285

Leu Gln Asp Thr Phe Pro Gln Gln Leu Glu Glu Ser Glu Lys Gln Arg
    290                 295                 300

Leu Gly Gly Asp Val Gln Ser Pro Asn Cys Pro Ser Glu Asp Val Val
305                 310                 315                 320

Ile Thr Pro Glu Ser Phe Gly Arg Asp Ser Ser Leu Thr Cys Leu Ala
                325                 330                 335

Gly Asn Val Ser Ala Cys Asp Ala Pro Ile Leu Ser Ser Ser Arg Ser
            340                 345                 350

Leu Asp Cys Arg Glu Ser Gly Lys Asn Gly Pro His Val Tyr Gln Asp
        355                 360                 365

Leu Leu Leu Ser Leu Gly Thr Thr Asn Ser Thr Leu Pro Pro Pro Phe
    370                 375                 380

Ser Leu Gln Ser Gly Ile Leu Thr Leu Asn Pro Val Ala Gln Gly Gln
385                 390                 395                 400
```

Pro Ile Leu Thr Ser Leu Gly Ser Asn Gln Glu Glu Ala Tyr Val Thr
405 410 415

Met Ser Ser Phe Tyr Gln Asn Gln Ser Arg Ser Asp Pro Lys Pro Glu
420 425 430

Asn Pro Ala Cys Pro Trp Thr Val Leu Pro Ala Gly Asp Leu Pro Thr
435 440 445

His Asp Gly Tyr Leu Pro Ser Asn Ile Asp Asp Leu Pro Ser His Glu
450 455 460

Ala Pro Leu Ala Asp Ser Leu Glu Glu Leu Glu Pro Gln
465 470 475

<210> SEQ ID NO 205
<211> LENGTH: 476
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 205

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

Asp Glu Asn Ile Thr Leu Glu Thr Val Cys His Asp Pro Lys Leu Pro
115 120 125

Tyr His Asp Phe Ile Leu Glu Asp Ala Ala Ser Pro Lys Cys Ile Met
130 135 140

Lys Glu Lys Lys Lys Pro Gly Glu Thr Phe Phe Met Cys Ser Cys Ser
145 150 155 160

Ser Asp Glu Cys Asn Asp Asn Ile Ile Phe Ser Glu Glu Tyr Asn Thr
165 170 175

Ser Asn Pro Asp Leu Leu Leu Val Ile Phe Gln Ser Asp Pro Thr Arg
180 185 190

Val His Leu Val Leu Gly Leu Ser Ala Val Leu Gly Leu Leu Leu Leu
195 200 205

Arg Trp Gln Phe Pro Ala His Tyr Arg Arg Leu Arg His Ala Leu Trp
210 215 220

Pro Ser Leu Pro Asp Leu His Arg Val Leu Gly Gln Tyr Leu Arg Asp
225 230 235 240

Thr Ala Ala Leu Ser Pro Pro Lys Ala Thr Val Ser Asp Thr Cys Glu
245 250 255

Glu Val Glu Pro Ser Leu Leu Glu Ile Leu Pro Lys Ser Ser Glu Arg
260 265 270

Thr Pro Leu Pro Leu Leu Glu Ala Arg Asp Glu Val Glu Gly Phe Leu
275 280 285

Gln Asp Thr Phe Pro Gln Gln Leu Glu Glu Ser Glu Lys Gln Arg Leu
290 295 300

Gly Gly Asp Val Gln Ser Pro Asn Cys Pro Ser Glu Asp Val Val Ile
305 310 315 320

Thr Pro Glu Ser Phe Gly Arg Asp Ser Ser Leu Thr Cys Leu Ala Gly
325 330 335

Asn Val Ser Ala Cys Asp Ala Pro Ile Leu Ser Ser Ser Arg Ser Leu
340 345 350

Asp Cys Arg Glu Ser Gly Lys Asn Gly Pro His Val Tyr Gln Asp Leu
355 360 365

Leu Leu Ser Leu Gly Thr Thr Asn Ser Thr Leu Pro Pro Pro Phe Ser
370 375 380

Leu Gln Ser Gly Ile Leu Thr Leu Asn Pro Val Ala Gln Gly Gln Pro
385 390 395 400

Ile Leu Thr Ser Leu Gly Ser Asn Gln Glu Glu Ala Tyr Val Thr Met
405 410 415

Ser Ser Phe Tyr Gln Asn Gln Ser Arg Ser Asp Pro Lys Pro Glu Asn
420 425 430

Pro Ala Cys Pro Trp Thr Val Leu Pro Ala Gly Asp Leu Pro Thr His
435 440 445

Asp Gly Tyr Leu Pro Ser Asn Ile Asp Asp Leu Pro Ser His Glu Ala
450 455 460

Pro Leu Ala Asp Ser Leu Glu Glu Leu Glu Pro Gln
465 470 475

<210> SEQ ID NO 206
<211> LENGTH: 475
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 206

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

Asp Glu Asn Ile Thr Leu Glu Thr Val Cys His Asp Pro Lys Leu Pro
115 120 125

Tyr His Asp Phe Ile Leu Glu Asp Ala Ala Ser Pro Lys Cys Ile Met
130 135 140

Lys Glu Lys Lys Lys Pro Gly Glu Thr Phe Phe Met Cys Ser Cys Ser
145 150 155 160

Ser Asp Glu Cys Asn Asp Asn Ile Ile Phe Ser Glu Glu Tyr Asn Thr
165 170 175

Ser Asn Pro Asp Leu Leu Leu Val Ile Phe Gln Ser Asp Pro Thr Arg
180 185 190

His Leu Val Leu Gly Leu Ser Ala Val Leu Gly Leu Leu Leu Leu Arg
195 200 205

Trp Gln Phe Pro Ala His Tyr Arg Arg Leu Arg His Ala Leu Trp Pro
210 215 220

Ser Leu Pro Asp Leu His Arg Val Leu Gly Gln Tyr Leu Arg Asp Thr
225 230 235 240

Ala Ala Leu Ser Pro Pro Lys Ala Thr Val Ser Asp Thr Cys Glu Glu
245 250 255

Val Glu Pro Ser Leu Leu Glu Ile Leu Pro Lys Ser Ser Glu Arg Thr
260 265 270

Pro Leu Pro Leu Leu Glu Ala Arg Asp Glu Val Glu Gly Phe Leu Gln
275 280 285

Asp Thr Phe Pro Gln Gln Leu Glu Glu Ser Glu Lys Gln Arg Leu Gly
290 295 300

Gly Asp Val Gln Ser Pro Asn Cys Pro Ser Glu Asp Val Val Ile Thr
305 310 315 320

Pro Glu Ser Phe Gly Arg Asp Ser Ser Leu Thr Cys Leu Ala Gly Asn
325 330 335

Val Ser Ala Cys Asp Ala Pro Ile Leu Ser Ser Ser Arg Ser Leu Asp
340 345 350

Cys Arg Glu Ser Gly Lys Asn Gly Pro His Val Tyr Gln Asp Leu Leu
355 360 365

Leu Ser Leu Gly Thr Thr Asn Ser Thr Leu Pro Pro Pro Phe Ser Leu
370 375 380

Gln Ser Gly Ile Leu Thr Leu Asn Pro Val Ala Gln Gly Gln Pro Ile
385 390 395 400

Leu Thr Ser Leu Gly Ser Asn Gln Glu Glu Ala Tyr Val Thr Met Ser
405 410 415

Ser Phe Tyr Gln Asn Gln Ser Arg Ser Asp Pro Lys Pro Glu Asn Pro
420 425 430

Ala Cys Pro Trp Thr Val Leu Pro Ala Gly Asp Leu Pro Thr His Asp
435 440 445

Gly Tyr Leu Pro Ser Asn Ile Asp Asp Leu Pro Ser His Glu Ala Pro
450 455 460

Leu Ala Asp Ser Leu Glu Glu Leu Glu Pro Gln
465 470 475

<210> SEQ ID NO 207
<211> LENGTH: 474
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 207

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

Asp Glu Asn Ile Thr Leu Glu Thr Val Cys His Asp Pro Lys Leu Pro
115 120 125

Tyr His Asp Phe Ile Leu Glu Asp Ala Ala Ser Pro Lys Cys Ile Met
130 135 140

Lys Glu Lys Lys Lys Pro Gly Glu Thr Phe Phe Met Cys Ser Cys Ser
145 150 155 160

Ser Asp Glu Cys Asn Asp Asn Ile Ile Phe Ser Glu Glu Tyr Asn Thr
165 170 175

Ser Asn Pro Asp Leu Leu Leu Val Ile Phe Gln Ser Asp Pro Thr His
180 185 190

Leu Val Leu Gly Leu Ser Ala Val Leu Gly Leu Leu Leu Leu Arg Trp
195 200 205

Gln Phe Pro Ala His Tyr Arg Arg Leu Arg His Ala Leu Trp Pro Ser
210 215 220

Leu Pro Asp Leu His Arg Val Leu Gly Gln Tyr Leu Arg Asp Thr Ala
225 230 235 240

Ala Leu Ser Pro Pro Lys Ala Thr Val Ser Asp Thr Cys Glu Glu Val
245 250 255

Glu Pro Ser Leu Leu Glu Ile Leu Pro Lys Ser Ser Glu Arg Thr Pro
260 265 270

Leu Pro Leu Leu Glu Ala Arg Asp Glu Val Glu Gly Phe Leu Gln Asp
275 280 285

Thr Phe Pro Gln Gln Leu Glu Glu Ser Glu Lys Gln Arg Leu Gly Gly
290 295 300

Asp Val Gln Ser Pro Asn Cys Pro Ser Glu Asp Val Val Ile Thr Pro
305 310 315 320

Glu Ser Phe Gly Arg Asp Ser Ser Leu Thr Cys Leu Ala Gly Asn Val
325 330 335

Ser Ala Cys Asp Ala Pro Ile Leu Ser Ser Ser Arg Ser Leu Asp Cys
340 345 350

Arg Glu Ser Gly Lys Asn Gly Pro His Val Tyr Gln Asp Leu Leu Leu
355 360 365

Ser Leu Gly Thr Thr Asn Ser Thr Leu Pro Pro Pro Phe Ser Leu Gln
370 375 380

Ser Gly Ile Leu Thr Leu Asn Pro Val Ala Gln Gly Gln Pro Ile Leu
385 390 395 400

Thr Ser Leu Gly Ser Asn Gln Glu Glu Ala Tyr Val Thr Met Ser Ser
405 410 415

Phe Tyr Gln Asn Gln Ser Arg Ser Asp Pro Lys Pro Glu Asn Pro Ala
420 425 430

```
Cys Pro Trp Thr Val Leu Pro Ala Gly Asp Leu Pro Thr His Asp Gly
        435                 440                 445

Tyr Leu Pro Ser Asn Ile Asp Asp Leu Pro Ser His Glu Ala Pro Leu
    450                 455                 460

Ala Asp Ser Leu Glu Glu Leu Glu Pro Gln
465                 470


<210> SEQ ID NO 208
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Met Ala Leu Pro Val Thr Ala Leu Leu Leu Pro Leu Ala Leu Leu Leu
1               5                   10                  15

His Ala Ala Arg Pro Met Gly Arg Gly Leu Leu Arg Gly Leu Trp Pro
            20                  25                  30

Leu His Ile Val Leu Trp Thr Arg Ile Ala Ser Thr Ile Pro Pro His
        35                  40                  45

Val Gln Lys Ser Val Asn Asn Asp Met Ile Val Thr Asp Asn Asn Gly
    50                  55                  60

Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser Asp Pro His Leu
            180                 185                 190

Val Leu Gly Leu Ser Ala Val Leu Gly Leu Leu Leu Leu Arg Trp Gln
        195                 200                 205

Phe Pro Ala His Tyr Arg Arg Leu Arg His Ala Leu Trp Pro Ser Leu
    210                 215                 220

Pro Asp Leu His Arg Val Leu Gly Gln Tyr Leu Arg Asp Thr Ala Ala
225                 230                 235                 240

Leu Ser Pro Pro Lys Ala Thr Val Ser Asp Thr Cys Glu Glu Val Glu
                245                 250                 255

Pro Ser Leu Leu Glu Ile Leu Pro Lys Ser Ser Glu Arg Thr Pro Leu
            260                 265                 270

Pro Leu Leu Glu Ala Arg Asp Glu Val Glu Gly Phe Leu Gln Asp Thr
        275                 280                 285

Phe Pro Gln Gln Leu Glu Glu Ser Glu Lys Gln Arg Leu Gly Gly Asp
    290                 295                 300

Val Gln Ser Pro Asn Cys Pro Ser Glu Asp Val Val Ile Thr Pro Glu
305                 310                 315                 320
```

Ser Phe Gly Arg Asp Ser Ser Leu Thr Cys Leu Ala Gly Asn Val Ser
325 330 335

Ala Cys Asp Ala Pro Ile Leu Ser Ser Ser Arg Ser Leu Asp Cys Arg
340 345 350

Glu Ser Gly Lys Asn Gly Pro His Val Tyr Gln Asp Leu Leu Leu Ser
355 360 365

Leu Gly Thr Thr Asn Ser Thr Leu Pro Pro Pro Phe Ser Leu Gln Ser
370 375 380

Gly Ile Leu Thr Leu Asn Pro Val Ala Gln Gly Gln Pro Ile Leu Thr
385 390 395 400

Ser Leu Gly Ser Asn Gln Glu Glu Ala Tyr Val Thr Met Ser Ser Phe
405 410 415

Tyr Gln Asn Gln Ser Arg Ser Asp Pro Lys Pro Glu Asn Pro Ala Cys
420 425 430

Pro Trp Thr Val Leu Pro Ala Gly Asp Leu Pro Thr His Asp Gly Tyr
435 440 445

Leu Pro Ser Asn Ile Asp Asp Leu Pro Ser His Glu Ala Pro Leu Ala
450 455 460

Asp Ser Leu Glu Glu Leu Glu Pro Gln
465 470

<210> SEQ ID NO 209
<211> LENGTH: 472
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 209

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

Asp Glu Asn Ile Thr Leu Glu Thr Val Cys His Asp Pro Lys Leu Pro
115 120 125

Tyr His Asp Phe Ile Leu Glu Asp Ala Ala Ser Pro Lys Cys Ile Met
130 135 140

Lys Glu Lys Lys Lys Pro Gly Glu Thr Phe Phe Met Cys Ser Cys Ser
145 150 155 160

Ser Asp Glu Cys Asn Asp Asn Ile Ile Phe Ser Glu Glu Tyr Asn Thr
165 170 175

Ser Asn Pro Asp Leu Leu Leu Val Ile Phe Gln Ser Asp His Leu Val
180 185 190

Leu Gly Leu Ser Ala Val Leu Gly Leu Leu Leu Leu Arg Trp Gln Phe
195 200 205

Pro Ala His Tyr Arg Arg Leu Arg His Ala Leu Trp Pro Ser Leu Pro
210 215 220

Asp Leu His Arg Val Leu Gly Gln Tyr Leu Arg Asp Thr Ala Ala Leu
225 230 235 240

Ser Pro Pro Lys Ala Thr Val Ser Asp Thr Cys Glu Glu Val Glu Pro
245 250 255

Ser Leu Leu Glu Ile Leu Pro Lys Ser Ser Glu Arg Thr Pro Leu Pro
260 265 270

Leu Leu Glu Ala Arg Asp Glu Val Glu Gly Phe Leu Gln Asp Thr Phe
275 280 285

Pro Gln Gln Leu Glu Glu Ser Glu Lys Gln Arg Leu Gly Gly Asp Val
290 295 300

Gln Ser Pro Asn Cys Pro Ser Glu Asp Val Val Ile Thr Pro Glu Ser
305 310 315 320

Phe Gly Arg Asp Ser Ser Leu Thr Cys Leu Ala Gly Asn Val Ser Ala
325 330 335

Cys Asp Ala Pro Ile Leu Ser Ser Ser Arg Ser Leu Asp Cys Arg Glu
340 345 350

Ser Gly Lys Asn Gly Pro His Val Tyr Gln Asp Leu Leu Leu Ser Leu
355 360 365

Gly Thr Thr Asn Ser Thr Leu Pro Pro Pro Phe Ser Leu Gln Ser Gly
370 375 380

Ile Leu Thr Leu Asn Pro Val Ala Gln Gly Gln Pro Ile Leu Thr Ser
385 390 395 400

Leu Gly Ser Asn Gln Glu Glu Ala Tyr Val Thr Met Ser Ser Phe Tyr
405 410 415

Gln Asn Gln Ser Arg Ser Asp Pro Lys Pro Glu Asn Pro Ala Cys Pro
420 425 430

Trp Thr Val Leu Pro Ala Gly Asp Leu Pro Thr His Asp Gly Tyr Leu
435 440 445

Pro Ser Asn Ile Asp Asp Leu Pro Ser His Glu Ala Pro Leu Ala Asp
450 455 460

Ser Leu Glu Glu Leu Glu Pro Gln
465 470

<210> SEQ ID NO 210
<211> LENGTH: 471
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 210

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

```
Ala Val Lys Phe Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
            100                 105                 110

Asp Glu Asn Ile Thr Leu Glu Thr Val Cys His Asp Pro Lys Leu Pro
        115                 120                 125

Tyr His Asp Phe Ile Leu Glu Asp Ala Ala Ser Pro Lys Cys Ile Met
    130                 135                 140

Lys Glu Lys Lys Lys Pro Gly Glu Thr Phe Phe Met Cys Ser Cys Ser
145                 150                 155                 160

Ser Asp Glu Cys Asn Asp Asn Ile Ile Phe Ser Glu Glu Tyr Asn Thr
                165                 170                 175

Ser Asn Pro Asp Leu Leu Leu Val Ile Phe Gln Ser His Leu Val Leu
            180                 185                 190

Gly Leu Ser Ala Val Leu Gly Leu Leu Leu Leu Arg Trp Gln Phe Pro
        195                 200                 205

Ala His Tyr Arg Arg Leu Arg His Ala Leu Trp Pro Ser Leu Pro Asp
    210                 215                 220

Leu His Arg Val Leu Gly Gln Tyr Leu Arg Asp Thr Ala Ala Leu Ser
225                 230                 235                 240

Pro Pro Lys Ala Thr Val Ser Asp Thr Cys Glu Glu Val Glu Pro Ser
                245                 250                 255

Leu Leu Glu Ile Leu Pro Lys Ser Ser Glu Arg Thr Pro Leu Pro Leu
            260                 265                 270

Leu Glu Ala Arg Asp Glu Val Glu Gly Phe Leu Gln Asp Thr Phe Pro
        275                 280                 285

Gln Gln Leu Glu Glu Ser Glu Lys Gln Arg Leu Gly Gly Asp Val Gln
    290                 295                 300

Ser Pro Asn Cys Pro Ser Glu Asp Val Val Ile Thr Pro Glu Ser Phe
305                 310                 315                 320

Gly Arg Asp Ser Ser Leu Thr Cys Leu Ala Gly Asn Val Ser Ala Cys
                325                 330                 335

Asp Ala Pro Ile Leu Ser Ser Ser Arg Ser Leu Asp Cys Arg Glu Ser
            340                 345                 350

Gly Lys Asn Gly Pro His Val Tyr Gln Asp Leu Leu Leu Ser Leu Gly
        355                 360                 365

Thr Thr Asn Ser Thr Leu Pro Pro Pro Phe Ser Leu Gln Ser Gly Ile
    370                 375                 380

Leu Thr Leu Asn Pro Val Ala Gln Gly Gln Pro Ile Leu Thr Ser Leu
385                 390                 395                 400

Gly Ser Asn Gln Glu Glu Ala Tyr Val Thr Met Ser Ser Phe Tyr Gln
                405                 410                 415

Asn Gln Ser Arg Ser Asp Pro Lys Pro Glu Asn Pro Ala Cys Pro Trp
            420                 425                 430

Thr Val Leu Pro Ala Gly Asp Leu Pro Thr His Asp Gly Tyr Leu Pro
        435                 440                 445

Ser Asn Ile Asp Asp Leu Pro Ser His Glu Ala Pro Leu Ala Asp Ser
    450                 455                 460

Leu Glu Glu Leu Glu Pro Gln
465                 470
```

<210> SEQ ID NO 211
<211> LENGTH: 470
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 211

Met Ala Leu Pro Val Thr Ala Leu Leu Leu Pro Leu Ala Leu Leu Leu
1 5 10 15

His Ala Ala Arg Pro Met Gly Arg Gly Leu Leu Arg Gly Leu Trp Pro
20 25 30

Leu His Ile Val Leu Trp Thr Arg Ile Ala Ser Thr Ile Pro Pro His
35 40 45

Val Gln Lys Ser Val Asn Asn Asp Met Ile Val Thr Asp Asn Asn Gly
50 55 60

Ala Val Lys Phe Pro Gln Leu Cys Lys Phe Cys Asp Val Arg Phe Ser
65 70 75 80

Thr Cys Asp Asn Gln Lys Ser Cys Met Ser Asn Cys Ser Ile Thr Ser
85 90 95

Ile Cys Glu Lys Pro Gln Glu Val Cys Val Ala Val Trp Arg Lys Asn
100 105 110

Asp Glu Asn Ile Thr Leu Glu Thr Val Cys His Asp Pro Lys Leu Pro
115 120 125

Tyr His Asp Phe Ile Leu Glu Asp Ala Ala Ser Pro Lys Cys Ile Met
130 135 140

Lys Glu Lys Lys Lys Pro Gly Glu Thr Phe Phe Met Cys Ser Cys Ser
145 150 155 160

Ser Asp Glu Cys Asn Asp Asn Ile Ile Phe Ser Glu Glu Tyr Asn Thr
165 170 175

Ser Asn Pro Asp Leu Leu Leu Val Ile Phe Gln His Leu Val Leu Gly
180 185 190

Leu Ser Ala Val Leu Gly Leu Leu Leu Leu Arg Trp Gln Phe Pro Ala
195 200 205

His Tyr Arg Arg Leu Arg His Ala Leu Trp Pro Ser Leu Pro Asp Leu
210 215 220

His Arg Val Leu Gly Gln Tyr Leu Arg Asp Thr Ala Ala Leu Ser Pro
225 230 235 240

Pro Lys Ala Thr Val Ser Asp Thr Cys Glu Glu Val Glu Pro Ser Leu
245 250 255

Leu Glu Ile Leu Pro Lys Ser Ser Glu Arg Thr Pro Leu Pro Leu Leu
260 265 270

Glu Ala Arg Asp Glu Val Glu Gly Phe Leu Gln Asp Thr Phe Pro Gln
275 280 285

Gln Leu Glu Glu Ser Glu Lys Gln Arg Leu Gly Gly Asp Val Gln Ser
290 295 300

Pro Asn Cys Pro Ser Glu Asp Val Val Ile Thr Pro Glu Ser Phe Gly
305 310 315 320

Arg Asp Ser Ser Leu Thr Cys Leu Ala Gly Asn Val Ser Ala Cys Asp
325 330 335

Ala Pro Ile Leu Ser Ser Ser Arg Ser Leu Asp Cys Arg Glu Ser Gly
340 345 350

Lys Asn Gly Pro His Val Tyr Gln Asp Leu Leu Leu Ser Leu Gly Thr
355 360 365

Thr Asn Ser Thr Leu Pro Pro Pro Phe Ser Leu Gln Ser Gly Ile Leu
    370                 375                 380

Thr Leu Asn Pro Val Ala Gln Gly Gln Pro Ile Leu Thr Ser Leu Gly
385                 390                 395                 400

Ser Asn Gln Glu Glu Ala Tyr Val Thr Met Ser Ser Phe Tyr Gln Asn
                405                 410                 415

Gln Ser Arg Ser Asp Pro Lys Pro Glu Asn Pro Ala Cys Pro Trp Thr
            420                 425                 430

Val Leu Pro Ala Gly Asp Leu Pro Thr His Asp Gly Tyr Leu Pro Ser
        435                 440                 445

Asn Ile Asp Asp Leu Pro Ser His Glu Ala Pro Leu Ala Asp Ser Leu
    450                 455                 460

Glu Glu Leu Glu Pro Gln
465                 470

<210> SEQ ID NO 212
<211> LENGTH: 434
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Met Ala Leu Pro Val Thr Ala Leu Leu Leu Pro Leu Ala Leu Leu Leu
1               5                   10                  15

His Ala Ala Arg Pro Gln Leu Cys Lys Phe Cys Asp Val Arg Phe Ser
            20                  25                  30

Thr Cys Asp Asn Gln Lys Ser Cys Met Ser Asn Cys Ser Ile Thr Ser
        35                  40                  45

Ile Cys Glu Lys Pro Gln Glu Val Cys Val Ala Val Trp Arg Lys Asn
    50                  55                  60

Asp Glu Asn Ile Thr Leu Glu Thr Val Cys His Asp Pro Lys Leu Pro
65                  70                  75                  80

Tyr His Asp Phe Ile Leu Glu Asp Ala Ala Ser Pro Lys Cys Ile Met
                85                  90                  95

Lys Glu Lys Lys Lys Pro Gly Glu Thr Phe Phe Met Cys Ser Cys Ser
            100                 105                 110

Ser Asp Glu Cys Asn Asp Asn Ile Ile Phe Ser Glu Glu Tyr Asn Thr
        115                 120                 125

Ser Asn Pro Asp Leu Leu Leu Val Ile Phe Gln Ser Asp Pro Thr Arg
    130                 135                 140

Val Glu Thr Ala Thr Glu Thr His Leu Val Leu Gly Leu Ser Ala Val
145                 150                 155                 160

Leu Gly Leu Leu Leu Leu Arg Trp Gln Phe Pro Ala His Tyr Arg Arg
                165                 170                 175

Leu Arg His Ala Leu Trp Pro Ser Leu Pro Asp Leu His Arg Val Leu
            180                 185                 190

Gly Gln Tyr Leu Arg Asp Thr Ala Ala Leu Ser Pro Pro Lys Ala Thr
        195                 200                 205

Val Ser Asp Thr Cys Glu Glu Val Glu Pro Ser Leu Leu Glu Ile Leu
    210                 215                 220

Pro Lys Ser Ser Glu Arg Thr Pro Leu Pro Leu Leu Glu Ala Arg Asp
225                 230                 235                 240

Glu Val Glu Gly Phe Leu Gln Asp Thr Phe Pro Gln Gln Leu Glu Glu
245 250 255

Ser Glu Lys Gln Arg Leu Gly Gly Asp Val Gln Ser Pro Asn Cys Pro
260 265 270

Ser Glu Asp Val Val Ile Thr Pro Glu Ser Phe Gly Arg Asp Ser Ser
275 280 285

Leu Thr Cys Leu Ala Gly Asn Val Ser Ala Cys Asp Ala Pro Ile Leu
290 295 300

Ser Ser Ser Arg Ser Leu Asp Cys Arg Glu Ser Gly Lys Asn Gly Pro
305 310 315 320

His Val Tyr Gln Asp Leu Leu Leu Ser Leu Gly Thr Thr Asn Ser Thr
325 330 335

Leu Pro Pro Pro Phe Ser Leu Gln Ser Gly Ile Leu Thr Leu Asn Pro
340 345 350

Val Ala Gln Gly Gln Pro Ile Leu Thr Ser Leu Gly Ser Asn Gln Glu
355 360 365

Glu Ala Tyr Val Thr Met Ser Ser Phe Tyr Gln Asn Gln Ser Arg Ser
370 375 380

Asp Pro Lys Pro Glu Asn Pro Ala Cys Pro Trp Thr Val Leu Pro Ala
385 390 395 400

Gly Asp Leu Pro Thr His Asp Gly Tyr Leu Pro Ser Asn Ile Asp Asp
405 410 415

Leu Pro Ser His Glu Ala Pro Leu Ala Asp Ser Leu Glu Glu Leu Glu
420 425 430

Pro Gln

<210> SEQ ID NO 213
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 213

Met Ala Leu Pro Val Thr Ala Leu Leu Leu Pro Leu Ala Leu Leu Leu
1 5 10 15

His Ala Ala Arg Pro Gln Leu Cys Lys Phe Cys Asp Val Arg Phe Ser
20 25 30

Thr Cys Asp Asn Gln Lys Ser Cys Met Ser Asn Cys Ser Ile Thr Ser
35 40 45

Ile Cys Glu Lys Pro Gln Glu Val Cys Val Ala Val Trp Arg Lys Asn
50 55 60

Asp Glu Asn Ile Thr Leu Glu Thr Val Cys His Asp Pro Lys Leu Pro
65 70 75 80

Tyr His Asp Phe Ile Leu Glu Asp Ala Ala Ser Pro Lys Cys Ile Met
85 90 95

Lys Glu Lys Lys Lys Pro Gly Glu Thr Phe Phe Met Cys Ser Cys Ser
100 105 110

Ser Asp Glu Cys Asn Asp Asn Ile Ile Phe Ser Glu Glu Tyr Asn Thr
115 120 125

Ser Asn Pro Asp Leu Leu Leu Val Ile Phe Gln Ser Asp Pro Thr Arg
130 135 140

Val Glu Thr Ala Thr Glu Thr Ala Trp Ile Leu Val Leu Ile Ser Leu
145 150 155 160

Val Thr Ala Leu His Leu Val Leu Gly Leu Ser Ala Val Leu Gly Leu
165 170 175

Leu Leu Leu Arg Trp Gln Phe Pro Ala His Tyr Arg Arg Leu Arg His
180 185 190

Ala Leu Trp Pro Ser Leu Pro Asp Leu His Arg Val Leu Gly Gln Tyr
195 200 205

Leu Arg Asp Thr Ala Ala Leu Ser Pro Pro Lys Ala Thr Val Ser Asp
210 215 220

Thr Cys Glu Glu Val Glu Pro Ser Leu Leu Glu Ile Leu Pro Lys Ser
225 230 235 240

Ser Glu Arg Thr Pro Leu Pro Leu Leu Glu Ala Arg Asp Glu Val Glu
245 250 255

Gly Phe Leu Gln Asp Thr Phe Pro Gln Gln Leu Glu Glu Ser Glu Lys
260 265 270

Gln Arg Leu Gly Gly Asp Val Gln Ser Pro Asn Cys Pro Ser Glu Asp
275 280 285

Val Val Ile Thr Pro Glu Ser Phe Gly Arg Asp Ser Ser Leu Thr Cys
290 295 300

Leu Ala Gly Asn Val Ser Ala Cys Asp Ala Pro Ile Leu Ser Ser Ser
305 310 315 320

Arg Ser Leu Asp Cys Arg Glu Ser Gly Lys Asn Gly Pro His Val Tyr
325 330 335

Gln Asp Leu Leu Leu Ser Leu Gly Thr Thr Asn Ser Thr Leu Pro Pro
340 345 350

Pro Phe Ser Leu Gln Ser Gly Ile Leu Thr Leu Asn Pro Val Ala Gln
355 360 365

Gly Gln Pro Ile Leu Thr Ser Leu Gly Ser Asn Gln Glu Glu Ala Tyr
370 375 380

Val Thr Met Ser Ser Phe Tyr Gln Asn Gln Ser Arg Ser Asp Pro Lys
385 390 395 400

Pro Glu Asn Pro Ala Cys Pro Trp Thr Val Leu Pro Ala Gly Asp Leu
405 410 415

Pro Thr His Asp Gly Tyr Leu Pro Ser Asn Ile Asp Asp Leu Pro Ser
420 425 430

His Glu Ala Pro Leu Ala Asp Ser Leu Glu Glu Leu Glu Pro Gln
435 440 445

<210> SEQ ID NO 214
<211> LENGTH: 430
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 214

Met Ala Leu Pro Val Thr Ala Leu Leu Leu Pro Leu Ala Leu Leu Leu
1 5 10 15

His Ala Ala Arg Pro Gln Leu Cys Lys Phe Cys Asp Val Arg Phe Ser
20 25 30

Thr Cys Asp Asn Gln Lys Ser Cys Met Ser Asn Cys Ser Ile Thr Ser
35 40 45

Ile Cys Glu Lys Pro Gln Glu Val Cys Val Ala Val Trp Arg Lys Asn
50 55 60

```
Asp Glu Asn Ile Thr Leu Glu Thr Val Cys His Asp Pro Lys Leu Pro
65                  70                  75                  80

Tyr His Asp Phe Ile Leu Glu Asp Ala Ala Ser Pro Lys Cys Ile Met
                85                  90                  95

Lys Glu Lys Lys Lys Pro Gly Glu Thr Phe Phe Met Cys Ser Cys Ser
            100                 105                 110

Ser Asp Glu Cys Asn Asp Asn Ile Ile Phe Ser Glu Glu Tyr Asn Thr
        115                 120                 125

Ser Asn Pro Asp Leu Leu Leu Val Ile Phe Gln Ser Asp Pro Thr Arg
    130                 135                 140

Val Glu Thr His Leu Val Leu Gly Leu Ser Ala Val Leu Gly Leu Leu
145                 150                 155                 160

Leu Leu Arg Trp Gln Phe Pro Ala His Tyr Arg Arg Leu Arg His Ala
                165                 170                 175

Leu Trp Pro Ser Leu Pro Asp Leu His Arg Val Leu Gly Gln Tyr Leu
            180                 185                 190

Arg Asp Thr Ala Ala Leu Ser Pro Pro Lys Ala Thr Val Ser Asp Thr
        195                 200                 205

Cys Glu Glu Val Glu Pro Ser Leu Leu Glu Ile Leu Pro Lys Ser Ser
    210                 215                 220

Glu Arg Thr Pro Leu Pro Leu Leu Glu Ala Arg Asp Glu Val Glu Gly
225                 230                 235                 240

Phe Leu Gln Asp Thr Phe Pro Gln Gln Leu Glu Glu Ser Glu Lys Gln
                245                 250                 255

Arg Leu Gly Gly Asp Val Gln Ser Pro Asn Cys Pro Ser Glu Asp Val
            260                 265                 270

Val Ile Thr Pro Glu Ser Phe Gly Arg Asp Ser Ser Leu Thr Cys Leu
        275                 280                 285

Ala Gly Asn Val Ser Ala Cys Asp Ala Pro Ile Leu Ser Ser Ser Arg
    290                 295                 300

Ser Leu Asp Cys Arg Glu Ser Gly Lys Asn Gly Pro His Val Tyr Gln
305                 310                 315                 320

Asp Leu Leu Leu Ser Leu Gly Thr Thr Asn Ser Thr Leu Pro Pro Pro
                325                 330                 335

Phe Ser Leu Gln Ser Gly Ile Leu Thr Leu Asn Pro Val Ala Gln Gly
            340                 345                 350

Gln Pro Ile Leu Thr Ser Leu Gly Ser Asn Gln Glu Glu Ala Tyr Val
        355                 360                 365

Thr Met Ser Ser Phe Tyr Gln Asn Gln Ser Arg Ser Asp Pro Lys Pro
    370                 375                 380

Glu Asn Pro Ala Cys Pro Trp Thr Val Leu Pro Ala Gly Asp Leu Pro
385                 390                 395                 400

Thr His Asp Gly Tyr Leu Pro Ser Asn Ile Asp Asp Leu Pro Ser His
                405                 410                 415

Glu Ala Pro Leu Ala Asp Ser Leu Glu Glu Leu Glu Pro Gln
            420                 425                 430
```

<210> SEQ ID NO 215
<211> LENGTH: 425
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

```
Met Ala Leu Pro Val Thr Ala Leu Leu Leu Pro Leu Ala Leu Leu Leu
1               5                   10                  15

His Ala Ala Arg Pro Gln Leu Cys Lys Phe Cys Asp Val Arg Phe Ser
            20                  25                  30

Thr Cys Asp Asn Gln Lys Ser Cys Met Ser Asn Cys Ser Ile Thr Ser
        35                  40                  45

Ile Cys Glu Lys Pro Gln Glu Val Cys Val Ala Val Trp Arg Lys Asn
    50                  55                  60

Asp Glu Asn Ile Thr Leu Glu Thr Val Cys His Asp Pro Lys Leu Pro
65                  70                  75                  80

Tyr His Asp Phe Ile Leu Glu Asp Ala Ala Ser Pro Lys Cys Ile Met
                85                  90                  95

Lys Glu Lys Lys Lys Pro Gly Glu Thr Phe Phe Met Cys Ser Cys Ser
            100                 105                 110

Ser Asp Glu Cys Asn Asp Asn Ile Ile Phe Ser Glu Glu Tyr Asn Thr
        115                 120                 125

Ser Asn Pro Asp Leu Leu Leu Val Ile Phe Gln Ser Asp Pro His Leu
    130                 135                 140

Val Leu Gly Leu Ser Ala Val Leu Gly Leu Leu Leu Leu Arg Trp Gln
145                 150                 155                 160

Phe Pro Ala His Tyr Arg Arg Leu Arg His Ala Leu Trp Pro Ser Leu
                165                 170                 175

Pro Asp Leu His Arg Val Leu Gly Gln Tyr Leu Arg Asp Thr Ala Ala
            180                 185                 190

Leu Ser Pro Pro Lys Ala Thr Val Ser Asp Thr Cys Glu Glu Val Glu
        195                 200                 205

Pro Ser Leu Leu Glu Ile Leu Pro Lys Ser Ser Glu Arg Thr Pro Leu
    210                 215                 220

Pro Leu Leu Glu Ala Arg Asp Glu Val Glu Gly Phe Leu Gln Asp Thr
225                 230                 235                 240

Phe Pro Gln Gln Leu Glu Glu Ser Glu Lys Gln Arg Leu Gly Gly Asp
                245                 250                 255

Val Gln Ser Pro Asn Cys Pro Ser Glu Asp Val Val Ile Thr Pro Glu
            260                 265                 270

Ser Phe Gly Arg Asp Ser Ser Leu Thr Cys Leu Ala Gly Asn Val Ser
        275                 280                 285

Ala Cys Asp Ala Pro Ile Leu Ser Ser Ser Arg Ser Leu Asp Cys Arg
    290                 295                 300

Glu Ser Gly Lys Asn Gly Pro His Val Tyr Gln Asp Leu Leu Leu Ser
305                 310                 315                 320

Leu Gly Thr Thr Asn Ser Thr Leu Pro Pro Pro Phe Ser Leu Gln Ser
                325                 330                 335

Gly Ile Leu Thr Leu Asn Pro Val Ala Gln Gly Gln Pro Ile Leu Thr
            340                 345                 350

Ser Leu Gly Ser Asn Gln Glu Glu Ala Tyr Val Thr Met Ser Ser Phe
        355                 360                 365

Tyr Gln Asn Gln Ser Arg Ser Asp Pro Lys Pro Glu Asn Pro Ala Cys
    370                 375                 380

Pro Trp Thr Val Leu Pro Ala Gly Asp Leu Pro Thr His Asp Gly Tyr
385                 390                 395                 400

Leu Pro Ser Asn Ile Asp Asp Leu Pro Ser His Glu Ala Pro Leu Ala
                405                 410                 415
```

```
Asp Ser Leu Glu Glu Leu Glu Pro Gln
            420                 425


<210> SEQ ID NO 216
<211> LENGTH: 424
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Met Ala Leu Pro Val Thr Ala Leu Leu Leu Pro Leu Ala Leu Leu Leu
1               5                   10                  15

His Ala Ala Arg Pro Gln Leu Cys Lys Phe Cys Asp Val Arg Phe Ser
            20                  25                  30

Thr Cys Asp Asn Gln Lys Ser Cys Met Ser Asn Cys Ser Ile Thr Ser
        35                  40                  45

Ile Cys Glu Lys Pro Gln Glu Val Cys Val Ala Val Trp Arg Lys Asn
    50                  55                  60

Asp Glu Asn Ile Thr Leu Glu Thr Val Cys His Asp Pro Lys Leu Pro
65                  70                  75                  80

Tyr His Asp Phe Ile Leu Glu Asp Ala Ala Ser Pro Lys Cys Ile Met
                85                  90                  95

Lys Glu Lys Lys Lys Pro Gly Glu Thr Phe Phe Met Cys Ser Cys Ser
            100                 105                 110

Ser Asp Glu Cys Asn Asp Asn Ile Ile Phe Ser Glu Glu Tyr Asn Thr
        115                 120                 125

Ser Asn Pro Asp Leu Leu Leu Val Ile Phe Gln Ser Asp His Leu Val
    130                 135                 140

Leu Gly Leu Ser Ala Val Leu Gly Leu Leu Leu Leu Arg Trp Gln Phe
145                 150                 155                 160

Pro Ala His Tyr Arg Arg Leu Arg His Ala Leu Trp Pro Ser Leu Pro
                165                 170                 175

Asp Leu His Arg Val Leu Gly Gln Tyr Leu Arg Asp Thr Ala Ala Leu
            180                 185                 190

Ser Pro Pro Lys Ala Thr Val Ser Asp Thr Cys Glu Glu Val Glu Pro
        195                 200                 205

Ser Leu Leu Glu Ile Leu Pro Lys Ser Ser Glu Arg Thr Pro Leu Pro
    210                 215                 220

Leu Leu Glu Ala Arg Asp Glu Val Glu Gly Phe Leu Gln Asp Thr Phe
225                 230                 235                 240

Pro Gln Gln Leu Glu Glu Ser Glu Lys Gln Arg Leu Gly Gly Asp Val
                245                 250                 255

Gln Ser Pro Asn Cys Pro Ser Glu Asp Val Val Ile Thr Pro Glu Ser
            260                 265                 270

Phe Gly Arg Asp Ser Ser Leu Thr Cys Leu Ala Gly Asn Val Ser Ala
        275                 280                 285

Cys Asp Ala Pro Ile Leu Ser Ser Ser Arg Ser Leu Asp Cys Arg Glu
    290                 295                 300

Ser Gly Lys Asn Gly Pro His Val Tyr Gln Asp Leu Leu Leu Ser Leu
305                 310                 315                 320

Gly Thr Thr Asn Ser Thr Leu Pro Pro Pro Phe Ser Leu Gln Ser Gly
                325                 330                 335
```

Ile Leu Thr Leu Asn Pro Val Ala Gln Gly Gln Pro Ile Leu Thr Ser
340 345 350

Leu Gly Ser Asn Gln Glu Glu Ala Tyr Val Thr Met Ser Ser Phe Tyr
355 360 365

Gln Asn Gln Ser Arg Ser Asp Pro Lys Pro Glu Asn Pro Ala Cys Pro
370 375 380

Trp Thr Val Leu Pro Ala Gly Asp Leu Pro Thr His Asp Gly Tyr Leu
385 390 395 400

Pro Ser Asn Ile Asp Asp Leu Pro Ser His Glu Ala Pro Leu Ala Asp
405 410 415

Ser Leu Glu Glu Leu Glu Pro Gln
420

<210> SEQ ID NO 217
<211> LENGTH: 105
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 217

Ser Asp Pro Thr Arg Val Glu Thr Ala Thr Glu Thr Ala Trp Ile Ser
1 5 10 15

Leu Val Thr Ala Leu Leu Leu Val Leu Gly Leu Asn Ala Val Leu Gly
20 25 30

Leu Leu Leu Leu Arg Lys Gln Phe Pro Ala His Tyr Arg Arg Leu Arg
35 40 45

His Ala Leu Trp Pro Ser Leu Pro Asp Leu His Arg Val Leu Gly Gln
50 55 60

Tyr Leu Arg Asp Thr Ala Ala Leu Ser Pro Pro Arg Ala Thr Val Ser
65 70 75 80

Asp Thr Cys Glu Glu Val Glu Pro Ser Leu Leu Glu Ile Leu Pro Arg
85 90 95

Ser Ser Glu Arg Thr Pro Leu Pro Leu
100 105

<210> SEQ ID NO 218
<211> LENGTH: 105
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 218

Ser Asp Pro Thr Arg Val Glu Thr Ala Thr Glu Thr Ala Trp Ile Ser
1 5 10 15

Leu Val Thr Ala Leu His Leu Val Leu Gly Leu Ser Ala Val Leu Gly
20 25 30

Leu Leu Leu Leu Arg Trp Gln Phe Pro Ala His Tyr Arg Arg Leu Arg
35 40 45

His Ala Leu Trp Pro Ser Leu Pro Asp Leu His Arg Val Leu Gly Gln
50 55 60

Tyr Leu Arg Asp Thr Ala Ala Leu Ser Pro Pro Arg Ala Thr Val Ser
65 70 75 80

Asp Thr Cys Glu Glu Val Glu Pro Ser Leu Leu Glu Ile Leu Pro Arg
85 90 95

Ser Ser Glu Arg Thr Pro Leu Pro Leu
100 105

<210> SEQ ID NO 219
<211> LENGTH: 98
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 219

Ser Asp Pro Thr Arg Val Glu Thr Ala Thr Glu Thr Ala Leu His Leu
1 5 10 15

Val Leu Gly Leu Asn Ala Val Leu Gly Leu Leu Leu Leu Arg Lys Gln
20 25 30

Phe Pro Ala His Tyr Arg Arg Leu Arg His Ala Leu Trp Pro Ser Leu
35 40 45

Pro Asp Leu His Arg Val Leu Gly Gln Tyr Leu Arg Asp Thr Ala Ala
50 55 60

Leu Ser Pro Pro Lys Ala Thr Val Ser Asp Thr Cys Glu Glu Val Glu
65 70 75 80

Pro Ser Leu Leu Glu Ile Leu Pro Lys Ser Ser Glu Arg Thr Pro Leu
85 90 95

Pro Leu

<210> SEQ ID NO 220
<211> LENGTH: 98
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 220

Ser Asp Pro Thr Arg Val Glu Thr Ala Thr Glu Thr Ala Leu His Leu
1 5 10 15

Val Leu Gly Leu Asn Ala Val Leu Gly Leu Leu Leu Leu Arg Lys Gln
20 25 30

Phe Pro Ala His Tyr Arg Arg Leu Arg His Ala Leu Trp Pro Ser Leu
35 40 45

Pro Asp Leu His Arg Val Leu Gly Gln Tyr Leu Arg Asp Thr Ala Ala
50 55 60

Leu Ser Pro Pro Arg Ala Thr Val Ser Asp Thr Cys Glu Glu Val Glu
65 70 75 80

Pro Ser Leu Leu Glu Ile Leu Pro Arg Ser Ser Glu Arg Thr Pro Leu
85 90 95

Pro Leu

<210> SEQ ID NO 221
<211> LENGTH: 97
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 221

Ser Asp Pro Thr Arg Val Glu Thr Ala Thr Glu Thr Leu His Leu Val
1 5 10 15

Leu Gly Leu Asn Ala Val Leu Gly Leu Leu Leu Leu Arg Lys Gln Phe
20 25 30

Pro Ala His Tyr Arg Arg Leu Arg His Ala Leu Trp Pro Ser Leu Pro
35 40 45

Asp Leu His Arg Val Leu Gly Gln Tyr Leu Arg Asp Thr Ala Ala Leu
50 55 60

Ser Pro Pro Lys Ala Thr Val Ser Asp Thr Cys Glu Glu Val Glu Pro
65 70 75 80

Ser Leu Leu Glu Ile Leu Pro Lys Ser Ser Glu Arg Thr Pro Leu Pro
85 90 95

Leu

<210> SEQ ID NO 222
<211> LENGTH: 97
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 222

Ser Asp Pro Thr Arg Val Glu Thr Ala Thr Glu Thr Leu His Leu Val
1 5 10 15

Leu Gly Leu Asn Ala Val Leu Gly Leu Leu Leu Leu Arg Lys Gln Phe
20 25 30

Pro Ala His Tyr Arg Arg Leu Arg His Ala Leu Trp Pro Ser Leu Pro
35 40 45

Asp Leu His Arg Val Leu Gly Gln Tyr Leu Arg Asp Thr Ala Ala Leu
50 55 60

Ser Pro Pro Arg Ala Thr Val Ser Asp Thr Cys Glu Glu Val Glu Pro
65 70 75 80

Ser Leu Leu Glu Ile Leu Pro Arg Ser Ser Glu Arg Thr Pro Leu Pro
85 90 95

Leu

<210> SEQ ID NO 223
<211> LENGTH: 96
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 223

Ser Asp Pro Thr Arg Val Glu Thr Ala Thr Glu Thr His Leu Val Leu
1 5 10 15

Gly Leu Asn Ala Val Leu Gly Leu Leu Leu Leu Arg Lys Gln Phe Pro
20 25 30

Ala His Tyr Arg Arg Leu Arg His Ala Leu Trp Pro Ser Leu Pro Asp
35 40 45

Leu His Arg Val Leu Gly Gln Tyr Leu Arg Asp Thr Ala Ala Leu Ser
50 55 60

Pro Pro Lys Ala Thr Val Ser Asp Thr Cys Glu Glu Val Glu Pro Ser
65 70 75 80

Leu Leu Glu Ile Leu Pro Lys Ser Ser Glu Arg Thr Pro Leu Pro Leu
85 90 95

<210> SEQ ID NO 224
<211> LENGTH: 96
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 224

```
Ser Asp Pro Thr Arg Val Glu Thr Ala Thr Glu Thr His Leu Val Leu
1               5                   10                  15

Gly Leu Asn Ala Val Leu Gly Leu Leu Leu Leu Arg Lys Gln Phe Pro
            20                  25                  30

Ala His Tyr Arg Arg Leu Arg His Ala Leu Trp Pro Ser Leu Pro Asp
        35                  40                  45

Leu His Arg Val Leu Gly Gln Tyr Leu Arg Asp Thr Ala Ala Leu Ser
    50                  55                  60

Pro Pro Arg Ala Thr Val Ser Asp Thr Cys Glu Glu Val Glu Pro Ser
65                  70                  75                  80

Leu Leu Glu Ile Leu Pro Arg Ser Ser Glu Arg Thr Pro Leu Pro Leu
                85                  90                  95
```

<210> SEQ ID NO 225
<211> LENGTH: 109
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 225

```
Ser Asp Pro Thr Arg Val Glu Thr Ala Thr Glu Thr Ala Trp Ile Leu
1               5                   10                  15

Val Leu Ile Ser Leu Val Thr Ala Leu His Leu Val Leu Gly Leu Asn
            20                  25                  30

Ala Val Leu Gly Leu Leu Leu Leu Arg Lys Gln Phe Pro Ala His Tyr
        35                  40                  45

Arg Arg Leu Arg His Ala Leu Trp Pro Ser Leu Pro Asp Leu His Arg
    50                  55                  60

Val Leu Gly Gln Tyr Leu Arg Asp Thr Ala Ala Leu Ser Pro Pro Lys
65                  70                  75                  80

Ala Thr Val Ser Asp Thr Cys Glu Glu Val Glu Pro Ser Leu Leu Glu
                85                  90                  95

Ile Leu Pro Lys Ser Ser Glu Arg Thr Pro Leu Pro Leu
            100                 105
```

<210> SEQ ID NO 226
<211> LENGTH: 109
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 226

```
Ser Asp Pro Thr Arg Val Glu Thr Ala Thr Glu Thr Ala Trp Ile Leu
1               5                   10                  15

Val Leu Ile Ser Leu Val Thr Ala Leu His Leu Val Leu Gly Leu Asn
            20                  25                  30

Ala Val Leu Gly Leu Leu Leu Leu Arg Lys Gln Phe Pro Ala His Tyr
        35                  40                  45
```

Arg Arg Leu Arg His Ala Leu Trp Pro Ser Leu Pro Asp Leu His Arg
50 55 60

Val Leu Gly Gln Tyr Leu Arg Asp Thr Ala Ala Leu Ser Pro Pro Arg
65 70 75 80

Ala Thr Val Ser Asp Thr Cys Glu Glu Val Glu Pro Ser Leu Leu Glu
85 90 95

Ile Leu Pro Arg Ser Ser Glu Arg Thr Pro Leu Pro Leu
100 105

<210> SEQ ID NO 227
<211> LENGTH: 95
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 227

Ser Asp Pro Thr Arg Val Glu Thr Ala Thr Glu His Leu Val Leu Gly
1 5 10 15

Leu Asn Ala Val Leu Gly Leu Leu Leu Leu Arg Lys Gln Phe Pro Ala
20 25 30

His Tyr Arg Arg Leu Arg His Ala Leu Trp Pro Ser Leu Pro Asp Leu
35 40 45

His Arg Val Leu Gly Gln Tyr Leu Arg Asp Thr Ala Ala Leu Ser Pro
50 55 60

Pro Lys Ala Thr Val Ser Asp Thr Cys Glu Glu Val Glu Pro Ser Leu
65 70 75 80

Leu Glu Ile Leu Pro Lys Ser Ser Glu Arg Thr Pro Leu Pro Leu
85 90 95

<210> SEQ ID NO 228
<211> LENGTH: 95
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 228

Ser Asp Pro Thr Arg Val Glu Thr Ala Thr Glu His Leu Val Leu Gly
1 5 10 15

Leu Asn Ala Val Leu Gly Leu Leu Leu Leu Arg Lys Gln Phe Pro Ala
20 25 30

His Tyr Arg Arg Leu Arg His Ala Leu Trp Pro Ser Leu Pro Asp Leu
35 40 45

His Arg Val Leu Gly Gln Tyr Leu Arg Asp Thr Ala Ala Leu Ser Pro
50 55 60

Pro Arg Ala Thr Val Ser Asp Thr Cys Glu Glu Val Glu Pro Ser Leu
65 70 75 80

Leu Glu Ile Leu Pro Arg Ser Ser Glu Arg Thr Pro Leu Pro Leu
85 90 95

<210> SEQ ID NO 229
<211> LENGTH: 92
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 229

Ser Asp Pro Thr Arg Val Glu Thr His Leu Val Leu Gly Leu Asn Ala
1               5                   10                  15

Val Leu Gly Leu Leu Leu Leu Arg Lys Gln Phe Pro Ala His Tyr Arg
            20                  25                  30

Arg Leu Arg His Ala Leu Trp Pro Ser Leu Pro Asp Leu His Arg Val
        35                  40                  45

Leu Gly Gln Tyr Leu Arg Asp Thr Ala Ala Leu Ser Pro Pro Lys Ala
    50                  55                  60

Thr Val Ser Asp Thr Cys Glu Glu Val Glu Pro Ser Leu Leu Glu Ile
65                  70                  75                  80

Leu Pro Lys Ser Ser Glu Arg Thr Pro Leu Pro Leu
                85                  90

<210> SEQ ID NO 230
<211> LENGTH: 92
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 230

Ser Asp Pro Thr Arg Val Glu Thr His Leu Val Leu Gly Leu Asn Ala
1               5                   10                  15

Val Leu Gly Leu Leu Leu Leu Arg Lys Gln Phe Pro Ala His Tyr Arg
            20                  25                  30

Arg Leu Arg His Ala Leu Trp Pro Ser Leu Pro Asp Leu His Arg Val
        35                  40                  45

Leu Gly Gln Tyr Leu Arg Asp Thr Ala Ala Leu Ser Pro Pro Arg Ala
    50                  55                  60

Thr Val Ser Asp Thr Cys Glu Glu Val Glu Pro Ser Leu Leu Glu Ile
65                  70                  75                  80

Leu Pro Arg Ser Ser Glu Arg Thr Pro Leu Pro Leu
                85                  90

<210> SEQ ID NO 231
<211> LENGTH: 87
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 231

Ser Asp Pro His Leu Val Leu Gly Leu Asn Ala Val Leu Gly Leu Leu
1               5                   10                  15

Leu Leu Arg Lys Gln Phe Pro Ala His Tyr Arg Arg Leu Arg His Ala
            20                  25                  30

Leu Trp Pro Ser Leu Pro Asp Leu His Arg Val Leu Gly Gln Tyr Leu
        35                  40                  45

Arg Asp Thr Ala Ala Leu Ser Pro Pro Lys Ala Thr Val Ser Asp Thr
    50                  55                  60

Cys Glu Glu Val Glu Pro Ser Leu Leu Glu Ile Leu Pro Lys Ser Ser
65                  70                  75                  80

Glu Arg Thr Pro Leu Pro Leu
                85

<210> SEQ ID NO 232
<211> LENGTH: 87
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 232

Ser Asp Pro His Leu Val Leu Gly Leu Asn Ala Val Leu Gly Leu Leu
1 5 10 15

Leu Leu Arg Lys Gln Phe Pro Ala His Tyr Arg Arg Leu Arg His Ala
20 25 30

Leu Trp Pro Ser Leu Pro Asp Leu His Arg Val Leu Gly Gln Tyr Leu
35 40 45

Arg Asp Thr Ala Ala Leu Ser Pro Pro Arg Ala Thr Val Ser Asp Thr
50 55 60

Cys Glu Glu Val Glu Pro Ser Leu Leu Glu Ile Leu Pro Arg Ser Ser
65 70 75 80

Glu Arg Thr Pro Leu Pro Leu
85

<210> SEQ ID NO 233
<211> LENGTH: 86
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 233

Ser Asp His Leu Val Leu Gly Leu Asn Ala Val Leu Gly Leu Leu Leu
1 5 10 15

Leu Arg Lys Gln Phe Pro Ala His Tyr Arg Arg Leu Arg His Ala Leu
20 25 30

Trp Pro Ser Leu Pro Asp Leu His Arg Val Leu Gly Gln Tyr Leu Arg
35 40 45

Asp Thr Ala Ala Leu Ser Pro Pro Lys Ala Thr Val Ser Asp Thr Cys
50 55 60

Glu Glu Val Glu Pro Ser Leu Leu Glu Ile Leu Pro Lys Ser Ser Glu
65 70 75 80

Arg Thr Pro Leu Pro Leu
85

<210> SEQ ID NO 234
<211> LENGTH: 86
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 234

Ser Asp His Leu Val Leu Gly Leu Asn Ala Val Leu Gly Leu Leu Leu
1 5 10 15

Leu Arg Lys Gln Phe Pro Ala His Tyr Arg Arg Leu Arg His Ala Leu
20 25 30

Trp Pro Ser Leu Pro Asp Leu His Arg Val Leu Gly Gln Tyr Leu Arg
35 40 45

```
Asp Thr Ala Ala Leu Ser Pro Pro Arg Ala Thr Val Ser Asp Thr Cys
    50                  55                  60

Glu Glu Val Glu Pro Ser Leu Leu Glu Ile Leu Pro Arg Ser Ser Glu
65                  70                  75                  80

Arg Thr Pro Leu Pro Leu
                85


<210> SEQ ID NO 235
<211> LENGTH: 55
<212> TYPE: PRT
<213> ORGANISM: Homo sapiens

<400> SEQUENCE: 235

Ser Asp Pro Thr Arg Val Glu Thr Ala Thr Glu Thr Ala Trp Ile Ser
1               5                   10                  15

Leu Val Thr Ala Leu His Leu Val Leu Gly Leu Ser Ala Val Leu Gly
            20                  25                  30

Leu Leu Leu Leu Arg Trp Gln Phe Pro Ala His Tyr Arg Arg Leu Arg
        35                  40                  45

His Ala Leu Trp Pro Ser Leu
    50                  55


<210> SEQ ID NO 236
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Ser Asp Pro Thr Arg Val Glu Thr Ala Thr Glu Thr Trp Ile Ser Leu
1               5                   10                  15

Val Thr Ala Leu His Leu Val Leu Gly Leu Ser Ala Val Leu Gly Leu
            20                  25                  30

Leu Leu Leu Arg Trp Gln Phe Pro Ala His Tyr Arg Arg Leu Arg His
        35                  40                  45

Ala Leu Trp Pro Ser Leu
    50


<210> SEQ ID NO 237
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Ser Asp Pro Thr Arg Val Glu Thr Ala Thr Glu Thr Ile Ser Leu Val
1               5                   10                  15

Thr Ala Leu His Leu Val Leu Gly Leu Ser Ala Val Leu Gly Leu Leu
            20                  25                  30

Leu Leu Arg Trp Gln Phe Pro Ala His Tyr Arg Arg Leu Arg His Ala
        35                  40                  45

Leu Trp Pro Ser Leu
    50


<210> SEQ ID NO 238
<211> LENGTH: 54
```

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 238

Ser Asp Pro Thr Arg Val Glu Thr Ala Thr Glu Thr Leu Ile Ser Leu
1 5 10 15

Val Thr Ala Leu His Leu Val Leu Gly Leu Ser Ala Val Leu Gly Leu
20 25 30

Leu Leu Leu Arg Trp Gln Phe Pro Ala His Tyr Arg Arg Leu Arg His
35 40 45

Ala Leu Trp Pro Ser Leu
50

<210> SEQ ID NO 239
<211> LENGTH: 52
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 239

Ser Asp Pro Thr Arg Val Glu Thr Ala Thr Glu Thr Ser Leu Val Thr
1 5 10 15

Ala Leu His Leu Val Leu Gly Leu Ser Ala Val Leu Gly Leu Leu Leu
20 25 30

Leu Arg Trp Gln Phe Pro Ala His Tyr Arg Arg Leu Arg His Ala Leu
35 40 45

Trp Pro Ser Leu
50

<210> SEQ ID NO 240
<211> LENGTH: 51
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 240

Ser Asp Pro Thr Arg Val Glu Thr Ala Thr Glu Thr Leu Val Thr Ala
1 5 10 15

Leu His Leu Val Leu Gly Leu Ser Ala Val Leu Gly Leu Leu Leu Leu
20 25 30

Arg Trp Gln Phe Pro Ala His Tyr Arg Arg Leu Arg His Ala Leu Trp
35 40 45

Pro Ser Leu
50

<210> SEQ ID NO 241
<211> LENGTH: 52
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 241

Ser Asp Pro Thr Arg Val Glu Thr Ala Thr Glu Thr Ile Leu Val Thr
1 5 10 15

Ala Leu His Leu Val Leu Gly Leu Ser Ala Val Leu Gly Leu Leu Leu
20 25 30

Leu Arg Trp Gln Phe Pro Ala His Tyr Arg Arg Leu Arg His Ala Leu
35 40 45

Trp Pro Ser Leu
50

<210> SEQ ID NO 242
<211> LENGTH: 50
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 242

Ser Asp Pro Thr Arg Val Glu Thr Ala Thr Glu Thr Val Thr Ala Leu
1 5 10 15

His Leu Val Leu Gly Leu Ser Ala Val Leu Gly Leu Leu Leu Leu Arg
20 25 30

Trp Gln Phe Pro Ala His Tyr Arg Arg Leu Arg His Ala Leu Trp Pro
35 40 45

Ser Leu
50

<210> SEQ ID NO 243
<211> LENGTH: 49
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 243

Ser Asp Pro Thr Arg Val Glu Thr Ala Thr Glu Thr Thr Ala Leu His
1 5 10 15

Leu Val Leu Gly Leu Ser Ala Val Leu Gly Leu Leu Leu Leu Arg Trp
20 25 30

Gln Phe Pro Ala His Tyr Arg Arg Leu Arg His Ala Leu Trp Pro Ser
35 40 45

Leu

<210> SEQ ID NO 244
<211> LENGTH: 48
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 244

Ser Asp Pro Thr Arg Val Glu Thr Ala Thr Glu Thr Ala Leu His Leu
1 5 10 15

Val Leu Gly Leu Ser Ala Val Leu Gly Leu Leu Leu Leu Arg Trp Gln
20 25 30

Phe Pro Ala His Tyr Arg Arg Leu Arg His Ala Leu Trp Pro Ser Leu
35 40 45

<210> SEQ ID NO 245
<211> LENGTH: 47
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 245

Ser Asp Pro Thr Arg Val Glu Thr Ala Thr Glu Thr Leu His Leu Val
1               5                   10                  15

Leu Gly Leu Ser Ala Val Leu Gly Leu Leu Leu Leu Arg Trp Gln Phe
            20                  25                  30

Pro Ala His Tyr Arg Arg Leu Arg His Ala Leu Trp Pro Ser Leu
        35                  40                  45

<210> SEQ ID NO 246
<211> LENGTH: 46
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 246

Ser Asp Pro Thr Arg Val Glu Thr Ala Thr Glu Thr His Leu Val Leu
1               5                   10                  15

Gly Leu Ser Ala Val Leu Gly Leu Leu Leu Leu Arg Trp Gln Phe Pro
            20                  25                  30

Ala His Tyr Arg Arg Leu Arg His Ala Leu Trp Pro Ser Leu
        35                  40                  45

<210> SEQ ID NO 247
<211> LENGTH: 56
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 247

Ser Asp Pro Thr Arg Val Glu Thr Ala Thr Glu Thr Ala Trp Leu Ile
1               5                   10                  15

Ser Leu Val Thr Ala Leu His Leu Val Leu Gly Leu Ser Ala Val Leu
            20                  25                  30

Gly Leu Leu Leu Leu Arg Trp Gln Phe Pro Ala His Tyr Arg Arg Leu
        35                  40                  45

Arg His Ala Leu Trp Pro Ser Leu
    50                  55

<210> SEQ ID NO 248
<211> LENGTH: 57
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 248

Ser Asp Pro Thr Arg Val Glu Thr Ala Thr Glu Thr Ala Trp Val Leu
1               5                   10                  15

Ile Ser Leu Val Thr Ala Leu His Leu Val Leu Gly Leu Ser Ala Val
            20                  25                  30

Leu Gly Leu Leu Leu Leu Arg Trp Gln Phe Pro Ala His Tyr Arg Arg
35 40 45

Leu Arg His Ala Leu Trp Pro Ser Leu
50 55

<210> SEQ ID NO 249
<211> LENGTH: 58
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 249

Ser Asp Pro Thr Arg Val Glu Thr Ala Thr Glu Thr Ala Trp Leu Val
1 5 10 15

Leu Ile Ser Leu Val Thr Ala Leu His Leu Val Leu Gly Leu Ser Ala
20 25 30

Val Leu Gly Leu Leu Leu Leu Arg Trp Gln Phe Pro Ala His Tyr Arg
35 40 45

Arg Leu Arg His Ala Leu Trp Pro Ser Leu
50 55

<210> SEQ ID NO 250
<211> LENGTH: 59
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 250

Ser Asp Pro Thr Arg Val Glu Thr Ala Thr Glu Thr Ala Trp Ile Leu
1 5 10 15

Val Leu Ile Ser Leu Val Thr Ala Leu His Leu Val Leu Gly Leu Ser
20 25 30

Ala Val Leu Gly Leu Leu Leu Leu Arg Trp Gln Phe Pro Ala His Tyr
35 40 45

Arg Arg Leu Arg His Ala Leu Trp Pro Ser Leu
50 55

<210> SEQ ID NO 251
<211> LENGTH: 60
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 251

Ser Asp Pro Thr Arg Val Glu Thr Ala Thr Glu Thr Ala Trp Leu Ile
1 5 10 15

Leu Val Leu Ile Ser Leu Val Thr Ala Leu His Leu Val Leu Gly Leu
20 25 30

Ser Ala Val Leu Gly Leu Leu Leu Leu Arg Trp Gln Phe Pro Ala His
35 40 45

Tyr Arg Arg Leu Arg His Ala Leu Trp Pro Ser Leu
50 55 60

<210> SEQ ID NO 252
<211> LENGTH: 61

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 252

Ser Asp Pro Thr Arg Val Glu Thr Ala Thr Glu Thr Ala Trp Leu Leu
1 5 10 15

Ile Leu Val Leu Ile Ser Leu Val Thr Ala Leu His Leu Val Leu Gly
20 25 30

Leu Ser Ala Val Leu Gly Leu Leu Leu Leu Arg Trp Gln Phe Pro Ala
35 40 45

His Tyr Arg Arg Leu Arg His Ala Leu Trp Pro Ser Leu
50 55 60

<210> SEQ ID NO 253
<211> LENGTH: 62
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 253

Ser Asp Pro Thr Arg Val Glu Thr Ala Thr Glu Thr Ala Trp Val Leu
1 5 10 15

Leu Ile Leu Val Leu Ile Ser Leu Val Thr Ala Leu His Leu Val Leu
20 25 30

Gly Leu Ser Ala Val Leu Gly Leu Leu Leu Leu Arg Trp Gln Phe Pro
35 40 45

Ala His Tyr Arg Arg Leu Arg His Ala Leu Trp Pro Ser Leu
50 55 60

<210> SEQ ID NO 254
<211> LENGTH: 63
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 254

Ser Asp Pro Thr Arg Val Glu Thr Ala Thr Glu Thr Ala Trp Leu Val
1 5 10 15

Leu Leu Ile Leu Val Leu Ile Ser Leu Val Thr Ala Leu His Leu Val
20 25 30

Leu Gly Leu Ser Ala Val Leu Gly Leu Leu Leu Leu Arg Trp Gln Phe
35 40 45

Pro Ala His Tyr Arg Arg Leu Arg His Ala Leu Trp Pro Ser Leu
50 55 60

<210> SEQ ID NO 255
<211> LENGTH: 45
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 255

Ser Asp Pro Thr Arg Val Glu Thr Ala Thr Glu Thr Leu Val Leu Gly
1 5 10 15

Leu Ser Ala Val Leu Gly Leu Leu Leu Leu Arg Trp Gln Phe Pro Ala
20 25 30

His Tyr Arg Arg Leu Arg His Ala Leu Trp Pro Ser Leu
35 40 45

<210> SEQ ID NO 256
<211> LENGTH: 44
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 256

Ser Asp Pro Thr Arg Val Glu Thr Ala Thr Glu Thr Val Leu Gly Leu
1 5 10 15

Ser Ala Val Leu Gly Leu Leu Leu Leu Arg Trp Gln Phe Pro Ala His
20 25 30

Tyr Arg Arg Leu Arg His Ala Leu Trp Pro Ser Leu
35 40

<210> SEQ ID NO 257
<211> LENGTH: 43
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 257

Ser Asp Pro Thr Arg Val Glu Thr Ala Thr Glu Thr Leu Gly Leu Ser
1 5 10 15

Ala Val Leu Gly Leu Leu Leu Leu Arg Trp Gln Phe Pro Ala His Tyr
20 25 30

Arg Arg Leu Arg His Ala Leu Trp Pro Ser Leu
35 40

<210> SEQ ID NO 258
<211> LENGTH: 42
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 258

Ser Asp Pro Thr Arg Val Glu Thr Ala Thr Glu Thr Gly Leu Ser Ala
1 5 10 15

Val Leu Gly Leu Leu Leu Leu Arg Trp Gln Phe Pro Ala His Tyr Arg
20 25 30

Arg Leu Arg His Ala Leu Trp Pro Ser Leu
35 40

<210> SEQ ID NO 259
<211> LENGTH: 41
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 259

Ser Asp Pro Thr Arg Val Glu Thr Ala Thr Glu Thr Leu Ser Ala Val
1 5 10 15

Leu Gly Leu Leu Leu Leu Arg Trp Gln Phe Pro Ala His Tyr Arg Arg
20 25 30

Leu Arg His Ala Leu Trp Pro Ser Leu
35 40

<210> SEQ ID NO 260
<211> LENGTH: 45
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 260

Ser Asp Pro Thr Arg Val Glu Thr Ala Thr Glu His Leu Val Leu Gly
1 5 10 15

Leu Ser Ala Val Leu Gly Leu Leu Leu Leu Arg Trp Gln Phe Pro Ala
20 25 30

His Tyr Arg Arg Leu Arg His Ala Leu Trp Pro Ser Leu
35 40 45

<210> SEQ ID NO 261
<211> LENGTH: 44
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 261

Ser Asp Pro Thr Arg Val Glu Thr Ala Thr His Leu Val Leu Gly Leu
1 5 10 15

Ser Ala Val Leu Gly Leu Leu Leu Leu Arg Trp Gln Phe Pro Ala His
20 25 30

Tyr Arg Arg Leu Arg His Ala Leu Trp Pro Ser Leu
35 40

<210> SEQ ID NO 262
<211> LENGTH: 43
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 262

Ser Asp Pro Thr Arg Val Glu Thr Ala His Leu Val Leu Gly Leu Ser
1 5 10 15

Ala Val Leu Gly Leu Leu Leu Leu Arg Trp Gln Phe Pro Ala His Tyr
20 25 30

Arg Arg Leu Arg His Ala Leu Trp Pro Ser Leu
35 40

<210> SEQ ID NO 263
<211> LENGTH: 42
<212> TYPE: PRT

<213> ORGANISM: Artificial Sequence
<220> FEATURE:
<223> OTHER INFORMATION: Description of Artificial Sequence: Synthetic
polypeptide

<400> SEQUENCE: 263

Ser Asp Pro Thr Arg Val Glu Thr His Leu Val Leu Gly Leu Ser Ala
1 5 10 15

Val Leu Gly Leu Leu Leu Leu Arg Trp Gln Phe Pro Ala His Tyr Arg
20 25 30

Arg Leu Arg His Ala Leu Trp Pro Ser Leu
35 40

<210> SEQ ID NO 264
<211> LENGTH: 41
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 264

Ser Asp Pro Thr Arg Val Glu His Leu Val Leu Gly Leu Ser Ala Val
1 5 10 15

Leu Gly Leu Leu Leu Leu Arg Trp Gln Phe Pro Ala His Tyr Arg Arg
20 25 30

Leu Arg His Ala Leu Trp Pro Ser Leu
35 40

<210> SEQ ID NO 265
<211> LENGTH: 40
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 265

Ser Asp Pro Thr Arg Val His Leu Val Leu Gly Leu Ser Ala Val Leu
1 5 10 15

Gly Leu Leu Leu Leu Arg Trp Gln Phe Pro Ala His Tyr Arg Arg Leu
20 25 30

Arg His Ala Leu Trp Pro Ser Leu
35 40

<210> SEQ ID NO 266
<211> LENGTH: 39
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 266

Ser Asp Pro Thr Arg His Leu Val Leu Gly Leu Ser Ala Val Leu Gly
1 5 10 15

Leu Leu Leu Leu Arg Trp Gln Phe Pro Ala His Tyr Arg Arg Leu Arg
20 25 30

His Ala Leu Trp Pro Ser Leu
35

<210> SEQ ID NO 267
<211> LENGTH: 38

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 267

Ser Asp Pro Thr His Leu Val Leu Gly Leu Ser Ala Val Leu Gly Leu
1 5 10 15

Leu Leu Leu Arg Trp Gln Phe Pro Ala His Tyr Arg Arg Leu Arg His
20 25 30

Ala Leu Trp Pro Ser Leu
35

<210> SEQ ID NO 268
<211> LENGTH: 37
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 268

Ser Asp Pro His Leu Val Leu Gly Leu Ser Ala Val Leu Gly Leu Leu
1 5 10 15

Leu Leu Arg Trp Gln Phe Pro Ala His Tyr Arg Arg Leu Arg His Ala
20 25 30

Leu Trp Pro Ser Leu
35

<210> SEQ ID NO 269
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 269

Ser Asp His Leu Val Leu Gly Leu Ser Ala Val Leu Gly Leu Leu Leu
1 5 10 15

Leu Arg Trp Gln Phe Pro Ala His Tyr Arg Arg Leu Arg His Ala Leu
20 25 30

Trp Pro Ser Leu
35

<210> SEQ ID NO 270
<211> LENGTH: 35
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 270

Ser His Leu Val Leu Gly Leu Ser Ala Val Leu Gly Leu Leu Leu Leu
1 5 10 15

Arg Trp Gln Phe Pro Ala His Tyr Arg Arg Leu Arg His Ala Leu Trp
20 25 30

Pro Ser Leu
35

<210> SEQ ID NO 271

<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 271

His Leu Val Leu Gly Leu Ser Ala Val Leu Gly Leu Leu Leu Leu Arg
1 5 10 15

Trp Gln Phe Pro Ala His Tyr Arg Arg Leu Arg His Ala Leu Trp Pro
20 25 30

Ser Leu

<210> SEQ ID NO 272
<211> LENGTH: 244
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 272

Met Ala Leu Pro Val Thr Ala Leu Leu Leu Pro Leu Ala Leu Leu Leu
1 5 10 15

His Ala Ala Arg Pro Ser Asp Pro Thr Arg Val Glu Thr Ala Thr Glu
20 25 30

Thr Ala Trp Ile Ser Leu Val Thr Ala Leu Leu Leu Val Leu Gly Leu
35 40 45

Asn Ala Val Leu Gly Leu Leu Leu Leu Arg Lys Gln Phe Pro Ala His
50 55 60

Tyr Arg Arg Leu Arg His Ala Leu Trp Pro Ser Leu Pro Asp Leu His
65 70 75 80

Arg Val Leu Gly Gln Tyr Leu Arg Asp Thr Ala Ala Leu Ser Pro Pro
85 90 95

Arg Ala Thr Val Ser Asp Thr Cys Glu Glu Val Glu Pro Ser Leu Leu
100 105 110

Glu Ile Leu Pro Arg Ser Ser Glu Arg Thr Pro Leu Pro Leu Leu Glu
115 120 125

Gln Gln Asp Lys Val Pro Glu Pro Ala Ser Leu Ser Ser Asn His Ser
130 135 140

Leu Thr Ser Cys Phe Thr Asn Gln Gly Tyr Phe Phe Phe His Leu Pro
145 150 155 160

Asp Ala Leu Glu Ile Glu Ala Cys Gln Asp Glu Gly Val Ala Gly Ala
165 170 175

Pro Thr Gly Ser Ser Pro Gln Pro Leu Gln Pro Leu Ser Gly Glu Asp
180 185 190

Asp Ala Tyr Cys Thr Phe Pro Ser Arg Asp Asp Leu Leu Leu Phe Ser
195 200 205

Pro Ser Gly Gln Gly Glu Phe Arg Ala Leu Asn Ala Arg Leu Pro Leu
210 215 220

Asn Thr Asp Ala Tyr Leu Ser Leu Gln Glu Leu Gln Gly Gln Asp Pro
225 230 235 240

Thr His Leu Val

<210> SEQ ID NO 273
<211> LENGTH: 203
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 273

Met Ala Leu Pro Val Thr Ala Leu Leu Leu Pro Leu Ala Leu Leu Leu
1 5 10 15

His Ala Ala Arg Pro Ser Asp Pro Thr Arg Val Glu Thr Ala Thr Glu
20 25 30

Thr Ala Trp Ile Ser Leu Val Thr Ala Leu His Leu Val Leu Gly Leu
35 40 45

Asn Ala Val Leu Gly Leu Leu Leu Leu Arg Lys Gln Phe Pro Ala His
50 55 60

Tyr Arg Arg Leu Arg His Ala Leu Trp Pro Ser Leu Pro Asp Leu His
65 70 75 80

Arg Val Leu Gly Gln Tyr Leu Arg Asp Thr Ala Ala Leu Ser Pro Pro
85 90 95

Arg Ala Thr Val Ser Asp Thr Cys Glu Glu Val Glu Pro Ser Leu Leu
100 105 110

Glu Ile Leu Pro Arg Ser Ser Glu Arg Thr Pro Leu Pro Leu Leu Glu
115 120 125

Asp Glu Gly Val Ala Gly Ala Pro Thr Gly Ser Ser Pro Gln Pro Leu
130 135 140

Gln Pro Leu Ser Gly Glu Asp Asp Ala Tyr Cys Thr Phe Pro Ser Arg
145 150 155 160

Asp Asp Leu Leu Leu Phe Ser Pro Ser Gly Gln Gly Glu Phe Arg Ala
165 170 175

Leu Asn Ala Arg Leu Pro Leu Asn Thr Asp Ala Tyr Leu Ser Leu Gln
180 185 190

Glu Leu Gln Gly Gln Asp Pro Thr His Leu Val
195 200

<210> SEQ ID NO 274
<211> LENGTH: 394
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 274

Met Ala Leu Pro Val Thr Ala Leu Leu Leu Pro Leu Ala Leu Leu Leu
1 5 10 15

His Ala Ala Arg Pro Pro Gly Trp Phe Leu Asp Ser Pro Asp Arg Pro
20 25 30

Trp Asn Pro Pro Thr Phe Ser Pro Ala Leu Leu Val Val Thr Glu Gly
35 40 45

Asp Asn Ala Thr Phe Thr Cys Ser Phe Ser Asn Thr Ser Glu Ser Phe
50 55 60

His Val Ile Trp His Arg Glu Ser Pro Ser Gly Gln Thr Asp Thr Leu
65 70 75 80

Ala Ala Phe Pro Glu Asp Arg Ser Gln Pro Gly Gln Asp Cys Arg Phe
85 90 95

Arg Val Thr Gln Leu Pro Asn Gly Arg Asp Phe His Met Ser Val Val
100 105 110

```
Arg Ala Arg Arg Asn Asp Ser Gly Thr Tyr Val Cys Gly Val Ile Ser
        115                 120                 125

Leu Ala Pro Lys Ile Gln Ile Lys Glu Ser Leu Arg Ala Glu Leu Arg
    130                 135                 140

Val Thr Glu Arg Arg Ala Glu Val Pro Thr Ala His Pro Ser Pro Ser
145                 150                 155                 160

Pro Arg Pro Ala Gly Gln Phe Gln Thr Leu Val Ser Asp Pro Thr Arg
                165                 170                 175

Val Glu Thr Ala Thr Glu Thr Ala Trp Ile Ser Leu Val Thr Ala Leu
            180                 185                 190

Leu Leu Val Leu Gly Leu Asn Ala Val Leu Gly Leu Leu Leu Leu Arg
        195                 200                 205

Lys Gln Phe Pro Ala His Tyr Arg Arg Leu Arg His Ala Leu Trp Pro
    210                 215                 220

Ser Leu Pro Asp Leu His Arg Val Leu Gly Gln Tyr Leu Arg Asp Thr
225                 230                 235                 240

Ala Ala Leu Ser Pro Pro Arg Ala Thr Val Ser Asp Thr Cys Glu Glu
                245                 250                 255

Val Glu Pro Ser Leu Leu Glu Ile Leu Pro Arg Ser Ser Glu Arg Thr
            260                 265                 270

Pro Leu Pro Leu Leu Glu Gln Gln Asp Lys Val Pro Glu Pro Ala Ser
        275                 280                 285

Leu Ser Ser Asn His Ser Leu Thr Ser Cys Phe Thr Asn Gln Gly Tyr
    290                 295                 300

Phe Phe Phe His Leu Pro Asp Ala Leu Glu Ile Glu Ala Cys Gln Asp
305                 310                 315                 320

Glu Gly Val Ala Gly Ala Pro Thr Gly Ser Ser Pro Gln Pro Leu Gln
                325                 330                 335

Pro Leu Ser Gly Glu Asp Asp Ala Tyr Cys Thr Phe Pro Ser Arg Asp
            340                 345                 350

Asp Leu Leu Leu Phe Ser Pro Ser Gly Gln Gly Glu Phe Arg Ala Leu
        355                 360                 365

Asn Ala Arg Leu Pro Leu Asn Thr Asp Ala Tyr Leu Ser Leu Gln Glu
    370                 375                 380

Leu Gln Gly Gln Asp Pro Thr His Leu Val
385                 390
```

<210> SEQ ID NO 275
<211> LENGTH: 353
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

```
Met Ala Leu Pro Val Thr Ala Leu Leu Leu Pro Leu Ala Leu Leu Leu
1               5                   10                  15

His Ala Ala Arg Pro Pro Gly Trp Phe Leu Asp Ser Pro Asp Arg Pro
            20                  25                  30

Trp Asn Pro Pro Thr Phe Ser Pro Ala Leu Leu Val Val Thr Glu Gly
        35                  40                  45

Asp Asn Ala Thr Phe Thr Cys Ser Phe Ser Asn Thr Ser Glu Ser Phe
    50                  55                  60
```

-continued

```
His Val Ile Trp His Arg Glu Ser Pro Ser Gly Gln Thr Asp Thr Leu
65                  70                  75                  80

Ala Ala Phe Pro Glu Asp Arg Ser Gln Pro Gly Gln Asp Cys Arg Phe
                85                  90                  95

Arg Val Thr Gln Leu Pro Asn Gly Arg Asp Phe His Met Ser Val Val
            100                 105                 110

Arg Ala Arg Arg Asn Asp Ser Gly Thr Tyr Val Cys Gly Val Ile Ser
        115                 120                 125

Leu Ala Pro Lys Ile Gln Ile Lys Glu Ser Leu Arg Ala Glu Leu Arg
    130                 135                 140

Val Thr Glu Arg Arg Ala Glu Val Pro Thr Ala His Pro Ser Pro Ser
145                 150                 155                 160

Pro Arg Pro Ala Gly Gln Phe Gln Thr Leu Val Ser Asp Pro Thr Arg
                165                 170                 175

Val Glu Thr Ala Thr Glu Thr Ala Trp Ile Ser Leu Val Thr Ala Leu
            180                 185                 190

His Leu Val Leu Gly Leu Asn Ala Val Leu Gly Leu Leu Leu Leu Arg
        195                 200                 205

Lys Gln Phe Pro Ala His Tyr Arg Arg Leu Arg His Ala Leu Trp Pro
    210                 215                 220

Ser Leu Pro Asp Leu His Arg Val Leu Gly Gln Tyr Leu Arg Asp Thr
225                 230                 235                 240

Ala Ala Leu Ser Pro Pro Arg Ala Thr Val Ser Asp Thr Cys Glu Glu
                245                 250                 255

Val Glu Pro Ser Leu Leu Glu Ile Leu Pro Arg Ser Ser Glu Arg Thr
            260                 265                 270

Pro Leu Pro Leu Leu Glu Asp Glu Gly Val Ala Gly Ala Pro Thr Gly
        275                 280                 285

Ser Ser Pro Gln Pro Leu Gln Pro Leu Ser Gly Glu Asp Asp Ala Tyr
    290                 295                 300

Cys Thr Phe Pro Ser Arg Asp Asp Leu Leu Leu Phe Ser Pro Ser Gly
305                 310                 315                 320

Gln Gly Glu Phe Arg Ala Leu Asn Ala Arg Leu Pro Leu Asn Thr Asp
                325                 330                 335

Ala Tyr Leu Ser Leu Gln Glu Leu Gln Gly Gln Asp Pro Thr His Leu
            340                 345                 350

Val
```